(12) United States Patent
O'Neill et al.

(10) Patent No.: US 7,119,207 B2
(45) Date of Patent: Oct. 10, 2006

(54) BENZOAMIDE PIPERIDINE CONTAINING COMPOUNDS AND RELATED COMPOUNDS

(75) Inventors: Brian Thomas O'Neill, Old Saybrook, CT (US); Arthur Adam Nagel, Gales Ferry, CT (US); John Michael Humphrey, Mystic, CT (US); Susan Beth Sobolov-Jaynes, Ivoryton, CT (US); Thomas Allen Chappie, Old Lyme, CT (US); Lawrence Albert Vincent, Moosup, CT (US); Eric Platt Arnold, Hebron, CT (US); Jianhua Huang, Waterford, CT (US)

(73) Assignee: Pfizer INC, New York, NY (US)

( * ) Notice: Subject to any disclaimer, the term of this patent is extended or adjusted under 35 U.S.C. 154(b) by 32 days.

(21) Appl. No.: 09/811,218

(22) Filed: Mar. 16, 2001

(65) Prior Publication Data

US 2003/0087925 A1    May 8, 2003

Related U.S. Application Data

(60) Provisional application No. 60/212,922, filed on Jun. 20, 2000, provisional application No. 60/195,922, filed on Apr. 10, 2000.

(51) Int. Cl.
| C07D 401/06 | (2006.01) |
| C07D 401/08 | (2006.01) |
| A61K 31/4523 | (2006.01) |
| A61P 25/06 | (2006.01) |

(52) U.S. Cl. .................. 546/199; 546/113; 546/18; 514/256; 514/322; 514/278; 544/333

(58) Field of Classification Search ............ 546/199, 546/113, 18
See application file for complete search history.

(56) References Cited

U.S. PATENT DOCUMENTS

| 3,539,584 A | 11/1970 | Suh et al. |
| 4,680,283 A | 7/1987 | Veber et al. |
| 5,604,252 A | 2/1997 | O'Neill |

FOREIGN PATENT DOCUMENTS

| EP | 0122494 | | 10/1984 |
| WO | 9206079 | | 4/1992 |
| WO | WO-94 13663 | * | 6/1994 |
| WO | 9703066 | | 1/1997 |
| WO | WO-97 03066 | * | 1/1997 |
| WO | 9958500 | | 11/1999 |
| WO | 0073312 | | 5/2000 |
| WO | 0073313 | | 5/2000 |

OTHER PUBLICATIONS

Cordero, et al.; Syntheses of 3-Phenyl Substituted Idolizidin-2-ones and a Pyrrolizidin-2-one on the Route to Constrained Potential NK$_1$ Receptor Antagonists; Tetrahedron; vol. 50, No. 44 pp. 12713-12726 (1994).

* cited by examiner

*Primary Examiner*—Venkataraman Balasubramanian
(74) *Attorney, Agent, or Firm*—Steve T. Zelson; Jolene W. Appleman

(57) ABSTRACT

The present invention relates to certain benzoamide piperidine containing compounds and related compounds that exhibit activity as NK-1 receptor antagonists, (e.g., substance P receptor antagonists), to pharmaceutical compositions containing them, and to their use in the treatment and prevention of central nervous system disorders, inflammatory disorders, cardiovascular disorders, ophthalmic disorders, gastrointestinal disorders, disorders caused by *helicobacter pylori*, disorders of the immune system, urinary incontinence, pain, migraine, emesis, angiogenesis and other disorders.

51 Claims, No Drawings

BENZOAMIDE PIPERIDINE CONTAINING COMPOUNDS AND RELATED COMPOUNDS

This application claims priority under 35 U.S.C. § 119(e) from U.S. Provisional Application Ser. No. 60/195,922, filed Apr. 10, 2000, and from U.S. Provisional Application Ser. No. 60/212,922, filed Jun. 20, 2000, which applications are hereby incorporated by reference.

The present invention relates to certain benzoamide piperidine containing compounds and related compounds that exhibit activity as NK-1 receptor antagonists, (e.g., substance P receptor antagonists), to pharmaceutical compositions containing them, and to their use in the treatment and prevention of central nervous system disorders, inflammatory disorders, cardiovascular disorders, ophthalmic disorders, gastrointestinal disorders, disorders caused by *helicobacter pylori*, disorders of the immune system, urinary incontinence, pain, migraine, emesis, angiogenesis and other disorders.

Substance P is a naturally occurring undecapeptide belonging to the tachykinin family of peptides, the latter being so-named because of their prompt stimulatory action on smooth muscle tissue. More specially, substance P is a pharmaceutically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art.

World Patent Application WO 97/03066, published Jan. 30, 1997, and U.S. Pat. No. 6,180,647, refer to substituted benzolactam and cyclicthioamide compounds that exhibit activity as substance P receptor antagonists. Other substance P receptor antagonists containing a fused bicyclic moiety are referred to in the following: U.S. patent application Ser. No. 09/011,271, filed Jun. 10, 1996; U.S. Provisional Patent Application No. 60/132,858, filed May 6, 1999; U.S. patent application Ser. No. 09/402,630, filed Oct. 26, 1998; and World Patent Application WO 99/13663, published Jun. 23, 1994.

The foregoing patent applications are incorporated herein by reference in their entirety.

SUMMARY OF THE INVENTION

The present invention relates to compounds of the formula

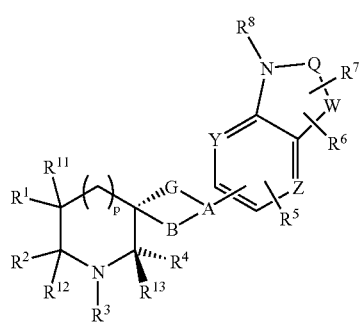

I wherein Q is C=NH, C=CH$_2$, C=S, C=O, SO or SO$_2$;

A is CH, CH$_2$, C(C$_1$–C$_6$)alkyl, CH(C$_1$–C$_6$)alkyl, C(CF$_3$) or CH(CF$_3$), with the proviso that when B is present, A must be either CH, C(C$_1$–C$_6$)alkyl or C(CF$_3$);

B is absent or is methylene or ethylene;

each of Y and Z is N or CH, with the proviso that Y and Z can not both be N;

G is NH(CH$_2$)$_q$, S(CH$_2$)$_q$ or O(CH$_2$)$_q$, wherein q is zero or one;

with the proviso that when q is zero, G is NH$_2$, SH or OH;

W is a one carbon linking group (i.e., methylene) or a saturated or unsaturated two or three carbon linking group, wherein each of the foregoing W groups can optionally be substituted with one substituent R$^7$ or two substituents R$^7$ and R$^6$, or W is a one carbon linking group that forms, together with a 2, 3, 4 or 5 carbon chain, a 3, 4, 5 or 6 membered spiro ring, respectively;

or W is a saturated two carbon chain linking group that forms, together with a separate 1, 2 or 3 carbon chain, a fused 3, 4 or 5 membered ring, respectively;

or W is a saturated two carbon chain linking group, wherein one of the two carbons in the chain forms, together with a separate 2, 3, 4 or 5 carbon chain, a 3, 4, 5 or 6 membered spiro ring, respectively;

p is zero, one or two;

R$^3$ is selected from hydrogen, COR$^9$, CO$_2$R$^9$, optionally substituted phenyl, optionally substituted heterocyclic rings, and optionally substituted (C$_1$–C$_8$)alkyl wherein one of the CH$_2$ groups of said (C$_1$–C$_8$)alkyl may optionally be replaced with a sulfur, oxygen or carbonyl group and wherein said (C$_1$–C$_8$)alkyl can optionally be substituted with from one to three substituents, preferably with zero substituents or one substituent, independently selected from hydroxy, oxo, phenyl-(C$_1$–C$_3$)alkoxy, phenyl, cyano, halo, optionally substituted heterocyclic rings, NR$^9$COR$^{10}$, NR$^9$CO$_2$R$^{10}$, CONR$^9$R$^{10}$, COR$^9$, CO$_2$R$^9$, NR$^9$R$^{10}$, and (C$_1$–C$_6$)alkoxy optionally substituted with from one to seven fluorine atoms, preferably with from zero to three fluorine atoms;

and wherein the heterocyclic rings of R$^3$ and the heterocyclic ring substituents on the alkyl groups of R$^3$ are selected, independently, from 3 to 7 membered saturated or unsaturated monocyclic rings containing from 1 to 4 ring heteroatoms, and 8 to 12 membered saturated or unsaturated bicyclic rings containing from 1 to 4 ring heteroatoms, wherein said heteroatoms are selected, independently, from oxygen, nitrogen and sulfur, with the proviso that there can not be two adjacent ring oxygen atoms or two adjacent ring sulfur atoms in either the monocyclic or bicyclic heterocyclic rings, and with the proviso that heterocyclic rings formed from NR$^9$R$^{10}$ or CONR$^9$R$^{10}$ must contain at least one nitrogen atom;

and wherein the heterocyclic rings of R$^3$ and the heterocyclic ring substituents on the alkyl groups of R$^3$ can optionally be substituted with one or more substituents, preferably with zero, one or two substituents, independently selected from oxo, hydroxy, thioxo, halo, cyano, phenyl, (CH$_2$)$_m$NR$^9$R$^{10}$, NR$^9$COR$^{10}$, (CH$_2$)$_m$OR$^9$, wherein m is zero, one or two, and (C$_1$–C$_6$)alkyl optionally substituted with one or more substituents, preferably with from zero to two substituents, independently selected from halo, CF$_3$, methoxy and phenyl;

and wherein the phenyl groups of R$^3$ and the phenyl substituents in the alkyl groups of R$^3$ can optionally be substituted with one or more substituents, preferably with from zero to two substitutents, independently selected from the group consisting of halo, cyano, nitro, CF$_3$, (CH$_2$)$_m$NR$^9$R$^{10}$, wherein m is zero, one or two, NR$^9$COR$^{10}$, NR$^9$CO$_2$R$^{10}$, CONR$^9$R$^{10}$, CO$_2$NR$^9$R$^{10}$, COR$^9$, CO$_2$R$^9$, ($C_1$–$C_6$)alkyl optionally substituted with from one to seven fluorine atoms, preferably with from zero to three fluorine atoms, ($C_1$–$C_6$)alkoxy optionally substituted with from one to seven fluorine atoms, preferably with from zero to three fluorine atoms, and ($C_2$–$C_6$)alkenyl optionally substituted with from one to seven fluorine atoms, preferably with from zero to three fluorine atoms;

each of $R^1$, $R^2$, $R^{11}$, $R^{12}$ and $R^{13}$ are selected, independently, from hydrogen and ($C_1$–$C_6$)alkyl optionally substituted with one or more substituents, preferably with zero, one or two substituents, that are selected, independently, from hydroxy, oxo, ($C_1$–$C_6$)alkoxy and cyano;

or $R^1$ and $R^2$, together with the carbon atoms to which they are attached, or $R^2$ and $R^3$, together with the carbon and nitrogen to which they are attached, respectively, form a 5 or 6 membered saturated heterocyclic ring containing one or two heteroatoms that are selected, independently, from nitrogen, oxygen and sulfur, with the proviso that said ring can not contain two adjacent oxygen atoms or two adjacent sulfur atoms; or $R^1$ and $R^2$, together with the carbons to which they are attached, form a 5 or 6 membered, saturated or unsaturated carbocyclic ring, and wherein said heterocyclic and carbocyclic rings formed by $R^1$ and $R^2$ or by $R^2$ and $R^3$ can be substituted with one or more substituents, preferably with zero substituents or one substituent, independently selected from halo, oxo, $NR^9R^{10}$, ($C_1$–$C_6$)alkyl optionally substituted with from one to seven fluorine atoms, preferably with from zero to three fluorine atoms, and ($C_1$–$C_6$)alkoxy optionally substituted with from one to seven fluorine atoms, preferably with from zero to three fluorine atoms;

or $R^{12}$ and $R^{13}$, together with the carbon atoms to which they are attached, form a 5 or 6 membered saturated heterocyclic ring containing one or two heteroatoms that are selected, independently, from nitrogen, oxygen and sulfur, with the proviso that said ring can not contain two adjacent oxygen atoms or two adjacent sulfur atoms, or $R^{12}$ and $R^{13}$, together with the carbons to which they are attached, form a 5 or 6 membered, saturated or unsaturated carbocyclic ring, and wherein said heterocyclic and carbocyclic rings formed by $R^{12}$ and $R^{13}$ can be substituted with one or more substituents, preferably with zero substituents or one substituent, independently selected from $NR^9R^{10}$, halo, phenyl-S—, phenyl-SO—, phenyl-$SO_2$—, oxo, ($C_1$–$C_6$)alkoxy optionally substituted with from one to three fluorine atoms, and ($C_1$–$C_6$)alkyl optionally substituted with from one to seven fluorine atoms, preferably with from zero to three fluorine atoms:

with the proviso that no more than one of $R^1$ and $R^2$, $R^2$ and $R^3$, and $R^{12}$ and $R^{13}$ can form a ring;

$R^4$ is selected from phenyl, 2-, 3- or 4-pyridyl, 2- or 3-thienyl, and pyrimidyl, wherein $R^4$ can be optionally substituted with one or more substituents, preferably with zero or one substituent, selected, independently, from halo, ($C_1$–$C_6$)alkyl optionally substituted with from one to seven fluorine atoms, preferably with from zero to three fluorine atoms, ($C_1$–$C_6$)alkoxy optionally substituted with from one to seven fluorine atoms, preferably with from zero to three fluorine atoms, and ($C_2$–$C_6$)alkenyl optionally substituted with from one to seven fluorine atoms, preferably with from zero to three fluorine atoms;

$R^5$ and $R^8$ are selected, independently, from hydrogen, —SO($C_1$–$C_6$)alkyl, —$SO_2$—($C_1$–$C_6$)alkyl, —SO-aryl, —$SO_2$-aryl, $CF_3$, halo, phenyl, phenyl-($C_1$–$C_2$)alkyl, hydroxy, aryloxy, heteroaryloxy, pyridyl, tetrazolyl, oxazolyl, thiazolyl, ($C_1$–$C_6$)alkoxy optionally substituted with from one to seven fluorine atoms, preferably with from zero to three fluorine atoms, ($C_1$–$C_6$)alkyl optionally substituted with from one to seven fluorine atoms, preferably with from zero to three fluorine atoms, and ($C_1$–$C_6$)alkyl substituted with one or more substituents, preferably with from zero to two substituents selected, independently, from hydroxy, oxo, ($C_1$–$C_6$)alkoxy, phenyl-($C_1$–$C_3$)alkoxy, phenyl, cyano, chloro, bromo, iodo, $NR^9R^{10}$, $NR^9COR^{10}$, $NR^9CO_2R^{10}$, $CONR^9R^{10}$, $COR^9$ and $CO_2R^9$;

$R^6$ and $R^7$ are selected, independently, from —SO($C_1$–$C_6$)alkyl, —$SO_2$—($C_1$–$C_6$)alkyl, —SO-aryl, —$SO_2$-aryl, $CF_3$, halo, phenyl, phenyl-($C_1$–$C_2$)alkyl, hydroxy, aryloxy, heteroaryloxy, pyridyl, tetrazolyl, oxazolyl, thiazolyl, ($C_1$–$C_6$)alkoxy optionally substituted with from one to seven fluorine atoms, preferably with from zero to three fluorine atoms, ($C_1$–$C_6$)alkyl optionally substituted with from one to seven fluorine atoms, preferably with from zero to three fluorine atoms, and ($C_1$–$C_6$)alkyl substituted with one or more substituents, preferably with from zero to two substituents selected, independently, from hydroxy, oxo, ($C_1$–$C_6$)alkoxy, phenyl-($C_1$–$C_3$)alkoxy, phenyl, cyano, chloro, bromo, iodo, $NR^9R^{10}$, $NR^9COR^{10}$, $NR^9CO_2R^{10}$, $CONR^9R^{10}$, $COR^9$ and $CO_2R^9$;

each $R^9$ and each $R^{10}$ is selected, independently, from hydrogen, ($C_1$–$C_6$)alkyl, hydroxy($C_1$–$C_6$)alkyl, phenyl and $CF_3$;

or $R^9$ and $R^{10}$, when $R^3$ is $NR^9R^{10}$ or $CONR^9R^{10}$, can form, together with the nitrogen to which they are attached, an optionally substituted heterocyclic ring that contains at least one nitrogen atom;

and wherein the phenyl groups in the definition of $R^5$, $R^6$, $R^7$ and $R^8$ and the phenyl moiety of phenyl ($C_1$–$C_2$)alkyl in the definition of $R^5$, $R^6$, $R^7$ and $R^8$ can optionally be substituted with one or more substituents, preferably with from zero to two substituents, that are selected, independently, from halo, hydroxy, ($C_1$–$C_6$)alkoxy optionally substituted with from one to seven fluorine atoms, preferably with from zero to three fluorine atoms, and ($C_1$–$C_6$)alkyl optionally substituted with from one to seven fluorine atoms, preferably with from zero to three fluorine atoms;

with the proviso that: (a) $R^8$ can not be halo, hydroxy, cyano, aryloxy, heteroaryloxy, substituted or unsubstituted ($C_1$–$C_6$)alkoxy or methyl substituted with from 1–3 fluorine atoms; and (b) when Q is C=O or C=S, and Y and Z are both carbon, and W is a methylene, ethylene or propylene group that is optionally substituted with ($C_1$–$C_6$)alkyl or fluoro substituted ($C_1$–$C_6$)alkyl, and all of $R^1$, $R^2$, $R^{11}$, $R^{12}$ and $R^{13}$ are hydrogen, and $R^5$, $R^6$, $R^7$, and $R^8$ are selected from hydrogen, halo, ($C_1$–$C_6$)alkyl optionally substituted with from 1 to 7 fluorine atoms, ($C_1$–$C_6$)alkoxy optionally substituted with from 1 to 7 fluorine atoms, then $R^3$ can not be hydrogen;

and the pharmaceutically acceptable salts of such compounds.

Examples of the optionally substituted heterocyclic rings of $R^3$ and the optionally substituted heterocyclic ring substitutents on the alkyl groups of $R^3$ are the following: pyrimidinyl, benzoxazolyl, 2,3-dihydro-3-oxobenzisosulfonazol-2-yl, morpholin-1-yl, thiomorpholin-1-yl, benzofuranyl, benzothienyl, indolyl, isoindolyl, isoquinolinyl, furyl, pyridyl, isothiazolyl, oxazolyl, triazolyl, tetrazolyl, quinolyl, thiazolyl, and thienyl, and groups of the formulas

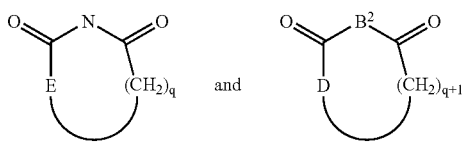

wherein $B^2$ and D are selected from carbon, oxygen and nitrogen, and at least one of $B^2$ and D is other than carbon; E is carbon or nitrogen; q is an integer from 1 to 5; any one of the carbon atoms of said $(CH_2)_q$ and $(CH_2)_{q+1}$ may be optionally substituted with $(C_1-C_6)$alkyl or $(C_1-C_6)$ spiroalkyl; and either any one pair of the carbon atoms of said $(CH_2)_q$ and $(CH_2)_{q+1}$ may be bridged by a one or two carbon atom linkage, or any one pair of adjacent carbon atoms of said $(CH_2)_q$ and $(CH_2)_{q+1}$ may form, together with from one to three carbon atoms that are not members of the carbonyl containing ring, a $(C_3-C_5)$ fused carbocyclic ring.

Compounds of formula I may contain chiral centers and therefore may exist in different enantiomeric and diastereomeric forms. This invention relates to all optical isomers and all stereoisomers of compounds of the formula I, both as racemic mixtures and as individual enantiomers and diastereoismers of such compounds, and mixtures thereof, and to all pharmaceutical compositions and methods of treatment defined above that contain or employ them, respectively.

As the compounds of formula I of this invention possess at least two asymmetric centers, they are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate.

In so far as the compounds of formula I of this invention are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts.

Individual enantiomers of the compounds of formula I may have advantages, as compared with the racemic mixtures of these compounds, in the treatment of various disorders or conditions. For example, the compounds prepared from the 2S-phenyl-piperidin-3S-ylamino template are preferred.

The present invention also includes isotopically labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like.

The term "alkoxy", as used herein, unless otherwise indicated, means "alkyl-O—", wherein "alkyl" is as defined above. Examples of "alkoxy" groups include, but are not limited to, methoxy, ethoxy, propoxy, butoxy and pentoxy.

The term "alkenyl", as used herein, unless otherwise indicated, includes unsaturated hydrocarbon radicals having one or more double bonds connecting two carbon atoms, wherein said hydrocarbon radical may have straight, branched or cyclic moieties or combinations thereof. Examples of "alkenyl" groups include, but are not limited to, ethenyl, propenyl, butenyl, pentenyl, and dimethylpentyl, and include E and Z forms where applicable.

The term "aryl", as used herein, unless otherwise indicated, includes an aromatic ring system with no heteroatoms, which can be either unsubstituted or substituted with one, two or three substituents selected from the group consisting of halo, $(C_1-C_4)$alkyl optionally substituted with from one to three fluorine atoms and $(C_1-C_4)$alkoxy optionally substituted with from one to three fluorine atoms.

The term "aryloxy", as used herein, unless otherwise indicated, means "aryl-O—", wherein "aryl" is as defined above.

The term "heteroaryl", as used herein, unless otherwise indicated, includes an aromatic heterocycle containing five or six ring members, of which from 1 to 4 can be heteroatoms selected, independently, from N, S and O, and which rings can be unsubstituted, monosubstituted or disubstituted with substituents selected, independently, from the group consisting of halo, $(C_1-C_4)$alkyl, and $(C_1-C_4)$alkoxy, optionally substituted with from one to three fluorine atoms;

The term "heteroaryloxy", as used herein, unless otherwise indicated, means "heteroaryl-O", wherein heteroaryl is as defined above.

The term "one or more substituents", as used herein, refers to a number of substituents that equals from one to the maximum number of substituents possible based on the number of available bonding sites.

The terms "halo" and "halogen", as used herein, unless otherwise indicated, include, fluoro, chloro, bromo and iodo.

The term "treating", as used herein, refers to reversing, alleviating, inhibiting the progress of, or preventing the disorder or condition to which such term applies, or preventing one or more symptoms of such condition or disorder. The term "treatment", as used herein, refers to the act of treating, as "treating" is defined immediately above.

The term "methylene", as used herein, means —$CH_2$—.
The term "ethylene", as used herein, means —$CH_2CH_2$—.
The term "propylene", as used herein, means —$CH_2CH_2CH_2$—.

More specific embodiments of the invention include compounds of the formula I wherein B is absent and A is $CH_2$.

Other more specific embodiments of the invention include compounds of the formula I wherein Q is a carbonyl group.

Other more specific embodiments of the invention include compounds of the formula I wherein Y and Z are both CH.

Other more specific embodiments of the invention include compounds of the formula I wherein B is ethylene, A is CH and G is $NHCH_2$.

Other more specific embodiments of the invention include compounds of the formula I wherein B is ethylene, A is CH and G is $SCH_2$.

Other more specific embodiments of the invention include compounds of the formula I wherein $R^3$ is hydrogen.

Other more specific embodiments of the invention include compounds of the formula I wherein B is ethylene, A is CH and G is $NHCH_2$.

Other more specific embodiments of the invention include compounds of the formula I wherein $R^3$ is $CO_2R^9$.

Other more specific embodiments of the invention include compounds of the formula I wherein B is absent, G is NH and A is $CH_2$.

Other more specific embodiments of the invention include compounds of the formula I wherein W is ethylene.

Other more specific embodiments of the invention include compounds of the formula I wherein $R^4$ is phenyl.

Other more specific embodiments of the invention include compounds of the formula I wherein $R^4$ is phenyl and $R^8$ is hydrogen.

Other more specific embodiments of the invention include compounds of the formula I wherein $R^4$ is phenyl and $R^8$ is methyl.

Other more specific embodiments of the invention include compounds of the formula I wherein p is one.

Other more specific embodiments of the invention include compounds of the formula I wherein $R^2$ is $(C_1-C_6)$alkyl.

Other more specific embodiments of the invention include compounds of the formula I wherein $R^2$ is $(C_1-C_6)$alkyl wherein the stereochemical configuration at the chiral carbon to which $R^2$ is attached is "S".

Other more specific embodiments of the invention include compounds of the formula I wherein $R^4$ is 2-, 3- or 4-pyridyl.

Other more specific embodiments of the invention include compounds of the formula I wherein $R^2$ and $R^{12}$ are selected, independently, from hydrogen, methyl, ethyl and propyl.

Other more specific embodiments of the invention include compounds of the formula I wherein both $R^2$ and $R^{12}$ are other than hydrogen.

Other more specific embodiments of the invention include compounds of the formula I wherein Y is CH.

Other more specific embodiments of the invention include compounds of the formula I wherein Y is CH and Z is CH.

Other more specific embodiments of the invention include compounds of the formula I wherein Y is CH and Z is nitrogen.

Other more specific embodiments of the invention include compounds of the formula I wherein Q is C=O and W is methylene optionally substituted with one or two substituents independently selected from $(C_1-C_6)$alkyl and $CF_3$.

Other more specific embodiments of the invention include compounds of the formula I wherein Q is C=O and W is ethylene optionally substituted with one or two substituents independently selected from $(C_1-C_6)$alkyl and $CF_3$.

Other more specific embodiments of the invention include compounds of the formula I wherein Q is SO.

Other more specific embodiments of the invention include compounds of the formula I wherein Q is $SO_2$.

Other more specific embodiments of the invention include compounds of the formula I wherein Y is nitrogen and Z is CH.

Other more specific embodiments of the invention include compounds of the formula I wherein Q is C=S.

Other more specific embodiments of the invention include compounds of the formula I wherein $R^8$ is hydrogen.

Other more specific embodiments of the invention include compounds of the formula I wherein $R^8$ is methyl.

Other more specific embodiments of the invention include compounds of the formula I wherein $R^3$ is a heterocyclic ring.

Other more specific embodiments of the invention include compounds of the formula I wherein $R^3$ is an alkyl group substituted with a heterocyclic ring.

Other more specific embodiments of the invention include compounds of the formula I wherein $R^3$ is an alkyl group substituted with a heterocyclic ring selected from imidazolyl, 5-oxo-4,5-dihydro-1H-[1,2,4]triazol-3-yl, benzoxazol-2-yl, and 5-oxo-pyrrolidin-2-yl.

Other more specific embodiments of the invention include compounds of the formula I wherein $R^8$ is a cycloalkyl group.

Other more specific embodiments of the invention include compounds of the formula I wherein $R^8$ is a cyclopropyl group.

Preferred compounds of the invention include compounds of the formula I wherein $R^4$ is optionally substituted pyridyl.

Other preferred compounds of the invention include compounds of the formula I wherein $R^2$ and $R^{12}$ are selected from $(C_1-C_3)$alkyl.

Examples of preferred compounds of this invention are the isomers of the following compounds that have the stereochemistry depicted in structural formula I, and their pharmaceutically acceptable salts:

7-[(1-Dimethylaminoacetyl-2-phenyl-piperidin-3-ylamino)-methyl]-6-methoxy-1-methyl-3,4-dihydro-1H-quinolin-2-one;

6-Methoxy-1-methyl-7-{[2-phenyl-1-(pyridin-2-yl-acetyl)-piperidin-3-ylamino]-methyl}-3,4-dihydro-1H-quinolin-2-one;
6-Methoxy-1-methyl-7-{[2-phenyl-1-(pyridin-3-yl-acetyl)-piperidin-3-ylamino]-methyl}-3,4-dihydro-1H-quinolin-2-one;
6-Methoxy-1-methyl-7-{[2-phenyl-1-(pyridin-4-yl-acetyl)-piperidin-3-ylamino]-methyl}-3,4-dihydro-1H-quinolin-2-one;
6-Cyclopropoxy-1-methyl-7-[(2-phenyl-piperidin-3-ylamino)-methyl]-3,4-dihydro-1H-quinolin-2-one;
(5-Chloro-2-methoxy-benzyl)-(2-phenyl-octahydro-cyclopenta[b]pyrrol-3-yl)-amine;
6-Methoxy-1-methyl-7-[(1-[1,2,4]oxadiazol-3-ylmethyl-2-phenyl-piperidin-3-ylamino)-methyl]-3,4-dihydro-1H-quinolin-2-one;
7-{[1-(Imidazol-1-yl-acetyl)-2-phenyl-piperidin-3-ylamino]-methyl}-6-methoxy-1-methyl-3,4-dihydro-1H-quinolin-2-one;
1-[3-(2-Methoxy-5-trifluoromethoxy-benzylamino)-2-phenyl-piperidin-1-yl]-2-pyridin-2-yl-ethanone;
1-[3-(2-Methoxy-5-trifluoromethoxy-benzylamino)-2-phenyl-piperidin-1-yl]-2-pyridin-3-yl-ethanone;
1-[3-(2-Methoxy-5-trifluoromethoxy-benzylamino)-2-phenyl-piperidin-1-yl]-2-pyridin-4-yl-ethanone;
2-Imidazol-1-yl-1-[3-(2-methoxy-5-trifluoromethoxy-benzylamino)-2-phenyl-piperidin-1-yl]-ethanone;
2-Dimethylamino-1-[3-(2-methoxy-5-trifluoromethoxy-benzylamino)-2-phenyl-piperidin-1-yl]-ethanone;
3-(2-Benzyloxy-5-trifluoromethoxy-phenyl)-6-phenyl-1-oxa-7-aza-spiro[4.5]decane;
1-[3-(2-Methoxy-5-trifluoromethoxy-benzylamino)-2-phenyl-piperidin-1-yl]-2-pyrrolidin-1-yl-ethanone;
(2-Methoxy-5-trifluoromethoxy-benzyl)-(1-[1,2,4]oxadiazol-3-ylmethyl-2-phenyl-piperidin-3-yl)-amine;
7-{[2-(4-Fluoro-phenyl)-piperidin-3-ylamino]-methyl}-6-methoxy-1-methyl-3,4-dihydro-1H-quinolin-2-one;
[1-(2-Imidazol-1-yl-ethyl)-2-phenyl-piperidin-3-yl]-(2-methoxy-5-trifluoromethoxy-benzyl)-amine;
7-{[1-(2-Dimethylamino-ethyl)-2-phenyl-piperidin-3-ylamino]-methyl}-6-methoxy-1-methyl-3,4-dihydro-1H-quinolin-2-one;
(5-Chloro-2-ethoxy-pyridin-3-ylmethyl)-(2-phenyl-piperidin-3-yl)-amine;
(5-Chloro-2-methoxy-pyridin-3-ylmethyl)-(2-phenyl-piperidin-3-yl)-amine;
Dibenzofuran-2-ylmethyl-(2-phenyl-piperidin-3-yl)-amine;
[3-(Indan-2-yloxy)-4-methoxy-benzyl]-(2-phenyl-piperidin-3-yl)-amine;
6-[(2-Phenyl-piperidin-3-ylamino)-methyl]-chroman-4-one;
(5-Methyl-benzo[b]thiophen-3-ylmethyl)-(2-phenyl-piperidin-3-yl)-amine;
(2,2-Dimethyl-chroman-6-ylmethyl)-(2-phenyl-piperidin-3-yl)-amine;
(1H-Benzoimidazol-5-ylmethyl)-(2-phenyl-piperidin-3-yl)-amine;
1-{2-[(2-Phenyl-piperidin-3-ylamino)-methyl]-phenyl}-pyrrolidin-2-one;
(2-Phenyl-piperidin-3-yl)-[3-(pyridin-2-yloxy)-benzyl]-amine
[3-(4-Methoxy-phenoxy)-benzyl]-(2-phenyl-piperidin-3-yl)-amine;
(4-Phenoxy-benzyl)-(2-phenyl-piperidin-3-yl)-amine;
(2-Phenyl-piperidin-3-yl)-thiophen-2-ylmethyl-amine;
Furan-2-ylmethyl-(2-phenyl-piperidin-3-yl)-amine;
(5-Methyl-furan-2-ylmethyl)-(2-phenyl-piperidin-3-yl)-amine;
(3-Methyl-thiophen-2-ylmethyl)-(2-phenyl-piperidin-3-yl)-amine;
(2-Phenyl-piperidin-3-yl)-thiophen-3-ylmethyl-amine;
(3-Methyl-benzo[b]thiophen-2-ylmethyl)-(2-phenyl-piperidin-3-yl)-amine;
Benzofuran-2-ylmethyl-(2-phenyl-piperidin-3-yl)-amine;
(5-Ethyl-furan-2-ylmethyl)-(2-phenyl-piperidin-3-yl)-amine;
(5-Chloro-3-methyl-1-phenyl-1H-pyrazol-4-ylmethyl)-(2-phenyl-piperidin-3-yl)-amine;
6-Methoxy-7-{[1-(2-methoxy-ethyl)-2-phenyl-piperidin-3-ylamino]-methyl}-1-methyl-3,4-dihydro-1H-quinolin-2-one;
(5-Methyl-3-phenyl-isoxazol-4-ylmethyl)-(2-phenyl-piperidin-3-yl)-amine;
(3-Phenoxy-benzyl)-(2-phenyl-piperidin-3-yl)-amine;
Furan-3-ylmethyl-(2-phenyl-piperidin-3-yl)-amine;
(3,5-Dimethyl-1-phenyl-1H-pyrazol-4-ylmethyl)-(2-phenyl-piperidin-3-yl)-amine;
(5,7-Dimethoxy-1H-indol-4-ylmethyl)-(2-phenyl-piperidin-3-yl)-amine;
(5-Methoxy-1H-indol-3-ylmethyl)-(2-phenyl-piperidin-3-yl)-amine;
(4-Oxy-quinoxalin-2-ylmethyl)-(2-phenyl-piperidin-3-yl)-amine;
(2-Phenyl-piperidin-3-yl)-quinoxalin-2-ylmethyl-amine;
7-{[1-(2,3-Dihydroxy-propyl)-2-phenyl-piperidin-3-ylamino]-methyl}-6-methoxy-1-methyl-3,4-dihydro-1H-quinolin-2-one;
(2-Methoxy-5-trifluoromethoxy-benzyl)-[2-phenyl-1-(2-pyrrolidin-1-yl-ethyl)-piperidin-3-yl]-amine;
6-Ethoxy-1-methyl-7-[(2-phenyl-piperidin-3-ylamino)-methyl]-3,4-dihydro-1H-quinolin-2-one;
[1-(2-Dimethylamino-ethyl)-2-phenyl-piperidin-3-yl]-(2-methoxy-5-trifluoromethoxy-benzyl)-amine;
3-(2-Cyclopropoxy-5-trifluoromethoxy-phenyl)-6-phenyl-1-oxa-7-aza-spiro[4.5]decane;
[1-(2-Methoxy-ethyl)-2-phenyl-piperidin-3-yl]-(2-methoxy-5-trifluoromethoxy-benzyl)-amine;
6-Hydroxy-1-methyl-7-[(2-phenyl-piperidin-3-ylamino)-methyl]-3,4-dihydro-1H-quinolin-2-one;
6-Methoxy-1-methyl-7-[(2-phenyl-octahydro-cyclopenta[b]pyrrol-3-ylamino)-methyl]-3,4-dihydro-1H-quinolin-2-one;
7-{[2-(4-Fluoro-phenyl)-piperidin-3-ylamino]-methyl}-6-methoxy-3,4-dihydro-1H-quinolin-2-one;
6-Methoxy-1-methyl-7-(6-phenyl-1-oxa-7-aza-spiro[4.5]dec-3-yl)-3,4-dihydro-1H-quinolin-2-one;
6-Methoxy-1,3,3-trimethyl-5-[(2-phenyl-octahydro-cyclopenta[b]pyrrol-3-ylamino)-methyl]-1,3-dihydro-indol-2-one;
[3-Chloro-2-(4-fluoro-phenoxy)-pyridin-4-ylmethyl]-(2-phenyl-piperidin-3-yl)-amine;
6-Ethoxy-1,3,3-trimethyl-5-[(2-phenyl-piperidin-3-ylamino)-methyl]-1,3-dihydro-indol-2-one;
6-Ethoxy-1,3,3-trimethyl-5-[(2-phenyl-octahydro-cyclopenta[b]pyrrol-3-ylamino)-methyl]-1,3-dihydro-indol-2-one;
6-Isopropoxy-1,3,3-trimethyl-5-[(2-phenyl-piperidin-3-ylamino)-methyl]-1,3-dihydro-indol-2-one;
6-Isopropoxy-1,3,3-trimethyl-5-[(2-phenyl-octahydro-cyclopenta[b]pyrrol-3-ylamino)-methyl]-1,3-dihydro-indol-2-one;
6-Ethoxy-1,3,3-trimethyl-5-[(2-phenyl-octahydro-cyclopenta[b]pyrrol-3-ylamino)-methyl]-1,3-dihydro-indol-2-one;

6-Isopropoxy-1,3,3-trimethyl-5-[(2-phenyl-octahydro-cyclopenta[b]pyrrol-3-ylamino)-methyl]-1,3-dihydro-indol-2-one;
7-Isopropoxy-1-methyl-6-[(2-phenyl-piperidin-3-ylamino)-methyl]-3,4-dihydro-1H-quinolin-2-one;
6-Methoxy-1-methyl-7-[(6-methyl-2-phenyl-piperidin-3-ylamino)-methyl]-3,4-dihydro-1H-quinolin-2-one;
6-Methoxy-1,3,3-trimethyl-7-[(2-phenyl-piperidin-3-ylamino)-methyl]-3,4-dihydro-1H-quinolin-2-one;
6-Methoxy-1,3-dimethyl-7-[(2-phenyl-piperidin-3-ylamino)-methyl]-3,4-dihydro-1H-quinolin-2-one;
6-Methoxy-1,3-dimethyl-5-[(2-phenyl-piperidin-3-ylamino)-methyl]-1,3-dihydro-indol-2-one;
6-Methoxy-1-methyl-5-[(2-phenyl-piperidin-3-ylamino)-methyl]-1,3-dihydro-indol-2-one;
5-[(1-Isopropyl-2-phenyl-piperidin-3-ylamino)-methyl]-6-methoxy-1,3,3-trimethyl-1,3-dihydro-indol-2-one;
6-Methoxy-1-methyl-7-[(2-phenyl-1-propyl-piperidin-3-ylamino)-methyl]-3,4-dihydro-1H-quinolin-2-one;
6-Methoxy-1-methyl-7-{[1-(5-methyl-3H-imidazol-4-ylmethyl)-2-phenyl-piperidin-3-ylamino]-methyl}-3,4-dihydro-1H-quinolin-2-one;
7-{[1-(1H-Imidazol-4-ylmethyl)-2-phenyl-piperidin-3-ylamino]-methyl}-6-methoxy-1-methyl-3,4-dihydro-1H-quinolin-2-one;
7-[(1-Isopropyl-2-phenyl-piperidin-3-ylamino)-methyl]-6-methoxy-1-methyl-3,4-dihydro-1H-quinolin-2-one;
6-Methoxy-1,3-dimethyl-7-[(1-methyl-2-phenyl-piperidin-3-ylamino)-methyl]-3,4-dihydro-1H-quinolin-2-one;
5-[(1-Isopropyl-2-phenyl-piperidin-3-ylamino)-methyl]-6-methoxy-1,3,3-trimethyl-1,3-dihydro-indol-2-one
6-Methoxy-1-methyl-7-{[1-(5-oxo-2,5-dihydro-1H-[1,2,4]triazol-3-ylmethyl)-2-phenyl-piperidin-3-ylamino]-methyl}-3,4-dihydro-1H-quinolin-2-one;
6-Methoxy-7-[(2-phenyl-piperidin-3-ylamino)-methyl]-3,4-dihydro-1H-quinolin-2-one;
1-Ethyl-6-methoxy-7-[(2-phenyl-piperidin-3-ylamino)-methyl]-3,4-dihydro-1H-quinolin-2-one;
1-Methanesulfonyl-6-methoxy-7-[(2-phenyl-piperidin-3-ylamino)-methyl]-3,4-dihydro-1H-quinolin-2-one;
6-Methoxy-1,4,4-trimethyl-7-[(2-phenyl-piperidin-3-ylamino)-methyl]-3,4-dihydro-1H-quinolin-2-one;
8-Fluoro-6-methoxy-1,4,4-trimethyl-7-[(2-phenyl-piperidin-3-ylamino)-methyl]-3,4-dihydro-1H-quinolin-2-one;
6-Methoxy-1-methyl-7-[(2-phenyl-piperidin-3-ylamino)-methyl]-3,4-dihydro-1H-quinolin-2-one;
6-Methoxy-1,4-dimethyl-7-[(2-phenyl-piperidin-3-ylamino)-methyl]-3,4-dihydro-1H-quinolin-2-one;
6-Methoxy-2-methyl-7-[(2-phenyl-piperidin-3-ylamino)-methyl]-3,4-dihydro-2H-isoquinolin-1-one;
6-Methoxy-3-methyl-5-[(2-phenyl-piperidin-3-ylamino)-methyl]-1,1a,3,7b-tetrahydro-3-aza-cyclopropa[a]naphthalen-2-one;
6-Methoxy-1-methyl-,3,3-cyclopropyl-5-[(2-phenyl-piperidin-3-ylamino)-methyl]-1,3-dihydro-indol-2-one;
5-Methoxy-1-methyl-,3,3-cyclopropyl-6-[(2-phenyl-piperidin-3-ylamino)-methyl]-1,3-dihydro-indol-2-one;
6-Methoxy-1-methyl-(6-phenyl-1,7-diaza-spiro[4.5]dec-3-yl)-3,4-dihydro-1H-quinolin-2-one;
6-Methoxy-1-methyl-7-phenyl-1,7-diaza-spiro[4.5]dec-3-yl)-3,4-dihydro-1H-quinolin-2-one;
6-Methoxy-3-methyl-5-[(1-phenyl-8-aza-bicyclo[3.2.1]oct-2-ylamino)-methyl]-1,1a,3,7b-tetrahydro-3-aza-cyclopropa[a]naphthalen-2-one;
(6-Methoxy-1-methyl-2,2-dioxo-1,2,3,4-tetrahydro-2-thiobenzo[c[1,2]thiazin-7-yl-methyl)-(2-phenyl-piperidin-3-yl)-amine;

6-Methoxy-3-methyl-5-[(6-methyl-2-phenyl-piperidin-3-ylamino)-methyl]-1,1a,3,7b-tetrahydro-3-aza-cyclopropa[a]naphthalen-2-one;
6-Methoxy-1-methyl-7-(6-phenyl-1,7-diaza-spiro[4.5]dec-3-yl)-3,4-dihydro-1H-quinolin-2-one;
6-Methoxy-1,3,3-trimethyl-5-[(2-phenyl-piperidin-3-ylamino)-methyl]-1,3-dihydro-pyrrolo[2,3-b]pyridin-2-one;
5-Methoxy-1,3,3-trimethyl-6-[(2-phenyl-piperidin-3-ylamino)-methyl]-1,3-dihydro-pyrrolo[3,2-b]pyridin-2-one;
6-Methoxy-1-methyl-7-[(2-phenyl-piperidin-3-ylamino)-methyl]-3,4-dihydro-1H-[1,5]naphthyridin-2-one;
7-[(6-Ethyl-2-phenyl-piperidin-3-ylamino)-methyl]-6-methoxy-1-methyl-3,4-dihydro-1H-quinolin-2-one;
5-[(6-Ethyl-2-phenyl-piperidin-3-ylamino)-methyl]-6-methoxy-1,3,3-trimethyl-1,3,-dihydro-indol-2-one;
6-Methoxy-1,3,3-trimethyl-5-[(2-phenyl-piperidin-3-ylamino)-methyl]-1,3-dihydro-pyrrolo[2,3-b]pyridin-2-one;
5-Methoxy-1,3,3-trimethyl-6-[(2-phenyl-piperidin-3-ylamino)-methyl]-1,3-dihydro-pyrrolo[3,2-b]pyridin-2-one;
6-Methoxy-1-methyl-7-[(2-phenyl-piperidin-3-ylamino)-methyl]-3,4-dihydro-1H-[1,5]naphthyridin-2-one;
6-Methoxy-1-methyl-7-[(6-methyl-2-phenyl-piperidin-3-ylamino)-methyl]-3,4-dihydro-1H-[1,5]naphthyridin-2-one;
7-[(6-Ethyl-2-phenyl-piperidin-3-ylamino)-methyl]-6-methoxy-1-methyl-3,4-dihydro-1H-[1,5]naphthyridin-2-one;
6-Methoxy-1-methyl-7-[(2-phenyl-6-propyl-piperidin-3-ylamino)-methyl]-3,4-dihydro-1H-[1,5]naphthyridin-2-one;
6-Methoxy-3-methyl-5-[(6-methyl-2-phenyl-piperidin-3-ylamino)-methyl]-1,1a,3,7b-tetrahydro-3-aza-cyclopropa[a]naphthalen-2-one; and
6-Methoxy-1-methyl-7-(6-phenyl-1,7-diaza-spiro[4.5]dec-3-yl)-3,4-dihydro-1H-quinolin-2-one.

Other examples of preferred compounds of this invention are the following compounds of the formula I and their pharmaceutically acceptable salts:
5-[(6-Ethyl-2-phenyl-piperidin-3-ylamino)-methyl]-6-methoxy-3-methyl-1,1a,3,7b-tetrahydro-3-aza-cyclopropa[a]naphthalen-2-one;
(7bS,1aR)-5-[(2S,3S,6S)-(6-Ethyl-2-phenyl-piperidin-3-ylamino)-methyl]-6-methoxy-3-methyl-1,1a,3,7b-tetrahydro-3-aza-cyclopropa[a]naphthalen-2-one;
(7bR,1aS)-5-[(2R,3R,6R)-(6-Ethyl-2-phenyl-piperidin-3-ylamino)-methyl]-6-methoxy-3-methyl-1,1a,3,7b-tetrahydro-3-aza-cyclopropa[a]naphthalen-2-one;
(7bR,1aS)-5-[(2S,3S,6S)-(6-Ethyl-2-phenyl-piperidin-3-ylamino)-methyl]-6-methoxy-3-methyl-1,1a,3,7b-tetrahydro-3-aza-cyclopropa[a]naphthalen-2-one;
(7bS,1aR)-5-[(2R,3R,6R)-(6-Ethyl-2-phenyl-piperidin-3-ylamino)-methyl]-6-methoxy-3-methyl-1,1a,3,7b-tetrahydro-3-aza-cyclopropa[a]naphthalen-2-one;
6-Methoxy-3-methyl-5-[(6-methyl-2-phenyl-piperidin-3-ylamino)-methyl]-1,1a,3,7b-tetrahydro-3-aza-cyclopropa[a]naphthalen-2-one;
(7bS,1aR)-6-Methoxy-3-methyl-5-[(2S,3S,6S)-(6-methyl-2-phenyl-piperidin-3-ylamino)-methyl]-1,1a,3,7b-tetrahydro-3-aza-cyclopropa[a]naphthalen-2-one;
(7bR,1aS)-6-Methoxy-3-methyl-5-[(2R,3R,6R)-(6-methyl-2-phenyl-piperidin-3-ylamino)-methyl]-1,1a,3,7b-tetrahydro-3-aza-cyclopropa[a]naphthalen-2-one;

(7bR,1aS)-6-Methoxy-3-methyl-5-[(2S,3S,6S)-(6-methyl-2-phenyl-piperidin-3-ylamino)-methyl]-1,1a,3,7b-tetrahydro-3-aza-cyclopropa[a]naphthalen-2-one;

(7bS,1aR)-6-Methoxy-3-methyl-5-[(2R,3R,6R)-(6-methyl-2-phenyl-piperidin-3-ylamino)-methyl]-1,1a,3,7b-tetrahydro-3-aza-cyclopropa[a]naphthalen-2-one;

6-Methoxy-3-methyl-5-[(2-phenyl-6-propyl-piperidin-3-ylamino)-methyl]-1,1a,3,7b-tetrahydro-3-aza-cyclopropa[a]naphthalen-2-one;

6-Methoxy-1-methyl-7-[(2-phenyl-6-propyl-piperidin-3-ylamino)-methyl]-3,4-dihydro-1H-quinolin-2-one;

7-[(6-Ethyl-2-phenyl-piperidin-3-ylamino)-methyl]-6-methoxy-1-methyl-3,4-dihydro-1H-quinolin-2-one;

6-Methoxy-1-methyl-7-[(6-methyl-2-phenyl-piperidin-3-ylamino)-methyl]-3,4-dihydro-1H-quinolin-2-one;

7-[((2S,3S,6S)-6-Isopropyl-2-phenyl-piperidin-3-ylamino)-methyl]-6-methoxy-1-methyl-3,4-dihydro-1H-quinoline-2-one;

7-[(6,6-Dimethyl-2-phenyl-piperidin-3-ylamino)-methyl]-6-methoxy-1-methyl-3,4-dihydro-1H-quinolin-2-one;

7-[((2S,3S,6S)-6-Isopropyl-2-phenyl-piperidin-3-ylamino)-methyl]-6-methoxy-1-methyl-3,4-dihydro-1H-[1,5]naphthyridin-2-one;

5-[(5-Ethyl-2-phenyl-piperidin-3-ylamino)-methyl]-6-methoxy-3-methyl-1,1a,3,7b-tetrahydro-3-aza-cyclopropa[a]naphthalen-2-one;

6-Methoxy-3-methyl-5-[(5-methyl-2-phenyl-piperidin-3-ylamino)-methyl]-1,1a,3,7b-tetrahydro-3-aza-cyclopropa[a]naphthalen-2-one;

6-Methoxy-3-methyl-5-[(2-phenyl-5-propyl-piperidin-3-ylamino)-methyl]-1,1a,3,7b-tetrahydro-3-aza-cyclopropa[a]naphthalen-2-one;

(6-Methoxy-1-methyl-2,2-dioxo-1,2,3,4-tetrahydro-2$^6$-benzo[c][1,2]thiazin-7-ylmethyl)-(2-phenyl-piperidin-3-yl)-amine;

6-Methoxy-1-methyl-,3,3-spirocyclopropyl-5-[(2-phenyl-piperidin-3-ylamino)-methyl]-1,3-dihydro-indol-2-one;

5-Methoxy-1-methyl-,3,3-spirocyclopropyl-6-[(2-phenyl-piperidin-3-ylamino)-methyl]-1,3-dihydro-indol-2-one;

5-Methoxy-1-methyl-,3,3-cyclobutyl-6-[(2-phenyl-piperidin-3-ylamino)-methyl]-1,3-dihydro-indol-2-one;

6-Methoxy-1-methyl-,3,3-cyclopentyl-5-[(2-phenyl-piperidin-3-ylamino)-methyl]-1,3-dihydro-indol-2-one;

6-Methoxy-1-methyl-,3,3-cyclohexyl-5-[(2-phenyl-piperidin-3-ylamino)-methyl]-1,3-dihydro-indol-2-one;

(7bS,1aR)-6-Methoxy-3-methyl-5-[(1S,2S,5R)-(1-phenyl-8-aza-bicyclo[3.2.1]oct-2-ylamino)-methyl]-1,1a,3,7b-tetrahydro-3-aza-cyclopropa[a]naphthalen-2-one;

(7bR,1aS)-6-Methoxy-3-methyl-5-[(1R,2R,5S)-(1-phenyl-8-aza-bicyclo[3.2.1]oct-2-ylamino)-methyl]-1,1a,3,7b-tetrahydro-3-aza-cyclopropa[a]naphthalen-2-one;

(2-Methoxy-5-trifluoromethoxy-benzyl)-((1S,2S,5R) 1-phenyl-8-azabicyclo[3.2.1]oct-2-yl)-amine;

(2-Methoxy-5-trifluoromethoxy-benzyl)-((1R,2R,5S) 1-phenyl-8-azabicyclo[3.2.1]oct-2-yl)-amine;

5-Methoxy-1-methyl-,3,3-cyclopropyl-6-[(1S,2S,5R)-(1-phenyl-8-azabicyclo[3.2.1]oct-2-yl)-amine)-methyl]-1,3-dihydro-indol-2-one; and (6-Methoxy-1-methyl-2,2-dioxo-1,2,3,4-tetrahydro-2$^6$-benzo[c][1,2]thiazin-7-ylmethyl)-(2-phenyl-piperidin-3-yl)-amine.

Other examples of preferred compounds of this invention are:

5-[(6-Ethyl-2-phenyl-piperidin-3-ylamino)-methyl]-6-methoxy-3-methyl-1,1a,3,7b-tetrahydro-3-aza-cyclopropa[a]naphthalen-2-one monohydrochloride;

(7bS,1aR)-5-[(2S,3S,6S)-(6-Ethyl-2-phenyl-piperidin-3-ylamino)-methyl]-6-methoxy-3-methyl-1,1a,3,7b-tetrahydro-3-aza-cyclopropa[a]naphthalen-2-one monohydrochloride;

(7bR,1aS)-5-[(2R,3R,6R)-(6-Ethyl-2-phenyl-piperidin-3-ylamino)-methyl]-6-methoxy-3-methyl-1,1a,3,7b-tetrahydro-3-aza-cyclopropa[a]naphthalen-2-one monohydrochloride;

(7bR,1aS)-5-[(2S,3S,6S)-(6-Ethyl-2-phenyl-piperidin-3-ylamino)-methyl]-6-methoxy-3-methyl-1,1a,3,7b-tetrahydro-3-aza-cyclopropa[a]naphthalen-2-one monohydrochloride;

(7bS,1aR)-5-[(2R,3R,6R)-(6-Ethyl-2-phenyl-piperidin-3-ylamino)-methyl]-6-methoxy-3-methyl-1,1a,3,7b-tetrahydro-3-aza-cyclopropa[a]naphthalen-2-one monohydrochloride;

6-Methoxy-3-methyl-5-[(6-methyl-2-phenyl-piperidin-3-ylamino)-methyl]-1,1a,3,7b-tetrahydro-3-aza-cyclopropa[a]naphthalen-2-one monohydrochloride;

(7bS,1aR)-6-Methoxy-3-methyl-5-[(2S,3S,6S)-(6-methyl-2-phenyl-piperidin-3-ylamino)-methyl]-1,1a,3,7b-tetrahydro-3-aza-cyclopropa[a]naphthalen-2-one monohydrochloride;

(7bR,1aS)-6-Methoxy-3-methyl-5-[(2R,3R,6R)-(6-methyl-2-phenyl-piperidin-3-ylamino)-methyl]-1,1a,3,7b-tetrahydro-3-aza-cyclopropa[a]naphthalen-2-one monohydrochlyoride;

(7bR,1aS)-6-Methoxy-3-methyl-5-[(2S,3S,6S)-(6-methyl-2-phenyl-piperidin-3-ylamino)-methyl]-1,1a,3,7b-tetrahydro-3-aza-cyclopropa[a]naphthalen-2-one monohydrochloride;

(7bS,1aR)-6-Methoxy-3-methyl-5-[(2R,3R,6R)-(6-methyl-2-phenyl-piperidin-3-ylamino)-methyl]-1,1a,3,7b-tetrahydro-3-aza-cyclopropa[a]naphthalen-2-one monohydrochloride;

6-Methoxy-3-methyl-5-[(2-phenyl-6-propyl-piperidin-3-ylamino)-methyl]-1,1a,3,7b-tetrahydro-3-aza-cyclopropa[a]naphthalen-2-one monohydrochloride;

6-Methoxy-1-methyl-7-[(2-phenyl-6-propyl-piperidin-3-ylamino)-methyl]-3,4-dihydro-1H-quinolin-2-one monohydrochloride;

7-[(6-Ethyl-2-phenyl-piperidin-3-ylamino)-methyl]-6-methoxy-1-methyl-3,4-dihydro-1H-quinolin-2-one monohydrochloride;

6-Methoxy-1-methyl-7-[(6-methyl-2-phenyl-piperidin-3-ylamino)-methyl]-3,4-dihydro-1H-quinolin-2-one monohydrochloride;

5-[(5-Ethyl-2-phenyl-piperidin-3-ylamino)-methyl]-6-methoxy-3-methyl-1,1a,3,7b-tetrahydro-3-aza-cyclopropa[a]naphthalen-2-one monohydrochloride;

6-Methoxy-3-methyl-5-[(5-methyl-2-phenyl-piperidin-3-ylamino)-methyl]-1,1a,3,7b-tetrahydro-3-aza-cyclopropa[a]naphthalen-2-one monohydrochloride; and 6-Methoxy-3-methyl-5-[(2-phenyl-5-propyl-piperidin-3-ylamino)-methyl]-1,1a,3,7b-tetrahydro-3-aza-cyclopropa[a]naphthalen-2-one monohydrochloride.

Other examples of preferred compounds of this invention are:

5-[(6-Ethyl-2-phenyl-piperidin-3-ylamino)-methyl]-6-methoxy-3-methyl-1,1a,3,7b-tetrahydro-3-aza-cyclopropa[a]naphthalen-2-one mono (D)-lactate;

(7bS,1aR)-5-[(2S,3S,6S)-(6-Ethyl-2-phenyl-piperidin-3-ylamino)-methyl]-6-methoxy-3-methyl-1,1a,3,7b-tetrahydro-3-aza-cyclopropa[a]naphthalen-2-one mono (D)-lactate;

(7bR,1aS)-5-[(2R,3R,6R)-(6-Ethyl-2-phenyl-piperidin-3-ylamino)-methyl]-6-methoxy-3-methyl-1,1a,3,7b-tetrahydro-3-aza-cyclopropa[a]naphthalen-2-one mono (D)-lactate;

(7bR,1aS)-5-[(2S,3S,6S)-(6-Ethyl-2-phenyl-piperidin-3-ylamino)-methyl]-6-methoxy-3-methyl-1,1a,3,7b-tetrahydro-3-aza-cyclopropa[a]naphthalen-2-one mono (D)-lactate;

(7bS,1aR)-5-[(2R,3R,6R)-(6-Ethyl-2-phenyl-piperidin-3-ylamino)-methyl]-6-methoxy-3-methyl-1,1a,3,7b-tetrahydro-3-aza-cyclopropa[a]naphthalen-2-one mono (D)-lactate;

6-Methoxy-3-methyl-5-[(6-methyl-2-phenyl-piperidin-3-ylamino)-methyl]-1,1a,3,7b-tetrahydro-3-aza-cyclopropa[a]naphthalen-2-one mono (D)-lactate;

(7bS,1aR)-6-Methoxy-3-methyl-5-[(2S,3S,6S)-(6-methyl-2-phenyl-piperidin-3-ylamino)-methyl]-1,1a,3,7b-tetrahydro-3-aza-cyclopropa[a]naphthalen-2-one mono (D)-lactate;

(7bR,1aS)-6-Methoxy-3-methyl-5-[(2R,3R,6R)-(6-methyl-2-phenyl-piperidin-3-ylamino)-methyl]-1,1a,3,7b-tetrahydro-3-aza-cyclopropa[a]naphthalen-2-one mono (D)-lactate;

(7bR,1aS)-6-Methoxy-3-methyl-5-[(2S,3S,6S)-(6-methyl-2-phenyl-piperidin-3-ylamino)-methyl]-1,1a,3,7b-tetrahydro-3-aza-cyclopropa[a]naphthalen-2-one mono (D)-lactate;

(7bS,1aR)-6-Methoxy-3-methyl-5-[(2R,3R,6R)-(6-methyl-2-phenyl-piperidin-3-ylamino)-methyl]-1,1a,3,7b-tetrahydro-3-aza-cyclopropa[a]naphthalen-2-one mono (D)-lactate;

6-Methoxy-3-methyl-5-[(2-phenyl-6-propyl-piperidin-3-ylamino)-methyl]-1,1a,3,7b-tetrahydro-3-aza-cyclopropa[a]naphthalen-2-one mono (D)-lactate;

6-Methoxy-1-methyl-7-[(2-phenyl-6-propyl-piperidin-3-ylamino)-methyl]-3,4-dihydro-1H-quinolin-2-one mono (D)-lactate;

7-[(6-Ethyl-2-phenyl-piperidin-3-ylamino)-methyl]-6-methoxy-1-methyl-3,4-dihydro-1H-quinolin-2-one mono (D)-lactate;

6-Methoxy-1-methyl-7-[(6-methyl-2-phenyl-piperidin-3-ylamino)-methyl]-3,4-dihydro-1H-quinolin-2-one mono (D)-lactate;

5-[(5-Ethyl-2-phenyl-piperidin-3-ylamino)-methyl]-6-methoxy-3-methyl-1,1a,3,7b-tetrahydro-3-aza-cyclopropa[a]naphthalen-2-one mono (D)-lactate;

6-Methoxy-3-methyl-5-[(5-methyl-2-phenyl-piperidin-3-ylamino)-methyl]-1,1a,3,7b-tetrahydro-3-aza-cyclopropa[a]naphthalen-2-one mono (D)-lactate; and 6-Methoxy-3-methyl-5-[(2-phenyl-5-propyl-piperidin-3-ylamino)-methyl]-1,1a,3,7b-tetrahydro-3-aza-cyclopropa[a]naphthalen-2-one mono (D)-lactate.

Other examples of preferred compounds of this invention are:

5-[(6-Ethyl-2-phenyl-piperidin-3-ylamino)-methyl]-6-methoxy-3-methyl-1,1a,3,7b-tetrahydro-3-aza-cyclopropa[a]naphthalen-2-one mono-(L)-lactate;

(7bS,1aR)-5-[(2S,3S,6S)-(6-Ethyl-2-phenyl-piperidin-3-ylamino)-methyl]-6-methoxy-3-methyl-1,1a,3,7b-tetrahydro-3-aza-cyclopropa[a]naphthalen-2-one mono-(L)-lactate;

(7bR,1aS)-5-[(2R,3R,6R)-(6-Ethyl-2-phenyl-piperidin-3-ylamino)-methyl]-6-methoxy-3-methyl-1,1a,3,7b-tetrahydro-3-aza-cyclopropa[a]naphthalen-2-one mono-(L)-lactate;

(7bR,1aS)-5-[(2S,3S,6S)-(6-Ethyl-2-phenyl-piperidin-3-ylamino)-methyl]-6-methoxy-3-methyl-1,1a,3,7b-tetrahydro-3-aza-cyclopropa[a]naphthalen-2-one mono-(L)-lactate;

(7bS,1aR)-5-[(2R,3R,6R)-(6-Ethyl-2-phenyl-piperidin-3-ylamino)-methyl]-6-methoxy-3-methyl-1,1a,3,7b-tetrahydro-3-aza-cyclopropa[a]naphthalen-2-one mono-(L)-lactate;

6-Methoxy-3-methyl-5-[(6-methyl-2-phenyl-piperidin-3-ylamino)-methyl]-1,1a,3,7b-tetrahydro-3-aza-cyclopropa[a]naphthalen-2-one mono-(L)-lactate;

(7bS,1aR)-6-Methoxy-3-methyl-5-[(2S,3S,6S)-(6-methyl-2-phenyl-piperidin-3-ylamino)-methyl]-1,1a,3,7b-tetrahydro-3-aza-cyclopropa[a]naphthalen-2-one mono-(L)-lactate;

(7bR,1aS)-6-Methoxy-3-methyl-5-[(2R,3R,6R)-(6-methyl-2-phenyl-piperidin-3-ylamino)-methyl]-1,1a,3,7b-tetrahydro-3-aza-cyclopropa[a]naphthalen-2-one mono-(L)-lactate;

(7bR,1aS)-6-Methoxy-3-methyl-5-[(2S,3S,6S)-(6-methyl-2-phenyl-piperidin-3-ylamino)-methyl]-1,1a,3,7b-tetrahydro-3-aza-cyclopropa[a]naphthalen-2-one mono-(L)-lactate;

(7bS,1aR)-6-Methoxy-3-methyl-5-[(2R,3R,6R)-(6-methyl-2-phenyl-piperidin-3-ylamino)-methyl]-1,1a,3,7b-tetrahydro-3-aza-cyclopropa[a]naphthalen-2-one mono-(L)-lactate;

6-Methoxy-3-methyl-5-[(2-phenyl-6-propyl-piperidin-3-ylamino)-methyl]-1,1a,3,7b-tetrahydro-3-aza-cyclopropa[a]naphthalen-2-one mono-(L)-lactate;

6-Methoxy-1-methyl-7-[(2-phenyl-6-propyl-piperidin-3-ylamino)-methyl]-3,4-dihydro-1H-quinolin-2-one mono-(L)-lactate;

7-[(6-Ethyl-2-phenyl-piperidin-3-ylamino)-methyl]-6-methoxy-1-methyl-3,4-dihydro-1H-quinolin-2-one mono-(L)-lactate;

6-Methoxy-1-methyl-7-[(6-methyl-2-phenyl-piperidin-3-ylamino)-methyl]-3,4-dihydro-1H-quinolin-2-one mono-(L)-lactate;

5-[(5-Ethyl-2-phenyl-piperidin-3-ylamino)-methyl]-6-methoxy-3-methyl-1,1a,3,7b-tetrahydro-3-aza-cyclopropa[a]naphthalen-2-one mono-(L)-lactate;

6-Methoxy-3-methyl-5-[(5-methyl-2-phenyl-piperidin-3-ylamino)-methyl]-1,1a,3,7b-tetrahydro-3-aza-cyclopropa[a]naphthalen-2-one mono-(L)-lactate; and 6-Methoxy-3-methyl-5-[(2-phenyl-5-propyl-piperidin-3-ylamino)-methyl]-1,1a,3,7b-tetrahydro-3-aza-cyclopropa[a]naphthalen-2-one mono-(L)-lactate.

Other examples of compounds of this invention are the following compounds and their pharmaceutically acceptable salts:

6-Methoxy-1-methyl-7-[(2-phenyl-6-propyl-piperidin-3-ylamino)-methyl]-3,4-dihydro-1H-quinolin-2-one;

7-[(6-Isopropyl-2-phenyl-piperidin-3-ylamino)-methyl]-6-methoxy-1-methyl-3,4-dihydro-1H-quinolin-2-one;

7-[(6-Tert-butyl-2-phenyl-piperidin-3-ylamino)-methyl]-6-methoxy-1-methyl-3,4-dihydro-1H-quinolin-2-one;

7-[(6-Isobutyl-2-phenyl-piperidin-3-ylamino)-methyl]-6-methoxy-1-methyl-3,4-dihydro-1H-quinolin-2-one;

7-[(1,2,3,4,5,6-Hexahydro-[2,3']bipyridinyl-3-ylamino)-methyl]-6-methoxy-1-methyl-3,4-dihydro-1H-quinolin-2-one;

7-[(1,2,3,4,5,6-Hexahydro-[2,4']bipyridinyl-3-ylamino)-methyl]-6-methoxy-1-methyl-3,4-dihydro-1H-quinolin-2-one;

(6-Methoxy-1-methyl-2,2-dioxo-1,2,3,4-tetrahydro-2-thiobenzo[c][1,2]thiazin-7-ylmethyl)-(2-phenyl-piperidin-3-yl)-amine;

6-Methoxy-3-methyl-5-[(6-methyl-2-phenyl-piperidin-3-ylamino)-methyl]-1,1a,3,7b-tetrahydro-3-aza-cyclopropa[a]naphthalen-2-one;

6-Methoxy-1-methyl-,3,3-cyclopropyl-5-[(6-methyl-2-phenyl-piperidin-3-ylamino)-methyl]-1,3-dihydro-indol-2-one;

5-Methoxy-1-methyl-,3,3-cyclopropyl-6-[(1-phenyl-8-aza-bicyclo[3.2.1]oct-2-ylamino)-methyl]-1,3-dihydro-indol-2-one;

6-Methoxy-1-methyl-,3,3-cyclohexane-5-[(2-phenyl-piperidin-3-ylamino)-methyl]-1,3-dihydro-indol-2-one;

6-Methoxy-1-methyl-,3,3-cyclopentyl-5-[(2-phenyl-piperidin-3-ylamino)-methyl]-1,3-dihydro-indol-2-one;

6-Methoxy-1-methyl-,3,3-cyclopropyl-5-[(2-(-4-fluorophenyl)-piperidin-3-ylamino)-methyl]-1,3-dihydro-indol-2-one;

6-Methoxy-1-methyl-,3,3-cyclobutyl-5-[(2-phenyl-piperidin-3-ylamino)-methyl]-1,3-dihydro-indol-2-one;

5-Methoxy-1-methyl-,3,3-cyclobutyl-6-[(2-phenyl-piperidin-3-ylamino)-methyl]-1,3-dihydro-indol-2-one;

5-Methoxy-1-methyl-,3,3-cyclopropyl-6-[(6-methyl-2-phenyl-piperidin-3-ylamino)-methyl]-1,3-dihydro-indol-2-one;

6-Methoxy-1,3-dimethyl-5-[(2-phenyl-piperidin-3-ylamino)-methyl]-1,1a,3,7b-tetrahydro-3-aza-cyclopropa[a]naphthalen-2-one;

7-[(1,2,3,4,5,6-Hexahydro-[2,2']bipyridinyl-3-ylamino)-methyl]-6-methoxy-1-methyl-3,4-dihydro-1H-quinolin-2-one; and 6-[(6-Ethyl-2-phenyl-piperidin-3-ylamino)-methyl]-5-methoxy-1,1-dimethyl-indan-2-one.

The compounds of formula I of this invention have useful pharmaceutical and medicinal properties. The compounds of formula I of this invention exhibit significant substance P receptor-binding activity and therefore are of value in the treatment of a wide variety of clinical conditions that are characterized by the presence of an excess of tachykinin, in particular, substance P, activity. Thus, for example, an excess of tachykinin, and in particular, substance P, activity is implicated in a variety of disorders of the central nervous system. Such disorders include, but are not limited to those enumerated in the paragraphs below.

This invention also relates to a method of treating a disorder or condition selected from the group consisting of mood disorders, such as depression, or more particularly, depressive disorders, for example, single episodic or recurrent major depressive disorders, dysthymic disorders, depressive neurosis and neurotic depression, melancholic depression, including anorexia, weight loss, insomnia, early morning waking and psychomotor retardation, atypical depression (or reactive depression), including increased appetite, hypersomnia, psychomotor agitation or irritability, seasonal affective disorder and pediatric depression; or bipolar disorders or manic depression, for example, bipolar I disorder, bipolar II disorder and cyclothymic disorder; conduct disorder and disruptive behavior disorder; anxiety disorders, such as panic disorder with or without agoraphobia, agoraphobia without history of panic disorder, specific phobias, for example, specific animal phobias, social anxiety, social phobia, obsessive-compulsive disorder, stress disorders, including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder, mood disorders associated with schizophrenia; behavioral disturbances associated with mental retardation, autistic disorder, and conduct disorder in a mammal, including a human, comprising administering to said mammal an amount of a compound of the formula I, or a pharmaceutically acceptable salt thereof, that is effective in treating such disorder or condition.

This invention also relates to a method of treating a disorder or condition selected from the group consisting of delerium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple aetiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium and withdrawal delerium; addictive behaviors such as gambling; epilepsy; Down's syndrome; acute pain, chronic pain and migraine; demyelinating diseases such as multiple sclerosis (MS) and amylolateral sclerosis (ALS), peripheral neuropathy, for example diabetic and chemotherapy-induced-neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema in a mammal, including a human, comprising administering to said mammal an amount of a compound of the formula I, or a pharmaceutically acceptable salt thereof, that is effective in treating such disorder or condition.

Examples of the types of pain that can be treated with the compounds of formula I of the present invention and their pharmaceutically acceptable salts include pain resulting from soft tissue and peripheral damage, such as acute trauma, pain associated with osteoarthritis and rheumatoid arthritis, musculo-skeletal pain, such as pain experienced after trauma; spinal pain, dental pain, myofascial pain syndromes, episiotomy pain, and pain resulting from burns; deep and visceral pain, such as heart pain, muscle pain, eye pain, orofacial pain, for example, odontalgia, abdominal pain, gynaecological pain, for example, dysmenorrhoea, labour pain and pain associated with endometriosis; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, trigeminal neuralgia, neuropathic lower back pain, HIV related neuropathic pain, cancer related neuropathic pain, diabetic neuropathic pain, and arachnoiditis; neuropathic and non-neuropathic pain associated with carcinoma, often referred to as cancer pain; central nervous system pain, such as pain due to spinal cord or brain stem damage; lower back pain; sciatica; phantom limb pain, headache, including migraine and other vascular headaches, acute or chronic tension headache, cluster headache, temperomandibular pain and maxillary sinus pain; pain resulting from ankylosing spondylitis and gout; pain caused by increased blader contractions; post operative pain; scar pain; and chronic non-neuropathic pain such as pain associated with fibromyalgia, HIV, rheumatoid and osteoarthritis, anthralgia and myalgia, sprains, strains and trauma such as broken bones; and post surgical pain.

This invention also relates to a method of treating a disorder or condition selected from the group consisting of respiratory diseases, particularly those associated with excess mucus secretion, such as chronic obstructive airways disease, bronchopneumonia, chronic bronchitis, cystic fibrosis, adult respiratory distress syndrome, and bronchospasm; inflammatory diseases such as inflammatory bowel disease, psoriasis, Reiter's syndrome, Raynaud's syndrome, anthropathies, fibrositis, osteoarthritis, rheumatoid arthritis, psoriatic arthritis, asthma, pruritis and sunburn; human immunodeficiency virus (HIV) infections; allergies such as eczema and rhinitis, and other allergies; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis in a mammal, including a human, comprising administering to said mammal an amount of a compound of the formula I, or a pharmaceutically acceptable salt thereof, that is effective in treating such disorder or condition.

This invention also relates to a method of treating a disorder or condition selected from the group consisting of neoplasms, including breast tumours, gastric carcinomas, gastric lymphomas, neuroganglioblastomas and small cell carcinomas such as small cell lung cancer in a mammal, including a human, comprising administering to said mammal an amount of a compound of the formula I, or a pharmaceutically acceptable salt thereof, that is effective in treating such disorder or condition.

This invention also relates to a method of treating a disorder or condition selected from the group consisting of gastrointestinal (GI) disorders, including inflammatory gastrointestinal disorders such as inflammation bowel disease, disorders caused by helicobacter pylori and diseases of the GI tract such as gastritis, gastroduodenal ulcers, disorders associated with the neuronal control of viscera, ulcerative colitis, Crohn's disease, irritable bowel syndrome and emesis, including post operative nausea and post operative vomiting, and including acute, delayed or anticipatory emesis in a mammal, including a human, comprising administering to said mammal an amount of a compound of the formula I, or a pharmaceutically acceptable salt thereof, that is effective in treating such disorder or condition.

Emesis, as referred to above, includes emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

This invention also relates to a method of treating a disorder or condition selected from the group consisting of stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy; disorders of bladder function such as cystitis, bladder detrusor hyper-reflexia, inflammation of the urinary tract and incontinence, including urinary urge incontinence, overactive bladder, stress incontinence and mixed incontinence; fibrosing and collagen diseases such as scleroderma and eosinophilic fascioliasis; blood flow disorders caused by vasodilation and vasospastic diseases such as angina and Reynaud's disease; angiogenesis; cardiovascular disorders; eating disorders, such as anorexia nervosa and bulimia nervosa; attention deficit hyperactivity disorder; chronic fatigue syndrome; sexual dysfunctions including premature ejaculation and male erectile dysfunction; premenstrual syndrome and premenstrual dysphoric disorder; fibromyalgia; and rheumatic diseases such as fibrositis in a mammal, including a human, comprising administering to said mammal an amount of a compound of the formula I, or a pharmaceutically acceptable salt thereof, that is effective in treating such disorder or condition.

The compounds of formula I are also of value in the treatment of a combination of the above conditions, in particular in the treatment of combined post-operative pain and post-operative nausea and vomiting.

The compounds of formula I are particularly useful in the treatment of emesis, including acute, delayed or anticipatory emesis, wherein the emetic agent or condition is chemotherapy, radiation, toxins, pregnancy, vestibular disorders, motion, surgery, migraine, variations in intercranial pressure, or any other emetic agent or condition. Most especially, the compounds of formula I are of use in the treatment of emesis induced by antineoplastic (cytotoxic) agents including those routinely used in cancer chemotherapy, and emesis induced by other pharmacological agents, for example, rolipram. Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics. Particular examples of chemotherapeutic agents are described, for instance, by D. J. Stewart in Nausea and Vomiting: Recent Research and Clinical Advances, Eds. J. Kucharczyk et al., CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil (R. J. Gralla et al. in Cancer Treatment Reports (1984) 68(I), 163–172). The compounds of formula I are also of use in the treatment of emesis induced by radiation, including radiation therapy such as in the treatment of cancer, or radiation sickness; and in the treatment of post-operative nausea and vomiting. It will be appreciated that the compounds of formula I may be presented together with another therapeutic agent as a combined preparation for simultaneous, separate or sequential use for the relief of emesis. Such combined preparations may be, for example, in the form of a twin pack.

This invention also relates to a pharmaceutical composition comprising a therapeutically effective amount of a compound of the formula I, or a pharmaceutically acceptable salt thereof, and a pharmaceutically acceptable carrier.

This invention also relates to a pharmaceutical composition for treating a disorder or condition selected from the group consisting of mood disorders, such as depression, or more particularly, depressive disorders, for example, single episodic or recurrent major depressive disorders, dysthymic disorders, depressive neurosis and neurotic depression, melancholic depression, including anorexia, weight loss, insomnia, early morning waking and psychomotor retardation, atypical depression (or reactive depression), including increased appetite, hypersomnia, psychomotor agitation or irritability, seasonal affective disorder and pediatric depression; or bipolar disorders or manic depression, for example, bipolar I disorder, bipolar II disorder and cyclothymic disorder; conduct disorder and disruptive behavior disorder; anxiety disorders, such as panic disorder with or without agoraphobia, agoraphobia without history of panic disorder, specific phobias, for example, specific animal phobias, social anxiety, social phobia, obsessive-compulsive disorder, stress disorders, including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder, mood disorders associated with schizophrenia; behavioral disturbances associated with mental retardation, autistic disorder, and conduct disorder, comprising a therapeutically effective amount of a compound of the formula I, or a pharmaceutically acceptable salt thereof, and a pharmaceutically acceptable carrier.

This invention also relates to a pharmaceutical composition for treating a disorder or condition selected from the group consisting of delerium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple aetiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium and withdrawal delerium; addictive behaviors such as gambling; epilepsy; Down's syndrome; acute pain, chronic pain and migraine; demyelinating diseases such as multiple sclerosis (MS) and amylolateral sclerosis (ALS), peripheral neuropathy, for example diabetic and chemotherapy-induced-neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema, comprising a therapeutically effective amount of a compound of the formula I, or a pharmaceutically acceptable salt thereof, and a pharmaceutically acceptable carrier.

This invention also relates to a pharmaceutical composition for treating a disorder or condition selected from the group consisting of respiratory diseases, particularly those associated with excess mucus secretion, such as chronic obstructive airways disease, bronchopneumonia, chronic bronchitis, cystic fibrosis, adult respiratory distress syndrome, and bronchospasm; inflammatory diseases such as inflammatory bowel disease, psoriasis, Reiter's syndrome, Raynaud's syndrome, anthropathies, fibrositis, osteoarthritis, rheumatoid arthritis, psoriatic arthritis, asthma, pruritis and sunburn; human immunodeficiency virus (HIV) infections; allergies such as eczema and rhinitis, and other allergies; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis, comprising a therapeutically effective amount of a compound of the formula I, or a pharmaceutically acceptable salt thereof, and a pharmaceutically acceptable carrier.

This invention also relates to a pharmaceutical composition for treating a disorder or condition selected from the group consisting of neoplasms, including breast tumours, gastric carcinomas, gastric lymphomas, neuroganglioblastomas and small cell carcinomas such as small cell lung cancer, comprising a therapeutically effective amount of a compound of the formula I, or a pharmaceutically acceptable salt thereof, and a pharmaceutically acceptable carrier.

This invention also relates to a pharmaceutical composition for treating a disorder or condition selected from the group consisting of gastrointestinal (GI) disorders, including inflammatory gastrointestinal disorders such as inflammation bowel disease, disorders caused by helicobacter pylori and diseases of the GI tract such as gastritis, gastroduodenal ulcers, disorders associated with the neuronal control of viscera, ulcerative colitis, Crohn's disease, irritable bowel syndrome and emesis, including post operative nausea and post operative vomiting, and including acute, delayed or anticipatory emesis, comprising a therapeutically effective amount of a compound of the formula I, or a pharmaceutically acceptable salt thereof, and a pharmaceutically acceptable carrier.

This invention also relates to a pharmaceutical composition for treating a disorder or condition selected from the group consisting of stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy;

disorders of bladder function such as cystitis, bladder detrusor hyper-reflexia, inflammation of the urinary tract and incontinence, including urinary urge incontinence, overactive bladder, stress incontinence and mixed incontinence; fibrosing and collagen diseases such as scleroderma and eosinophilic fascioliasis; blood flow disorders caused by vasodilation and vasospastic diseases such as angina and Reynaud's disease; angiogenesis; cardiovascular disorders; eating disorders, such as anorexia nervosa and bulimia nervosa; attention deficit hyperactivity disorder; chronic fatigue syndrome; sexual dysfunctions including premature ejaculation and male erectile dysfunction; premenstrual syndrome and premenstrual dysphoric disorder; fibromyalgia; and rheumatic diseases such as fibrositis, comprising a therapeutically effective amount of a compound of the formula I, or a pharmaceutically acceptable salt thereof, and a pharmaceutically acceptable carrier.

The present invention also relates to compounds of the formula

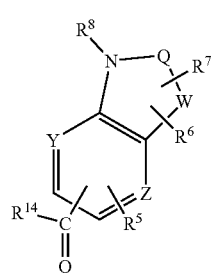

(II)

wherein Q is C=NH, C=CH$_2$, C=S, C=O, SO or SO$_2$;

each of Y and Z is N or CH, with the proviso that Y and Z can not both be N;

W is a one carbon linking group (i.e., methylene) or a saturated or unsaturated two or three carbon linking group, wherein each of the foregoing W groups can optionally be substituted with one substituent R$^7$ or two substituents R$^7$ and R$^6$, or W is a one carbon linking group that forms, together with a 2, 3, 4 or 5 carbon chain, a 3, 4, 5 or 6 membered spiro ring, respectively;

or W is a saturated two carbon chain linking group that forms, together with a separate 1, 2 or 3 carbon chain, a fused 3, 4 or 5 membered ring, respectively;

or W is a saturated two carbon chain linking group, wherein one of the two carbons in the chain forms, together with a separate 2, 3, 4 or 5 carbon chain, a 3, 4, 5 or 6 membered spiro ring, respectively;

R$^5$ and R$^8$ are selected, independently, from hydrogen, —SO(C$_1$–C$_6$)alkyl, —SO$_2$—(C$_1$–C$_6$)alkyl, —SO-aryl, —SO$_2$-aryl, CF$_3$, halo, phenyl, phenyl-(C$_1$–C$_2$)alkyl, hydroxy, aryloxy, heteroaryloxy, pyridyl, tetrazolyl, oxazolyl, thiazolyl, (C$_1$–C$_6$)alkoxy optionally substituted with from one to seven fluorine atoms, preferably with from zero to three fluorine atoms, (C$_1$–C$_6$)alkyl optionally substituted with from one to seven fluorine atoms, preferably with from zero to three fluorine atoms, and (C$_1$–C$_6$)alkyl substituted with one or more substituents, preferably with from zero to two substituents selected, independently, from hydroxy, oxo, (C$_1$–C$_6$)alkoxy, phenyl-(C$_1$–C$_3$)alkoxy, phenyl, cyano, chloro, bromo, iodo, NR$^9$R$^{10}$, NR$^9$COR$^{10}$, NR$^9$CO$_2$R$^{10}$, CONR$^9$R$^{10}$, COR$^9$ and CO$_2$R$^9$;

R$^6$ and R$^7$ are selected, independently, from —SO(C$_1$–C$_6$)alkyl, —SO$_2$—(C$_1$–C$_6$)alkyl, —SO-aryl, —SO$_2$-aryl, CF$_3$, halo, phenyl, phenyl-(C$_1$–C$_2$)alkyl, hydroxy, aryloxy, heteroaryloxy, pyridyl, tetrazolyl, oxazolyl, thiazolyl, (C$_1$–C$_6$)alkoxy optionally substituted with from one to seven fluorine atoms, preferably with from zero to three fluorine atoms, (C$_1$–C$_6$)alkyl optionally substituted with from one to seven fluorine atoms, preferably with from zero to three fluorine atoms, and (C$_1$–C$_6$)alkyl substituted with one or more substituents, preferably with from zero to two substituents selected, independently, from hydroxy, oxo, (C$_1$–C$_6$)alkoxy, phenyl-(C$_1$–C$_3$)alkoxy, phenyl, cyano, chloro, bromo, iodo, NR$^9$R$^{10}$, NR$^9$COR$^{10}$, NR$^9$CO$_2$R$^{10}$, CONR$^9$R$^{10}$, COR$^9$ and CO$_2$R$^9$;

each R$^9$ and each R$^{10}$ is selected, independently, from hydrogen, (C$_1$–C$_6$)alkyl, hydroxy(C$_1$–C$_6$)alkyl, phenyl and CF$_3$;

and wherein the phenyl groups in the definition of R$^5$, R$^6$, R$^7$ and R$^8$ and the phenyl moiety of phenyl (C$_1$–C$_2$)alkyl in the definition of R$^5$, R$^6$, R$^7$ and R$^8$ can optionally be substituted with one or more substituents, preferably with from zero to two substituents, that are selected, independently, from halo, hydroxy, (C$_1$–C$_6$)alkoxy optionally substituted with from one to seven fluorine atoms, preferably with from zero to three fluorine atoms, and (C$_1$–C$_6$)alkyl optionally substituted with from one to seven fluorine atoms, preferably with from zero to three fluorine atoms; and R$^{14}$ is hydrogen, (C$_1$–C$_6$)alkyl or CF$_3$;

with the proviso that: (a) R$^8$ can not be halo, hydroxy, cyano, aryloxy, heteroaryloxy, substituted or unsubstituted (C$_1$–C$_6$)alkoxy or methyl substituted with from 1–3 fluorine atoms;

and the pharmaceutically acceptable salts of such compounds.

Compounds of the formula II are useful as intermediates in the preparation of compounds of the formula I.

Compounds of formula II may contain chiral centers and therefore may exist in different enantiomeric and diastereomeric forms. This invention relates to all optical isomers and all stereoisomers of compounds of the formula II, both as racemic mixtures and as individual enantiomers and diastereoismers of such compounds, and mixtures thereof.

Other examples of preferred compounds of this invention are the following compounds of the formula II and their pharmaceutically acceptable salts:

5-Dimethoxymethyl-6-methoxy-3-methyl-1,1a,3,7b-tetrahydro-3-aza-cyclopropa[a]naphthalen-2-one;

(1S,1aR)-5-Dimethoxymethyl-6-methoxy-3-methyl-1,1a,3,7b-tetrahydro-3-aza-cyclopropa[a]naphthalen-2-one;

(1R,1aS)-5-Dimethoxymethyl-6-methoxy-3-methyl-1,1a,3,7b-tetrahydro-3-aza-cyclopropa[a]naphthalen-2-one;

6-Methoxy-3-methyl-2-oxo-1a,2,3,7b-tetrahydro-1H-3-aza-cyclopropa[a]naphthalene-5-carbaldehyde;

(1S,1aR)-6-Methoxy-3-methyl-2-oxo-1a,2,3,7b-tetrahydro-1H-3-aza-cyclopropa[a]naphthalene-5-carbaldehyde;

(1R,1aS)-6-Methoxy-3-methyl-2-oxo-1a,2,3,7b-tetrahydro-1H-3-aza-cyclopropa[a]naphthalene-5-carbaldehyde;

5-Methoxy-1,3,3-trimethyl-2-oxo-2,3-dihydro-1H-pyrrolo[3,2-b]pyridine-6-carbaldehyde;

6-Methoxy-1,3,3-trimethyl-2-oxo-2,3-dihydro-1H-pyrrolo[2,3-b]pyridine-5-carbaldehyde;

3-Methoxy-8-methyl-7-oxo-5,6,7,8-tetrahydro-[1,8]naphthyridine-2-carbaldehyde; and 2-Methoxy-5-methyl-6-oxo-5,6,7,8-tetrahydro-[1,5]naphthyridine-3-carbaldehyde. The present invention also relates to compounds of the formula T-NH$_2$ wherein T-NH$_2$ is

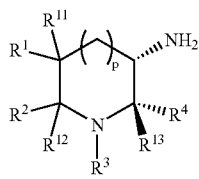

and wherein p is zero, one or two;

$R^3$ is selected from hydrogen, $COR^9$, $CO_2R^9$, optionally substituted phenyl, optionally substituted heterocyclic rings, and optionally substituted $(C_1–C_8)$alkyl wherein one of the $CH_2$ groups of said $(C_1–C_8)$alkyl may optionally be replaced with a sulfur, oxygen or carbonyl group and wherein said $(C_1–C_8)$alkyl can optionally be substituted with from one to three substituents, preferably with zero substituents or one substituent, independently selected from hydroxy, oxo, phenyl-$(C_1–C_3)$alkoxy, phenyl, cyano, halo, optionally substituted heterocyclic rings, $NR^9COR^{10}$, $NR^9CO_2R^{10}$, $CONR^9R^{10}$, $COR^9$, $CO_2R^9$, $NR^9R^{10}$, and $(C_1–C_6)$alkoxy optionally substituted with from one to seven fluorine atoms, preferably with from zero to three fluorine atoms;

and wherein the heterocyclic rings of $R^3$ and the heterocyclic ring substituents on the alkyl groups of $R^3$ are selected, independently, from 3 to 7 membered saturated or unsaturated monocyclic rings containing from 1 to 4 ring heteroatoms, and 8 to 12 membered saturated or unsaturated bicyclic rings containing from 1 to 4 ring heteroatoms, wherein said heteroatoms are selected, independently, from oxygen, nitrogen and sulfur, with the proviso that there can not be two adjacent ring oxygen atoms or two adjacent ring sulfur atoms in either the monocyclic or bicyclic heterocyclic rings, and with the proviso that heterocyclic rings formed from $NR^9R^{10}$ or $CONR^9R^{10}$ must contain at least one nitrogen atom;

and wherein the heterocyclic rings of $R^3$ and the heterocyclic ring substituents on the alkyl groups of $R^3$ can optionally be substituted with one or more substituents, preferably with zero, one or two substituents, independently selected from oxo, hydroxy, thioxo, halo, cyano, phenyl, $(CH_2)_mNR^9R^{10}$, $NR^9COR^{10}$, $(CH_2)_mOR^9$, wherein m is zero, one or two, and $(C_1–C_6)$alkyl optionally substituted with one or more substituents, preferably with from zero to two substituents, independently selected from halo, $CF_3$, methoxy and phenyl;

and wherein the phenyl groups of $R^3$ and the phenyl substituents in the alkyl groups of $R^3$ can optionally be substituted with one or more substitutents, preferably with from zero to two substituents, independently selected from the group consisting of halo, cyano, nitro, $CF_3$, $(CH_2)_mNR^9R^{10}$, wherein m is zero, one or two, $NR^9COR^{10}$, $NR^9CO_2R^{10}$, $CONR^9R^{10}$, $CO_2NR^9R^{10}$, $COR^9$, $CO_2R^9$, $(C_1–C_6)$alkyl optionally substituted with from one to seven fluorine atoms, preferably with from zero to three fluorine atoms, $(C_1–C_6)$alkoxy optionally substituted with from one to seven fluorine atoms, preferably with from zero to three fluorine atoms, and $(C_2–C_6)$alkenyl optionally substituted with from one to seven fluorine atoms, preferably with from zero to three fluorine atoms;

each of $R^1$, $R^2$, $R^{11}$, $R^{12}$ and $R^{13}$ are selected, independently, from hydrogen and $(C_1–C_6)$alkyl optionally substituted with one or more substituents, preferably with zero, one or two substituents, that are selected, independently, from hydroxy, oxo, $(C_1–C_6)$alkoxy and cyano;

or $R^1$ and $R^2$, together with the carbon atoms to which they are attached, or $R^2$ and $R^3$, together with the carbon and nitrogen to which they are attached, respectively, form a 5 or 6 membered saturated heterocyclic ring containing one or two heteroatoms that are selected, independently, from nitrogen, oxygen and sulfur, with the proviso that said ring can not contain two adjacent oxygen atoms or two adjacent sulfur atoms; or $R^1$ and $R^2$, together with the carbons to which they are attached, form a 5 or 6 membered, saturated or unsaturated carbocyclic ring, and wherein said heterocyclic and carbocyclic rings formed by $R^1$ and $R^2$ or by $R^2$ and $R^3$ can be substituted with one or more substituents, preferably with zero substituents or one substituent, independently selected from halo, oxo, $NR^9R^{10}$, $(C_1–C_6)$alkyl optionally substituted with from one to seven fluorine atoms, preferably with from zero to three fluorine atoms, and $(C_1–C_6)$alkoxy optionally substituted with from one to seven fluorine atoms, preferably with from zero to three fluorine atoms;

or $R^{12}$ and $R^{13}$, together with the carbon atoms to which they are attached, form a 5 or 6 membered saturated heterocyclic ring containing one or two heteroatoms that are selected, independently, from nitrogen, oxygen and sulfur, with the proviso that said ring can not contain two adjacent oxygen atoms or two adjacent sulfur atoms, or $R^{12}$ and $R^{13}$, together with the carbons to which they are attached, form a 5 or 6 membered, saturated or unsaturated carbocyclic ring, and wherein said heterocyclic and carbocyclic rings formed by $R^{12}$ and $R^{13}$ can be substituted with one or more substituents, preferably with zero substituents or one substituent, independently selected from $NR^9R^{10}$, halo, phenyl-S—, phenyl-SO—, phenyl-$SO_2$—, oxo, $(C_1–C_6)$alkoxy optionally substituted with from one to seven fluorine atoms, preferably with from zero to three fluorine atoms, and $(C_1–C_6)$alkyl optionally substituted with from one to seven fluorine atoms, preferably with from zero to three fluorine atoms:

with the proviso that no more than one of $R^1$ and $R^2$, $R^2$ and $R^3$, and $R^{12}$ and $R^{13}$ can form a ring;

$R^4$ is selected from phenyl, 2-, 3- or 4-pyridyl, 2- or 3-thienyl, and pyrimidyl, wherein $R^4$ can be optionally substituted with one or more substituents, preferably with zero or one substituent, selected, independently, from halo, $(C_1–C_6)$alkyl optionally substituted with from one to seven fluorine atoms, preferably with from zero to three fluorine atoms, $(C_1–C_6)$alkoxy optionally substituted with from one to seven fluorine atoms, preferably with from zero to three fluorine atoms, and $(C_2–C_6)$alkenyl optionally substituted with from one to seven fluorine atoms, preferably with from zero to three fluorine atoms;

each $R^9$ and each $R^{10}$ is selected, independently, from hydrogen, $(C_1–C_6)$alkyl, hydroxy$(C_1–C_6)$alkyl, phenyl and $CF_3$;

or $R^9$ and $R^{10}$, when $R^3$ is $NR^9R^{10}$ or $CONR^9R^{10}$, can form, together with the nitrogen to which they are attached, an optionally substituted heterocyclic ring that contains at least one nitrogen atom;

and the pharmaceutically acceptable salts of such compounds.

Compounds of the formula $T-NH_2$ as defined above are useful as intermediates in the preparation of compunds of the formula I.

Compounds of formula $T-NH_2$ as defined above may contain chiral centers and therefore may exist in different enantiomeric and diastereomeric forms. This invention relates to all optical isomers and all stereoisomers of compounds of the formula $T-NH_2$ as defined above, both as racemic mixtures and as individual enantiomers and diastereoismers of such compounds, and mixtures thereof.

Other examples of preferred compounds of this invention are the following compounds of the formula T-NH$_2$ and their pharmaceutically acceptable salts:
6-Methyl-2-phenyl-piperidin-3-ylamine;
(2S,3S,6S)-6-Methyl-2-phenyl-piperidin-3-ylamine;
(2R,3R,6R)-6-Methyl-2-phenyl-piperidin-3-ylamine;
6-Ethyl-2-phenyl-piperidin-3-ylamine;
(2S,3S,6S)-6-Ethyl-2-phenyl-piperidin-3-ylamine;
(2R,3R,6R)-6-Ethyl-2-phenyl-piperidin-3-ylamine;
5-Methyl-2-phenyl-piperidin-3-ylamine;
5-Ethyl-2-phenyl-piperidin-3-ylamine;
5-propyl-2-phenyl-piperidin-3-ylamine;
5,5-diethyl-2-phenyl-piperidin-3-ylamine;
5,5-dimethyl-2-phenyl-piperidin-3-ylamine;
6,6-dimethyl-2-phenyl-piperidin-3-ylamine;
8-Benzyl-1-phenyl-8-aza-bicyclo[3.2.1]oct-2-ylamine; and
(1S,2S,5R) or (1R,2R,5S) 1-Phenyl-8-aza-bicyclo[3.2.1]oct-2-ylamine.

A further aspect of the present invention comprises the compounds of formula I in combination with a 5-HT$_3$ antagonist, such as ondansetron, granisetron or tropisetron, or other anti-emetic medicaments, for example, a dopamine antagonist such as metoclopramide or domperidone, or GABA-B receptor agonists such as baclofen. Additionally, a compound of formula I either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118; 2,990,401; 3,048,581; 3,126,375; 3,929,768; 3,996,359; 3,928,326; and 3,749,712. Dexamethasone (Decadron™) is particularly preferred, Furthermore, a compound of formula I may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable. When tested in the ferret model of cisplatin-induced emesis described by F. D. Tattersall et al. in Eur. J. Pharmacol., (1993) 250, R5–R6, the compounds of the present invention were found to attenuate the retching and vomiting induced by cisplatin.

For the treatment of certain conditions it may be desirable to employ a compound according to the present invention in conjunction with another pharmacologically active agent. For example, for the treatment of respiratory diseases such as asthma, a compound of formula I may be used in conjunction with a bronchodilator, such as an α$_2$-adrenergic receptor agonist or tachykinin antagonist which acts at NK-2 receptors. The compound of formula I and the bronchodilator may be administered to a patient simultaneously, sequentially or in combination. Likewise, a compound of the present invention may be employed with a leukotriene antagonist, such as a leukotriene D4 antagonist such as a compound selected from those disclosed in European Patent Application Nos. 0 480 717 and 0 604 114 and in U.S. Pat. Nos. 4,859,692 and 5,210,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula I and an effective amount of a bronchodilator. The present invention also provides a composition comprising a compound of formula I, a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$ agonists, especially sumatriptan, naratriptan, zolmatriptan or rizatriptan. Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist. Specific antiinflammatory agents include diclofenac, ibuprofen, indomethacin, ketoprofen, naproxen, piroxicam and sulindac.

It will be appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Suitable opioid analgesics of use in conjunction with a compound of the present invention include morphine, codeine, dihydrocodeine, diacetylmorphine, bydrocodone, hydromorphone, levorphanol, oxymorphone, alfentanil, buprenorphine, butorphanol, fentanyl, sufentanyl, meperidine, methadone, nalbuphine, propoxyphene and pentazocine, or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanii hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient. In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other antidepressant or anti-anxiety agents. Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical antidepressants. Suitable norepinephrine reuptake inhibitors include tertiary amine tricyclics and secondary amine tricyclics. Suitable examples of tertiary amine tricyclics include amitriptyline, clomipramine, doxepin, imipramine and trimipramine, and pharmaceutically acceptable salts thereof. Suitable examples of secondary amine tricyclics include amoxapine, desipramine, maprotiline, nortriptyline and protriptyline, and pharmaceutically acceptable salts thereof. Suitable selective serotonin reuptake inhibitors include fluoxetine, fluvoxamine, paroxetine and sertraline, and pharmaceutically acceptable salts thereof. Suitable monoamine oxidase inhibitors include isocarboxazid, phenelzine, tranylcypromine and selegiline, and pharmaceutically acceptable salts thereof. Suitable reversible inhibitors of monoamine oxidase include moclobemide, and pharmaceutically acceptable salts thereof. Suitable serotonin and noradrenaline reuptake inhibitors of use in the present invention include venlafaxine, and pharmaceutically acceptable salts thereof. Suitable CRF antagonists include those compounds described in International Patent Application Nos. WO 94/13643, WO 94113644, WO 94/13661, WO 94/13676 and WO 94/13677. Suitable atypical anti-depressants include bupropion, lithium, nefazodone, trazodone and viloxazine, and pharmaceutically acceptable salts thereof. Suitable classes of antianxiety agents include benzodiazepines and 5-$HT_{1A}$ agonists or antagonists, especially 5-HT1A partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam, and pharmaceutically acceptable salts thereof. Suitable 5-$HT_{1A}$ receptor agonists or antagonists include, in particular, the 5-$HT_{1A}$ receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient. In a further or alternative aspect of the present invention, there is provided a product comprising a compound of the present invention and an anti depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents. The present invention accordingly provides the use of a compound of formula I and an anorectic agent for the manufacture of a medicament for the treatment or prevention of eating disorders. The present invention also provides a method for the treatment or prevention of eating disorders, which method comprises administration to a patient in need of such treatment an amount of a compound of formula I and an amount of an anorectic agent, such that together they give effective relief. In a further aspect of the present invention, there is provided a pharmaceutical composition comprising a compound of formula I and an anorectic agent, together with at least one pharmaceutically acceptable carrier or excipient. It will be appreciated that the compound of formula I and anorectic agent may be present as a combined preparation for simultaneous, separate or sequential use for the treatment or prevention of eating disorders. Such combined preparations may be, for example, in the form of a twin pack. In a further or alternative aspect of the present invention, there is therefore provided a product comprising a compound of formula I and an anorectic agent as a combined preparation for simultaneous, separate or sequential use in the treatment or prevention of eating disorders.

In a further embodiment of the present invention there is provided the use of a compound of formula I and an anorectic agent for the manufacture of a medicament for the treatment or prevention of obesity. The present invention also provides a method for the treatment or prevention of obesity, which method comprises administration to a patient in need of such treatment an amount of a compound of formula I and an amount of an anorectic agent, such that together they give effective relief.

In an alternative embodiment of the present invention there is provided the use of a compound of formula I and an anorectic agent for the manufacture of a medicament for the treatment or prevention of bulimia nervosa. The present invention also provides a method for the treatment or prevention of bulimia nervosa, which method comprises administration to a patient in need of such treatment an amount of a compound of formula I and an amount of an anorectic agent, such that together they give effective relief.

In a further embodiment of the present invention there is provided the use of a compound of formula I and an anorectic agent for the manufacture of a medicament for the treatment or prevention of compulsive eating disorders. The present invention also provides a method for the treatment or prevention of compulsive eating disorders, which method comprises administration to a patient in need of such treatment an amount of a compound of formula I and an amount of an anorectic agent, such that together they give effective relief.

In an alternative embodiment of the present invention there is provided the use of a compound of formula I and an anorectic agent for the manufacture of a medicament for reducing the total body fat mass in an obese mammal, especially a human. The present invention also provides a method for reducing the total body fat mass in an obese mammal, especially a human, which method comprises administration to a patient in need of such treatment an amount of a compound of formula I and an amount of an anorectic agent, such that together they give effective relief.

Suitable anoretic agents for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof. Particularly preferred anorectic agents include amphetamine and derivatives thereof such as amphetamine, benzphetamine, chlorphentermine, clobenzorex, cloforex, clotermine, dexfenfluramine, dextroamphetamine, diethylpropion, N-ethylamphetamine, fenfluramine, fenproporex, furfurylmethylamphetamine, levamfetamine, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine, and pharmaceutically acceptble salts thereof. Particularly preferred halogenated amphetamine derivatives of use in combination with a compound of the present invention include fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI). The present invention accordingly provides the use of a compound of formula I and an SSRI for the manufacture of a medicament for the treatment or prevention of obesity. The present invention also provides a method for the treatment or prevention of obesity, which method comprises administration to a patient in need of such treatment an amount of a compound of formula I and an amount of an SSRI, such that together they give effective relief. In a further aspect of the present invention, there is provided a pharmaceutical composition for the treatment or prevention of obesity comprising a compound of formula I and an SSRI, together with at least one pharmaceutically acceptable carrier or excipient. It will be appreciated that the compound of formula I and SSRI may be present as a combined preparation for simultaneous, separate or sequential use for the treatment or prevention of obesity. Such combined preparations may be, for example, in the form of a twin pack. In a further or alternative aspect of the present invention, there is therefore provided a product comprising a compound of formula I and an SSRI as a combined preparation for simultaneous, separate or sequential use in the treatment or prevention of obesity.

In an alternative embodiment of the present invention, there is provided the use of a compound of formula I and an SSRI for the manufacture of a medicament for reducing the total body fat mass in an obese mammal, especially a human. The present invention also provides a method for reducing the total body fat mass in an obese mammal, especially a human, which method comprises administration to the mammal an amount of a compound of formula I and an amount of an SSRI, such that together they give effective relief. In a further aspect of the present invention, there is provided a pharmaceutical composition for reducing the total body fat mass in an obese mammal, especially a human, comprising a compound of formula I and an SSRI, together with at least one pharmaceutically acceptable carrier or excipient. Suitable selective serotonin reuptake inhibitors for use in combination with a compound of the present invention include fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared (kg/m²), of at least 25.9. Conventionally, those persons with normal weight, have a BMI of 19.9 to less than 25.9. The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia. "Treatment" (of obesity) refers to reducing the BMI of the mammal to less than about 25.9, and maintaining that weight for at least 6 months. The treatment suitably results in a reduction in food or calorie intake by the mammal. "Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycycstic ovarian disease, cardiovascular diseases, osteoarthritis, dermatological disorders, hypertension, insulin resistance, hypercholesterolemia, hypertriglyceridemia, and cholelithiasis. Thus, in one aspect, this invention relates to the inhibition and/or complete suppression of lipogenesis in obese mammals, i.e., the excessive accumulation of lipids in fat cells, which is one of the major features of human and animal obesity, as well as loss of total body weight. In another aspect, the invention ameliorates the conditions that are a consequence of the disease, such as preventing or arresting the progression of polycystic ovarian disease so that the patient is no longer infertile, and increasing the insulin sensitivity and/or decreasing or eliminating the need or usage of insulin in a diabetic patient, e.g., one with adult-onset diabetes or Type II diabetes.

In a further embodiment of the present invention there is provided the use of a compound of formula I and a nicotine recpetor partial agonist for the treatment of chronic pain, neuropathic pain and migraine. Nicotine receptor partial agonists that can be used in such embodiments of this invention include, but are not limited to, those referred to in World Patent Applications WO 98/18798, WO 99/55680 and WO 99/35131, which were published, respectively, on May 7, 1998, Nov. 4, 1999 and Jul. 15, 1999, and in United States Provisional Application No. 60/083,556, which was filed on Apr. 29, 1998.

DETAILED DESCRIPTION OF THE INVENTION

The compounds of formula I of the present invention may be prepared as described in the following reaction schemes. Unless otherwise indicated, in the reaction schemes that follow, $R^1$ through $R^{13}$, Q, Z, G, B, $B^2$, A, W, E, D and Y are defined as above.

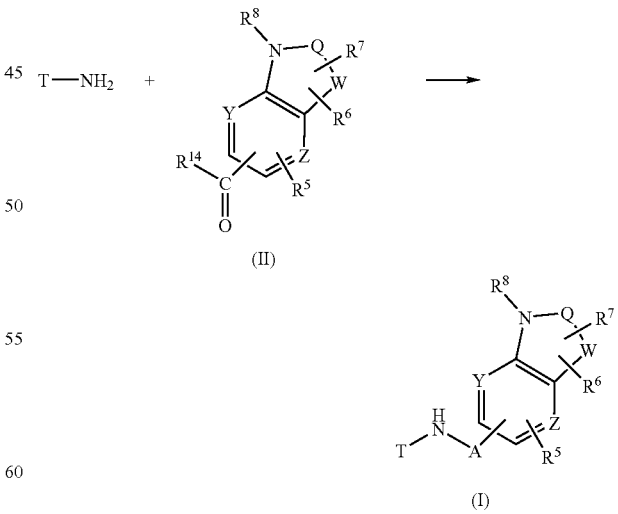

Scheme A-I illustrates a method for preparing compounds of the formula (I) wherein A is $CH_2$, B is absent and G is NH by reductive amination of a compound of the formula (II) with a compound of the formula T-$NH_2$ wherein T-NH2 is

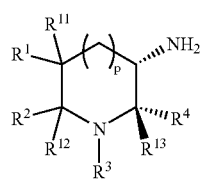

and $R^{14}$ is hydrogen, $(C_1-C_6)$alkyl or $CF_3$.

The above reaction may be carried out in one vessel without isolation of the imine intermediate, or T-NH$_2$ and (II) may be combined in an inert solvent such as methylene chloride, dichloroethane, toluene or benzene, either at room temperature or the reflux point of the solvent, with or without removal of the byproduct water, to form the imine, which is then reduced. The reduction can be carried out by catalytic hydrogenation, or with several hydride reagents in a reaction inert solvent. The catalytic hydrogenation may be carried out in the presence of a metal catalyst such as palladium or Raney nickel. Suitable hydride reagents include borohydrides such as sodium borohydride (NaBH$_4$), sodium cyanoborohydride (NaBH$_3$CN) and sodium triacetoxyborohydride (NaB(OAc)$_3$H), boranes, aluminum based reagents and trialkylsilanes. Suitable solvents include polar solvents such as methanol, ethanol, methylene chloride, dichloroethane, tetrahydrofuran (THF), dioxane, toluene, benzene and ethylacetate. This reaction is typically carried out at a temperature from about –78° C. to about the reflux temperature of the solvent, preferably from about 0° C. to about 25° C., for a period of about 5 minutes to about 48 hours, preferably from 0.5 to 16 hours.

Alternatively, the compounds of the formula (I) of this invention may be prepared as shown in the following scheme A-II.

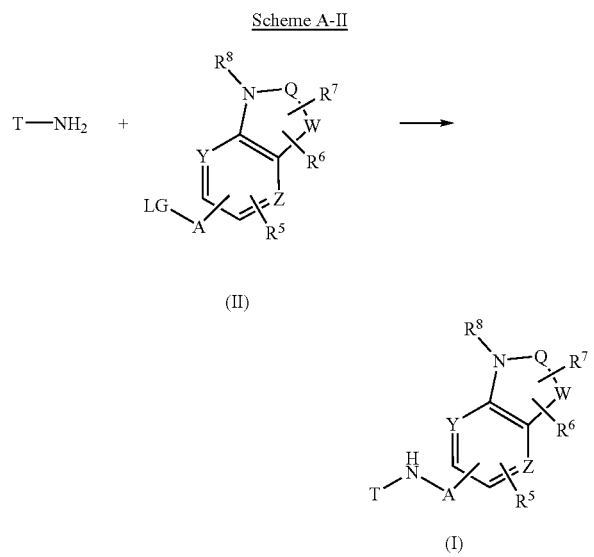

(wherein LG is a leaving group such as halo or sulfonate including tosylate, triflate or mesylate)

Referring to Scheme A-II, the compounds of the formula (I) wherein B is absent and G is NH may be prepared by a reaction of a compound of the formula (III) with a compound of the formula T-NH$_2$, wherein T-NH$_2$ is as previously defined. The compound of formula (III) is treated with T-NH$_2$ in the presence of a base (e.g., K$_2$CO$_3$ or Na$_2$CO$_3$) in a polar solvent (e.g., methanol, ethanol, isopropylalcohol, THF, dioxane, dimethylformamide (DMF) or dimethylsulfoxide (DMSO)). This reaction is typically carried out at a temperature from about –78° C. to about the reflux temperature of the solvent, preferably from 0° C. to 25° C., for a period of about 5 minutes to about 48 hours, preferably for between 0.5 and 16 hours.

The compounds of formula (III) can be prepared by reduction of an aldehyde of the formula (II), followed by conversion of a hydroxy group of the resultant compound into a leaving group, LG (e.g., halo such as chloro, bromo, iodo or fluoro, or sulfonate including tosylate or mesylate). Reduction of the aldehyde of formula (II) can be accomplished using a variety of reducing agents in a reaction inert solvent. Suitable reducing agents/solvent systems include sodium tetrahydroborate (NaBH$_4$) in methanol or ethanol; lithium tetrahydroborate (LiBH$_4$) in THF or diethyl ether; lithium tetrahydroaluminium (LiAlH$_4$), lithium triethoxyhydroaluminium (LiAl(OEt)$_3$H), lithium tert-buthoxyhydroaluminium (LiAl(OBut)$_3$H) or aluminium trihydride (AlH$_3$) in THF or diethyl ether; and iso-buthyl aluminium hydride(i-BuAlH$_2$) or diisopropyl aluminum hydride (DIBAL-H) in dichloromethane, THF or n-hexane. This reaction is generally carried out at a temperature from about –20° C. to about 25° C. for a period of about 5 minutes to about 12 hours. Then, the hydroxy group of the resultant compound is converted into a leaving group LG using methods known to those skilled in the art. For example, when LG is a sulfonate such as tosylate or mesylate, the hydroxy compound is reacted with sulfonyl chloride in the presence of pyridine or triethylamine in dichloromethane. When LG is halo such as chloro or bromo, the hydroxy compound may be treated with SOX$_2$ (wherein X is Cl or Br) in the presence of pyridine.

Compounds of formula (II) can be prepared as illustrated in the following scheme B.

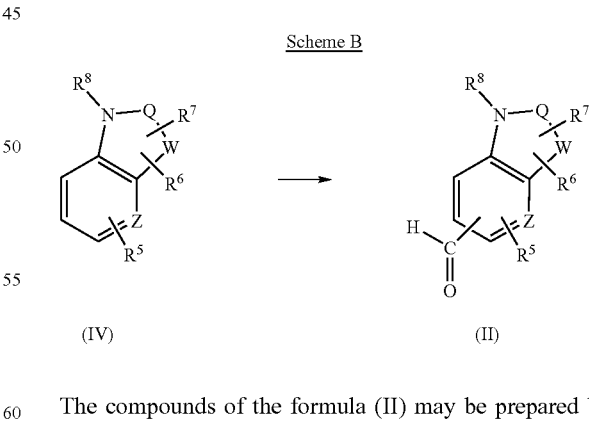

The compounds of the formula (II) may be prepared by direct or indirect formylation of a compound of the formula (IV). Any formylation methods known to those skilled in the art may be used to introduce a formyl group into a benzene ring. For example, direct formylation may be accomplished by contacting the compound of formula (IV) with a suitable formylating agent in the presence of a suitable catalyst.

Suitable formylating agent/catalyst systems include dichloromethyl methyl ether/titanium (IV) chloride ($Cl_2CHOCH_3$/$TiCl_4$), dichloromethyl methyl ether/aluminum chloride ($Cl_2CHOCH_3$/$AlCl_3$), dichloromethyl methyl ether/tin (IV) chloride ($Cl_2CHOCH_3$/$SnCl_4$) dichloromethyl methyl ether/boron trifluoride etherate ($Cl_2CHOCH_3$/$BF_3$-OEt), trifluoroacetic acid ($CF_3CO_2H$)/hexamethylenetetramine (modified Duff's conditions) and phosphoryl trichloride ($POCl_3$)/DMF (Vilsmeier's conditions). Indirect formylation may be achieved by halogenating the compound of formula (IV), displacing the halogen atom introduced with a cyano group, and then subjecting the resultant cyano substituted compound to reduction. Alternatively, the halogen may be subjected to halogen metal exchange with butyl lithium. The lithium intermediate may then be treated with dimethylformamide to afford the compound of formula (II). The halogenation as used herein may be carried out according to the procedure reported in G. A. Olah et al., *J. Org Chem*, 58, 3194 (1993). The displacement of the halogen atom with a cyano group may be performed according to the methods reported in D. M. Tschaem et al., *Synth Commun*, 24, 887 (1994), and K. Takagi et al., 64 *Bull Chem. Soc. Jpn.* 64, 1118 (1991). The reduction can be performed in the presence of diisopropyl aluminiumhydride (DIBAL-H) in dichloromethane or Raney nickel in formic acid.

In addition, compounds of formula (II) wherein W is vinylene can be prepared by dehydrogenation of the analogous compounds of formula (II) wherein W is ethylene in a suitable solvent such as dioxane.

The starting materials of the formula (IV) either are known compounds which are commercially available, or can be prepared by known methods. For example, compounds of the formula (IV) wherein $R^1$ is alkyl can be prepared by N-alkylation of the corresponding compounds (IV) wherein $R^1$ is hydrogen, in the presence of a base (e.g., NaH or KH), in a suitable solvent (e.g., DMSO, DMF and THF). Compounds of the formula (IV) wherein $R^2$ or $R^3$ is other than hydrogen, can also be prepared from the corresponding compounds of the formula (IV) wherein $R^2$ or $R^3$, respectively, is hydrogen, using similar techniques as described above. Compounds of the formula (IV) can be also prepared by other methods as described in European Patent No. 385662 and C. Crestini et al., *Synth. Commun.* 24 2853 (1994) and G. W. Rewcastle et al., *J. Med Chem*, 37, 2033 (1994). Compounds of the formula (IV) wherein Q is S can be prepared by thionation of the corresponding compounds of formula (IV) wherein Q is O. Suitable thionation agents are Lawesson's reagent (*Tetrahedron*, 41, 5061 (1985)) and $P_4S_{10}$ (*Chem. Pharm. Bull.*, 10, 647 (1962)).

Alternatively, compounds of the formula (I) wherein B is absent G is NH and A is $CH_2$ may be prepared as shown in the following Scheme A-III.

Scheme A-III

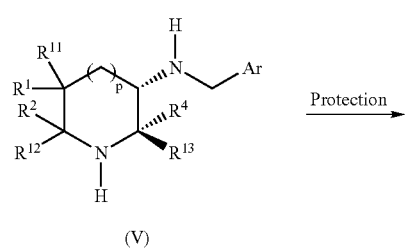

(V)

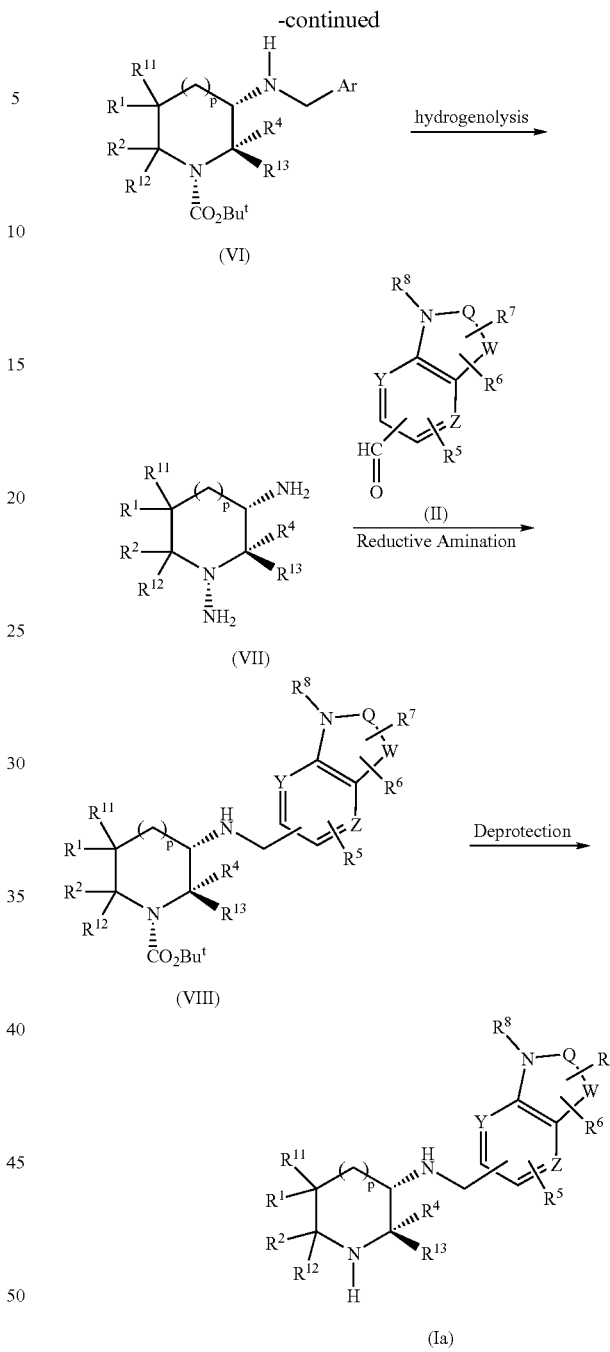

Scheme A-III illustrates the preparation of compounds of the formula (Ia) (which are compounds of the formula (I) wherein T is 2-phenylpiperidinyl).

Referring to Scheme A-III, N-protection of a compound of the formula (V) (Ar is phenyl or the like) may be carried out by treatment with (t-BuOCO)$_2$O (Boc$_2$O) in the presence of a base such as sodium bicarbonate (NaHCO$_3$) or triethylamine (Et$_3$N) to obtain a compound of the formula (VI). Other nitrogen protecting groups that are well known to those of skill in the art can also be used, e.g., FMOC (via reaction with FMOC-Cl), benzyl (via reaction with benzyl chloride), trifluoroacetyl (via reaction with trifluoroacetic anhydride) and benzoyl (via reaction with benzoylchloride).

For a discussion of such protecting groups and methods of attaching and removing them, see Greene, Theodora W. and Wiuts, Peter G. M., *Protective Groups In Organic Synthesis*, Second Edition, John Wiley & Sons, Inc., New York, 1991. The compound of formula (VI) is subjected to hydrogenolysis to obtain a compound of the formula (VII) An alternative route for N-protection of a compound of the formula (V) may be carried out by treatment with carbobenzoxy chloride (Cbz-Cl) in the presence of a base such as sodium bicarbonate ($NaHCO_3$) or triethylamine ($Et_3N$). The hydrogenolysis may be carried out by treatment with $H_2$ or ammonium formate ($HCO_2NH_4$) in the presence of a metal catalyst such as a palladium on charcoal (e.g., 20% palladium on charcoal) in a suitable solvent. Then, the compound of formula (VII) is subjected to the reductive amination as described in Scheme A-I to form the corresponding compound of formula (VIII), which can then be converted into a compound of the formula (Ia) by treatment with an acid catalyst such as hydrochloride (HCl) in methanol, concentrated HCl in ethylacetate or $CF_3CO_2H$ in dichloroethane.

The compounds of formula (I), and the intermediates shown in the above reaction schemes can be isolated and purified by conventional procedures, such as recrystallization or chromatographic separation.

Selected intermediates depicted as compound IV in Scheme B can be prepared by the transformations depicted in Schemes C and D.

Preferably, the compound of formula XIII is formed by the reaction of acetic anhydride in methylene chloride, using triethyl amine as the base, at about 0° C. for about 2 hours.

Compounds of the formula XIII wherein $R^8$=H can be alkylated with a suitable electrophile chosen from methyl iodide, dimethyl sulfate and methyl triflate. This reaction is conducted in the presence of a base such as sodium or potassium t-butoxide or sodium or potassium hydride. A suitable inert solvent such as THF, ether or dimethoxyethane may be used. The reaction is conveniently carried out at a temperature from about −50° C. to about ambient temperature. Preferred conditions involve using dimethylsulfate in THF in the presence of potassium t-butoxide, at a temperature from 0° C. to ambient temperature, for 16 hours.

Alternatively, when $R^8$ is hydrogen, the compound of formula XIII can be acylated with a sulfonyl or sulfinyl halide or anhydride (e.g., methanesulfonyl chloride or bromide or anhydride, trifluoromethanesulfonyl anhydride, phenyl sulfonyl chloride, bromide or anhydride, or tosyl chloride or anhydride) after treatment of such compound with a suitable base (e.g., sodium or potassium hydride, sodium or potassium carbonate, or sodium or potassium t-butoxide), in a solvent such as DMF, THF, N-methylpyrrolidinine, dichloroethane or dichloromethane. Preferably, this reaction is carried out with methane sulfonyl chloride as

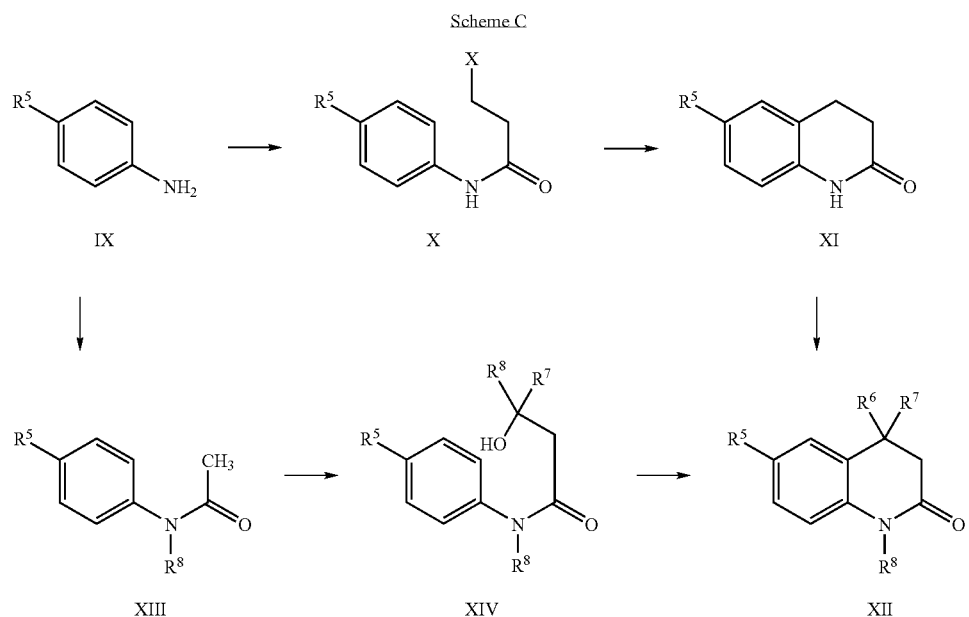

Scheme C

IX    X    XI

XIII    XIV    XII

Acylation of the aniline of formula IX with an acylating agent such as acetic anhydride, acetyl bromide, acetyl chloride, acetyl sulfonates, acetyl phosphates or mixed anhydrides of acetic acid and a phenyl or alkyl chloroformate affords a compound of the formula XIII. Typically, this transformation is carried out in an inert solvent or mixtures of solvents such as methylene chloride, dichloroethane, toluene, ether, benzene, THF, dioxane, water or chloroform, or any inert solvent, in the presence of a base such as a bicarbonate or carbonate or triethyl amine, at a temperature from about −50° C. to about the reflux temperature of the solvent, for a period of about 15 minutes to about 24 hours.

the reactant, using DMF as the solvent and sodium hydride as the base.

The compound of formula XIV can be prepared from the corresponding compound of formula XIII through formation of the enolate with a suitable base such as lithium diisopropyl amide, sodium, lithium or potassium hexamethyldisilazane or potassium t-butoxide, in a solvent such as THF or dimethoxyetane, at a temperature from about −100° C. to about −25° C., for a period of about 15 minutes to about 5 hours. Suitable electrophiles include acetone, acetaldehyde, benzaldehyde, formaldehyde, cyclopenanone and cyclohexanone. Preferred conditions for this transformation involve using lithium diisopropyl amide in THF at about −78° C. with either acetone or acetaldehyde as the electrophile, for about 2 hours.

Formation of the compound of formula XII from the corresponding compound of formula XIV can be accomplished in an acid such as sulfuric, phosphoric, triflic, hydrofluoric or polyphosphoric acid, with or without an additional inert solvent, at a temperature from about 50° C. to about 150° C. for a period of about 5 minutes to about 2 hours. Preferred conditions involve heating the compound of formula XIV in neat polyphosphoric acid for about 15 minutes at about 100° C.

Compounds of the formula X can be formed via acylation of the aniline of formula IX with an acylating agent such as 3-chloropropionyl chloride or chloroacetyl chloride. Typically, this transformation is carried out in an inert solvent or mixtures of solvents such as methylene chloride, dichloroethane, toluene, ether, benzene, THF, dioxane, water or chloroform, or any inert solvent, in the presence of a base such as a bicarbonate, a carbonate or triethyl amine, at a temperature between about −50° C. and about the reflux temperature of the solvent, for a period of about 15 minutes to about 24 hours. Preferably, the compound of formula X is formed by the reaction of 3-chloropropionyl chloride in methylene chloride/water, using sodium bicarbonate as the base, at about ambient temperature for about 16 hours. The compound of formula XI is formed by reacting the corresponding compound of formula X with a Lewis acid such as aluminum chloride, stannic chloride, stannous chloride, or titanium chloride, either neat or in an inert solvent such as methylene chloride, dichloroethane, chloroform, benzene or toluene, at a temperature from about ambient temperature to about 300° C., for a period of about 5 minutes to about 2 hours. Preferably, the compound of formula XI is formed by the reaction of the corresponding compound of formula X with aluminum chloride, neat, at about 210° C. for a period of about 10 minutes.

Compounds of the formula XI wherein $R^5$ is hydroxy and/or $R^8$ is hydrogen can be converted into the corresponding compounds wherein $R^5$ or $R^8$ is, respectively, an alkoxy or alkyl group by reacting them with a suitable electrophile chosen from methyl iodide, dimethyl sulfate and methyl triflate. This reaction is conducted in the presence of a base such as sodium or potassium t-butoxide or sodium or potassium hydride. A suitable inert solvent such as THF, ether or dimethoxyethane can be used. The reaction is conveniently carried out at a temperature from about −50° C. to about ambient temperature. Preferred conditions involve using methyl iodide in THF, in the presence of potassium t-butoxide, at a temperature from about 0° C. to about ambient temperature, for about 16 hours.

Scheme D

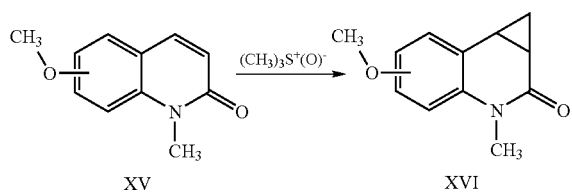

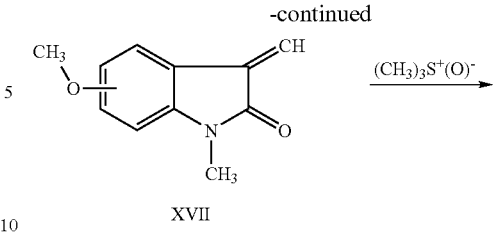

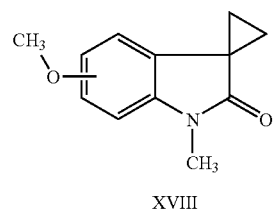

Compounds XVI and XVIII may be prepared as shown in Scheme D using conditions described by Bernard et al. CAN 67: 120195. The reaction may be conducted with trimethylsulfonium iodide, chloride or bromide, in a solvent such as DMSO, THF, DME, ether or DMF using a base such as sodium or potassium hydride, butyl or hexyl lithium at a temperature from about 0° C. to about 200° C. for about 1 hour to about 2 days. Preferred conditions involve using trimethylsulfonium chloride in DMSO with sodium hydride at a temperature of about 100° C. for about 1 week. More preferred conditions involve using trimethylsulfonium iodide in THF with hexyl lithium at a temperature of about 0° C. to the reflux point of the solvent for about 1.5 hours. Compounds XVI and XVIII can then be transformed as above into compounds of the formula II (see Scheme B) and further transformed into compounds of the formula I (see Schemes A-I and A-III).

Scheme E

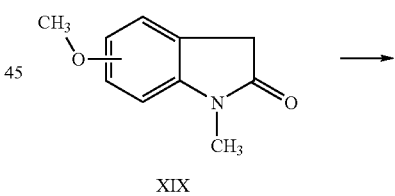

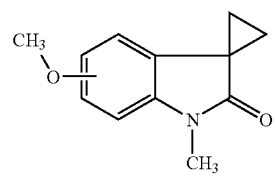

Compounds of the formula XVIII are preferably prepared directly from the corresponding compounds of formula XIX through the use of a suitable base and alkylating agent in an inert solvent. Suitable bases include but are not limited to sodium, potassium or lithium hydride, and lithium dialky lamides such as lithium diisopropyl amide, lithium hexam ethyldisilazide, sodium hexamethyldisilazide or potassium hexamethyldisilazide. Suitable alkylating agents include dibromoethane, iodobromoethane, ethylene glycol dimesylate or ditosylate, iodochloroethane and the like. Suitable inert solvents include THF, ether, dimethoxyethane and DMF. The reaction can be conducted at temperatures from about 0° C. to about the reflux temeperature of the solvent. The most preferred conditions involve reaction of the substrate XIX in DMF with sodium hydride as the base and dibromoethane as the alkylating agent at about room temperature for about 4 hours.

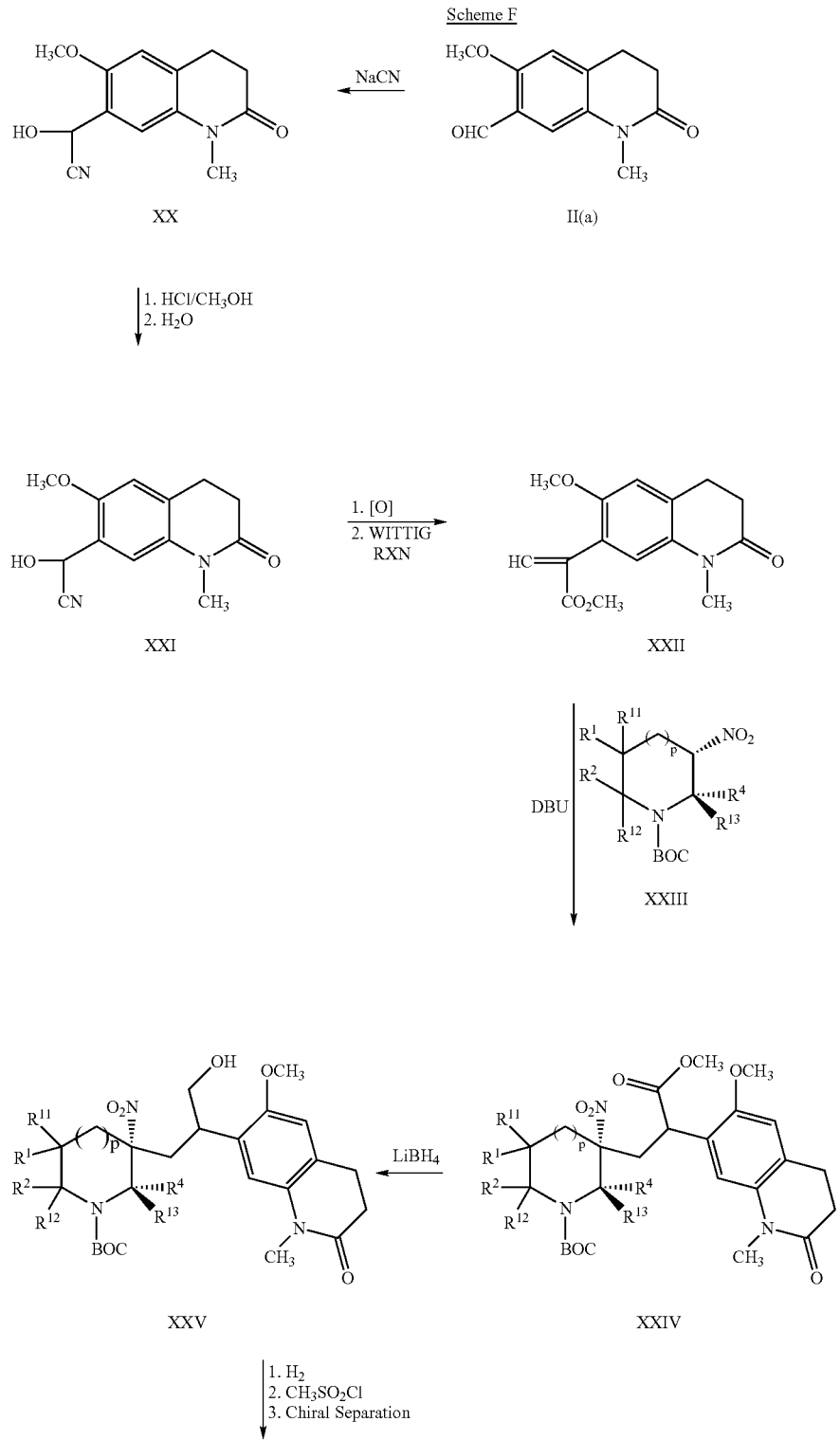

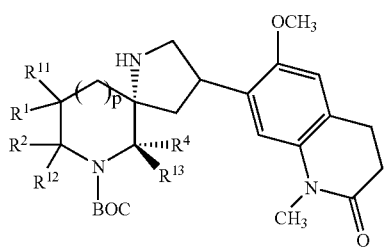

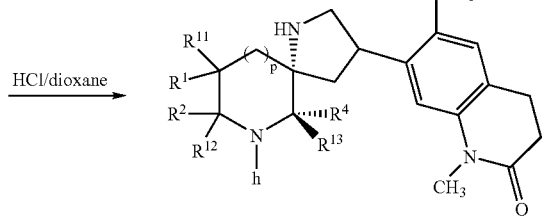

XXVI → XXVI (HCl/dioxane)

The spirocyclic compounds outlined in Scheme F can be prepared using the following general reaction sequence. The starting aldehyde of formula II(a) is dissolved in a non-polar solvent, preferably ethyl acetate, at a temperature from about −50° C. to about 50° C., preferably at about room temperature, and to this solution is added aqueous sodium bisulfite, followed by aqueous sodium cyanide (NaCN). The mixture is stirred for about 1 to about 24 hours, preferably for about 4 hours, a second portion of aqueous NaCN is added, and stirring is continued for about 18 hours. The resulting cyanohydrin of formula XX is isolated and dissolved in methanol saturated with hydrogen chloride (HCl) gas. The resulting solution is then refluxed for about 3 hours. From this solution the desired hydroxy-ester of formula XX can be isolated.

The hydroxy-ester of formula XXI can be oxidized to the corresponding keto-ester using a variety of oxidizing reagents (preferably $CrO_3/H_2SO_4$; Jones reagent) in a non-protic solvent, preferably acetone. The keto-acid is then reacted with methyl-triphenylphosphonium bromide using standard Wittig conditions (n-Bu Li/THF; about −20° C. to about room temperature) to afford the unsaturated ester derivative of formula XXII. The unsaturated ester derivative of formula XXII is then mixed with the compound of formula XXIII in a non-polar solvent, preferably tetrahydrofuran (THF), and treated with a non-aqueous base, preferably 1,8-diazabicylclo[5.4.0]undec-7-ene (DBU). The reaction is then heated to reflux for about 4 to about 36 hours, preferably for about 18 hours. The resulting ester adduct of formula XXIV can then be reduced using a variety of known reducing agents, preferably $LiBH_4$, in a nonprotic ether solvent, preferably ethyl ether, to afford the nitro alcohol derivative of formula XXV.

Reduction of the nitro group can be accomplished using standard methodology, preferably hydrogenation in ethanol using a Raney nickel catalyst, and cyclization to the spirocycle can be accomplished by activation of the alcohol, preferably using methanesulfonyl chloride in methylene chloride at about −20 to about 40° C., preferably about 5° C. Separation of the resulting enantiomers by chiral chromatography is a standard procedure known to those skilled in the art. Final removal of the nitrogen protecting group using standard conditions, preferably dioxane/HCl, affords the final product of formula I(b).

Compounds of the formula I wherein B is $CH_2$, A is CH and G is $OCH_2$ can be prepared using the method illustrated in Scheme G. Compounds of the formula QQ can be replaced with the appropriate compound of formula IV, as defined above for Scheme B to obtain compounds of the formula I having desired definitions of Q, W, Y, Z, $R^5$, $R^6$, $R^7$ and $R^8$.

Scheme G

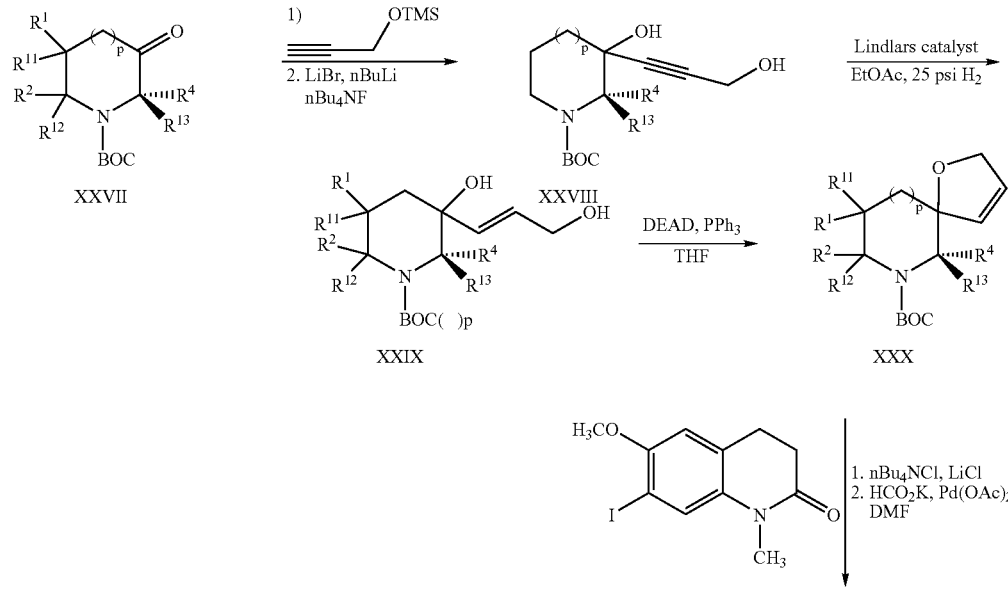

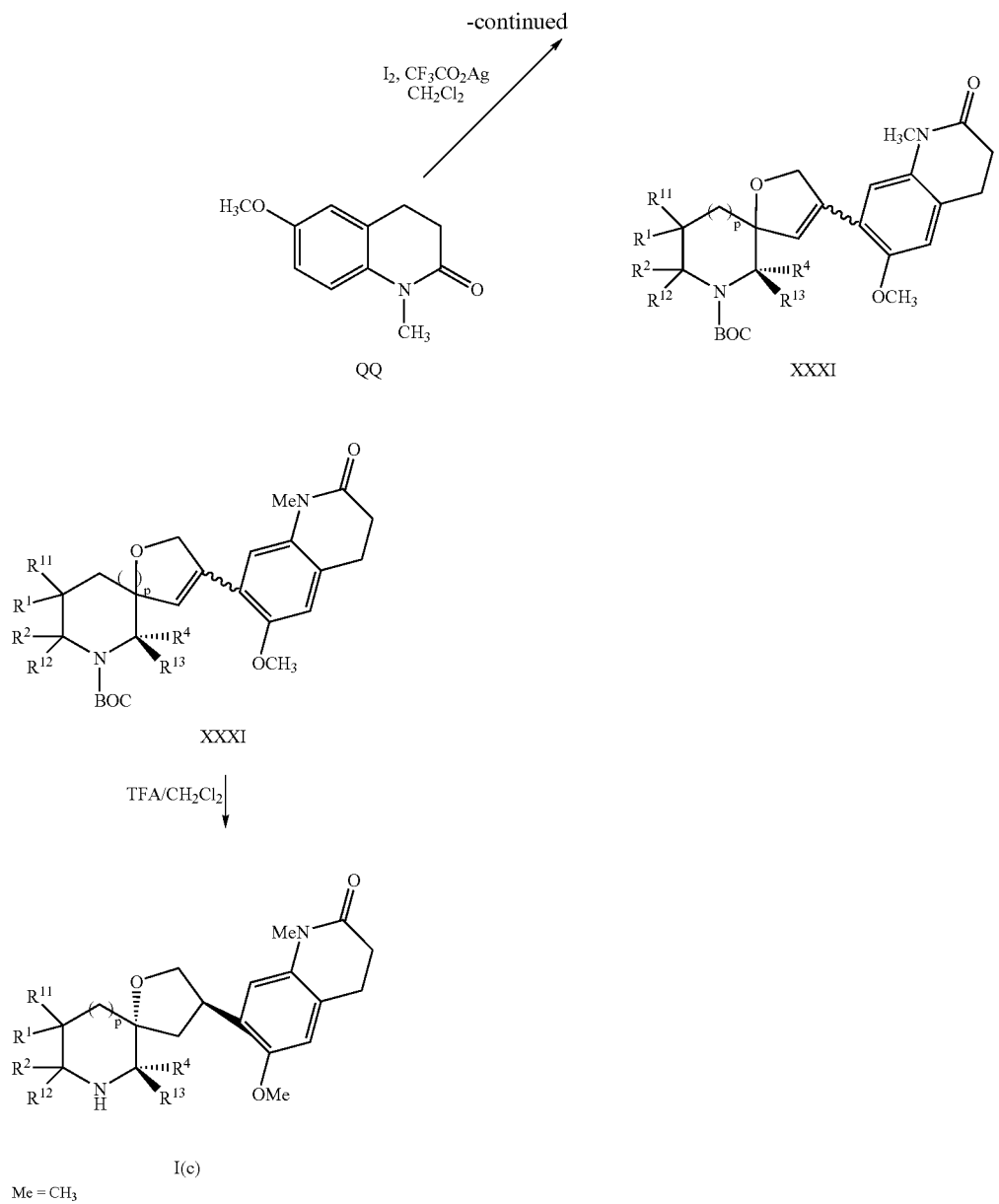

Scheme H illustrates a method of adding a Het-CH$_2$—C(=O)— group, as substituent R$^3$, to an analogous compound of the formula I wherein R$^3$ is hydrogen. (Het is defined as the heterocyclic substituents on R$^3$ are defined above, with the proviso that Het must contain a secondary amine). Het-H is condensed with methoxy bromoacetate or ethoxy bromoacetate, in the presence of a tertiary amine hydrochloride base catalyst such as diethyl benzyl amine, pyridinium hydrochloride, or diisopropyl ethyl amine hydrochloride at a temperature of from about 0° C. to about ambient temperature. The ester is hydrolyzed with a slurry of potassium carbonate in an aqueous potassium hydroxide solution at a temperature of from about 0° C. to about the reflux temperature for a period of from about 16 hours to about 48 hours. The substituted acetic acid and piperidine I(d) are coupled with any standard peptide coupling agent such as Bop (benzotriazol-1-yloxytris(dimethylamino)phosphonium hexafluorophosphate), Py-Brop (bromo-tris-pyrrolidinophosphonium hexafluorophosphate) or T3P(1-propanephosphonic acid cyclic anhydride), at a temperature of from about 0° C. to about ambient temperature for a period of from about 1 hour to about 24 hours, to form the final product.

Scheme H

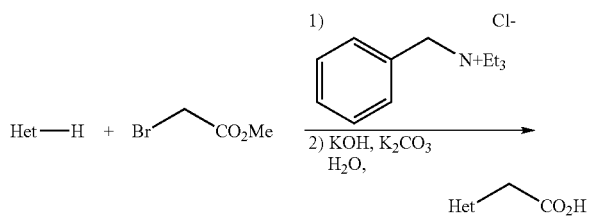

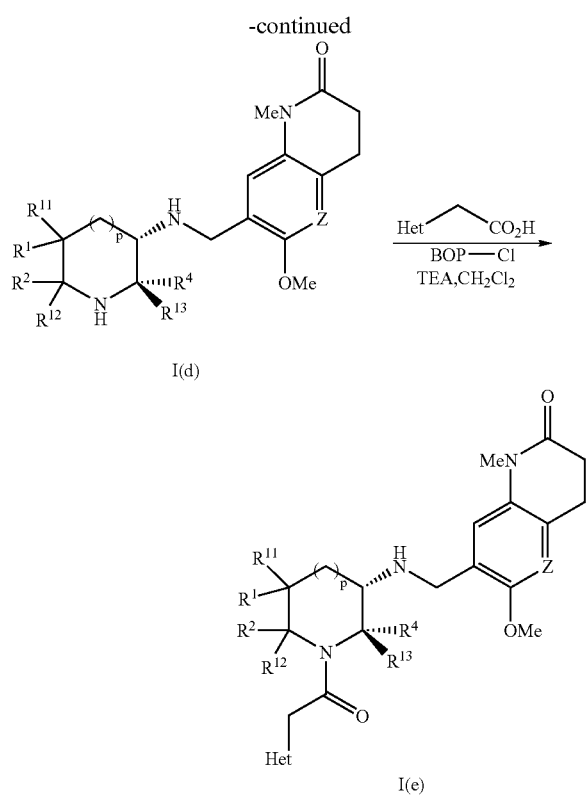

Me = CH₃, Et = CH₂CH₃

Scheme J illustrates the synthesis of certain compounds of the formula I wherein $R^2$ is alkyl.

The starting materials used in this scheme (compounds of the formula XXXII) can be prepared from commercially available alkyl vinyl ketones by reaction with nitromethane in the presence of a suitable base such as sodium or potassium alkoxide, triethylamine, diisopropylethyl amine, N-methyl morpholine, or sodium and potassium carbonate, in an organic solvent such as methanol, ethanol, propanol, isopropanol, tert-butanol, methylene chloride, chloroform, toluene, THF, DMF, DMSO, ether, or ethyl acetate, at a temperature from about −78° C. to about 100° C. (*J. Am. Chem. Soc.*, 74, 3664–3668 (1952)). Preferably, the reaction is carried out using nitromethane in methanol at between about −30° C. and about 0° C. with sodium methoxide as the base, and methyl vinyl ketone as the electrophile. Alternatively, the reaction can be conducted under neutral aqueous conditions as described in the literature, e.g., *Tetrahedron Lett.* 1929–1932 (1982).

Compounds of the formula XXXIII can be prepared by using a modified Henry reaction that condenses to give substituted cyclic imines. Firstly, the ketone is protected as a ketal by use of a mineral acid such as hydrochloric acid, sulfuric acid, and nitric acid or a catalytic organic acid such as camphor sulfonic acid or toluene sulfonic acid, in an alcoholic solvent such as methanol, ethanol, propanol, or ethylene glycol, with a water scavenger such as trimethyl orthoformate, triethyl orthoformate, magnesium sulfate, or molecular sieves, at a temperature from about 0° C. to about 75° C. Then, the nitroacetal is condensed in situ with an imine created by an amine source such as ammonium acetate, ammonium chloride, or ammonium formate, and an aldehyde such as one of variously substituted aromatic aldehydes, at a temperature from about 0° C. to about 75° C. The acetal is then converted into the ketone by addition of a mineral acid such as hydrochloric acid, sulfuric acid, or nitric acid in water, at a temperature from about 0° C. to about 75° C., which causes cyclization to occur, giving the compound XXXIII. Preferably, the nitroketone is dissolved in methanol at about room temperature with a catalytic amount of camphor sulfonic acid and trimethyl orthoformate. Ammonium formate is then added, followed by benzaldehyde. Aqueous sulfuric acid is added and stirred to give the cyclic imine XXXIII.

The resulting compound of formula XXXIII is dissolved in an alcoholic solvent such as methanol, ethanol, propanol, isopropanol, or t-butanol and its lithium, sodium, or potassium base and added to a solution of a mineral acid such as hydrochloric acid, sulfuric acid, or nitric acid in an alcoholic solvent with a water scavenger such as trimethyl orthoformate, triethyl orthoformate, magnesium sulfate, or molecular sieves, at a temperature from about −30° C. to about 75° C. This reaction yeilds the corresponding compound of formula XXXIV. Preferably, the nitroimine is dissolved in sodium methoxide in methanol and added to a 0° C. solution of sulfuric acid and trimethyl orthoformate in methanol.

The corresponding compound of formula XXXV-a is created by the stereoselective reduction of the imine of formula XXXIV. The imine is reduced with a Lewis acid such as trimethylaluminum, triethylaluminum, and trichloroaluminum and a hydride source such as lithium aluminum hydride or diisobutyl aluminum hydride. Typically, this reaction is conducted in an organic solvent such as THF, ether, or glyme at a temperature from about 0° C. to about −78° C. Preferably, the imine is reduced with triethylaluminum and lithium aluminum hydride in THF at about −78° C.

The compound of formula XXXV-a is converted into the corresponding compound of formula XXXVI-a by conversion of the acetal to the oxime and then reduction to give the amine. The acetal is stirred in water and an organic cosolvent such as THF with a mineral acid such as hydrochloric acid, sulfuric acid, or nitric acid, hydroxylamine, and a buffer such as ammonium acetate or ammonium chloride at a temperature from about 0° C. to about 100° C. Reduction of the oxime is accomplished in an organic solvent such as methanol, ethanol, ethyl acetate, or acetic acid, using a catalyst such as Raney-Nickel, platinum, or palladium, under a hydrogen atmosphere of about 1 to about 50 psi at a temperature from about room temperature to about 60° C. Preferably, the compound of formula XXXV-a and hydroxylamine hydrochloride are dissolved in water, THF, and concentrated hydrochloric acid, and then ammonium acetate is added at about room temperature. The oxime is then reduced by Raney-Nickel in ethanol under 40 psi of hydrogen at about room temperature.

The final products of formula XXXVII-a are made by reductive amination of the corresponding compounds of formula XXXVI-a using an appropriate aldehyde, acid such as acetic acid, hydrochloric acid, sulfuric acid, camphor sulfonic acid, or toluene sulfonic acid, and hydride source such as sodium borohydride, sodium cyanoborohydride, or sodium triacetoxyborohydride, in an organic solvent such as methanol, ethanol, or THF at a temperature from about 0° C. to about 75° C. Preferably, the compound of formula XXXVI-a, an appropriate aromatic aldehyde, acetic acid, and sodium cyanoborohydride are stirred in methanol at about room temperature to give desired product of formula XXXVII-a.

Starting materials of the type of formula XXXVII-b, which possess the opposite stereochemistry at the $R^2$ site from those of formula XXXVII-a, can be prepared through a similar reaction sequence whereby the only change is in the set of conditions used in the imine reduction. For example, substitution of $NaBH_3CN/MeOH$ for triethyl aluminum/$LiAlH_4$ gives the compound XXXV-b. Many other reduction methods are available for this transformation and are commonly known to those skilled in the art. Preferred conditions include reduction with $NaBH_4$ in alcoholic or ethereal solvents or reduction with $NaBHOAc_3$ in the presence of an acid such as acetic acid in chlorinated solvents such as $CH_2Cl_2$ or $CHCl_3$ or in other inert solvents such as benzene, toluene, ether, THF or glyme. $LiAl_4$ in ether, THF or glyme in the absence of triethyl aluminum may also be used. These reductions are generally carried out at temperatures from about −78° C. to about 100° C., preferably from about 0° C. to about 60° C. The subsequent reaction sequences which yield the compound of formula XXXVII-b may take place under the same conditions as the reaction sequences which yield the compound of formula XXXVII-a.

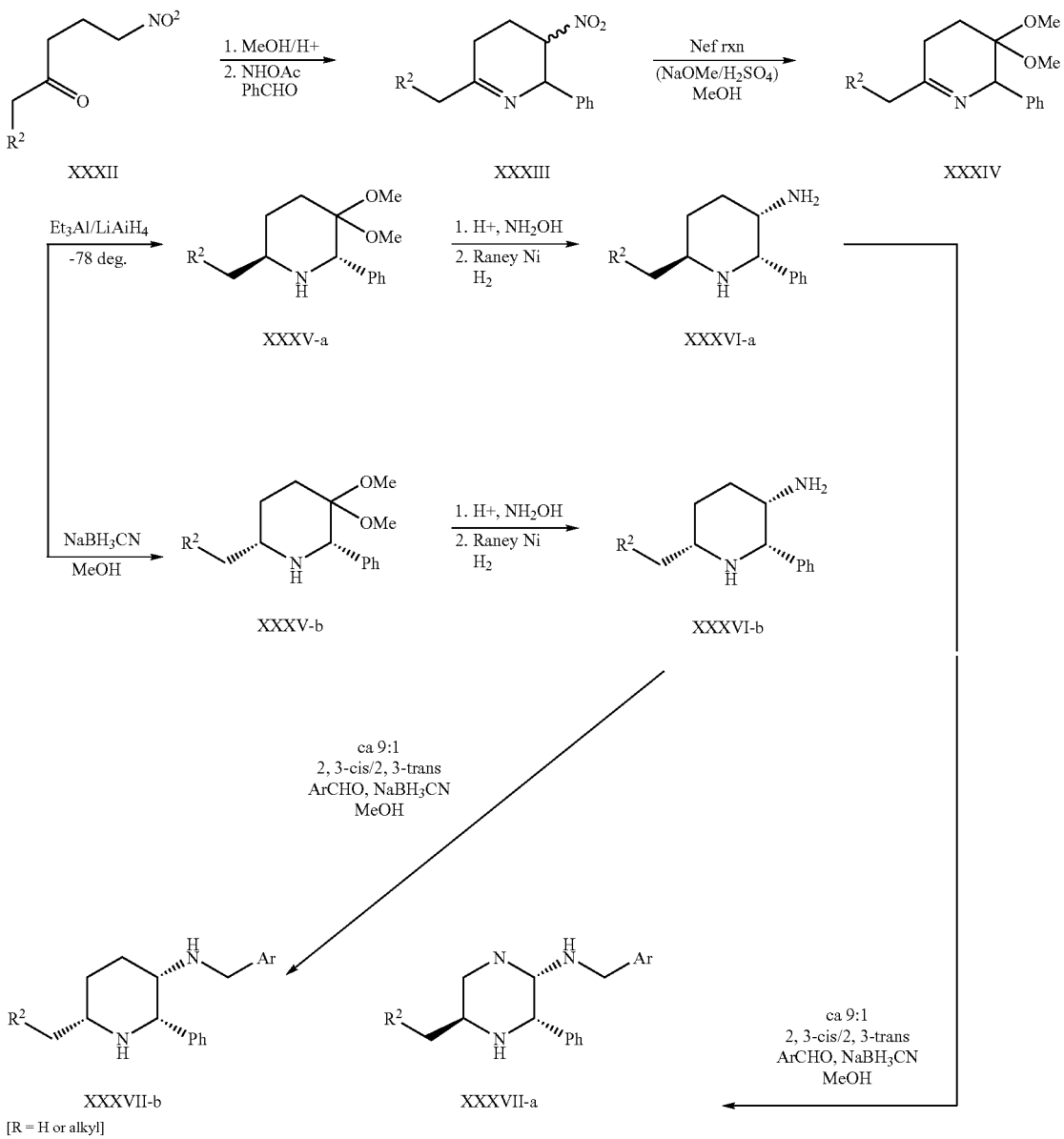

Scheme J

Scheme K illustrates the synthesis of certain compounds of the formula I wherein Q is $SO_2$ and W is ethylene.

The starting material used in this scheme (compound XXXVIII) can be prepared from commercially available 4-methoxy-2-methyl aniline by reaction with methanesulfonyl chloride (or bromide) or methanesulfonic anhydride in the presence of a suitable base such as pyridine, triethylamine, diisopropylethyl amine, N-methylmorpholine, or sodium or potassium carbonate or bicarbonate, in an organic solvent such as methylene chloride, dichloroethane, toluene, ether, ethyl acetate, carbon tetrachloride or chloroform. Preferably, the reaction is carried out in methylene chloride with methansulfonyl chloride in the presence of pyridine. The resulting sulfonamide is treated with a suitable base such as sodium or potassium hydride or sodium or potassium tert-butoxide in a solvent such as DMF, N-methylpyrrolidinone, dimethyl acetamide, THF or DMSO. The resulting salt is reacted with methyl iodide or dimethyl sulfate to form the compound of formula XXXVIII. Preferably, the reaction is conducted in DMF at ambient temperature using methyl iodide, with sodium hydride as the base. Reaction of the compound of fromula XXXVIII in carbon tetrachloride or dichloroethane with N-bromosuccinimide or dibromodimethyl hydantoin, dibromodiphenyl hydantoin or elemental bromine, with or without irradiation by a flood light, at a temperature near the reflux point of the solvent, yeilds the bromide of formula XXXIX. Preferably, the reaction is conducted in carbon tetrachloride with N-bromosuccinimide, under reflux, in the presence of high intensity visible light.

The bromide of formula XXXIX is then cyclized to form the sultam of formula XL as follows. Formation of an anion with a base such as sodium or potassium hydride or sodium or potassium tert-butoxide in a solvent such as DMF, N-methylpyrrolidinone, dimethyl acetamide, THF or DMSO produces an intermediate sultam that has a structure identical to that of compound XL except that the aldehyde of compound XL is replaced with a hydrogen atom. Direct or indirect formylation of such intermediate sultam yields the compound of formula XL. Any of a variety of formylation methods known to those skilled in the art may be used to introduce a formyl group onto the benzene ring. For example, direct formylation may be accomplished by contacting the compound of formula with a suitable formylating agent in the presence of a suitable catalyst. Suitable formylating agents/catalyst systems include dichloromethyl methyl ether/titanium (IV) chloride (Cl$_2$CHOCH$_3$/TiCl$_4$), dichloromethyl methyl ether/aluminum chloride (Cl$_2$CHOCH$_3$/AlCl$_3$), dichloromethyl methyl ether/tin (IV) chloride (Cl$_2$CHOCH$_3$/SnCl$_4$), dichloromethyl methyl ether/boron trifluoride etherate (Cl$_2$CHOCH$_3$/BF$_3$-OEt), trifluoroacetic acid (CF$_3$CO$_2$H)/hexamethylenetetramine (modified Duff's conditions) and phosphoryl trichloride (POCl$_3$)/DMF (Vilsmeier's conditions).

Indirect formylation may be achieved by halogenating the intermediate sultam referred to above, displacing the halogen atom with a cyano group, and then subjecting the resultant cyano-substituted compound to reduction. Alternatively, the halogen can be subjected to halogen metal exchange with butyl lithium. The lithium intermediate can then be treated with dimethylformamide to afford II. The halogenation can be carried out according to the procedure reported by G. A. Olah et. al., *J. Org Chem*, 58, 3194 (1993). The displacement of the halogen atom with a cyano group may be perfomred according to the methods reported by D. M. Tschaem et. al., *Synth Commun*, 24, 887 (1994) and by K. Takagi et. al., 64 *Bull Chem. Soc. Jpn.* 64, 1118 (1991). The reduction can be performed in the presence of diisopropyl aluminiumhydride (DIBAL-H) in dichloromethane or Raney nickel in formic acid. The aldehyde of formula XL is then coupled to the appropriate compound of formula T-NH$_2$, which is defined as above for Scheme A-I except that R$^3$ is BOC, as described in Schemes A-I through A-III.

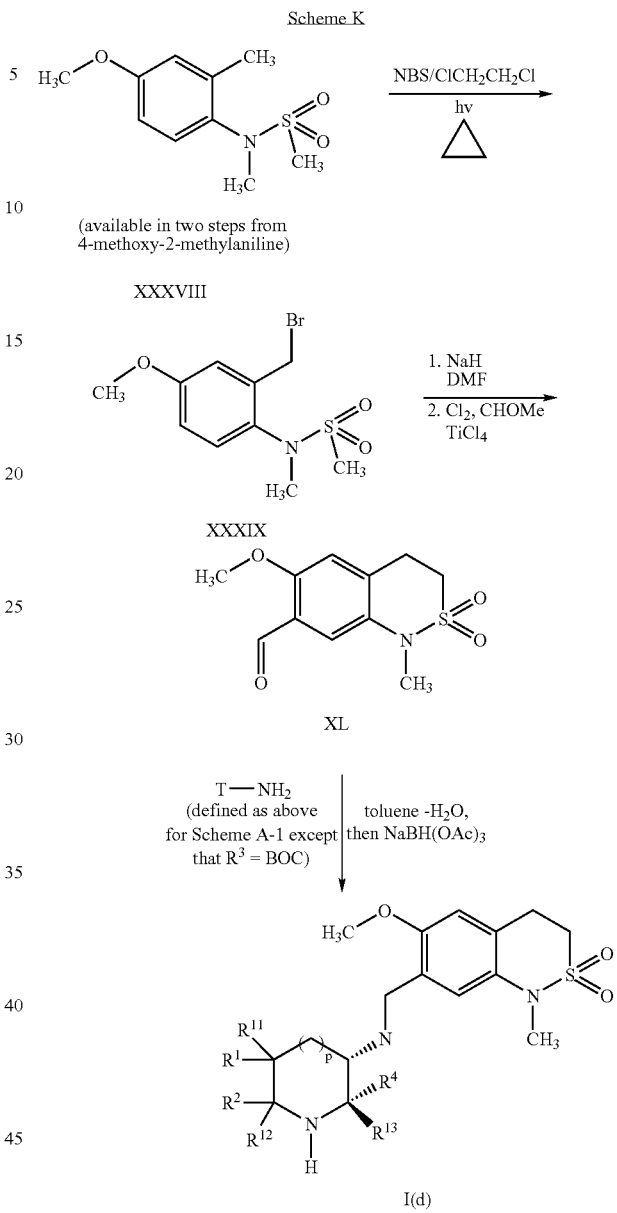

Scheme L illustrates a method of preparing compounds of the formula I wherein R$^3$ is benzyl and wherein R$^{12}$ and R$^{13}$, together with the carbon atoms to which they are attached, from a ring.

The starting materials for Scheme L can be prepared from 2-bromo-3-hydroxypyridine, or, in a similar fashion, from 2-iodo-3-hydroxypyridine. The reaction may be conducted using either of these starting materials and a nucleophile such as phenyl (or substituted phenyl) boronic acid or another aryl substituted boronic ester or phenylalkyl borane and/or an aryl (or substituted aryl) stannane such as phenyl tri-n-butylstannane or phenyltrimethylstannane. A palladium catalyst is usually employed. It can be either a palladium (0) source with a variety of phosphine ligands, including but not limited to palladium tetrakis[triphenylphosphine], or a non-phosphine source such as palladium dibenzylidene acetone (dba) or a palladium (II) source such as palladium acetate or palladium dichloride bis triphenylphosphine. The reaction can be carried out in a variety of solvents or mixtures of solvents such as ethyl acetate, methylene chloride, dichloroethane, toluene, benzene, ether, THF, or DMF and water, at a temperature from about ambient temperature to about the reflux point of the solvent in the presence of a suitable base such as sodium or potassium carbonate or bicarbonate. Preferably, 2-bromo-3-hydroxypyridine and phenylboronic acid, with palladium tetrakistriphenyl phosphine as the catalyst, in a mixture of benzene water and sodium carbonate, are used.

The product from this step (compound of formula XLII) is alkylated with benzyl bromide, chloride, mesylate, triflate or iodide or a substituted benzyl bromide in one of a variety of solvents such as acetonitrile, ethanol, methanol or water, at a temperature from about ambient temperature to about the reflux point of the solvent. The product of this reaction is a pyridine salt (salt of formula XLIII). The most preferred conditions involve the use of acetonitrile at reflux with benzyl bromide to form a pyridinium bromide. The resulting salt of formula XLIII can be converted into a betaine with a suitable base, either as a separate step or in situ via the following reaction. Typically, the pyridium salt is treated with amberlite™ or another type of basic ion exchange resin or triethyl amine, diisopropylethyl amine, sodium hydroxide, sodium carbonate or bicarbonate at about ambient temperature. The most preferred conditions involve using amberlite™, a strongly basic ion exchange resin. The betaine is then reacted with a vinyl sulfone such as phenyl vinyl sulfone or substituted phenyl vinyl sulfone in an inert solvent such as ethyl acetate, methylene chloride, dichloroethane, toluene, benzene, ether, THF, or DMF, at about the reflux point of the solvent. Typically, a radical inhibitor such as hydroquinone or a related inhibitor is added to prevent radical polymerization of the vinyl sulfone. Most preferably, phenyl vinylsulfone in refluxing toluene with hydroquinone is used.

The resulting product, an enone (compound of formula XLIV), contains a carbon-carbon double bond, which can be reduced under 1–110 psi of hydrogen pressure using a suitable catalyst such as palladium on carbon, palladium hydroxide, platinum oxide or platinum on carbon. This reaction may be carried out in a solvent such as methanol, ethanol or water, at a temperature from about ambient temperature to about the reflux point of the solvent. Alternatively, the reaction can be conducted using ammonium formate or another formate salt as the source of hydrogen. Preferably, ammonium formate in methanol at reflux is used with Pd(OH)$_2$/C. The resulting ketone is converted into an oxime ether or an oxime using hydroxylamine methyl ether or, alternatively, ethyl or benzyl ether as well as hydroxyl amine itself. The reaction is carried out in a solvent or mixture of solvents selected from ethyl acetate, methylene chloride, dichloroethane, toluene, benzene, ether, THF, DMF, methanol, ethanol and water, or mixtures thereof, at a temperature from about ambient temperature to about the reflux point of the solvent, with a suitable buffer such as sodium or potassium acetate. The most preferred conditions involve using a refluxing mixture of methylene chloride, methanol and water with hydroxylamine methyl ether and sodium acetate. The resulting oxime methyl ether (compound of formula XLV) can be selectively reduced with a suitable reducing agent such as sodium cyanoborohydride or sodium triacetoxy borohydride or triethyl silane in a solvent under acidic conditions. Suitable solvents include acetic formic and trifluoroacetic acid. This reaction is usually run at about ambient temperature. Most preferably, sodium cyanoborohydride in acetic acid is used to afford a compound of formula I(g).

Reduction of the hydroxylamine ether can be combined with removal of the phenylsulfone functionality. The reducing agent is typically sodium, lithium or potassium metal, or sodium amalgam, aluminum amalgam or samarium diiodide. The reaction can be conducted in a solvent or a mixture of solvents selected from liquid ammonia, ethanol, methanol, toluene, THF, t-butanol and similar solvents. The reaction is usually conducted at a temperature from about –33° C. to about ambient temperature or about the reflux point of the solvent. The most preferred conditions involve using sodium metal in liquid ammonia/THF at reflux to afford a compound of formula XLVI. Removal of the N-benzyl protecting group can be accomplished under 1–110 psi of hydrogen pressure using a suitable catalyst such as palladium on carbon or palladium hydroxide. This reaction can be carried out in a solvent such as methanol, ethanol or water, at a temperature from about ambient temperature to about the reflux point of the solvent. Alternatively, this reaction can be conducted using ammonium formate or another formate salt as the source of hydrogen. Preferably, ammonium formate in methanol is used, with palladium hydroxide on carbon as the catalyst and the reaction is conducted at the reflux point of the solvent. In the final step, the aldehyde of formula XLVII is coupled to the diazabicyclo[3.2.1]octane of formula XLVI (wherein the N-benzyl protecting group, Bn, has been removed) under the conditions described above for schemes A-I–A-III.

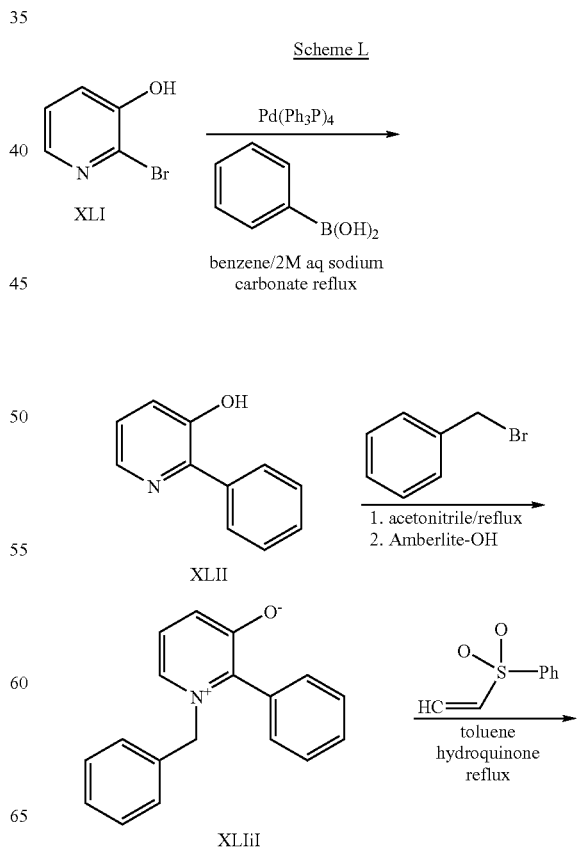

-continued

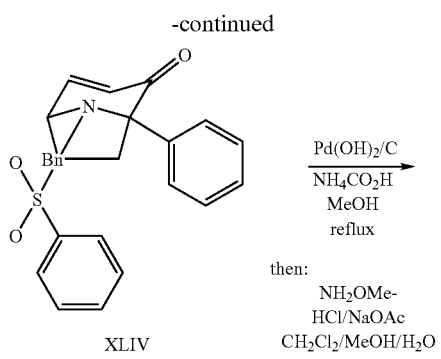

XLIV

Pd(OH)$_2$/C
NH$_4$CO$_2$H
MeOH
reflux then:
NH$_2$OMe-
HCl/NaOAc
CH$_2$Cl$_2$/MeOH/H$_2$O
reflux

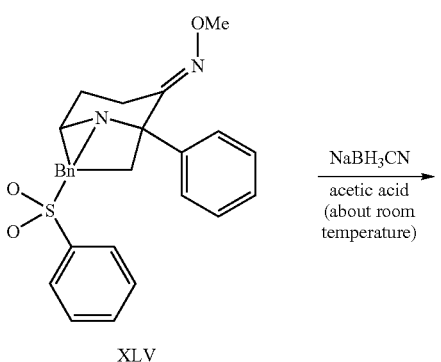

XLV

NaBH$_3$CN
acetic acid
(about room
temperature)

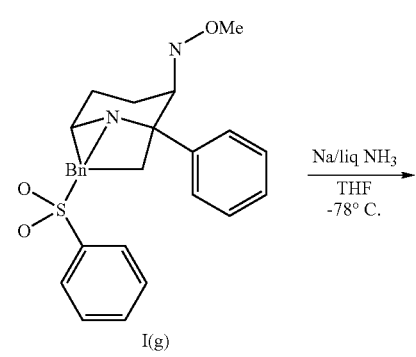

I(g)

[the benzyl (Bn) group
is bonded to the tertiary nitrogen]

Na/liq NH$_3$
THF
−78° C.

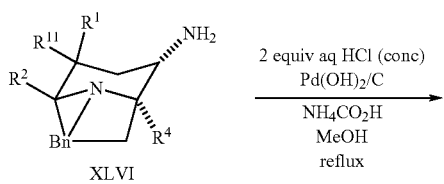

XLVI 2 equiv aq HCl (conc)
Pd(OH)$_2$/C
NH$_4$CO$_2$H
MeOH
reflux

-continued

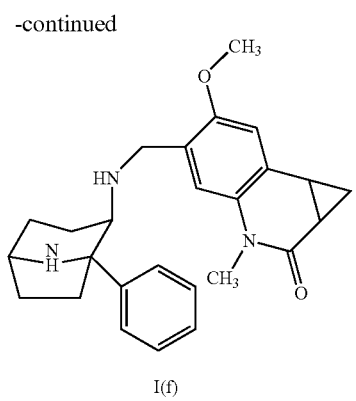

I(f)

then: 1. Ar—CHO
toluene/H$_2$O
2. NaBH(OAc)$_3$
DCE

Ar =

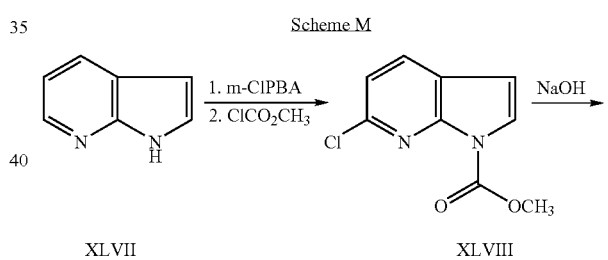

XLVII

Scheme M

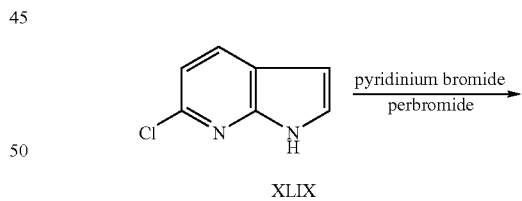

XLVII → XLVIII

NaOH

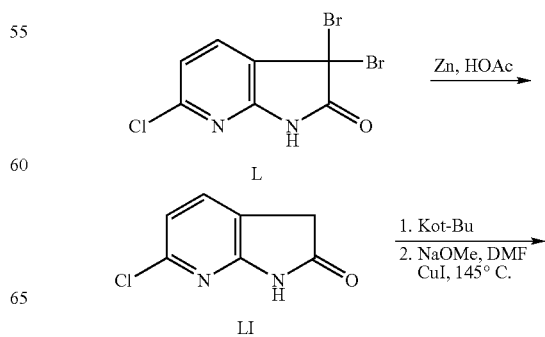

XLIX pyridinium bromide
perbromide

L

Zn, HOAc

LI

1. Kot-Bu
2. NaOMe, DMF
CuI, 145° C.

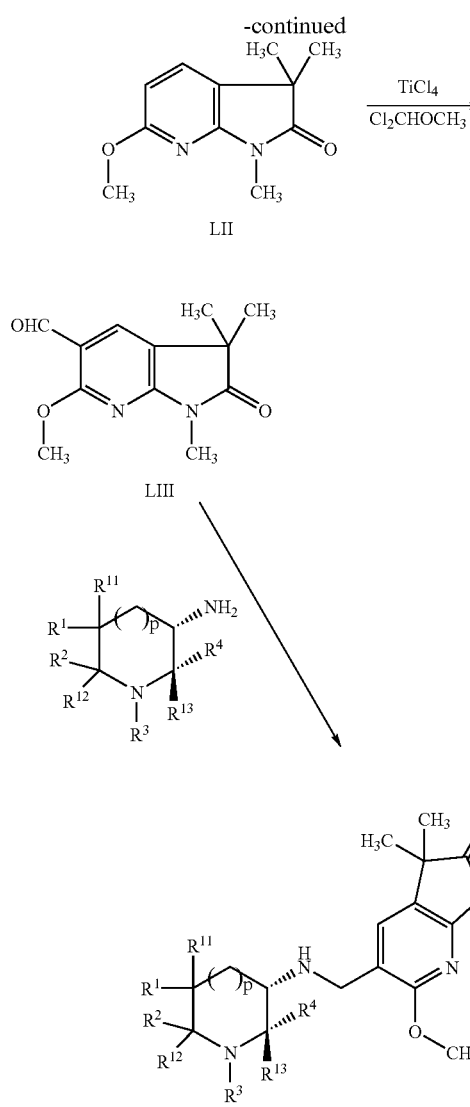

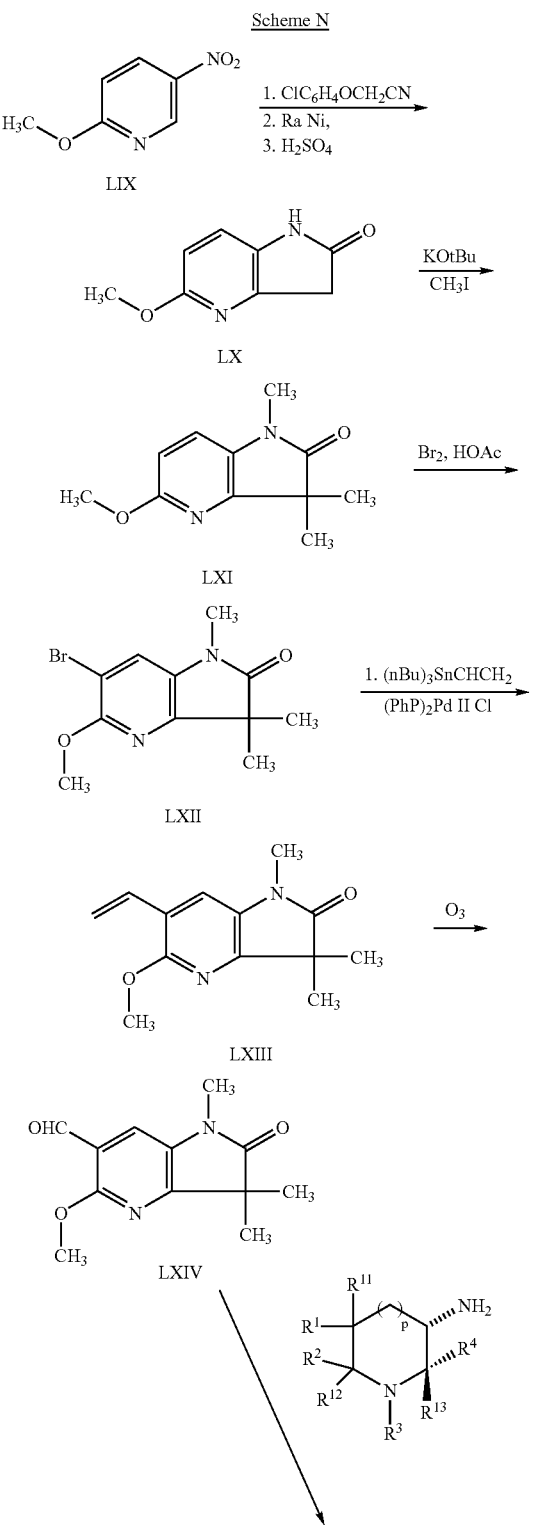

reacting the compound of formula LII with titanium tetrachloride (TiCl$_4$)/α,α-dichloromethyl methyl ether at about ambient temperture for about 16 hours. Standard reductive amination conditions to couple the compound of formula LIII to the apprporiate compound of formula T-NH$_2$ will yeild the desired final product of formula I(h).

Referring to Scheme M, 7-azaindole (formula XLVII) (Aldrich) is treated with 1.4 equivalents of m-chloroperbenzoic acid in dichloroethane at about ambient temperature for a period of about 4 hours. The product from the foregoing reaction is isolated and dissolved in THF and treated with 1 equivalent of hexamethyldisilane and 2.5 equivalents of methylchloroformate at about ambuient temperature for about 16 hours. This reaction yeilds the chlorinated compound having formula XLVIII. Sodium hydroxide hydrolysis in methanol/water at about ambient temperature, for about 2 hours yeilds 6-chloro-7-azaindole (formula XLIX). Sequential treatment of this intermediate with pyridininium bromide perbromide in t-butanol (t-BuOH) at about ambient temperature for about 16 hours, followed by treatment with Zn in acetic acid (HOAc) at about ambient temperature for about 20 minutes affords 6-chloro-7-azaoxindol-2-one (compound LI). The compound of formula LI is then permethylated using methyl iodide/potassium t-butoxide at about ambient temperature for about 16 hours and then converted to the 6-methoxy derivative of formula LII using sodium methoxide (NaOMe) in DMF and a copper (I) iodide (CuI) catylist at about 145° C., for about 6 hours. The resulting aldehyde of formula LIII can then be formed by

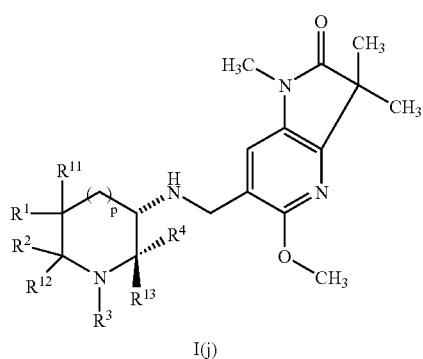

I(j)

Referring to Scheme N, the 4-aza-5-methoxy-oxindole intermediate (LX) can be prepared according to the literature (See Robinson et al., *J. Het. Chem.*, 1996, 33, 287–293). It is permethylated using methyl iodide/potassium t-butoxide at about ambient temperature for about 16 hours, and then brominated (using liquid bromine (Br$_2$) and acetic acid) at about 60° C. for about 1 hour). Vinylation of the compound of formula LXII is accomplished using tri-n-butyl-vinyl tin, hexamethylphosphoramide (HMPA), and a (Ph$_3$P)$_2$PdCl$_2$ catalyst at about 65° C. for about 14 hours. Ozonolysis of the vinyl group in methylene chloride for about 5 minutes afforded the aldehyde derivative of formula LXIV. The desired final product of formula I(j) is formed using standard reductive amination conditions with the appropriate compound of formula T-NH$_2$, as described above for Schemes A-I–A-III.

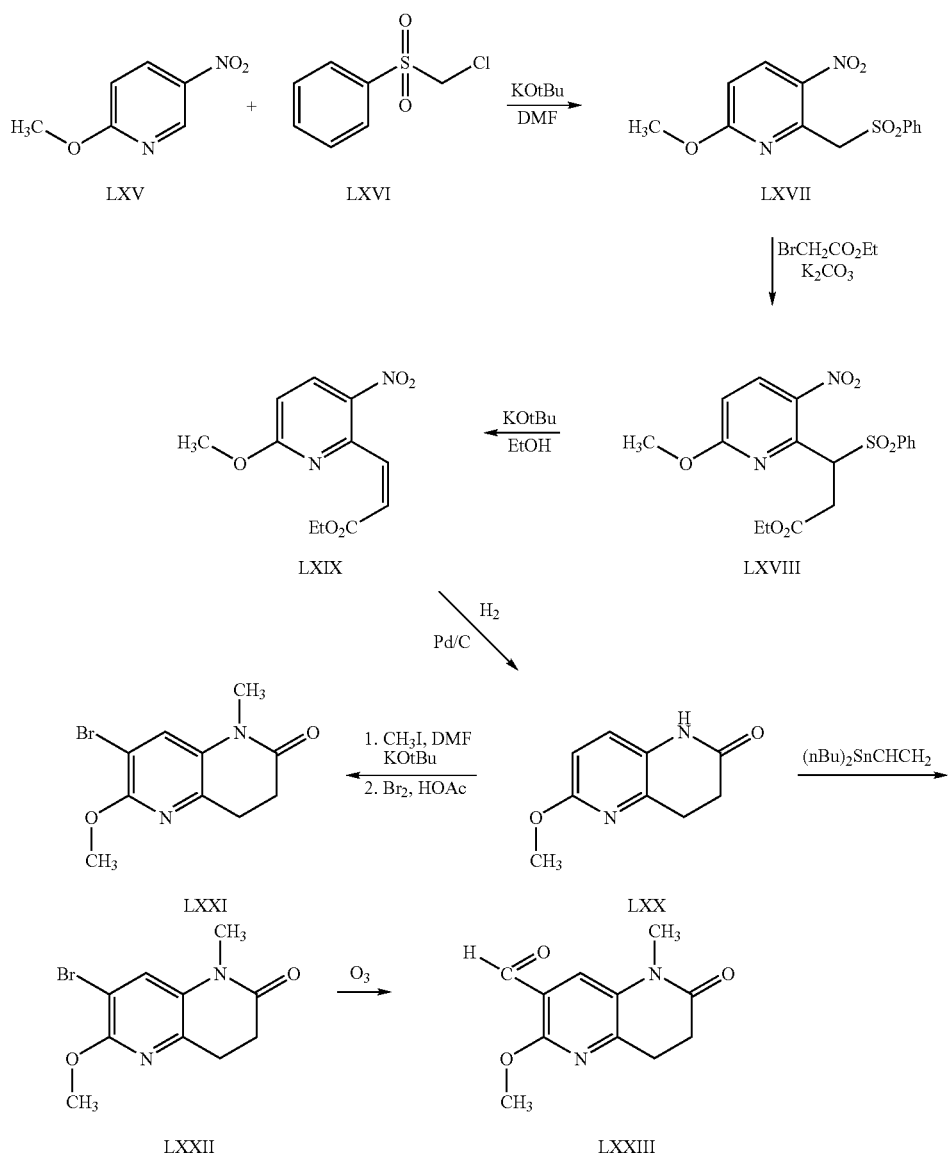

Scheme O

-continued

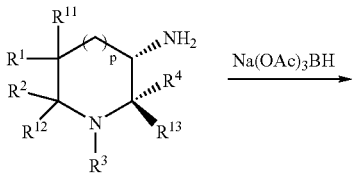

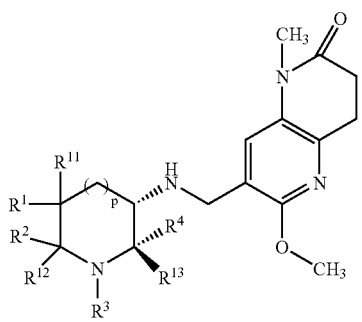

I(k)

Referring to Scheme O, 2-methoxy-5-nitropyridine (formula LXV) is converted into the phenyl sulfone derivative having formula LXVII by reacting it with potassium t-butoxide in DMF at about ambient temperature for about 16 hours. The latter compound is then alkylated with ethyl bromoacetate in DMF, in the presence of potassium carbonate ($K_2CO_3$) at about 45° C. for about 2 hours. Hydrogenation (using hydrogen gas at about 40 psi, a palladium on carbon catalyst and an ethanol solvent) for about 18 hours affords the ring cyclized product of formula LXX. The compound of formula LXX isthen reacted with methyl iodide at about 0° C. in DMF for about from 1 to about 4 hours, in the presence of an organic bas, preferably potassium t-butoxide. After the reactants are mixed at about 0° C., the reaction mixture is allowed to warm to ambient temperature. Bromination of the resulting intermediate using liquid bromine and acetic acid at about 60° C., for about 1 hour, yeilds the compound of formula LXXI. Vinylation to produce the compound of formula LXXII can then be accomplished using tri-n-butyl-vinyl tin, HMPA, and a $(Ph_3P)_2PdCl_2$ catalyst at about 65° C. for about 14 hours. Ozonolysis of the vinyl group in methylene chloride for about 5 minutes affords the aldehyde derivative of formula LXXIII. The desired final product of formula I(k) is formed using standard reductive amination conditions with the appropriate compound of formula T-$NH_2$, as described above for Schemes A-I–A-III.

Scheme P

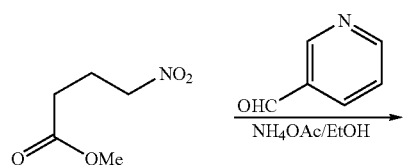

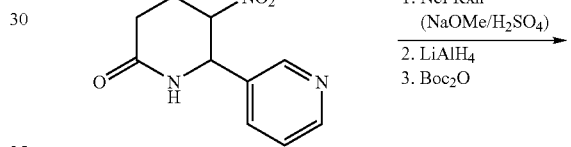

LXXIV

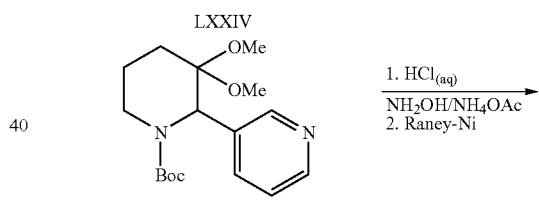

LXXV

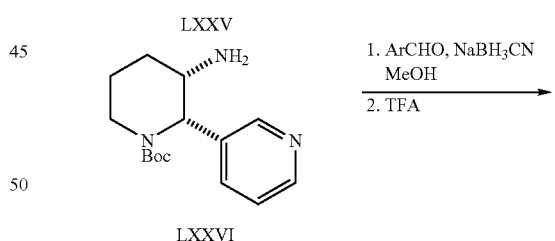

LXXVI

LXXVII

Referring to Scheme P, 4-nitrobutyric acid methyl ester is converted into the nitropyridyl derivative of formula LXXIV by reaction with pyridine-3-carboxaldehyde in the presence of an ammonia source such as ammonium acetate, ammonium chloride or ammonium formate. The reaction can be conducted in alcoholic solvents such as methanol or ethanol at temperatures ranging from about −78° C. to about the reflux temperature, with reflux being the preferred temperature. The nitro-group is converted into the dimethyl acetal by subjection to Nef reaction conditions as described ealier. Reduction of the amide group yields a piperidine compound. This reduction can be brought about by a number of conditions known to those skilled in the art. Preferred conditions include LiAlH$_4$ or borane-dimethylsulfide reduction in inert solvents such as ether or THF. This is followed by N-Boc protection via standard protocols as described earlier which yields the compound of formula LXXV Conversion of the acetal of formula LXXV into the oxime is carried out under acidic conditions catalyzed by mineral acids such as HCl, HBr HNO$_3$ or H$_2$SO$_4$, or organic acids such as carboxylic acids or sulfonic acids, at temperatures ranging from about −78° C. to about 100° C. Suitable solvents include water or mixtures of water with a variety of organic solvents such as THF, ether, toluene, DMF, ethanol and methanol. Preferred conditions are HCl-catalyzed hydrolysis at about room temperature in water/THF or water/alcohol. The initially formed ketone is converted into the oxime by treatment with hydroxylamine hydrochloride and ammonium acetate at about room temperature. The oxime is reduced by catalytic hydrogenation as described earlier. Preferred conditions for the reduction of the oxime are treatment with Raney nickel in methanol or ethanol under 52 psi of hydrogen. The resultant amine of formula LXXVI is converted into the benzylamine derivatives via reductive amination under standard conditions as described previously. The N-Boc group is cleaved under standard conditions as described earlier to yield the compound of formula LXXVII.

ene. The Boc group is installed under standard conditions using di-tert-butyldicarbonante in THF/water or dioxane/water in the presence of a carbonante base such as NaHCO$_3$ or K$_2$CO$_3$. Alternatively, this group may be installed in CH$_2$Cl$_2$, CHCl$_3$, THF, ether, toluene or related solvents in the presence of triethylamine or an alternative amine base. Oxidation of the alcohol to the aldehyde is accomplished under standard conditions associated with the use of Dess-Martin periodinane, Swern oxidation or MnO$_2$ oxidation. These methods are well known to those skilled in the art. A Henry reaction sequence yielding the nitroalkene of formula LXXXII is brought about by treatment of the aldehyde with nitromethane and a suitable base. Typical conditions include an alcoholic solvent such as methanol or ethanol and an alkoxide base such as sodium methoxide or sodium ethoxide. Alternative conditions include CH$_2$Cl$_2$, CHCl$_3$, THF or ether solvents and an amine base such as triethylamine. These conditions provide an intermediate nitroalcohol which can be converted into the nitroalkene by activation of the alcohol in the presence of base. This dehydration reaction is commonly known to those skilled in the art. The preferred method for this transformation involves activation of the alcohol with methanesulfonyl chloride or toluenesulfonyl chloride in the presence of triethylamine. The resultant nitroalkene is reduced to the nitroalkane under standard conditions. Preferred conditions for this transformation include treatment with NaBH$_4$ or LiBH$_4$ in alcoholic solvents such as methanol or ethanol. THF may also be used. The reaction may be conducted at temperatures between about −78° C. and about 88° C., with about 0° C. to about ambient temperature being preferred. Cyclization to the 2,3-trans piperidine ring is brought about by condensation with an aryl aldehyde such as benzaldehyde in the presence of a catalyst such as ammonium acetate or amonium chloride. The preferred solvent for this transformation is an alcoholic solvent such as methanol or ethanol and the typical temperature for this transformation lies between about −20° C. and about 100° C. Alternatively, the transformation may be brought about in solvents such as CH$_2$Cl$_2$, CHCl$_3$, THF, ether, toluene, ethyl acetate or related solvents, with or without acid or base catalysis. The 2,3-cis piperidine ring is obtained by treatment of the trans-piperidine with base followed by quenching in a kinetic fashion via addition of the nitronate solution to an excess of an acid in solution. Typical bases range from metal alkoxides or hydroxides in alcoholic solution to amine bases such as triethylamine or Hunig's base to LHMDS, KHMDS, NaHMDS in organic solvents such as CH$_2$Cl$_2$, CHCl$_3$, THF, ether, toluene, or ethylacetate. Alternative bases include the butyllithiums in THF or ether solution. Temperatures for this transformation can range between about −78° C. and about 100° C. The nitropiperidine is transformed into the aminopiperidine by reduction according to a variety of possible methods known to those skilled in the art. Preferred methods include zinc/HCl, zinc/acetic acid, or iron/HCl reduction in suitable solvents including water, THF/water, or water/alcohol mixtures. Suitable temperatures range from about −20° C. to about 118° C. The reduction may also be brought about by Raney nickel reduction in alcoholic solvents of in water/alcohol mixtures under an atmosphere of hydrogen. Typical reation temperatures range from about 0° C. to about 100° C. The resultant amine is subjected to reductive amination conditions as previously described to provide the compounds of interest.

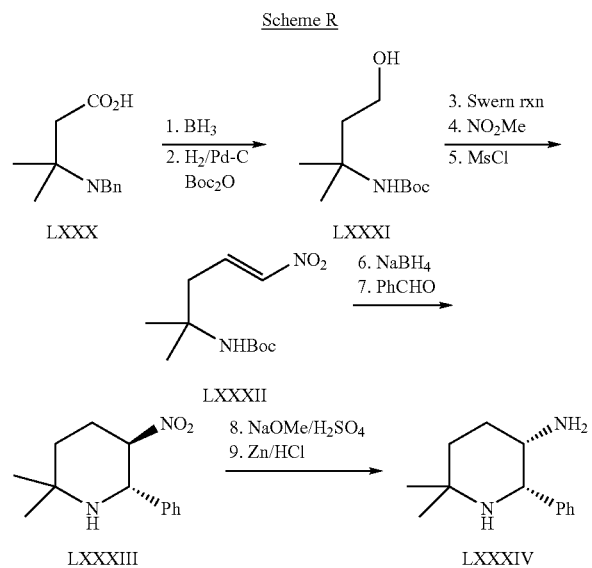

Scheme R

Referring to Scheme R, 3-Benzylamino-3-methyl-butyric acid is reduced to the corresponding N-Boc amino alcohol under standard conditions which are known to those skilled in the art. Preferably, this series of reactions is brought about by reduction of the carboxylic acid with borane or borane-dimethylsulfide complex in THF or ether. This is followed by hydrogenolysis of the N-benzyl group with palladium on carbon catalysis in ethanol or methanol at about room temperature under an atmosphere of hydrogen. Alternative hydrogen sources include ammonium formate or cyclohex- Scheme S

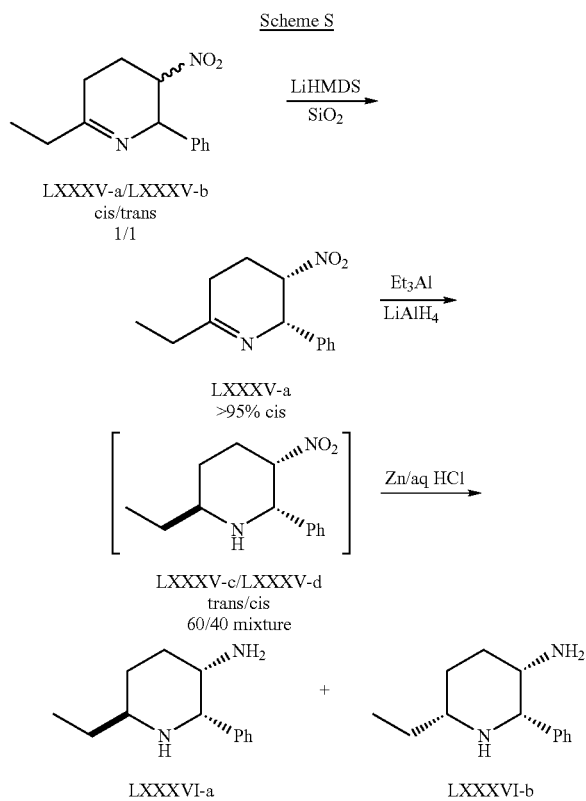

The mixture of cis and trans nitroimine of the formula LXXXV-a/LXXXV-b (compound of formula XXXIII prepared in Scheme J) may be transformed by the process of base induced epimerization to a single diastereomer LXXXV-a. A variety of bases may be used for this process including but not limited to lithium diisopropyl amide, sodium, lithium or potassium hexamethyldisilazane or potassium t-butoxide, potassium or sodium hydride diazabicycloundecene (DBU), diazabicyclononane (DBN), tetramethylguanidine, triethyl amine, diisopropylethylamine, sodium or potassium or lithium carbonate with or without accompanying 18-crown-6 or 15 crown-5, 12-crown-4, lithium sec-butylborohydride (L-selectride) in a solvent such as THF, ether or dimethoxyethane, at a temperature from about −100° C. to about −25° C., for a period of about 15 minutes to about 5 hours. The reaction mixture is quenched into a suitable acidic reagent which is either suspended or dissolved in an inert solvent to afford the desired diastereomer LXXXV-a. Suitable quenching agents include silica gel, alumina, hydrated sodium sulfate, para-toluenesulfonic acid pyridinium salt (PPTS), boric acid, hydrogen chloride, aqueous hydrogen chloride or aqueous sulfuric acid, nafion resin, molecular sieves, acidic ion exchange resins and the like. Preferred conditions utilize lithium hexamethyldisilazane in THF at about −78° C. followed by quench into a suspension of silica gel in THF.

Reduction of the imine of formula LXXXV-a to afford a mixture favoring either diastereomer of formula LXXXV-c/LXXXV-d may be accomplished through the use of a reducing agent and optionally a Lewis acid activating agent. Thus the imine may be reduced with lithium aluminum hydride with or without added triethyl or trimethyl aluminum. Other aluminum reagents may be used such as diethyl aluminum chloride or ethylaluminum dichloride. Other reducing agents include Vitride™ or Red-Al or diisobutylaluminum hydride and also sodium borohydride, sodium cyanoborohydride and sodium triacetoxy borohydride with or without borontrifluoride etherate, lithium sec-butylborohydride (L-selectride) and/or lithium borohydride in the presence of borontrifluoride etherate. A suitable inert solvent is used during this transformation and may be selected from THF, ether, dimethoxyethane, toluene, hexane, methylene chloride or other suitable solvents. The reaction is generally run below room temperature from about −78° C. to about 0° C. The most preferred conditions use lithium aluminum hydride in THF at about −78° C. with triethyl aluminum.

The resulting imine of formula LXXXV-c or LXXXV-d or the mixture of compounds of formulas LXXXV-c/LXXXV-d may be reduced to either a compound of formula LXXXVI-a or a compound of formula LXXXVI-b or a mixture of compounds of formulas LXXXVI-a/LXXXVI-b with a suitable reducing agent. Agents capable of reducing compounds of formulas LXXXV-c/LXXXV-d include, but are not limited to, zinc, tin, stannous chloride, zinc amalgam, palladium on carbon, palladium hydroxide, platinum oxide, platinum on carbon and Raney nickel, with or with out the presence of from 1–1000 psi hydrogen pressure, in a suitable solvent such as hydrochloric acid (aq), water, methanol, ethanol, isopropanol, ethyl acetate or similar inert solvents. The most preferred conditions include zinc metal in aqueous hydrochloric acid at a temperature from about room temperature to about the reflux temperature of the solvent.

Scheme T

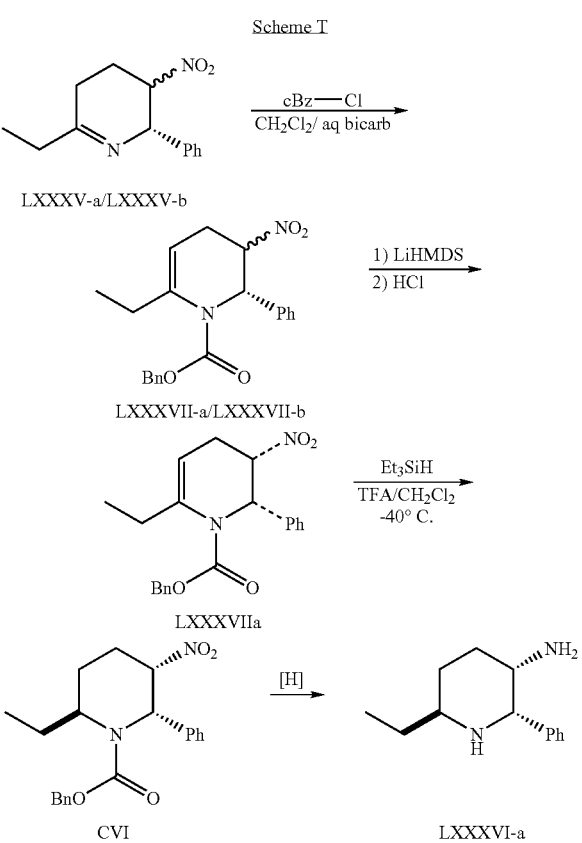

Alternatively, according to Scheme T, a compound of the formula LXXXVI-a may also be prepared from compounds of the formulas LXXXV-a/LXXXV-b in a straightforward manner. The imine of formula LXXXV-a/LXXXV-b prepared above can be converted to an enamine of the formula LXXXVII-a/LXXXVII-b through reaction with an activated acyl compound such as, but not limited to, carbobenzyloxychoroformate (cBz-Cl) benzoyl chloride, 9-fluorenylmethyl choroformate(FMOC-Cl), t-butoxychloroformate, phenyl chloroformate, nitro and dinitrophenylchloroformate, methyl, ethyl and isopropyl chloroformate in an inert solvent and in the presence of a suitable base. Suitable solvents include methylene chloride, chloroform, dichloroethane, benzene, toluene, water, ethyl acetate, dioxane and other suitable organic solvents. Typical bases include aqueous sodium, lithium arid potassium carbonate or bicarbonate solutions, pyridine, triethylamine, diisopropylethylamine, lutidine, collidine and other suitable bases. The reaction may be run at about room temperature up to about the reflux temperature of the solvent. The most preferred conditions involve reaction of a compound of formula LXXXV-a/LXXXV-b with cBz-Cl in methylene chloride and aqueous sodium bicarbonate solution at about the reflux temperature of the solvent mixture.

The desired cis isomer of formula LXXXVII-a may be obtained directly from the foregoing reaction by direct crystallization of the crude product from a suitable solvent such as diethyl ether or diisopropyl ether. Alternatively, the mixture of cis and trans isomers of formula LXXXVII-a/LXXXVII-b may be converted to mainly the cis isomer of formula LXXXVII-a by treatment with a suitable base such as lithium or sodium bis (trimethylsilyl)amide, lithium diisopropylamide, DBU, sodium or potassium carbonate in a suitable solvent such as THF or DME at a temperature of about −78° C. to about ambient temperature followed by quenching in a suitable aqueous acid such as dilute aqueous hydrochloric acid or dilute acetic acid. The most preferred conditions involve reaction of the compound of formula LXXXVII-a/LXXXVII-b with lithium bis (trimethylsilyl)amide in THF at about −78° C. followed by quenching in 1N aqueous HCl.

The reduction of the compound of formula LXXXVII-a to form the compound of formula CVI may be carried out in several ways. The reduction may be conducted under acidic or neutral conditions in an inert solvent at a temperature between about −78° C. and about room temperature. Suitable reducing agents include 1–1000 psi hydrogen gas, ammonium formate, sodium cyanoborohydride, sodium triacetoxyborohydride, tetrabutylammonium triacetoxyborohydride, triethylsilane, polyhydroxysilane, and sodium and lithium borohydride. If the reaction requires a suitable acid, then acetic or trifluoroacetic acid may be added. Additionally, hydrogen chloride triflic acid or sulfuric acid may be used. Typical solvents include methylene chloride, dichloroethane, chloroform, methanol, ethanol, toluene, dioxane and water. The most preferred conditions involve reaction of the compound of formula LXXXVII-a with sodium cyanoborohydride in methylene chloride with trifluoroacetic acid at about −40° C. Equally preferred are conditions involving reaction of the compound of formula LXXXVII-a with triethylsilane in methylene chloride with trifluoroacetic acid at about −40° C.

Deprotection of the acyl group and reduction of the nitro to an amine as in the compound of formula LXXXVI-a may be done in either order. For instance, reduction of the nitrogroup may be carried out with agents such as zinc, tin, stannous chloride, zinc amalgam, palladium on carbon, palladium hydroxide, platinum oxide, platinum on carbon or Raney nickel, with or with out the presence of from 1–1000 psi hydrogen pressure, in a suitable solvent such as hydrochloric acid (aq), water, methanol, ethanol, isopropanol, ethyl acetate or similar inert solvents. The most preferred conditions include zinc metal in aqueous hydrochloric acid at a temperature from about room temperature to about the reflux temperature of the solvent. Removal of the acyl group may be carried out in a variety of ways. If the acyl group is cBz- then catalytic hydrogenation is successful and may or may not be coupled with reduction of the nitro group. General conditions include hydrogenation with 1–1000 psi hydrogen over palladium on carbon or palladium hydroxide or oxide in methanol or ethanol. Alternatively, hydrogenolysis may be carried out with ammonium formate or cyclohexene under reflux in methanol or ethanol over a catalyst such as palladium on carbon or palladium hydroxide or oxide. An alternative method for cBz cleavage is treatment with HBr in acetic acid or propionic acid solution. For other acyl groups such as tertiary butoxy- (t-BOC), simple treatment with strong acid is sufficient, whereas with other acyl groups, treatment with aqueous sodium hydroxide solution at a temperature from ambient temperature to about the reflux temperature of the solvent is necessary. Alternatively, cBz or t-BOC groups may be removed by treatment with HBr/acetic acid.

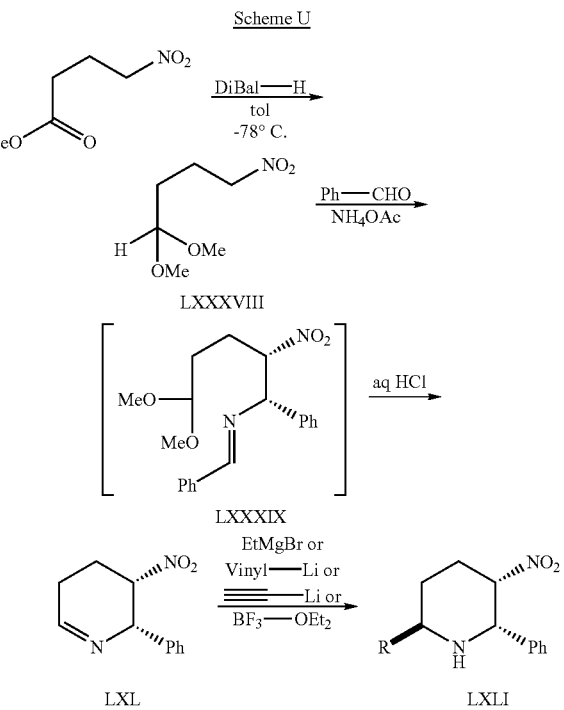

Scheme U

Alternatively, compounds of formula LXLI may be prepared by the sequence of reactions illustrated in Scheme U. 4-nitrobutyric acid methyl ester or 4-nitrobutyric acid ethyl ester may be reduced to an aldehyde and said aldehyde be protected as a nitro acetal of formula LXXXVIII. Reduction of the 4-nitrobutyric acid methyl ester may be completed in one step through reaction in toluene, hexane or methylene chloride at about −78° C. with diisobutylaluminum hydride. Alternatively, this reduction may be carried out over two steps via reduction of the 4-nitrobutyric acid methyl ester in THF or ether at about 0° C. to about ambient temperature through the use of lithium aluminum hydride, lithium borohydride or borane in THF. The resulting nitroalcohol may then be oxidized to the aldehyde through a Swern oxidation in methylene chloride or a Dess-Martin oxidation. The aldehyde is protected as a nitroacetal of formula LXXXVIII by use of a mineral acid such as hydrochloric acid, sulfuric acid, and nitric acid or a catalytic organic acid such as camphor sulfonic acid or toluene sulfonic acid, in an alcoholic solvent such as methanol, ethanol, propanol, or ethylene glycol, with a water scavenger such as trimethyl orthoformate, triethyl orthoformate, magnesium sulfate, or molecular sieves, at a temperature from about 0° C. to about 75° C.

Compounds of formula LXL can be prepared by using a modified Henry reaction that condenses to give substituted cyclic imines. The nitroacetal of formula LXXXVIII is condensed in situ with an imine created by an amine source such as ammonium acetate, ammonium chloride, or ammonium formate, and an aldehyde such as one of variously substituted aromatic aldehydes, at a temperature from about 0° C. to about 75° C. The acetal of formula LXXXIX is then converted into a nitroaldehyde by addition of a mineral acid such as hydrochloric acid, sulfuric acid, or nitric acid in water, at a temperature from about 0° C. to about 75° C., which causes cyclization to occur, giving the compound of formula LXL. Preferably, the nitroaldehyde is dissolved in methanol at about room temperature with a catalytic amount of camphor sulfonic acid and trimethyl orthoformate. Ammonium formate is then added, followed by benzaldehyde. Aqueous hydrochloric acid is added and stirred to give the cyclic imine of formula LXL.

The imine of formula LXL may be transformed to the compound of formula LXLI through the use of organometallic reagents. For instance, addition of ethyl lithium, ethylmagnesium bromide, diethyl magnesium, diethylzinc, ethylzinc chloride, diethyl cuprate or other cuprate reagents such as higher order cuprates in a solvent such as THF or ether, toluene or dimethoxyethane at a temperature from about −78° C. to about 0° C. Alternatively, in a two step process, one may add vinyl lithium, vinylmagnesium bromide, divinyl magnesium, divinylzinc, vinylzinc chloride, divinyl cuprate or other cuprate reagents such as higher order cuprates in a solvent such as THF or ether, toluene or dimethoxyethane at a temperature from about −78° C. to about 0° C. Once addition is complete the resulting product is hydrogenated under 1–1000 psi hydrogen pressure over palladium on carbon, palladium hydroxide, platinum oxide, platinum on carbon or Raney nickel. Alternatively, in another two step process, one may add an acetylenic lithium under similar conditions to those listed above for vinyl. This process is also followed by hydrogenation. Optionally, one may include a Lewis acid in the above additions to the imine. Typical Lewis acids include boron trifluoride etherate, zinc chloride and trimethyl or triethylaluminum.

The resulting amine of formula LXLI may be reduced to the compound of formula LXXXVI-a (Scheme T) with a suitable reducing agent. Agents capable of reducing LXLI include, but are not limited to, zinc, tin, stannous chloride, zinc amalgam, palladium on carbon, palladium hydroxide, platinum oxide, platinum on carbon and Raney nickel, with or with out the presence of from 1–1000 psi hydrogen pressure, in a suitable solvent such as hydrochloric acid (aq), water, methanol, ethanol, isopropanol, ethyl acetate or similar inert solvents. The most preferred conditions include zinc metal in aqueous hydrochloric acid at a temperature from about room temperature to about the reflux temperature of the solvent.

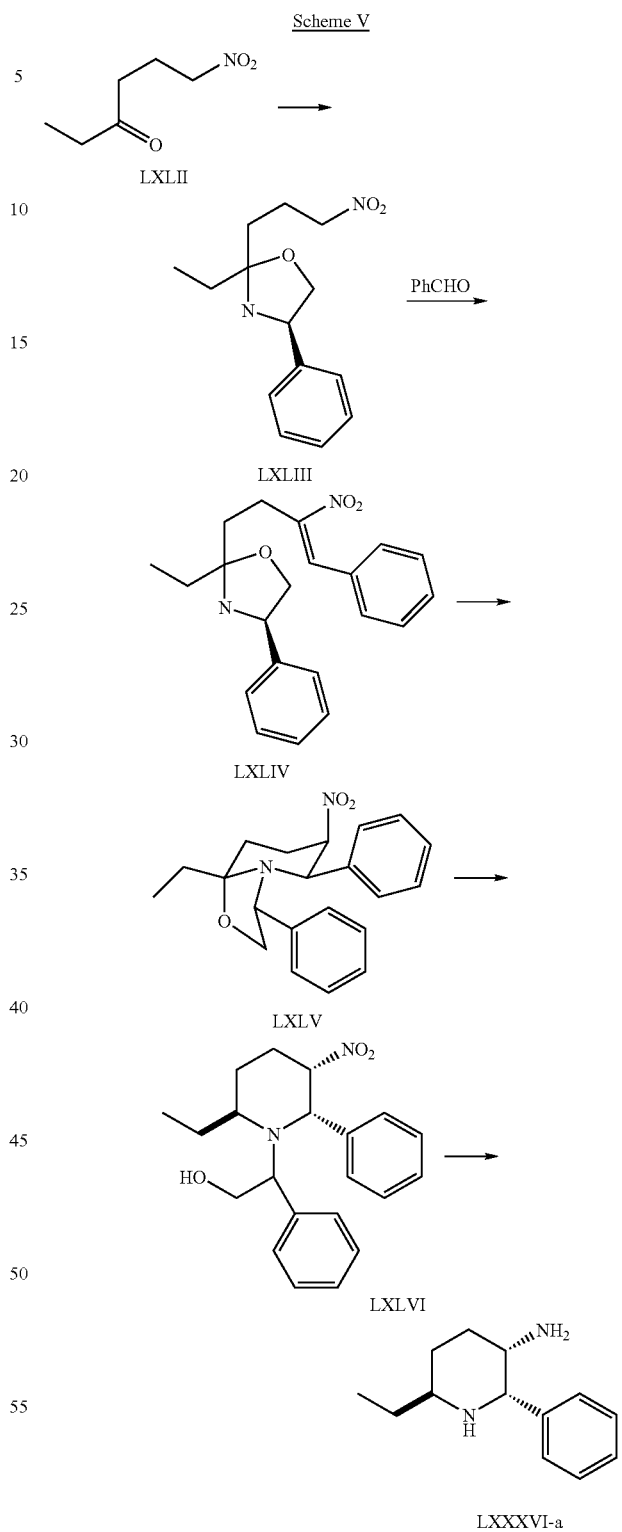

Alternatively, a compound of the formula LXXXVI-a may be prepared by the sequence of reactions shown in Scheme V. 1-nitrohex-4-one (the compound of formula LXLII) prepared above, may be reacted to form a hemiacetal of formula LXLIII through reaction of phenylglycinol with either configuration in a suitable solvent such as benzene, toluene, dichloroethane, methanol or ethanol with optional removal of water by molecular sieves or through the use of a Dean Stark water separator while under reflux. Compounds of the formula LXLIV can be prepared by using a modified Henry reaction which then condenses to give the substituted cyclic acetal of formula LXLV. The cyclic acetal of formula LXLV is condensed in situ with an imine created by an amine source such as ammonium acetate, ammonium chloride, or ammonium formate, and an aldehyde such as benzaldehyde or one of variously substituted aromatic aldehydes, at a temperature from about 0° C. to about 75° C. In most cases the compound of formula LXLIV is not isolated but directly cyclizes to the compound of formula LXLV.

The reduction of the compound of formula LXLV to form the compound of formula LXLVI may be carried out in several ways. The reduction may be conducted under acidic or neutral conditions in an inert solvent at a temperature between about −78° C. and about room temperature. Suitable reducing agents include 1–1000 psi hydrogen gas, ammonium formate, sodium cyanoborohydride, sodium triacetoxyborohydride, tetrabutylammonium triacetoxyborohydride, triethylsilane, polyhydroxysilane, and sodium and lithium borohydride. If the reaction requires a suitable acid, then acetic or trifluoroacetic acid and boron trifluoride etherate or trimethyl aluminum may be added. Additionally, hydrogen chloride triflic acid or sulfuric acid may be used. Typical solvents include methylene chloride, dichloroethane, chloroform, methanol, ethanol, toluene, dioxane and water.

The compound of formula LXLVI may be deprotected through hydrogenolysis. Typically, the nitro group is also reduced to the amine of formula LXXXVI-a during this process. General conditions include hydrogenation with 1–1000 psi hydrogen over palladium on carbon or palladium hydroxide or oxide in methanol or ethanol. Alternatively, hydrogenolysis may be carried out with ammonium formate or cyclohexene under reflux in methanol or ethanol over a catalyst such as palladium on carbon or palladium hydroxide or oxide. If the nitro group is to be removed prior to hydrgenolysis, then suitable reaction conditions include the following. The nitro functionality may be reduced by agents which include, but are not limited to, zinc, tin, stannous chloride, zinc amalgam, palladium on carbon, palladium hydroxide, platinum oxide, platinum on carbon and Raney nickel, with or with out the presence of from 1–1000 psi hydrogen pressure, in a suitable solvent such as hydrochloric acid (aq), water, methanol, ethanol, isopropanol, ethyl acetate or similar inert solvents. The most preferred conditions include zinc metal in aqueous hydrochloric acid at a temperature from about room temperature to the about reflux temperature of the solvent.

Scheme W

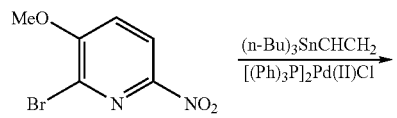

LXLVII

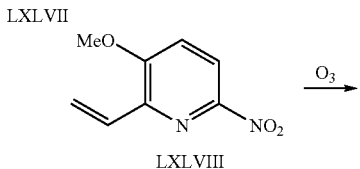

LXLVIII

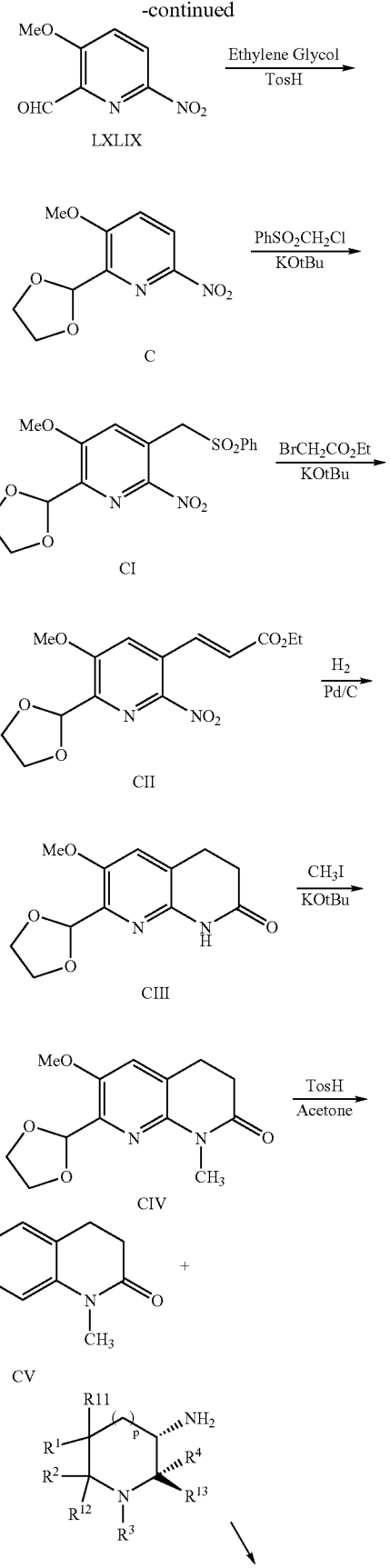

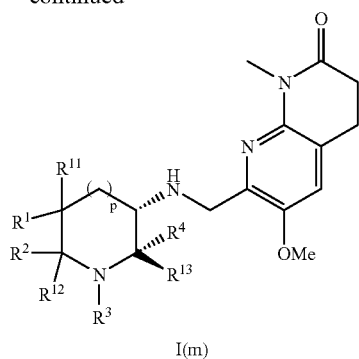

I(m)

2-Bromo-3-methoxy-5-nitropyridine (J. Lombardino, *J. Med. Chem.* 1981, 24, 39–42) was converted to the 2-aldehyde derivative of formula LXLIX using a two step sequence. The compound of formula LXLVII was treated with tri-n-butyl-vinyltin using a catalytic amount of bis (triphenylphosphine)-palladium(II) chloride in a non-protic solvent (preferably toluene) at about room temperature to about 150° C. (preferably 111° C.) for about 1 hour to about 24 hours (preferably 2 hours). Chromatography of the reaction mixture yields the vinyl compound of formula LXLVIII. The vinyl compound of formula LXLVIII was treated with ozone at about −100° C. to about 0° C. (preferably −78° C.) in methylene chloride and then quenched with dimethyl sulfide to afford the aldehyde of formula LXLIX. The aldehyde of formula LXLIX was protected using methods well known to those of skill in the art, e.g., reaction with ethylene glycol in benzene in the presence of a catalytic amount of acid (preferably p-toluenesulfonic acid) to afford the acetal of formula C. The pyridine derivative of formual C was reacted with benzylsulfonyl chloride using a strong base (preferably potassium t-butoxide) in a non-protic solvent (preferably a mixture of THF and DMF) to afford the sulfone derivative of formula CI. The methylene group of the sulfone of formula CI can be alkylated with ethyl bromoacetate in a protic solvent (preferably ethanol) using a strong base (preferably potassium t-butoxide). During these reaction conditions benzenesulfinic acid is eliminated to form the ester of formula CII. The ester of formula CII is hydrogenated in a protic solvent (preferably ethanol) using a metal catalyst (preferably 10% palladium on carbon) at about atmospheric pressure to about 50 PSI (preferably 50 PSI). During this reaction the nitro group is reduced to an amine, the double bond is reduced, and cyclization to the 6-membered amide is accomplished to yield the amide of formula CIII. Alkylation of the amide of formula CIII is accomplished with methyl iodide using a strong base (preferably potassium-t-butoxide) in a non-protic solvent (preferably THF) to afford the amide of formula CIV. The aldehyde in the amide of formula CIV is unmasked using acid (preferably p-toluenesulfonic acid) in a non-protic solvent (preferably acetone) to afford the aldehyde of formula CV. Reductive amination using aminopiperidine T-$NH_2$ as described in Scheme A-1 affords the product of formula I(m).

The preparation of other compounds of the formula I not specifically described in the foregoing experimental section can be accomplished using combinations of the reactions described above that will be apparent to those skilled in the art.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of formula 1, and the intermediates shown in the above reaction schemes can be isolated and purified by conventional procedures, such as recrystallization or chromatographic separation.

The compounds of the formula I and their pharmaceutically acceptable salts can be administered to mammals via either the oral, parenteral (such as subcutaneous, intravenous, intramuscular, intrasternal and infusion techniques), rectal, intranasal or topical routes. In general, these compounds are most desirably administered in doses ranging from about 0.01 to about 1500 mg per day, in single or divided doses (i.e., from 1 to 4 doses per day), although variations will necessarily occur depending upon the species, weight and condition of the subject being treated and the particular route of administration chosen. However, a dosage level that is in the range of about 0.5 mg to about 500 mg per kg of body weight per day is most desirably employed. Nevertheless, variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such higher dose levels are first divided into several small doses for administration throughout the day.

The compounds of the present invention may be administered alone or in combination with pharmaceutically acceptable carriers or diluents by either of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intramuscular and subcutaneous injection purposes The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may be done by way of creams, jellies, gels, pastes, patches, ointments and the like, in accordance with standard pharmaceutical practice.

The activity of the compounds of the present invention as substance P antagonists is determined by their ability to inhibit the binding of substance P at its receptor sites in IM-9 cells employing radioactive ligands. The substance P antagonist activity of the compounds described herein is evaluated by using the standard assay procedure described by D. G. Payan et al., as reported in the *The Journal of Immunology*, 133, 3260 (1984). This method essentially involves determining the concentration of the individual compound required to reduce by 50% the amount of radio-labelled substance P ligands at their receptor sites in said isolated cow tissues or IM-9 cells, thereby affording characteristic $IC_{50}$ values for each compound tested. More specifically, inhibition of [$^3$H]SP binding to human IM-9 cells by compounds are determined in assay buffer (50 mM Tris-HCl (pH 7.4), 1 mM $MnCl_2$, 0.02% bovine serum albumin, bacitracin (40 μg/ml), leupeptin (4 μg/ml), chymostatin (2 μg/ml) and phosphoramidon (30 μg/ml)) The reaction is initiated by the addition of cells to assay buffer containing 0.56 nM [$^3$H]SP and various concentrations of compounds (total volume 0.5 ml) and allowed to incubate for 120 min at 4° C. Incubation is terminated by filtration onto GF/B filters (presoaked in 0.1% polyethylenamine for 2 hours). Nonspecific binding is defined as the radioactivity remaining in the presence of 1 μM SP. The filters are placed into tubes and counted using liquid scintillation counter.

All of the title compounds of the examples were tested and at least one stereoisomer of each such compound exhibited a binding affinity, measured as $K_i$, of at least 600 nM.

The activity of the compounds of this invention against generalized anxiety disorder can be determined by inhibition of GR73632-induced tapping test in gerbils. More specifically, gerbils are lightly anesthetized with ether and the skull surface is exposed. GR73632 or vehicle (PBS, 5 μl) are administered directly into the lateral ventricles via a 25 gauge needle inserted 4.5 mm below bregma (preceded by pretreatment with an antagonist, 0.1–32.0 mg/kg, s.c. or p.o.). Following injection, gerbils are placed in 1 L beaker individually and monitored for repetitive hind paw tapping. Some compounds prepared in the following Examples were tested in accordance with these testing methods. As a result, it was found that the compounds of the present inventions have good antagonist activity toward substance P, particularly good activity against CNS disorders with decreased side effects.

The present invention is illustrated by the following examples. It will be understood, however, that the invention is not limited to the specific details of these examples. Melting points are uncorrected. Proton nuclear magnetic resonance spectra ($^1$H NMR) and $^{13}$C nuclear magnetic resonance spectra were measured for solutions in deuterochloroform ($CDCl_3$) or in $CD_3OD$ or $CD_3SOCD_3$ and peak positions are expressed in parts per million (ppm) downfield from tetramethylsilane (TMS). The peak shapes are denoted as follows: s, singlet; d, doublet; t, triplet; q, quartet; m, multiplet; b, broad.

EXPERIMENTAL PROCEDURES

Preparation 1

6-Hydroxy-2-oxo-1,2,3,4-tetrahydro-quinoline

P-aminophenol [0.5 gm (4.58 mmol)] was dissolved in 30 ml of each methylene chloride and saturated aqueous bicarbonate solution and it was stirred for 5 min at ambient temperature. 3-chloropropionyl chloride [0.49 ml (5.04 mmol.)] was added over 10 min. and the reaction mixture was stirred at ambient temperature for 4 hours. A large amount of precipitate was observed. The solids were filtered and dried to afford 0.82 gm (90%) of an off white solid. MS APCI m/e 200 (p+1)

Combine 0.82 gm (4.1 mmol.) and 1.6 gm (12.3 mmol.) aluminum chloride as a mixture of solids. The mixture was then heated in an oil bath at 210° C. for 10 min or until the gas evolution ceases. The reaction mixture was then allowed to cool to ambient temperature and then quenched in ice/water mixture. The aqueous phase was extracted with ethyl acetate which was separated, dried over sodium sulfate and evaporated in vacuo to a light brown solid 0.58 gm (87%) MS APCI m/e 164 (p+1)

Preparation 2

6-Methoxy-2-oxo-1,2,3,4-tetrahydro-quinoline

A solution of 0.58 gm (3.56 mmol.) 6-hydroxy-2-oxo-1,2,3,4-tetrahydro-quinoline was prepared in 10 ml acetone followed by the addition of 1.46 gm (10.58 mmol.) potassium carbonate and 0.51 ml (5.36 mmol.) dimethyl sulfate. The reaction mixture was stirred at ambient temperature for 16 hours and then evaporated in vacuo. The residue was partitioned between saturated aqueous bicarbonate solution and methylene chloride. The organic phase was dried over sodium sulfate and evaporated. The residue was purified by silica gel chromatography eluting with 96/4 methylene chloride/methanol to afford 0.53 gm (85%) of the desired product as a white solid. MS APCI m/e 178 (p+1)

Preparation 3

6-Methoxy-2-oxo-1,2,3,4-tetrahydro-quinoline-7-carbaldehyde

A mixture of 0.29 gm (2.19 mmol) aluminum chloride in 5 ml of methylene chloride was prepared under nitrogen gas $N_2$ and stirred for 15 minutes and then cooled to 0° C. The mixture was treated with 0.2 gm (1.13 mmol) 6-Methoxy-3,4-dihydro-1H-quinolin-2-one in 5 ml of methylene chloride. The reaction mixture was stirred for 10 minutes at this temperature and was then cooled to −5° C. α,α-dichloromethyl methyl ether 0.28 ml (3.07 mmol) was added over a 5 minutes period and the green reaction mixture was slowly warmed to room temperature and stirred for 6 hours. The reaction mixture was diluted with 2N HCl and extracted with methylene chloride (4×10 ml). The combined organics were dried over sodium sulfate, filtered and concentrated to yield an off white solid. The crude product was chromatographically purified on silica gel, eluting with 7/3 ethyl acetate/hexane. There was obtained 125 mg (54%) of an off white solid. MS APCI m/e 206 (p+1)

Example 1

6-Methoxy-7-[(2-phenyl-piperidin-3-ylamino)-methyl]-3,4-dihydro-1H-quinolin-2-one To a flame dried round bottom flask fitted with Dean-Stark trap, condenser and nitrogen atmosphere was placed: 66 mg (0.37 mmole) cis-(2S,3S)-3-amino, 2-phenylpiperidine and 77 mg (0.37 mmole) 6-Methoxy-2-oxo-1,2,3,4-tetrahydro-quinoline-7-carbaldehyde in 15 ml of toluene containing 3 Å molecular sieves. The reaction mixture was heated under reflux for 6 hours and monitored by mass spectrum analysis for the presence of the imine intermediate. The reaction mixture was allowed to cool to ambient temperature and then evaporated in vacuo. The residue was taken up in approximately 15 ml of dichloroethane and was treated with 102 mg (0.48 mmol.) sodium triacetoxybrohydride and then stirred for 16 hours under nitrogen at ambient temperature. The reaction mixture was then washed with aqueous saturated sodium bicarbonate solution, washed with brine and then dried and evaporated in vacuo. The residue was purified by column chromatography on silica gel eluting with 95/5 CHCl/MeOH containing 3 drops of concentrated $NH_4OH$ solution. There was obtained 100 mg of the free base (75%) which was converted to the above named product as the hydrochloride in the following manner. Treatment of methanol with 3 equivalents (53 µl, 0.82 mmol) acetyl chloride afforded a methanolic hydrochloric acid (HCl) solution, which was stirred for 10 minutes. The free base was added in methanol and the mixture was again stirred for 10 minutes and then evaporated in vacuo. The residue was taken up in the minimum amount of methanol and treated with ether until a cloudy precipitate form. Upon standing the di-HCl salt was obtained in 46% overall yield (75 mg). Mp 233–235° C. MS, APCI m/e 366 (p+1).

Preparation 4

1-Ethyl-6-methoxy-2-oxo-1,2,3,4-tetrahydro-quinoline-7-carbaldehyde

6-Methoxy-2-oxo-1,2,3,4-tetrahydro-quinoline-7-carbaldehyde (preparation 3) 60 mg (0.293 mmol) was dissolved in 5 ml of anhydrous THF and the solution was cooled to 0° C. The reaction mixture was treated with 33 mg (0.293 mmol) of potassium t-butoxide whereupon it became yellow in color. After stirring for 30 minutes, the mixture was treated with 23 µl (0.293 mmol) ethyl iodide and slowly warmed to room temperature while stirring for 16 hours (h). The reaction mixture was diluted with saturated aqueous sodium bicarbonate solution and extracted with ethyl acetate. The organic phase was dried over sodium sulfate and concentrated to an oil. The residue was chromatographed on silica gel eluting with 6/4 ethyl acetate/hexane to afford 34 mg (40%) as a white solid. MS APCI m/e 234 (p+1)

Preparation 5

1-Methyl-6-methoxy-2-oxo-1,2,3,4-tetrahydro-quinoline-7-carbaldehyde

6-Methoxy-2-oxo-1,2,3,4-tetrahydro-quinoline-7-carbaldehyde 30 mg (0.146 mmol) was dissolved in 5 ml of anhydrous THF and the solution was cooled to 0° C. The reaction mixture was treated with 16 mg (0.146 mmol) of potassium t-butoxide whereupon it became yellow in color. After stirring for 30 minutes, the mixture was treated with 14 µl (0.146 mmol) dimethylsulfate and slowly warmed to room temperature while stirring for 16 hours. The reaction mixture was diluted with saturated aqueous sodium bicarbonate solution and extracted with ethyl acetate. The organic phase was dried over sodium sulfate and concentrated to an oil. The residue was chromatographed on silica gel eluting with 6/4 ethyl acetate/hexane to afford 16 mg (50%) as a white solid. MS APCI m/e 220 (p+1)

Example 2

1-Ethyl-6-methoxy-7-[(2-phenyl-piperidin-3-ylamino)-methyl]-3,4-dihydro-1H-quinolin-2-one To a 50 ml round bottom flask fitted with a Dean Stark water separator, condenser and nitrogen cap was placed 0.027 gm (0.151 mmole) cis-(2S,3S)-3-amino, 2-phenylpiperidine and 0.033 gm (0.151 mmole) 1-Ethyl-6-methoxy-2-oxo-1,2,3,4-tetrahydro-quinoline-7-carbaldehyde (preparation 5) in 10 ml of toluene containing 3 Å molecular sieves. The reaction mixture was heated for 18 hours under reflux. The solution was then allowed to cool to room temperature and then evaporated in vacuo. The residue was taken up in 25 ml of dichloroethane and treated with 0.048 gm (0.229 mmol) sodium triacetoxyborohydride and the solution was stirred at ambient temperature for 16 hours. The reaction was then partitioned between saturated aqueous bicarbonate solution and dichloromethane. The organic phase was washed with saturated brine and then dried over sodium sulfate before evaporation in vacuo. The crude product was chromatographed on silica gel eluting with 95 $CHCl_3$, 4 MeOH, 1 $NH_4OH$. The resulting oil was taken up in methanol which had previously been treated with 17.5 µl of acetyl chloride. The solution was evaporated in vacuo and the dihydrochloride salt of the desired product was obtained by recrystallization from methanol-ether; 33 mg (47%). Mp 253–255° C.; MS, APCI m/e 394 (p+1).

Preparation 6

1-Methanesulfonyl-6-methoxy-3,4-dihydro-1H-quinolin-2-one

To a flame dried round bottom flask equipped with a nitrogen cap was placed 87 mg (2.17 mmol) of 60% sodium hydride in mineral oil and 15 ml of dimethylformaminde (DMF). The mixture was cooled to 0° C. and was treated with 350 mg (1.97 mmol) of 6-Methoxy-2-oxo-1,2,3,4-tetrahydro-quinoline (Preparation 2) in the minimum amount of DMF. The reaction mixture was stirred for 0.5 hours at 0° C. and was then treated with 226 mg (1.97 mmol) mesyl chloride. The mixture was slowly allowed to warm to room temperature and stirred for 16 hours. The reaction mixture was quenched by the addition of 30 ml of saturated aqueous sodium bicarbonate solution and the mixture was extracted with methylene chloride (3×30 ml). The combined organics were washed with brine, dried over sodium sulfate and evaporated in vacuo. The crude oil was purified by silica gel chromatography eluting with 1/1 ethyl acetate/hexane to afford a light yellow oil in 35% yield (177 mg). Mass spectrum APCI m/e 256 (p+1).

Preparation 7

1-Methanesulfonyl-6-methoxy-2-oxo-1,2,3,4-tetrahydro-quinoline-7-carbaldehyde

To a flame dried round bottom flask equipped with a nitrogen cap was added 180 mg (1.35 mmol) aluminum chloride and 10 ml of methylene chloride. The mixture was stirred at ambient temperature for 0.25 hour and then cooled to 0° C. followed by the addition of 177 mg (0.69 mmol) 1-methanesulfonyl-6-methoxy-3,4-dihydro-1H-quinolin-2-one. The reaction mixture was stirred for 10 minutes at this temperature and was then treated with 171 µl (1.89 mmol) of α,α-dichloromethyl methyl ether before allowing the reaction to slowly warm to room temperature over 16 hours. The reaction mixture was quenched with 30 ml of 2M HCl and extracted with ethyl acetate (3×30 ml). The combined organics were then washed with saturated aqueous bicarbonate solution and brine followed by drying over sodium sulfate and evaporation in vacuo. The crude residue was purified on silica gel eluting with 95/5 methylene chloride/methanol to afford an off white solid in 66% yield (130 mg). Mass spectrum APCI m/e 284 (p+1).

Example 3

1-Methanesulfonyl-6-methoxy-7-[(2-phenyl-piperidin-3-ylamino)-methyl]-3,4-dihydro-1H-quinolin-2-one By a procedure similar to the previous examples 1 and 2: 81 mg (0.46 mmole) cis-(2S,3S)-3-amino, 2-phenylpiperidine and 130 mg (0.46 mmole) 1-Methanesulfonyl-6-methoxy-2-oxo-1,2,3,4-tetrahydro-quinoline-7-carbaldehyde were converted to the above named product as the hydrochloride in 6% overall yield (12.5 mg). Mp 237–241° C. MS, APCI m/e 444 (p+1).

Preparation 8

4-Methoxy-N-methylacetanilide

To a flame dried round bottom flask equipped with a nitrogen cap was added 10 gm (6.05 mmol) 4-methoxyacetanilide and 20 ml of THF. The solution was cooled to 0° C. and was treated with a 1M solution of 680 mg (6.05 mmol) potassium t-butoxide (K—O-t-Bu) in tetrahydrofuran (THF) and stirred for 30 minutes. The reaction mixture was treated with 570 µl (6.05 mmol) dimethyl sulfate by dropwise addition followed by slow warming to ambient temperature over 16 hours. During this time the clear reaction mixture became a cloudy mixture. The reaction mixture was quenched with aqueous saturated sodium bicarbonate solution and extracted with chloroform (3×30 ml). The combined extracts were washed with brine, dried over sodium sulfate and evaporated in vacuo. The residue was triturated with petroleum ether and the resulting solid was removed as it was determined to be unreacted starting material. The mother liquor was concentrated to an oil 780 mg (72%) to afford the above named product. Mass spectrum APCI m/e 180 (p+1).

Preparation 9

3-Hydroxy-N-(4-methoxy-phenyl)-3,N-dimethyl-butyramide

To a flame dried round bottom flask equipped with a nitrogen cap was added 10 ml of anhydrous THF followed by 390 µl (2.79 mmol) diisopropyl amine. The solution was cooled to −78° C. followed by the dropwise addition of 1.1 ml (2.79 mmol) of 2.5 M n-butyl lithium in hexane. The reaction mixture was stirred for 0.5 hour at this temperature and then warmed briefly to −50° C. before cooling once again to −78° C. A solution of 0.5 gm (2.79 mmol) 4-methoxy-N-methylacetanilide in 5 ml of anhydrous THF was added to the solution of the base and the reaction mixture was stirred for 1 hour at −78° C. Acetone (205 µl (2.79 mmol)) was then added dropwise and the reaction mixture was allowed to slowly warm to ambient temperature over 1 hour. The reaction mixture was quenched with an aqueous saturated solution of sodium bicarbonate and then extracted with chloroform (CHCl$_3$) (3×30 ml). The combined organics were washed with brine, dried over sodium sulfate and evaporated in vacuo. The crude residue was purified on silica gel eluting with ethyl acetate/hexane 1/1 to afford 375 mg (57%) of the desire product. Mass spectrum APCI m/e 238 (p+1).

Preparation 10

6-Methoxy-1,4,4-trimethyl-3,4-dihydro-1H-quinolin-2-one

To 0.2 gm (0.84 mmol) 3-Hydroxy-N-(4-methoxy-phenyl)-3,N-dimethyl-butyramide was added approximately 5 ml of polyphosphoric acid and the mixture was heated to 150° C. for 15 minutes. The reaction mixture was then poured over ice/water and stirred for 15 minutes followed by extraction with chloroform (2×20 ml). The combined organics were washed with brine, dried over sodium sulfate and evaporated in vacuo. The residue weighed 158 mg (85%) and was identified as the desire product. Mass spectrum APCI m/e 220 (p+1).

Preparation 11

6-Methoxy-1,4,4-trimethyl-3,4-dihydro-1H-quinolin-2-one-7-carboxaldehyde

To a flame dried round bottom flask equipped with a nitrogen cap was added 89 mg (66 mmol) aluminum chloride and 5 ml of methylene chloride (CHCl$_2$). The mixture was stirred at ambient temperature for 0.25 hour and then cooled to 0° C. followed by the addition of 75 mg (0.34 mmol) 6-methoxy-1,4,4-trimethyl-3,4-dihydro-1H-quinolin-2-one. The reaction mixture was stirred for 10 minutes at this temperature and was then treated with 84 µl (0.93 mmol) of α,α-dichloromethyl methyl ether before allowing the reaction to slowly warm to room temperature over 16 hours. The reaction mixture was quenched with 30 ml of 2M HCl and extracted with ethyl acetate (3×30 ml). The combined organics were then washed with saturated aqueous bicarbonate solution and brine followed by drying over sodium sulfate and evaporation in vacuo. The crude residue was purified on silica gel eluting with 1:1 ethyl acetate/hexane to afford two products. The more polar material was identified as the desired product: Mass spectrum APCI m/e 248 (p+1). The less polar product was identified as 7-Dichloromethyl-6-methoxy-1-methyl-3,4-dihydro-1H-quinolin-2-one (Mass spectrum APCI m/e 302 (p+1)) from which the desire product was isolated after a brief stirring in pH 7 phosphate buffer. Total yield 56 mg (66%).

Preparation 12

6-Methoxy-1,4,4-trimethyl-3,4-dihydro-1H-quinolin-2-one-7-carboxaldehyde

To a flame dried round bottom flask equipped with a nitrogen cap was added 83 mg (0.38 mmol) 6-methoxy-1,4,4-trimethyl-3,4-dihydro-1H-quinolin-2-one, 3 ml of trifluoroacetic acid and 53 mg (0.38 mmol) of hexamethylene tetraamine. The mixture was stirred under reflux for 1.5 hours and then cooled to ambient temperature. The reaction mixture was quenched with 30 ml of saturated aqueous bicarbonate solution and extracted with ethyl acetate (3×30 ml). The combined organics were then washed with brine followed by drying over sodium sulfate and evaporation in vacuo. The crude residue (64 mg; 68%) was used directly in the following step. Mass spectrum APCI m/e 248 (p+1).

Example 4

6-Methoxy-1,4,4-trimethyl-7-[(2-phenyl-piperidin-3-ylamino)-methyl]-3,4-dihydro-1H-quinolin-2-one By a procedure similar to previous examples 1 and 2: 86 mg (0.49 mmole) cis-(2S,3S)-3-amino, 2-phenylpiperidine and 120 mg (0.49 mmole) 6-methoxy-1,4,4-trimethyl-3,4-dihydro-1H-quinolin-2-one-7-carboxaldehyde were converted to the above named product as the hydrochloride in 29% overall yield (68 mg). Mp>280° C. MS, APCI m/e 408 (p+1).

Preparation 13

2-Fluoro-4-methoxy-N-methylacetanilide

To a flame dried round bottom flask equipped with a nitrogen cap was added 4 gm (24.46 mmol) 2-fluoro-4-hydroxyaniline and 200 ml of methylene chloride. The solution was treated with 10.25 ml (73.39 mmol) triethyl amine and 4.62 ml (48.92 mmol) acetic anhydride and was stirred at room temperature for 16 hours. The reaction mixture was quenched with aqueous saturated sodium bicarbonate solution and extracted with methylene chloride (3×30 ml). The combined extracts were washed with brine, dried over sodium sulfate (Na$_2$SO$_4$) and evaporated in vacuo to afford an off white solid (4.82 gm) (93%). Mass spectrum APCI m/e 212 (p+1)) 2-fluoro-4-acetoxyacetanilide which was used directly in the next preparation.

To a flame dried round bottom flask equipped with a nitrogen cap was added 1.75 gm (8.29 mmol) of the previous product and 100 ml of methanol. The solution was treated with 1.1 gm (8.29 mmol) potassium carbonate and the reaction mixture was stirred at room temperature for 16 hours. The mixture was filtered and concentrated in vacuo to afford a tacky solid 1.4 gm (100%) which was used directly in the next step.

To a flame dried round bottom flask equipped with a nitrogen cap was added 663 mg (16.57 mmol) of 60% sodium hydride in mineral oil and 10 ml of DMF. The mixture was treated with 1.4 gm (8.28 mmol) 2-Fluoro-4-hydroxyacetanilide in a minimum amount of DMF followed by stirring for 1 hour at ambient temperature. The mixture was treated with 1.03 ml (16.57 mmol) methyl iodide and stirred for 16 hours at room temperature. The reaction mixture was quenched with aqueous saturated sodium bicarbonate solution and extracted with chloroform (3×30 ml). The combined extracts were washed with brine, dried over sodium sulfate and evaporated in vacuo. The residue was purified on silica gel eluting with a gradient of ethyl acetate/hexane 3/7 to ethyl acetate/hexane 1/1 to afford 510 mg (32%) of the desired product. Mass spectrum APCI m/e 198 (p+1).

Preparation 14

3-Hydroxy-N-(2-fluoro-4-methoxy-phenyl)-3,N-dimethyl-butyramide

To a flame dried round bottom flask equipped with a nitrogen cap was added 10 ml of anhydrous THF followed by 360 μl (2.58 mmol) diisopropyl amine. The solution was cooled to −78° C. followed by the dropwise addition of 1.03 ml (2.58 mmol) of 2.5 M n-butyl lithium in hexane. The reaction mixture was stirred for 0.5 hour at this temperature and then warmed briefly to −50° C. before cooling once again to −78° C. A solution of 0.51 gm (2.58 mmol) 2-fluoro-4-methoxy-N-methylacetanilide in 5 ml of anhydrous THF was added to the solution of the base and the reaction mixture was stirred for 1.5 hours at −78° C. Acetone (200 μl (2.58 mmol)) was then added dropwise and the reaction mixture was allowed to slowly warm to ambient temperature over 1 hour. The reaction mixture was quenched with an aqueous saturated solution of sodium bicarbonate and then extracted with chloroform (3×30 ml). The combined organics were washed with brine, dried over sodium sulfate and evaporated in vacuo. The crude residue was purified on silica gel eluting with ethyl acetate/hexane 3/7 to afford 315 mg (48%) of the desired product. Mass spectrum APCI m/e 255 (p+1).

Preparation 15

8-Fluoro-6-methoxy-1,4,4-trimethyl-3,4-dihydro-1H-quinolin-2-one

To 0.11 gm (0.43 mmol) 3-Hydroxy-N-(2-fluoro-4-methoxy-phenyl)-3,N-dimethyl-butyramide was added approximately 5 ml of polyphosphoric acid and the mixture was heated to 110° C. for 1 hour. The reaction mixture was then poured over ice/water and stirred for 15 minutes followed by extraction with chloroform (3×30 ml). The combined organics were washed with brine, dried over sodium sulfate and evaporated in vacuo. The residue weighed 93 mg. The crude product was purified on silica gel eluting with ethyl acetate/hexane 2/8 to afford 84 mg (82%) of the desired product. Mass spectrum APCI m/e 238 (p+1).

Preparation 16

8-Fluoro-6-methoxy-1,4,4-trimethyl-3,4-dihydro-1H-quinolin-2-one-7-carboxaldehyde To a flame dried round bottom flask equipped with a nitrogen cap was added 74 mg (0.312 mmol) 8-fluoro-6- methoxy-1,4,4-trimethyl-3,4-dihydro-1H-quinolin-2-one, 3 ml of trifluoroacetic acid and 53 mg (0.38 mmol) of hexamethylene tetraamine. The mixture was stirred under reflux for 16 hours and then cooled to ambient temperature. The reaction mixture was quenched first with water and then 30 ml of saturated aqueous bicarbonate solution and extracted with ethyl acetate (3×30 ml). The combined organics were then washed with brine followed by drying over sodium sulfate and evaporation in vacuo. The crude product was purified on silica gel eluting with ethyl acetate to afford 43 mg (52%) of the desired product. Mass spectrum APCI m/e 266 (p+1).

Example 5

8-Fluoro-6-methoxy-1,4,4-trimethyl-7-[(2-phenyl-piperidin-3-ylamino)-methyl]-3,4-dihydro-1H-quinolin-2-one By a procedure similar to a previous examples 1 and 2: 27 mg (0.151 mmole) cis-(2S,3S)-3-amino, 2-phenylpiperidine and 40 mg (0.151 mmole) 8-fluoro-6-methoxy-1,4,4-trimethyl-2-oxo-1,2,3,4-tetrahydro-quinoline-7-carbaldehyde were converted to the above named product as the hydrochloride in 46% overall yield (35 mg). Mp>270° C. MS, APCI m/e 426 (p+1).

Example 6

6-Methoxy-1-methyl-7-[cis-(2R,3R)(2-phenyl-piperidin-3-ylamino)-methyl]-3,4-dihydro-1H-quinolin-2-one By a procedure similar to a previous examples 1 and 2: 355 mg (2.02 mmole) cis-(2R,3R)-3-amino, 2-phenylpiperidine and 420 mg (1.92 mmole) 6-Methoxy-1-methyl-2-oxo-1,2,3,4-tetrahydro-quinoline-7-carbaldehyde were converted to the above named product as the dihydrochloride in 24% overall yield (210 mg). Mp>270° C. MS, APCI m/e 380 (p+1).

Preparation 17

3-Hydroxy-N-(4-methoxy-phenyl)-N-methyl-butyramide

To a flame dried round bottom flask equipped with a nitrogen cap was added 5 ml of anhydrous THF followed by 230 μl (1.68 mmol) diisopropyl amine. The solution was cooled to −78° C. followed by the dropwise addition of 0.67 ml (1.68 mmol) of 2.5 M n-butyl lithium (nBuLi)in hexane. The reaction mixture was stirred for 0.5 hour at this temperature and then warmed briefly to −50° C. before cooling once again to −78° C. A solution of 0.3 gm (1.68 mmol) 4-methoxy-N-methylacetanilide in 5 ml of anhydrous THF was added to the solution of the base and the reaction mixture was stirred for 1 hour at −78° C. Acetaldehyde (94 μl (1.68 mmol)) was then added dropwise and the reaction mixture was allowed to slowly warm to ambient temperature over 16 hours. The reaction mixture was quenched with an aqueous saturated solution of sodium bicarbonate and then extracted with chloroform (3×30 ml). The combined organics were washed with brine, dried over sodium sulfate and evaporated in vacuo. The crude residue was purified on silica gel eluting with ethyl acetate/hexane 1/1 to afford 201 mg (54%) of the desire product. Mass spectrum APCI m/e 223 (p+1).

Preparation 18

6-Methoxy-1,4,-dimethyl-3,4-dihydro-1H-quinolin-2-one

To 0.201 gm (0.91 mmol) 3-hydroxy-N-(4-methoxy-phenyl)-N-methyl-butyramide was added approximately 5 ml of polyphosphoric acid and the mixture was heated to 110° C. for 1 hour. The reaction mixture was then poured over ice/water and stirred for 15 minutes followed by extraction with chloroform (2×20 ml). The combined organics were washed with brine, dried over sodium sulfate and evaporated in vacuo. The residue weighed 110 mg (60%) and was identified as the desired product. Mass spectrum APCI m/e 206 (p+1).

Preparation 19

6-Methoxy-1,4-dimethyl-3,4-dihydro-1H-quinolin-2-one-7-carboxaldehyde

To a flame dried round bottom flask equipped with a nitrogen cap was added 110 mg (0.54 mmol) 6-methoxy-1,4-dimethyl-3,4-dihydro-1H-quinolin-2-one, 3 ml of trifluoroacetic acid and 90 mg (0.64 mmol) of hexamethylene tetraamine. The mixture was stirred under reflux for 1.5 hours and then cooled to ambient temperature. The reaction mixture was quenched first with water and then with 30 ml of saturated aqueous bicarbonate solution and extracted with chloroform (3×30 ml). The combined organics were then washed with brine followed by drying over sodium sulfate and evaporation in vacuo. The crude residue, 72 mg, was purified by silica gel column chromatography eluting with 4/6 ethyl acetate/hexane to afford 50 mg (40%) of a yellow solid which was used directly in the following step. Mass spectrum APCI m/e 234 (p+1). Enantiomeric separation was completed on a Chiralpak AD column eluting with 9/1 hexane/ethanol(EtOH) containing 1% diethylamine. The retention times were 12 minutes and 13.8 minutes respectively.

Example 7

6-Methoxy-1,4-dimethyl-7-[(2-phenyl-piperidin-3-ylamino)-methyl]-3,4-dihydro-1H-quinolin-2-one By a procedure similar to previous examples 1 and 2: 30 mg (0.172 mmole) cis-(2S,3S)-3-amino, 2-phenylpiperidine and 40 mg (0.172 mmole) 6-methoxy-1,4-dimethyl-3,4-dihydro-1H-quinolin-2-one-7-carboxaldehyde were converted to the above named product in 31% overall yield (21 mg). MS, APCI m/e 394 (p+1). Diastereomeric separation was completed on a Chiralcel OD column eluting with 9/1 hex/EtOH containing 1% diethylamine. The retention times were 14.7 minutes and 16.2 minutes respectively.

Example 8

6-Methoxy-2-methyl-7-[(2-phenyl-piperidin-3-ylamino)-methyl]-3,4-dihydro-2H-isoquinolin-1-one By a procedure similar to previous examples 1and 2: 80 mg (0.456 mmole) cis-(2S,3S)-3-amino, 2-phenylpiperidine and 100 mg (0.456 mmole) 6-Methoxy-2-methyl-1-oxo-1,2,3,4-tetrahydro-isoquinoline-7-carbaldehyde were converted to the above named product in 6% overall yield (12.5 mg). MS, APCI m/e 379 (p+1).

Preparation 20

6-Methoxy-1-methyl-1H-quinolin-2-one

A solution of 10 gm (63 mmol) 6-methoxyquinoline in 150 ml of acetone was treated with 4.4 ml (70 mmol) of methyl iodide and heated under reflux for 4.5 hours followed by stirring at ambient temperature for 16 hours. The desired product was obtained by filtration of the solution. [14 gm (74%)]. This material was suspended in 360 ml of water and was cooled to 5° C. The mixture was treated with 90 gm (0.273 mol) potassium ferricyanide in a portionwise fashion over 1 hour. This mixture was kept at 5° C. for 30 minutes and was then treated over 30 minutes with a solution of 31 gm (0.56 mol) KOH in 65 ml of water which had been previously cooled in an ice bath. The mixture becomes very very thick. Added 250 ml of toluene and heated to 40° C. in a water bath for 30 minutes. The organic layer was separated and the aqueous phase was extracted in the same fashion twice more. The combined organic phase was washed with brine, dried over sodium sulfate and evaporated in vacuo to afford 8.2 gm of the desired product. Mass Spectrum APCI m/e 190 (p+1).

Preparation 20A

6-Methoxy-1-methyl-1H-quinolin-2-one

A solution of 50 gm (314.1 mmol) 6-methoxyquinoline in 650 ml of acetone was treated with 21.5 ml (345.5 mmol) of methyl iodide and heated under reflux for 6 hours followed by stirring at ambient temperature for 16 hours. The desired product was obtained by filtration of the solution. [81.4 gm (91%)]. This material (285.4 mmol) was suspended in 2000 ml of water and was cooled to 5° C. The mixture was treated with 552.6 gm (1.68 mol) potassium ferricyanide in a portionwise fashion over 1 hour. This mixture was kept at 5° C. for 30 minutes and was then treated over 30 minutes with a solution of 191.8 gm (3.43 mol) KOH in 400 ml of water which had been previously cooled in an ice bath. The mixture becomes very very thick. Added 250 ml of toluene and heated to 45° C. in a water bath for 45 minutes. The reaction mixture was treated with 100 ml of saturated aqueous sodium thiosulfate solution. The organic layer was separated and the aqueous phase was extracted in the same fashion with ethyl acetate twice more. The combined organic phase was washed with brine, dried over sodium sulfate and evaporated in vacuo to afford 48.9 gm of the desired product (91%). Mass Spectrum APCI m/e 190 (p+1).

Preparation 21

6-Methoxy-3-methyl-1,1a,3,7b-tetrahydro-3-aza-cyclopropa[a]naphthalen-2-one

A suspension of 7.0 gm (42.0 mmol) potassium iodide and 4.89 gm (38.0 mmol) trimethylsulfoxonium chloride in 30 ml of DMSO under nitrogen was treated portionwise with 1.69 gm (42.0 mmol) of 60% sodium hydride in mineral oil. The mixture was stirred for one hour and then treated with 2.0 gm (11.0 mmol) 6-Methoxy-1-methyl-1H-quinolin-2-one followed by stirring for 0.5 hours at ambient temperature and 4 days at 90° C. The reaction mixture was allowed to cool to ambient temperature before quenching into ice followed by extraction into ether. The ether layer was washed with brine, dried over sodium sulfate and evaporated. The residue was partitioned between acetonitrile and pentane. The acetonitrile layer was concentrated. The residue was partitioned between 1:1 hexane/ethyl acetate and 50% saturated (sat'd) brine solution. The organic layer was washed with saturated brine, dried over sodium sulfate and evaporated in vacuo to afford 1.6 gm of a mixture of desired product and starting material. The residue was purified by silica gel chromatography eluting with 7/3 hexane/ethyl acetate to afford 972 mg (44%). Mass spectrum APCI m/e 204 (p+1).

Preparation 21A

6-Methoxy-3-methyl-1,1a,3,7b-tetrahydro-3-aza-cyclopropa[a]naphthalen-2-one

A suspension of 3.35 gm (15.1 mmol) trimethylsulfoxonium iodide in 10 ml of THF at 0° C. under nitrogen was treated portionwise with 5.8 ml (14.6 mmol) of 2.5 M n-hexyllithium in heptane over 30 minutes. The mixture was stirred for 30 minutes at 0° C. and then treated with 1.0 gm (5.02 mmol) 6-Methoxy-1-methyl-1H-quinolin-2-one followed by heating under reflux for 1.5 hours. The reaction mixture was allowed to cool to ambient temperature before quenching with 35 ml of water followed by extraction into ethyl acetate. The organic layer was washed with brine, dried over sodium sulfate and evaporated to afford 1.1 gm of desired product. Mass spectrum APCI m/e 204 (p+1).

Preparation 22

6-Methoxy-3-methyl-2-oxo-1a,2,3,7b-tetrahydro-1H-3-aza-cyclopropa[a]naphthalene-5-carbaldehyde To a flame dried round bottom flask equipped with a nitrogen cap was added 972 mg (4.8 mmol) 6-Methoxy-3-methyl-1,1a,3,7b-tetrahydro-3-aza-cyclopropa[a]naphthalen-2-one, 40 ml of trifluoroacetic acid and 806 mg (5.7 mmol) of hexamethylene tetraamine. The mixture was stirred under reflux for 1.5 hours and then cooled to ambient temperature. The reaction mixture was quenched in 200 ml ice and then treated with solid sodium carbonate until pH 9 was reached. The aqueous phase was extracted with chloroform (3×30 ml). The combined organics were then washed with brine followed by drying over sodium sulfate and evaporation in vacuo. The crude residue was taken up in ethyl acetate whereupon crystals formed. Four crops totaling 373 mg were obtained. The mother liquors were purified by silica gel column chromatography eluting with 1/1 ethyl acetate/hexane to afford another 98 mg (total yield 42%) of a white solid which was used directly in the following step. Mass spectrum APCI m/e 232 (p+1).

Preparation 22A

6-Methoxy-3-methyl-2-oxo-1a,2,3,7b-tetrahydro-1H-3-aza-cyclopropa[a]naphthalene-5-carbaldehyde To a flame dried round bottom flask equipped with a nitrogen cap was added 935 mg (4.6 mmol) 6-Methoxy-3-methyl-1,1a,3,7b-tetrahydro-3-aza-cyclopropa[a]naphthalen-2-one, and 40 ml of methylene chloride. The solution was cooled to 0° C. and 46.1 ml (46.1 mmol) of 1.0 M titanium tetrachloride was added. Dichloromethylmethylether (2.09 ml (23.05 mmol) was added and the reaction mixture was stirred at room temperature overnight. The reaction mixture was quenched in 100 ml ice/1N HCl. The aqueous phase was extracted with chloroform (3×30 ml).

The combined organics were then washed with saturated bicarbonate solution and then brine followed by drying over sodium sulfate and evaporation in vacuo. The crude residue was taken up in ethyl acetate whereupon crystals formed. Four crops totaling 902 mg were obtained. Mass spectrum APCI m/e 232 (p+1).

Preparation 22B

Separation of enantiomers: 6-Methoxy-3-methyl-2-oxo-1a,2,3,7b-tetrahydro-1H-3-aza-cyclopropa[a]naphthalene-5-carbaldehyde To a flame dried round bottomed flask under nitrogen atmosphere was introduced 7.5 gm (32.5 mmol) 6-Methoxy-3-methyl-2-oxo-1a,2,3,7b-tetrahydro-1H-3-aza-cyclopropa[a]-naphthalene-5-carbaldehyde and 150 ml methanol. The solution was treated with a catalytic amount of toluenesulfonic acid and 4.26 ml (38.9 mmol) trimetylorthoformate. The reaction was stirred for 1.5 hours and was then treated with a small amount of solid sodium bicarbonate. The reaction mixture was diluted with chloroform that had been passed through a plug of neutral or basic alumina and filtered to clarify the solution. The filtrate was concentrated in vacuo to afford 8.0 gm. The acetal was separated by chiral HPLC chromatography on a Chiralpak AS 10 cm×50 cm column eluting with 60:40/heptane:ethanol at a flow rate of 200 ml/min. The desired isomer (4.13 gm) had a retention time of 4.5 min and was estimated to be 100% ee. This material was taken up in 100 chloroform and 5 drops of 1N HCl. The mixture was stirred at room temperature for 16 hours and then dried over sodium sulfate. The solvent was removed n vacuo to afford 3.6 gm of the aldehyde as a single enantiomer.

Example 9

6-Methoxy-3-methyl-5-[(–2-phenyl-piperidin-3-ylamino)-methyl]-1,1,a,3,7b-tetrahydro-3-aza-cyclopropa[a]naphthalen-2-one By a procedure similar to previous examples 1 and 2: 331 mg (1.88 mmole) cis-(2S,3S)-3-amino, 2-phenylpiperidine and 443 mg (1.92 mmole) 6-Methoxy-3-methyl-2-oxo-1a,2,3,7b-tetrahydro-1H-3-aza-cyclopropa[a]naphthalene-5-carbaldehyde were combined in 100 ml of toluene and heated under reflux for 4 hours over a Dean-Stark trap. The crude imine (MS APCI m/e=390 p+1) solution was evaporated in vacuo and redissolved in 100 ml dichloroethane. The solution was treated with 528 mg (2.49 mmol) sodium triacetoxyborohydride and stirred at room temperature for 16 hours. The reaction mixture was washed with saturated aqueous bicarbonate solution followed by brine and then dried over sodium sulfate. The product dissolved in dichloroethane (MS, APCI m/e 392 (p+1) was treated with 392 µl (2.8 mmol) triethylamine and 541 mg (2.48 mmol) t-boc carbonate and the reaction mixture was stirred for 24 hours at ambient temperature. The reaction mixture was washed with saturated aqueous bicarbonate solution followed by brine and then dried over sodium sulfate. After evaporation, the crude residue was chromatographed on silica gel eluting with 98/2/1 methylene chloride, methanol, ($CH_3OH$), ammonium hydroxide ($NH_4OH$) to afford 780 mg of the desired product with protection of the N-1 nitrogen with the tertiary butoxycarbonyl group (t-BOC) in 84% yield (MS, APCI m/e 492 (p+1). Diastereomeric separation was completed on a Chirlpak AD column eluting with 8/2 hex/IPA.

The retention times were 7.0 minutes and 10.8 minutes respectively. Removal of the t-BOC protecting group was achieved by exposure of each substrate to ten molar equivalents of trifluoroacetic acid in dichloroethane at 65° C. for 5 hours followed by washing with saturated carbonate solution and brine. Chromatography on silica gel eluting with 95:5 methylene chloride:methanol containing ammonium hydroxide afforded the above titled products in 62 and 86% yields. (MS, APCI m/e 392 (p+1).

Example 9A

6-Methoxy-3-methyl-5-[(-2-phenyl-piperidin-3-ylamino)-methyl]-1,1a,3,7b-tetrahydro-3-aza-cyclopropa[a]naphthalen-2-one By a procedure similar to previous examples 1 and 2: 331 mg (1.88 mmole) cis-(2S,3S)-3-amino, 2-phenylpiperidine and 443 mg (1.92 mmole) enantiomerically pure 6-Methoxy-3-methyl-2-oxo-1a,2,3,7b-tetrahydro-1H-3-aza-cyclopropa[a]naphthalene-5-carbaldehyde were combined in 100 ml of toluene and heated under reflux for 4 hours over a Dean-Stark trap. The crude imine (MS APCI m/e=390 p+1) solution was evaporated in vacuo and redissolved in 100 ml dichloroethane. The solution was treated with 528 mg (2.49 mmol) sodium triacetoxyborohydride and stirred at room temperature for 16 hours. The reaction mixture was washed with saturated aqueous bicarbonate solution followed by brine and then dried over sodium sulfate. Chromatography on silica gel eluting with 95:5 methylene chloride:methanol containing ammonium hydroxide afforded the above titled product (550 mg) in 75% yield. (MS, APCI m/e 392 (p+1).

Example 10

6-Methoxy-1-methyl-7-[(2S,3S)-(2-phenyl-1-trifluoroacetyl-piperidin-3-ylamino)-methyl]-3,4-dihydro-1H-quinolin-2-one To 313 mg (0.825 mmol) of 6-methoxy-1-methyl-7-[(2-phenyl-piperidin-3-yl-amino)-methyl]-3,4-dihydro-1H-quinolin-2-one in $CH_2Cl_2$ at room temperature was added rapidly dropwise 208 mg (0.99 mmol) of trifluoroacetic anhydride. After 5 minutes, the mixture was partitioned between water (5 mL) and $CHCl_3$ (5 mL). The organic layer was washed with 5 mL satd sodium biocarbonate ($NaHCO_3$), dried via filtration through a plug of cotton, and concentrated. The residue was chromatographed (10:90 EtOAc/hexanes) to give 250 mg (89%) of the title compound as the free amine, a colorless oil. $^1$H NMR (major rotomer, 400 MHz, $CDCl_3$) δ 7.60 (d, J=6.8, 2H), 7.20–7.40 (m, 3H), 6.82 (s, 1H), 6.61 (s, 1H), 6.00 (d, J=5.6, 1H), 3.82 (s, 3H), 3.19 (dt, J=2.4, 14.4, 1H), 3.19 (dt, J=2.4, 14.4, 1H), 3.06–3.12 (m, 1H), 2.80–2.86 (m, 2H), 2.57–2.62 (m, 2H), 1.60–2.10 (comp, 5H). The residue was dissolved in methanol (4 mL) and treated with 3.3 mL of a 0.5 M solution of HCl in methanol. Concentration in vacuo gave the hydrochloride salt as a white powder (mp 222–224° (dec)); mass spectrum m/e calcd. for M+H=476.2. Found 476.4.

Preparation 23

6-Methoxy-1,3,3-trimethyl-1,3-dihydro-indol-2-one

To a stirred ice cold suspension of sodium hydride (60% in mineral oil, 3.9 g, 98.1 mmol) in 50 mL of dry DMF was added solid 6-methoxy-1,3-dihydro-indol-2-one (4.00 g, 24.5 mmol) portionwise over 10 minutes. To the resultant gray mixture was added dropwise MeI (2.68 g, 98.1 mmol). The mixture was warmed to room temperature and stirred for 45 minutes, and then was cooled back to 0° C. and quenched with 90 mL of water. The mixture was extracted with an ethyl acetate (EtOAc)/toluene mixture (2:1), and the extracts were dried with magnesium sulfate ($MgSO_4$), treated with activated charcoal, filtered and concentrated to give a red syrup. Silica gel chromatography (1:10 EtOAc/hexanes) gave 4.16 g (83%) of the title compound as a white solid (mp 67–69° C.). Mass spectrum m/e calcd for M+H=234.1. Found 234.2.

Preparation 24

6-Methoxy-1,3,3-trimethyl-2-oxo-2,3-dihydro-1H-indole-5-carbaldehyde

To a stirred ice-cold solution of 6-Methoxy-1,3,3-trimethyl-1,3-dihydro-indol-2-one (1.0 g, 4.87 mmol) in 30 mL of $CH_2Cl_2$ was added $TiCl_4$ (4.80 mL, 43.8 mmol) followed by α,α-dichloromethyl methyl ether (1.98 mL, 21.9 mmol). The reaction was stirred overnight at room temperature and was then quenched with 20 mL of water. The aqueous layer was extracted with $CH_2Cl_2$ (2×20 mL) and the combined organic portions were washed successively with satd $NaHCO_3$, brine and water, dried with $Na_2SO_4$, and concentrated. The crude product was recrystallized from isopropanol/isopropyl ether to give 680 mg (60%) of a white solid (mp 192–194° C.). A second crop afforded an additional 213 mg for a total yield of 78%.

Preparation 24A (2S,3S)-6-Methoxy-1,3,3-trimethyl-5-[(2-phenyl-piperidin-3-ylamino)-methyl]-1,3-dihydro-indol-2-one To 6-Methoxy-1,3,3-trimethyl-2-oxo-2,3-dihydro-1H-indole-5-carbaldehyde (936 mg, 4.0 mmol) in 50 mL of toluene was added (2S,3S)-2-Phenyl-piperidin-3-ylamine (1.0 g, 4.0 mmol) and 3 mL of methanol. The solution was heated to reflux with azeotropic water removal for 48 h. The solution was then concentrated and the residue was dissolved in $CH_2Cl_2$. Sodiumtriacetoxyborohydride (1.0 g, 4.7 mmol) was added and the mixture was stirred overnight. The mixture was then quenched with satd $NaHCO_3$ and the layers were separated. The aqueous portion was extracted with $CH_2Cl_2$ (2×20 mL). The combined organic portions were washed successively with brine and water and concentrated. Silica gel chromatography (10:1 EtOAc/MeOH) gave 1.27 g (81%) of the title compound as an orange oil. Treatment of the oil with ethereal HCl gave 1.44 g of the dihydrochloride salt as an off-white solid.

Preparation 25

6-Methoxy-1,3,3-trimethyl-3,4-dihydro-1H-quinolin-2-one

To 6-Methoxy-1-methyl-3,4-dihydro-1H-quinolin-2-one (1.00 g, 5.23 mmol) in 30 mL of THF at room temperature was added KHMDS (0.5 M in toluene; 22.0 mL, 10.9 mmol). After 15 minutes, methyl iodide (1.55 g, 10.9 mmol) was added and the reaction was stirred overnight. The KHMDS/MeI addition was repeated in the morning, and after stirring for several hours the mixture was quenched with water and extracted twice with ethyl acetate. The extracts were washed successively with water and brine, dried over sodium sulfate and concentrated. Silica gel chromatography (3:1 hexanes/EtOAc) gave 356 mg (31%) of the title compound as a yellow oil.

Preparation 26

6-Methoxy-1,3,3-trimethyl-2-oxo-1,2,3,4-tetrahydro-quinoline-7-carbaldehyde

To 6-Methoxy-1,3,3-trimethyl-3,4-dihydro-1H-quinolin-2-one (350 mg, 1.50 mmol) in 20 mL of $CH_2Cl_2$ was added $TiCl_4$ (1.0 M in $CH_2Cl_2$; 15 mL, 15 mmol) and α,α-dichloromethyl methyl ether (862 mg, 7.5 mmol). After stirring at room temperature overnight, the reaction was quenched with water and extracted with $CH_2Cl_2$. The combined organic extracts were washed successively with satd $NaHCO_3$, water, and brine, dried over $Na_2SO_4$ and concentrated. Silica gel chromatography (1:1 hexanes/EtOAc) provided 162 mg (43%) of a colorless oil.

Example 11 Deleted

Example 12

(2S,3S)-6-Methoxy-1,3,3-trimethyl-7-[(2-phenyl-piperidin-3-ylamino)-methyl]-3,4-dihydro-1H-quinolin-2-one To 6-Methoxy-1,3,3-trimethyl-2-oxo-1,2,3,4-tetrahydro-quinoline-7-carbaldehyde (150 mg, 0.6 mmol) in 15 mL of toluene and 2 mL of MeOH was added triethylamine (134 mg, 1.32 mmol) and (2S,3S)-3-amino-2-phenylpiperidine dihydrochloride (150 mg, 0.60 mmol). After heating at reflux for 24 hours and concentrating, the residue was dissolved in $CH_2Cl_2$ and treated with sodium triacetoxyborohydride (200 mg). The reaction was stirred at room temperature overnight and quenched with satd $NaHCO_3$. The aqueous portion was extracted with $CH_2Cl_2$, and the combined organic phases were washed with water and brine, dried over $NaHCO_3$ and concentrated. Silica gel chromatography (90:9:1 EtOAc/MeOH/$NH_4OH$) gave 52 mg (23%) of a colorless oil. Treatment with excess ethereal HCl and concentration gave 67 mg of the dihydrochloride salt as a white solid.

Example 13

5-[{(2S,3S)-1-Isopropyl-2-phenyl-piperidin-3-ylamino}-methyl]-6-methoxy-1,3,3-trimethyl-1,3-dihydro-indol-2-one To 6-Methoxy-1,3,3-trimethyl-5-[{(2S,3S)-2-phenyl-piperidin-3-ylamino)-methyl]-1,3-dihydro-indol-2-one (102 mg, 0.260 mmol) in 3 mL of $CH_3CN$ was added triethylamine (108 mg, 1.04 mmol) and isopropyliodide (87 mg, 0.52 mmol). The mixture was heated to 60° C. overnight, and then was diluted with $CH_2Cl_2$ and washed with satd $NaHCO_3$. The organic portion was dried over $MgSO_4$, concentrated and chromatographed (5:95 MeOH/EtOAc) to give a pale yellow oil. Mass spectrum m/e calcd for M+H=436.3. Found 436.3. Concentration from excess HCl in ether gave the dihydrochloride salt as a white solid.

Example 14

5-[{(2S,3S)-1-Methyl-2-phenyl-piperidin-3-ylamino}-methyl]-6-methoxy-1,3,3-trimethyl-1,3-dihydro-indol-2-one To 6-Methoxy-1,3,3-trimethyl-5-[{(2S,3S)-2-phenyl-piperidin-3-ylamino)-methyl]-1,3-dihydro-indol-2-one (102 mg, 0.26 mmol) and triethylamine (150 mg, 1.04 mmol) in 3 mL of acetonitrile was added methyl iodide. The solution was stirred for 48 h, and was then partitioned between satd NaHCO$_3$ and CH$_2$Cl$_2$. The organic portion was washed with brine, dried with Na$_2$SO$_4$ and concentrated. Chromatography (5:95 MeOH/EtOAc) gave the tile compound as a pale yellow oil. Mass spectrum m/e calcd for M+H=408.2. Found 408.2. The solid dihydrochloride salt was generated by treatment with excess HCl in ether followed by concentration in vacuo [mp>250° C. (dec)].

Example 15

(2S,3S)-6-Methoxy-1-methyl-5-[(2-phenyl-piperidin-3-ylamino)-methyl]-1,3-dihydro-indol-2-one To a slurry of added (2S,3S)-2-Phenyl-piperidin-3-ylamine dimalonate (1.26 g, 2.6 mmol) and 6-Methoxy-1-methyl-2-oxo-2,3-dihydro-1H-indole-5-carbaldehyde in 15 mL CH$_2$Cl$_2$ was added sodium triacetoxyborohydride (1.01 g, 4.8 mmol) in one portion. After 30 minutes the mixture was diluted with 10 mL of water and then basified with 3 N NaOH to a pH of ca. 11. The layers were separated and the aqueous portion was extracted once with CH$_2$Cl$_2$. The combined organic material was washed successively with 1 N NaOH and water, and was then dried with Na$_2$SO$_4$ and concentrated. Silica gel chromatography (90:9:1 EtOAc/MeOH/NH$_4$OH) gave 127 mg (14%) of the title compound as a white solid. Mass spectrum m/e calcd for M+H=366.2. Found 366.0. The solid dihydrochloride salt was generated by treatment with excess HCl in ether followed by concentration in vacuo.

Example 16 Deleted

Example 17

(3S)- and (3R)-6-Methoxy-1,3-dimethyl-5-{[(2S,3S)-2-phenyl-piperidin-3-ylamino]-methyl}1,3-dihydro-indol-2-one (A mixture of two diastereomers.) To (+/−)-6-Methoxy-1,3-dimethyl-2-oxo-2,3-dihydro-1H-indole-5-carbaldehyde (220 mg, 1.0 mmol) and (2S,3S)-2-phenyl-piperidin-3-ylamine dihydrochloride (249 mg, 1.0 mmol) in toluene (20 mL) and methanol (2 mL) was added triethylamine (222 mg, 2.2 mmol). The solution was heated to reflux with azeotropic water removeal for 72 hours. The resultant mixture was concentrated, and the residue was suspended in 10 mL of CH$_2$Cl$_2$. Sodium triacetoxyborohydride (1.8 mmol, 1.8 mL of a 1 M solution in CH$_2$Cl$_2$) was added and the mixture was stirred at room temperature for 30 minutes. The mixture was then quenched with saturated NaHCO$_3$ and extracted twice with CH$_2$Cl$_2$. The combined organic material was washed with brine, dried over NaHCO$_3$ and concentrated. Silica gel chromatography (90:9:1 EtOAc/MeOH/NH$_4$OH) gave 109 mg (29%) of a 1:1 mixture of title compounds as a pale yellow oil. The solid dihydrochloride salt was generated by treatment with excess HCl in ether followed by concentration in vacuo.

Example 18

6-Methoxy-1,3,3-trimethyl-5-{[(2S,3S)-1-(5-oxo-4,5-dihydro-1H-[1,2,4]triazol-3-ylmethyl)-2-phenyl-piperidin-3-ylamino]-methyl}-1,3-dihydro-indol-2-one To (2S,3S)-5-Methoxy-1,3,3-trimethyl-6-[(2-phenyl-piperidin-3-ylamino)-methyl]-1,3-dihydro-indol-2-one and N'-(2-Chloro-1-imino-ethyl)-hydrazinecarboxylic acid methyl ester in 5 mL of DMF was added K$_2$CO$_3$ (280 mg, 2.0 mmol). The mixture was heated to 70° C. for 18 h, and then the temperature was raised to 140° C. to achieve ring closure. The mixture was partitioned between EtOAc and water. The aqueous layer was extracted with an additional portion of EtOAc, and the combined orgainc layers were washed with brine, dried over Na$_2$SO$_4$ and concentrated. Silica gel chromatography (EtOAc/MeOH gave 27 mg (9%) of an off-white solid [mp>250° C. (dec)]. Mass spectrum m/e calcd for M+H=491.5. Found 491.5.

Example 19

6-Methoxy-1-methyl-7-{[1-(5-oxo-2,5-dihydro-1H-[1,2,4]triazol-3-ylmethyl)-2-phenyl-piperidin-3-ylamino]-methyl}-3,4-dihydro-1H-quinolin-2-one Similarly prepared:
NMR (CDCl$_3$) δ 1.50 (m, 2H), 1.9–2.2 (m, 4H), 2.50 (m, 2H), 2.6–2.8 (m, 4H), 3.05 (m, 1H), 3.15 (s, 3H), 3.22 (s, 3H), 3.35–3.5 (m, 2H), 3.6–3.8 (m, 2H), 6.4 (s, 1H), 6.7 (s, 1H), 7.25 (m, 2H), 7 38 (m, 3H), 7 4–7 8 (br s, 2H). Mass spectrum M/e=477 1 (p+1) TLC (10/1 CHCl$_3$/CH$_3$OH Rf=0.7.

Preparation 27

(+/−)-3-(3-Bromo-butyl)-1-(tert-butyl-dimethyl-silanyl)-4-phenyl-azetidin-2-one

To diethylamine (4.32 g, 59.0 mmol) in 22 mL of THF at 0° C. was added nBuLi (2.5 M in hexanes; 50.6 mmol, 20.2 mL). After 15 minutes the solution was added via cannula to a −50° C. solution of 1-(tert-Butyl-dimethyl-silanyl)-4-phenyl-azetidin-2-one (11.0 g, 42.2 mmol) in 110 mL of THF. After stirring for 20 minutes, 1,3-dibromobutane was added and the solution was stirred for 1 hour. Saturated aqueous NH$_4$Cl was added and the mixture was warmed to room temperature and extracted once with ether. The extract was dried with MgSO$_4$, concentrated and chromatographed (9:1 hexanes/EtOAc) to give 11.4 g (68%) of the title compound as a pale yellow oil. $^1$H NMR (400 MHz, CDCl$_3$) δ comp, 10H), 4.21 (d, J=2.5 Hz, 1H), 4.16 (d, J=2.5 Hz, 1H), 4.08 (m, 1H), 3.02 (m, 1H), 1.80–2.10 (comp, 4H), 1.67 (d, J=6.6 Hz, 3H), 0.90 (s, 9H), 0.18 (s, 3H), −0.22 (s, 3H); Mass spectrum m/e calcd for M+H=396.2. Found 396.0 (base), 316.

Preparation 28

(2R,5R)-, (2R,5S), (2S,5R)- and (2S,5S)-2-(Aminophenyl-methyl)-5-bromo-hexanoic acid methyl ester (A mixture of two diastereomers and their enantiomers.) 3-(3-Bromo-butyl)-1-(tert-butyl-dimethyl-silanyl)-4-phenyl-azetidin-2-one was refluxed in 75 mL of 5% sulfuric acid in methanol for 24 hours. The acid was neutralized with solid NaHCO$_3$ and the mixture was concentrated in vacuo to give 2.6 g of the title compound as a pale yellow oil which was used in the next step without purification.

Preparation 29

(2S,3S,6R), (2R,3R,6S), (2S,3S,6S), and (2R,3R, 6R)-6-Methyl-2-phenyl-piperidine-3-carboxylic acid methyl ester (A mixture of two diastereomers and their enantiomers.) To 2-(amino-phenyl-methyl)-5-bromo-hexanoic acid methyl ester in DMF was added NaI and NaHCO$_3$ The resultant mixture was stirred in DMF at 100° C. for 1 hour, and then was cooled to room temperature and partitioned between ether and water. The organic layer was washed with brine, dried with MgSO$_4$, filtered and concentrated. Silica gel chromatography (97:3 CHCl$_3$/MeOH) gave 1.63 g (90%) of the the product as an inseparable mixture of two diastereomers. $^1$H NMR (400 MHz, CDCl$_3$) δ 7.17–7.32 (comp, 10H, both diastereomers), 4.47 (d, J=5.0 Hz, 1H), 3.97 (d, J=3.5 Hz, 1H), 3.45 (s, 3H), 3.38 (s, 3H), 3.02–3.08 (m, 1H), 2.92–2.99 (m, 1H), 2.75–2.85 (comp, 2H), 2.0–2.2 (comp, 2H), 1.80–2.00 (comp, 3H), 1.40–1.60 (comp, 2H), 1.20–1.30 (m, 1H), 1.20 (d, J=6.4 Hz, 3H), 1.07 (d, J=6.4 Hz, 3H); Mass spectrum m/e calcd. for M+H=234.1. Found 234.2.

Preparation 30

(2S,3S,6R), (2R,3R,6S), (2S,3S,6S), and (2R,3R, 6R)-6-Methyl-2-phenyl-piperidine-1,3-dicarboxylic acid 1-benzyl ester 3-methyl ester (A mixture of two diastereomers and their enantiomers.) To 6-Methyl-2-phenyl-piperidine-3-carboxylic acid methyl ester (1.63 g, 7.0 mmol) in 20 mL of 10% aqueous NaHCO$_3$ at 0° C. was added benzylchloroformate (1.25 g, 7.35 mmol). The mixture was stirred for 45 minutes at 0° C., and was then warmed to room temperature and stirred for an additional 30 minutes. The mixture was partitioned with ether, and the organic phase was dried over MgSO$_4$ and concentrated. Silica gel chromatography (9:1 hexanes/EtOAc) gave 1.62 g (63%) of the title compound as a colorless oil. $^1$H NMR (400 MHz, CDCl$_3$) δ 7.1–7.4 (comp, 20H, both diastereomers), 6.1 (br, 1H, minor diastereomer), 5.74 (d, J=3.6, 1H, major diastereomer), 5.05–5.26 (comp, 8H, both diastereomers), 4.67 (d, J=6.0 Hz, 1H, major diastereomer), 4.57 (m, 1H, minor diastereomer), 4.10–4.20 (m, 2H, major diastereomer), 3.70 (s, 3H, major diastereomer), 3.59 (s, 3H, major diastereomer), 3.29 (app dt, J=4.5, 9.4 Hz, 1H, major diastereomer), 2.85 (m, 1H, minor diastereomer), 2.27 (app dq, J=4.1, 13.7 Hz, minor diastereomer), 1.85–2.15 (comp, 4H, both diastereomers), 1.55–1.80 (comp, 3H, both diastereomers), 1.34 (d, J=6.8 Hz, 3H, major diastereomer), 0.37 (d, J=7.1 Hz, 3H, minor diastereomer); $^{13}$C NMR (100 MHz) δ 172.8, 140.0, 136.7, 128.5, 128.4, 128.2, 128.0, 127.8, 127.7, 127.6, 127.2, 127.1, 127.0, 126.9, 126.4, 67.5, 66.9, 65.3, 56.4, 52.0, 47.5, 46.6, 44.3, 42.6, 30.2, 25.6, 22.1, 19.8, 17.2, 16.0; mass spectrum m/e calcd. for M+H=368.2. Found 368.2, 324.2 (base).

Preparation 31

(2S,3S,6R), (2R,3R,6S), (2S,3S,6S), and (2R,3R, 6R)-3-Carbamoyl-6-methyl-2-phenyl-piperidine-1-carboxylic acid benzyl ester (A mixture of two diastereomers and their enantiomers.). To ammonium chloride (1.18 g, 22.1 mmol) in 20 mL of benzene at 0° C. was added trimethylaluminum (22.1 mmol, 11.0 mL of a 2.0 M solution in toluene) The resultant mixture was stirred for 30 minutes at 0° C., and warmed to room temperature for an additional 30 minutes. To the mixture was then added 6-Methyl-2-phenyl-piperidine-1,3-dicarboxylic acid 1-benzyl ester 3-methyl ester as a solution in 20 mL of benzene, and the resultant mixture was heated to reflux for 6 hours. The reaction was then cooled to 0° C. and quenched carefully with 10 mL of 1 M HCl. The mixture was stirred for 30 minutes, filtered through celite, and the filter pad was rinsed with CH$_2$Cl$_2$. The filtrate was concentrated and the residue was dissolved in EtOAc, washed with saturated NaHCO$_3$, dried over MgSO$_4$ and concentrated. Silica gel chromatography (CHCl$_3$ to eluted nonpolar material followed by 95:5 CHCl$_3$/MeOH to elute the product) gave 560 mg (36%) of a mixture of the title compounds as a white foam. $^1$H NMR (400 MHz, CDCl$_3$) δ 7.10–7.42 (comp, 20H, both diastereomers), 5.99 (d, J=5.1 Hz, 1H), 5.68–5.90 (br, 2H, both diastereomers), 5.67 (d, J=4.3 Hz, 1H), 5.00–5.26 (comp, 4H, both diastereomers), 4.53 (m, 1H), 4.17 (br, 1H), 3.15 (m, 1H), 2.75 (m, 1H), 2.28 (app dq, J=4.1, 13.2 Hz, 1H), 1.9–2.08 (m, 2H), 1.50–1.90 (comp, 5H), 1.34 (d, J=6.6 Hz, 3H), 0.68 (d, J=7.1 Hz, 3H); $^{13}$C NMR (100 MHz) δ 174.2, 128.6, 128.4, 128.3, 128.2, 128.1, 127.8, 127.6, 127.2, 127.1, 126.7, 67.6, 67.1, 56.9, 52.8, 47.4, 46.6, 30.2, 25.5, 22.3, 19.8, 16.3; Mass spectrum m/e calcd. for M+H=353.2. Found 353.0, 309.1, 219.0 (base).

Preparation 32

(2S,3S,6R), (2R,3R,6S), (2S,3S,6S), and (2R,3R, 6R)-3-Amino-6-methyl-2-phenyl-piperidine-1-carboxylic acid benzyl ester (A mixture of two diastereomers and their enantiomers.) 3-Carbamoyl-6-methyl-2-phenyl-piperidine-1-carboxylic acid benzyl ester (525 mg, 1.49 mmol) and lead (IV) acetate (2.18 g, 4.92 mmol) were refluxed in tert-butyl alcohol for 19 h. The reaction mixture was poured into a mixture of ice cold 1 M HCL and EtOAc and stirred for 45 minutes. The mixture was then filtered through celite and the organic layer was washed with satd NaHCO$_3$, dried with MgSO$_4$ and concentrated to give 598 mg of a yellow solid. The solid was dissolved in CHCl$_3$ and 2M HCl in ether and was then stirred for 2 hours. The mixture was concentrated and the residue was partitioned between CHCl$_3$ and saturated NaHCO$_3$. The organic phase was dried over MgSO$_4$, filtered and concentrated. Silica gel chromatography (3:1 EtOAc/hexanes) gave 169 mg (35%) of a mixture of the title compounds as a colorless oil. $^1$H NMR (400 MHz, CDCl$_3$) δ 7.1–7.6 (comp, 20H, both diastereomers), 5.36 (d, J=6.6 Hz, 1H), 4.90–5.19 (comp, 5H), 4.40–4.50 (m, 1H), 4.32–4.40 (m, 1H), 3.58–3.61 (m, 1H), 3.19–3.22 (m, 1H) 2.20–2.30 (m, 1H), 1.80–2.10 (comp, 3H, both diastereomers), 1.60–1.75 (m, 2H), 1.35 (d, J=6.6 Hz, 3H), 1.07 (d, J=7.1 Hz, 3H). $^{13}$C NMR (100 MHz) δ 156.0, 155.7, 139.8, 139.0, 136.7, 136.7, 129.4, 128.4, 128.2, 128.1, 128.07, 127.9, 127.83, 127.81, 127.7, 127.6, 127.4, 127.1, 127.0, 77.4, 77.2, 76.9, 67.2, 66.7, 62.2, 59.2, 51.4, 47.7, 46.5, 46.0, 29.8, 25.4, 25.3, 24.0, 23.2, 21.1.

Preparation 33

3-[(6-Methoxy-1-methyl-2-oxo-1,2,3,4-tetrahydro-quinolin-7-ylmethyl)-amino]-6-methyl-2-phenyl-piperidine-1-carboxylic acid benzyl ester To 3-Amino-6-methyl-2-phenyl-piperidine-1-carboxylic acid benzyl ester and 6-Methoxy-1-methyl-2-oxo-1,2,3,4-tetrahydro-quinoline-7-carbaldehyde in 5 mL of methanol was added NaBH$_3$CN (3.13 mmol, 3.13 mL of a 1.0 M solution in THF) and 250 µl of acetic acid. The mixture was heated to 50° C. for 3 days. The mixture was diluted with CH$_2$Cl$_2$, washed with saturated NaHCO$_3$, dried over MgSO$_4$ and concentrated. Silica gel chromatography (1:1 hexanes/EtOAc) gave 315 mg a white solid consisting of an inseparable mixture of the title compound and the reduced aldehyde. The mixture was used in the next step without further purification.

Examples 20–23

6-Methoxy-1-methyl-7-[(2R,3R,6R)-(6-methyl-2-phenyl-piperidin-3-ylamino)-methyl]-3,4-dihydro-1H-quinolin-2-one, 6-Methoxy-1-methyl-7-[(2S,3S,6S)-(6-methyl-2-phenyl-piperidin-3-ylamino)-methyl]-3,4-dihydro-1H-quinolin-2-one, 6-Methoxy-1-methyl-7-[(2S,3S,6R)-(6-methyl-2-phenyl-piperidin-3-ylamino)-methyl]-3,4-dihydro-1H-quinolin-2-one, and 6-Methoxy-1-methyl-7-[(2R,3R,6S)-(6-methyl-2-phenyl-piperidin-3-ylamino)-methyl]-3,4-dihydro-1H-quinolin-2-one To 3-[(6-Methoxy-1-methyl-2-oxo-1,2,3,4-tetrahydro-quinolin-7-ylmethyl)-amino]-6-methyl-2-phenyl-piperidine-1-carboxylic acid benzyl ester (275 mg, 0.52 mmol) and 10% Pd-C (25 mg) in 10 mL of EtOH was added ammonium formate (164 mg, 2.60 mmol). The mixture was refluxed for 2 hours, and was then cooled to room temperature and filtered through celite. The filtrate was concentrated and the residue was chromatographed (9:1:0.05 EtOAc/MeOH/satdNH$_4$OH) to give 48 mg (23%) of the 2,5-cis isomer, and 88 mg (43%) of the 2,5-trans isomer of the title compounds as racemates. Chiral resolution of each sample by HPLC (chiralcel OD 2.1 cm×25 cm column, 90:10:0.025 hexanes/isopropanol/diethylamine) gave 4.3 mg of the (2S,3S,6R)-isomer, 20 mg of the (2S,3S,6S)-isomer, 25 mg of the (2R,3R,6R)-isomer, and 4.0 mg of the (2R,3R,6S,)-isomer.

(2R,3R,6R)- and (2S,3S,6S)-enantiomers: $^1$H NMR (400 MHz, CDCl$_3$) δ 7.2–7.4 (comp, 5H), 6.64 (s, 1H), 6.49 (s, 1H), 4.23 (d, 1H, J=3 2 Hz), 3.62 (d, 1H, J=13.8 Hz), 3.49 (s, 3H), 3.45 (d, 1H, J=13.8 Hz), 3.36–3.40 (m, 1H), 3.19 (s, 3H), 2.84 (m, 1H), 2.78 (m, 1H), 2.56 (m, 1H), 2.01–2.09 (m, 1H), 1.81–1.90 (m, 2H), 1.64–1.80 (m, 2H), 1.20–1.24 (m, 1H), 1.17 (d, 3H, J=6.8 Hz). $^{13}$C NMR (100 MHz) δ 170.0, 153.0, 142.6, 133.5, 128.2, 127.3, 126.7, 125.3, 116.3, 109.9, 57.0, 55.5, 54.4, 46.8, 46.1, 31.8, 29.6, 26.2, 25.5, 24.0, 19.0.

(2S,3S,6R)- and (2R,3R,6S)-enantiomers: $^{13}$C NMR (100 MHz) δ 170.0, 153.0, 142.7, 133.4, 128.1, 127.3, 126.6, 125.1, 116.2, 125.1, 116.2, 109.8, 64.5, 55.4, 54.4, 53.4, 45.8, 31.8, 29.6, 28.3, 28.2, 25.5, 22.9; $^1$H NMR (400 MHz, CDCl$_3$) δ 7.18–7.32 (m, 7H), 6.62 (s, 1H), 6.48 (s, 1H), 3.92 (s, 1H), 3.60 (d, J=14.0 Hz, 1H), 3.48 s, 3H), 3.38 (d, J=14.0 Hz, 1H), 3.16 (s, 3H), 2.70–2.83 (comp, 4H), 2.50–2.60 (m, 2H), 2.08 (m, 1H), 1.7 (br, 2H), 1.58 (m, 1H), 1.40–1.53 (comp, 2H), 1.14 (d, J=6.4 Hz, 3H).

Example 24 (Procedure A)

(2S,3S)-6-Methoxy-1-methyl-7-{[1-(5-methyl-3H-imidazol-4-ylmethyl)-2-phenyl-piperidin-3-ylamino]-methyl}-3,4-dihydro-1H-quinolin-2-one To 6-Methoxy-1-methyl-7-[(2S,3S)-(2-phenyl-piperidin-3-ylamino)-methyl]-3,4-dihydro-1H-quinolin-2-one (100 mg, 0.26 mmol), 4-methyl-5-imidazolecarboxaldehyde (116 mg, 1.06 mmol), and 5 drops acetic acid in 2 mL of methanol at room temperature was added 1.58 mL (1.58 mmol) of 1.0 M sodium cyanoborohydride in THF. The resultant mixture was stirred for 1 hour at room temperature and then at 50° C. for 3 days. The reaction was then diluted with methylene chloride and washed 1× with sat'd. NaHCO$_3$, dried over MgSO$_4$, filtered, and concentrated. Silica gel chroatography (9:1 ethyl acetate/methanol) gave 83 mg (66%) of the title compound, a white foam. R$_f$=0.05 (9:1 ethyl acetate/methanol). MS (M+H)$^+$=474.2; $^1$H NMR (400 MHz, CDCl$_3$): δ 1.35–1.45 (m, 2H), 1.85–1.95 (bd, 1H), 1.99 (s, 3H), 1.99–2.15 (m, 2H), 2.45–2.55 (t, J=7.4 Hz, 2H), 2.62–2.65 (bs, 1H), 2.70–2.80 (t, J=7.4 Hz, 2H), 2.90–2.95 (d, J=13.9 Hz, 1H), 3.00–3.05 (d, J=10.7 Hz, 1H), 3.10 (s, 3H), 3.35–3.40 (m, 2H), 3.47 (s, 3H), 3.60–3.65 (d, J=14.3 Hz, 2H), 6.46 (s, 1H), 6.60 (s, 1H), 7.15–7.30 (m, 3H), 7.35–7.45 (m, 2H); $^{13}$C NMR (100 MHz, CDCl$_3$): δ 11.4, 20.1, 25.5, 27.4, 29.6, 31.8, 45.3, 50.3, 53.7, 55.5, 56.2, 71.8, 109.8, 116.1, 125.2, 127.1, 128.2, 128.8, 133.2, 133.4, 141.2, 152.9, 170.0. The dihydrochloride salt was prepared by the addition of 2 M HCl in ether to a solution of the product in ethyl acetate. Concentration gave a white solid (Mp=225–229° C.).

Example 25

7-{[1-(3H-Imidazol-4-ylmethyl)-(2S,3S)-2-phenyl-piperidin-3-ylamino]-methyl}-6-methoxy-1-methyl-3,4-dihydro-1H-quinolin-2-one This compound was prepared according to Procedure A, substituting 4(5)-imidazolecarboxaldehyde for 4-methyl-5-imidazolecarboxaldehyde. Silica gel chromatography (9:1 ethyl acetate/methanol) gave 65 mg (54%) of the title compound, a white foam. R$_f$=0.10 (9:1 ethyl acetate/methanol). MS (M+H)$^+$=460.2; $^1$H NMR (400 MHz, CDCl$_3$): δ 1.40–1.50 (m, 2H), 1.85–1.95 (m, 1H), 1.99–2.15 (m, 3H), 2.50–2.55 (t, J=7.3 Hz, 2H), 2.62–2.65 (bs, 1H), 2.70–2.80 (t, J=7.3 Hz, 2H), 3.00–3.05 (d, J=14.3 Hz, 1H), 3.13 (s, 3H), 3.35–3.45 (m, 2H), 3.42 (s, 3H), 3.60–3.75 (dd, J=20.1 Hz, 14.3 Hz, 2H), 6.46 (s, 1H), 6.57 (s, 1H), 6.68 (s, 1H), 7.20–7.30 (m, 3H), 7.35–7.40 (m, 2H), 7.42 (s, 1H); $^{13}$C NMR (100 MHz, CDCl$_3$): δ 20.0, 25.5, 27.2, 29.6, 31.7, 45.7, 51.9, 53.8, 55.4, 56.3, 109.9, 116.3, 125.8, 126.2, 127.1, 128.3, 128.6, 133.8, 134.8, 141.0, 153.0, 170.1. The dihydrochloride salt was prepared by the addition of 2 M HCl in ether to a solution of the product in ethyl acetate. Concentration gave a white solid.

Preparation 34

3,5-Dimethyl-3H-imidazole-4-carbaldehyde and 1,5-Dimethyl-1H-imidazole-4-carbaldehyde To 5-Methyl-3H-imidazole-4-carbaldehyde (5.00 g, 45.4 mmol) in 50 mL of THF was added DBU (6.91 g, 45.4 mmol) and MeI (6.45 g, 45.4 mmol). The solution was stirred overnight, and then was partitioned between 100 mL of EtOAc and 100 mL of water. The aqueous portion was extracted with 2-butanol (3×100 mL) and the combined extracts were washed with brine, dried with $Na_2SO_4$ and concentrated. Chromatography (1:99 MeOH/$CHCl_3$) gave 1.03 g (23%) of 44015-106-1 ($R_f$=0.58, 12:78 MeOH/$CH_2Cl_2$) and 1.26 g (18%) of 44015-106-2 ($R_f$=0.5, 12:78 MeOH/$CH_2Cl_2$).

Example 26

7-{[1-(1,5-Dimethyl-1H-imidzol-4-ylmethyl)-(2S,3S)-2-phenyl-piperidin-3-ylamino]-methyl}-6-methoxy-1-methyl-3,4-dihydro-1H-quinolin-2-one This compound was prepared according to Procedure A, substituting 1,5-dimethyl-1H-imidazole-4-carbaldehyde; synthesis described above) for 4-methyl-5-imidazolecarboxaldehyde. Silica gel chromatography (9:1 ethyl acetate/methanol) gave 90 mg (70%) of the title compound, a white foam. $R_f$=0.09 (9:1 ethyl acetate/methanol). MS $(M+H)^+$=488.2; $^1$H NMR (400 MHz, $CDCl_3$): δ 1.37–1.46 (m, 2H), 1.87 (s, 3H), 1.88–1.92 (m, 1H), 1.98–2.03 (m, 1H), 2.22–2.28 (t, J=11.5 Hz, 1H), 2.50–2.53 (t, J=7.3 Hz, 2H), 2.68 (s, 1H), 2.72–2.75 (t, J=7.3 Hz, 2H), 2.89–2.92 (d, J=6.9 Hz, 1H), 3.09 (s, 3H), 3.20–3.22 (d, J=10.6 Hz, 1H), 3.33–3.38 (m, 2H), 3.40 (s, 3H), 3.52 (s, 3H), 3.59–3.62 (d, J=14.1 Hz, 2H), 6.46 (s, 1H), 6.66 (s, 1H), 7.17–7.29 (m, 4H), 7.43–7.45 (m, 2H). $^{13}$C NMR (100 MHz, $CDCl_3$): δ 8.1, 20.0, 25.4, 27.5, 29.5, 31.2, 31.7, 44.7, 52.2, 53.6, 55.4, 56.4, 71.9, 109.7, 115.8, 124.7, 126.6, 127.7, 129.0, 133.4, 135.6, 141.6, 152.7, 169.9. The dihydrochloride salt was prepared by the addition of 2 M HCl in ether to a solution of the product in ethyl acetate. Concentration gave a white solid.

Example 27

6-Methoxy-1-methyl-7-[(2S,3S)-(2-phenyl-1-propyl-piperidin-3-ylamino)-methyl]-3,4-dihydro-1H-quinolin-2-one 2-Imidazolidinethione (10 g, 97.89 mmol) and methyl iodide (6.70 mL, 107.67 mmol) were stirred in 20 mL of absolute ethanol at reflux for 2 hours. The reaction was cooled and an equal volume of diethyl ether was added. The suspension was filtered to give 22.9 g (96%) of 2-methylsulfanyl-4,5-dihydro-1H-imidazole hydrogen iodide as an off-white solid that was used in the next reaction. 6-Methoxy-1-methyl-7-[(2S,3S)-(2-phenyl-piperidin-3-ylamino)-methyl]-3,4-dihydro-1H-quinolin-2-one (500 mg, 1.32 mmol) and 2-methylsulfanyl-4,5-dihydro-1H-imidazole hydrogen iodide (402 mg, 1.65 mmol) were stirred in 5 mL of n-propanol at reflux for 2 days. The reaction was diluted with ethyl acetate, washed 1× with satd. $K_2CO_3$, dried over $MgSO_4$, filtered, and concentrated. Silica gel chromatography using (95:5 ethyl acetate/methanol) gave 123 mg (21%) of the title compound, a pale yellow oil. $R_f$=0.12 (9:1 ethyl acetate/methanol). $^1$H NMR (400 MHz, $CDCl_3$): δ 0.67–0.70 (t, J=7.4 Hz, 3H), 1.36–1.49 (m, 4H), 1.72–1.79 (m, 1H), 1.92–2.04 (m, 3H), 2.39–2.43 (m, 1H), 2.51–2.55 (t, J=7.3 Hz, 2H), 2.63 (s, 1H), 2.73–2.78 (t, J=7.3 Hz, 2H), 3.12 (s, 3H), 3.16–3.19 (m, 1H), 3.30 (s, 1H), 3.34–3.38 (d, J=14.4 Hz, 1H), 3.49 (s, 3H), 3.60–3.64 (d, J=14.4 Hz, 1H), 6.46 (s, 1H), 6.60 (s, 1H), 7.15–7.32 (m, 5H). $^{13}$C NMR (100 MHz, $CDCl_3$): δ 11.8, 19.3, 20.3, 25.4, 27.5, 29.5, 31.7, 45.1, 53.4, 55.4, 56.2, 57.9, 72.1, 109.7, 115.9, 124.8, 126.5, 127.7, 128.7, 133.3, 141.7, 152.8, 169.9. The dihydrochloride salt was prepared by the addition of 2 M HCl in ether to a solution of the product in ethyl acetate. Concentration gave a white solid.

Example 28

7-[(2S,3S)-(1-Benzooxazol-2-yl-2-phenyl-piperidin-3-ylamino)-methyl]-6-methoxy-1-methyl-3,4-dihydro-1H-quinolin-2-one To 6-Methoxy-1-methyl-7-[(2S,3S)-(2-phenyl-piperidin-3-ylamino)-methyl]-3,4-dihydro-1H-quinolin-2-one dihydrochloride (50 mg, 0.11 mmol), freshly ground potassium carbonate (61 mg, 0.44 mmol), and catalytic KI in 3 mL of 1,4-dioxane was added 2-chlorobenzoxazole (126 mg, 0.11 mmol). After heating at reflux for 5 days, the reaction was cooled and partitioned between ethyl acetate and water. The organic portion was separated, dried over $MgSO_4$, filtered, and concentrated. Silica gel chromatography (99:1 chloroform/methanol followed by 3:1 ethyl acetate/hexane) gave 31 mg (56%) of the title compound as a light brown oil. MS $(M+H)^+$=497.2; $^1$H NMR (400 MHz, $CDCl_3$): δ 1.75–1.85 (m, 1H), 1.85–1.95 (m, 3H), 2.55–2.60 (t, J=7 Hz, 2H), 2.80–2.85 (t, J=7 Hz, 2H), 3.15–3.25 (m, 1H), 3.30 (s, 3H), 3.30–3.40 (t, J=13 Hz, 1H), 3.71 (s, 3H), 3.82–3.92 (q, J=13.5 Hz, 2H), 4.16–4.21 (dd, J=13 Hz, 3.8 Hz, 1H), 5.74–5.76 (d, J=5.6 Hz, 1H), 6.62 (s, 1H), 6.90 (s, 1H), 6.95–6.99 (t, J=8.5 Hz, 1H), 7.10–7.14 (t, J=8.5 Hz, 1H), 7.19–7.21 (d, J=7.9 Hz, 1H), 7.24–7.28 (m, 4H), 7.68–7.70 (d, J=7.5 Hz, 2H); $^{13}$C NMR (100 MHz, $CDCl_3$): δ 24.2, 25.5, 26.8, 29.6, 31.7, 41.4, 46.0, 55.5, 56.9, 58.5, 108.5, 110.2, 116.0, 116.4, 120.3, 123.8, 125.7, 126.8, 127.5, 128.3, 129.3, 133.7, 137.7, 143.2, 148.5, 152.9, 162.3, 169.9. The dihydrochloride salt was prepared by the addition of 2 M HCl in ether to a solution of the product in ethyl acetate. Concentration gave a white solid (Mp=181–183° C.).

Example 29

6-Methoxy-1-methyl-7-{[1-((2S)-5-oxo-pyrrolidin-2-ylmethyl)-(2S,3S)-2-phenyl-piperidin-3-ylamino]-methyl}-3,4-dihydro-1H-quinolin-2-one To of (S)-(+)-5-(Hydroxymethyl)-2-pyrrolidinone (1.0 g 8.69 mmol) and triethylamine (1.21 ml, 8.69 mmol) in 50 mL of methylene chloride was added 1.66 g (8.69 mmol) of p-toluenesulfonyl chloride. The resultant solution was stirred at room temperature for 3 days. The organic solution was washed 1× with water, dried over $MgSO_4$, filtered, and concentrated. Silica gel chromatography (95:5 ethyl acetate/methanol) gave 1.65 g (71%) of toluene-4-sulfonic acid 5-oxo-pyrrolidin-2-ylmethyl ester as a white powder that was used in the next step. $R_f$=0.29 (95:5 ethyl acetate/methanol). $^1$H NMR (400 MHz, $CDCl_3$): δ 1.65–1.80 (m, 1H), 2.15–2.35 (m, 3H), 2.42 (s, 3H), 3.80–3.90 (m, 2H), 3.95–4.05 (m, 1H), 6.53 (bs, 1H), 7.30–7.35 (d, J=8.4 Hz, 2H), 7.74–7.76 (d, J=8.4 Hz, 2H); $^{13}$C NMR (100 MHz, $CDCl_3$): δ 21.7, 22.8, 29.3, 52.6, 72.0, 127.9, 130.1, 132.4, 145.4, 178.0. To 150 mg (0.40 mmol) of 6-Methoxy-1-methyl-7-[(2S,3S)-(2-phenyl-piperidin-3-ylamino)-methyl]-3,4-dihydro-1H-quinolin-2-one, potassium carbonate (55 mg, 0.40 mmol), and catalytic KI in 4 mL of DMF was added toluene-4-sulfonic acid 5-oxo-pyrrolidin-2-ylmethyl ester (107 mg, 0.40 mmol) The suspension was heated to 60° C. for 16 hours. The reaction was diluted with methylene chloride and washed 3× with water, 2× with brine, dried over MgSO$_4$, filtered, and concentrated. Silica gel chromatography using (85:15 ethyl acetate/methanol) gave 19 mg (10%) of the title compound, a white foam. R$_f$=0.10 (85:15 ethyl acetate/methanol). MS (M+H)$^+$=477.2; $^1$H NMR (400 MHz, CDCl$_3$): δ 1.30–1.60 (m, 3H), 1.78–1.82 (dd, J=12.6, 3.0 Hz, 1H), 1.98–2.16 (m, 6H), 2.20–2.30 (m, 1H), 2.50–2.52 (dd, J=12.6, 11.0 Hz, 1H), 2.54–2.58 (t, J=7.4 Hz, 2H), 2.68 (bs, 1H), 2.76–2.80 (t, J=7.4 Hz, 2H), 3.14 (s, 3H), 3.25–3.29 (m, 1H), 3.30 (bs, 1H), 3.37–3.40 (d, J=13.9 Hz, 1H), 3.49 (s, 3H), 3.62–3.66 (d, J=13.9 Hz, 1H), 3.86–3.91 (m, 1H), 6.49 (s, 1H), 6.50–6.55 (bs, 1H), 6.60 (s, 1H), 7.20–7.30 (m, 5H); $^{13}$C NMR (100 MHz, CDCl$_3$): δ 20.1, 25.0, 25.5, 27.3, 29.6, 29.9, 31.8, 45.6, 50.8, 53.7, 55.5, 56.3, 61.1, 72.4, 109.9, 116.28, 127.1, 128.3, 128.9, 133.6, 140.6, 152.9, 170.0, 177.5. The dihydrochloride salt was prepared by the addition of 2 M HCl in ether to a solution of the product in ethyl acetate. Concentration gave a white solid (Mp=203–207° C.).

Example 30

6-Methoxy-1-methyl-7-{[1-((2R)-5-oxo-pyrrolidin-2-ylmethyl)-(2S,3S)-2-phenyl-piperidin-3-ylamino]-methyl}-3,4-dihydro-1H-quinolin-2-one To 1.0 g (8.69 mmol) of (R)-(−)-5-(Hydroxymethyl)-2-pyrrolidinone and triethylamine (2.42 ml, 17.37 mmol) in 80 mL of methylene chloride at 0° C. was added 1.01 mL (13.03 mmol) of methanesulfonyl chloride. The resultant solution was stirred at 0° C. for 1 hour. The solvent was removed. Silica gel chromatography using (10:1 ethyl acetate/methanol) gave 1.54 g (92%) of methanesulfonic acid 5-oxo-pyrrolidin-2-ylmethyl ester as an off-white solid that was used in the next step. R$_f$=0.21 (10:1 ethyl acetate/methanol). $^1$H NMR (400 MHz, CDCl$_3$): δ 1.82–1.88 (m, 1H), 2.25–2.40 (m, 3H), 3.06 (s, 3H), 3.98–4.02 (m, 1H), 4.05–4.09 (dd, J=10.2, 7.1 Hz 1H), 4.22–4.25 (dd, J=9.1, 3.7 Hz 1H), 6.96 (bs, 1H). To 150 mg (0.40 mmol) of 6-Methoxy-1-methyl-7-[(2S,3S)-(2-phenyl-piperidin-3-ylamino)-methyl]-3,4-dihydro-H-quinolin-2-one, potassium carbonate (55 mg, 0.40 mmol), and and catalytic KI in 5 mL of DMF was added methanesulfonic acid 5-oxo-pyrrolidin-2-ylmethyl ester (92 mg, 0.47 mmol) The suspension was heated to 70° C. for 16 hours. The reaction was diluted with methylene chloride and washed three times with water, twice with brine, dried over MgSO$_4$, filtered, and concentrated. Silica gel chromatography using (9:1 ethyl acetate/methanol) gave 30 mg (16%) of the title compound, a white foam. R$_f$=0.20 (9:1 ethyl acetate/methanol). MS (M+H)$^+$=477.2; $^1$H NMR (400 MHz, CDCl$_3$): δ 1.45–1.60 (m, 2H), 1.65–1.78 (m, 1H), 1.90–2.15 (m, 5H), 2.18–2.30 (m, 3H), 2.36–2.41 (dd, J=13.1, 6.7 Hz, 1H), 2.53–2.57 (t, J=7.4 Hz, 2H), 2.75–2.80 (m, 3H), 3.03–3.06 (m, 1H), 3.14 (s, 3H), 3.45–3.49 (m, 2H), 3.53 (s, 3H), 3.67–3.75 (m, 2H), 6.08 (bs, 1H), 6.50 (s, 1H), 6.66 (s, 1H), 7.24–7.36 (m, 5H); $^{13}$C NMR (100 MHz, CDCl$_3$): δ 21.2, 25.3, 25.5, 27.0, 29.7, 31.8, 45.3, 52.5, 55.5, 56.2, 61.5, 72.0, 109.9, 116.1, 127.3, 128.1, 129.4, 133.6, 140.4, 152.9, 170.0, 178.0. The dihydrochloride salt was prepared by the addition of 2 M HCl in ether to a solution of the product in ethyl acetate. Concentration gave a white solid.

Example 31

7-[(2S,3S)-(1-Isopropyl-2-phenyl-piperidin-3-ylamino)-methyl]-6-methoxy-1-methyl-3,4-dihydro-1H-quinolin-2-one 6-Methoxy-1-methyl-7-[(2S,3S)-(2-phenyl-piperidin-3-ylamino)-methyl]-3,4-dihydro-1H-quinolin-2-one (100 mg, 0.26 mmol) and 2-iodopropane (0.058 mL, 0.58 mmol) were stirred in acetonitrile at 60° C. for 2 days. The reaction was diluted with methylene chloride, washed once with satd. NaHCO$_3$, dried over MgSO$_4$, filtered, and concentrated. Silica gel chromatography using (9.1 ethyl acetate/methanol) gave 38 mg (34%) of the title compound, a yellow oil. R$_f$=0.08 (9:1 ethyl acetate/methanol). MS (M+H)$^+$=422.1; $^1$H NMR (400 MHz, CDCl$_3$): δ 0.66–0.68 (d, J=6.5 Hz, 3H), 1.00–1.02 (d, J=6.5 Hz, 3H), 1.35–1.42 (m, 1H), 1.50–1.53 (bd, J=13.0 Hz, 1H), 1.91–1.97 (m, 1H), 2.02–2.07 (m, 1H), 2.22–2.28 (t, J=11.5 Hz, 1H), 2.53–2.57 (t, J=7.4 Hz, 2H), 2.64 (s, 1H), 2.75–2.79 (t, J=7.4 Hz, 2H), 2.94–3.02 (m, 2H), 3.12 (s, 3H), 3.38–3.42 (d, J=14.6 Hz, 1H), 3.54 (s, 3H), 3.60 (s, 1H), 3.66–3.69 (d, J=14.6 Hz, 1H), 6.49 (s, 1H), 6.66 (s, 1H), 7.19–7.29 (m, 3H), 7.36–7.38 (m, 2H). $^{13}$C NMR (100 MHz, CDCl$_3$): δ 12.0, 20.3, 21.1, 25.5, 27.7, 29.6, 31.8, 44.1, 45.0, 48.5, 55.5, 56.3, 109.8, 112.8, 116.0, 124.9, 126.7, 127.8, 129.2, 133.5, 141.5, 152.9, 170.0. The dihydrochloride salt was prepared by the addition of 2 M HCl in ether to a solution of the product in ethyl acetate. Concentration gave a white solid.

Examples 32 AND 33

(3R)- and (3S)-6-Methoxy-1,3-dimethyl-7-[(2S,3S)-(1-methyl-2-phenyl-piperidin-3-ylamino)-methyl]-3,4-dihydro-1H-quinolin-2-one (a mixture of diastereomers) and (3R)- and (3S)-6-Methoxy-1,3-dimethyl-7-[(2S,3S)-(2-phenyl-piperidin-3-ylamino)-methyl]-3,4-dihydro-1H-quinolin-2-one (a mixture of diastereomers)

To 6-Methoxy-1-methyl-7-[(2S,3S)-(2-phenyl-piperidin-3-ylamino)-methyl]-3,4-dihydro-1H-quinolin-2-one (250 mg, 0.66 mmol) in 10 mL of THF at 0° C. was added KHMDS (0.726 mmol, 1.45 mL of a 0.5 M solution in toluene), and the resultant solution was stirred for 10 minutes. Methyliodide (0.045 mL, 0.726 mmol) was then added, and after stirring 10 minutes the procedure was repeated with an additional portion of the KHMDS solution (0.726 mmol, 1.45 mL) and methyl iodide. (0.045 mL, 0.726 mmol). The resultant solution was stirred for 10 minutes at 0° C. and for 1 hour at room temperature. The solution was diluted with water and extracted with ethyl acetate. The organic portion was washed once with water, dried over MgSO$_4$, filtered, and concentrated. Silica gel chromatography (9:1 ethyl acetate/methanol) gave the two title compound mixtures X (two inseparable diastereomers, 36 mg, 13% yield) and Y (two inseparable diastereomers, 60 mg, 22% yield).

X: R$_f$=0.26 (9:1 ethyl acetate/methanol); $^1$H NMR (400 MHz, CDCl$_3$): δ 1.18–1.19 (d, J=6.4 Hz, 3H), 1.39–1.49 (m, 2H), 2.03 (s, 3H), 2.06–2.11 (m, 4H), 2.49–2.62 (m, 3H), 2.67 (s, 1H), 2.79–2.81 (d, J=9.8 Hz, 1H), 3.04–3.07 (m, 2H), 3.15 (s, 3H), 3.36–3.39 (d, J=14.2 Hz, 1H), 3.49–3.51

(d, J=6.4 Hz, 3H), 3.62–3.67 (d, J=14.2 Hz, 1H), 6.47 (s, 1H), 6.61–6.63 (d, J=8.9 Hz, 1H), 7.21–7.34 (m, 5H). $^{13}$C NMR (100 MHz, CDCl$_3$): δ 15.6, 20.1, 27.3, 29.8, 33.3, 35.5, 45.0, 45.5, 55.4, 56.1, 57.5, 74.0, 109.9, 115.8, 124.4, 126.7, 127.8, 128.6, 133.2, 141.5, 152.8, 172.6; MS (M+H)$^+$ =408.1

Y: R$_f$=0.11 (9:1 ethyl acetate/methanol); $^1$H NMR (400 MHz, CDCl$_3$): δ 1.18–1.20 (d, J=6.4 Hz, 3H), 1.39–1.42 (m, 1H), 1.58–1.62 (m, 1H), 1.86–2.10 (m, 3H), 2.10–2.13 (d, J=12.6 Hz, 1H), 2.54–2.63 (m, 2H), 2.74–2.82 (m, 2H), 3.18 (s, 3H), 3.22–3.26 (d, J=12.0 Hz, 1H), 3.37–3.41 (d, J=14.5 Hz, 1H), 3.47–3.49 (d, J=4.0 Hz, 3H), 3.50–3.63 (m, 2H), 3.86 (s, 1H), 6.47 (s, 1H), 6.60–6.61 (d, J=5.8 Hz, 1H), 7.19–7.28 (m, 5H). $^{13}$C NMR (100 MHz, CDCl$_3$): δ 15.7, 20.1, 28.2, 29.9, 33.4, 35.5, 46.1, 47.7, 55.2, 64.2, 110.1, 116.1, 124.7, 126.4, 128.1, 133.2, 138.2, 142.5, 153.0, 172.7. The dihydrochloride salt of each compound was prepared by the addition of 2 M HCl in ether to a solution of the product in ethyl acetate. Concentration of each gave a white solid.

Example 34

7-{[1-(4,5-Dihydro-1H-imidazol-2-yl)-(2S,3S)-2-phenyl-piperidin-3-ylamino]-methyl}-6-methoxy-1-methyl-3,4-dihydro-1H-quinolin-2-one Step 1: 6-Methoxy-1-methyl-7-[(2S,3S)-(2-phenyl-piperidin-3-ylamino)-methyl]-3,4-dihydro-1H-quinolin-2-one (750 mg, 1.98 mmol) and N-BOC-2-isothiocyanatoethylamine (400 mg, 1.98 mmol) were stirred in 20 mL of benzene at room temperature for 16 hours. The reaction was diluted with diethyl ether and washed 1× with water, dried over MgSO$_4$, filtered, and concentrated. Silica gel chromatography using (6:1 ethyl acetate/hexane) gave 800 mg (70% yield) of [2-({3-[(6-Methoxy-1-methyl-2-oxo-1,2,3,4-tetrahydro-quinolin-7-ylmethyl)-amino]-2-phenyl-piperidine-1-carbothioyl}-amino)-ethyl]-carbamic acid tert-butyl ester. R$_f$=0.11 (6:1 ethyl acetate/hexane).

Step 2: [2-({3-[(6-Methoxy-1-methyl-2-oxo-1,2,3,4-tetrahydro-quinolin-7-ylmethyl)-amino]-(2S,3S)-2-phenyl-piperidine-1-carbothioyl}-amino)-ethyl]-carbamic acid tert-butyl ester (800 mg, 1.38 mmol) was stirred in a mixture of 30 mL methylene chloride and 10 mL trifluoroacetic acid at room temperature for 4 hours. The solvent was removed and the residue was partitioned between ethyl acetate and satd. K$_2$CO$_3$. The organics were separated, dried over MgSO$_4$, filtered, and concentrated to give 3-[(6-Methoxy-1-methyl-2-oxo-1,2,3,4-tetrahydro-quinolin-7-ylmethyl)-amino]-2-phenyl-piperidine-1-carbothioic acid (2-amino-ethyl)-amide. R$_f$=0.18 (90:10:1 methylene chloride/methanol/satd. aq. NH$_4$OH).

Step 3: 3-[(6-Methoxy-1-methyl-2-oxo-1,2,3,4-tetrahydro-quinolin-7-ylmethyl)-amino]-(2S,3S)-2-phenyl-piperidine-1-carbothioic acid (2-amino-ethyl)-amide (660 mg, 1.38 mmol) and mercury (II) oxide (600 mg, 2.75 mmol) were stirred in 30 mL of ethanol at reflux for 4 hours. The black reaction was filtered through Celite and the filtrate was concentrated. Silica gel chromatography using (9:1 chloroform/methanol) gave 225 mg (37% yield) of the title compound, a yellow oil. R$_f$=0.06 (9:1 chloroform/methanol). MS (M+H)$^+$=448.2; $^1$H NMR (400 MHz, CD$_3$OD): δ 1.79–2.00 (m, 4H), 2.49–2.53 (t, J=7.2 Hz, 2H), 2.80–2.84 (t, J=7.2 Hz, 2H), 3.19–3.23 (m, 1H), 3.25 (s, 3H), 3.28–3.31 (m, 1H), 3.48–3.54 (m, 1H), 3.61 (bs, 1H), 3.66 (s, 3H), 3.69 (s, 4H), 3.75–3.89 (m, 4H), 5.14–5.15 (d, J=5.6 Hz, 1H), 6.77 (s, 1H), 6.97 (s, 1H), 7.33–7.42 (m, 3H), 7.57–7.59 (d, J=7.3 Hz, 2H). $^{13}$C NMR (100 MHz, CD$_3$OD): δ 24.0, 35.5, 26.1, 30.2, 32.6, 44.0, 44.2, 47.1, 562, 57.8, 61.6, 61.9, 111.5, 118.1, 127.5, 127.8, 129.5, 129.9, 130.1, 134.6, 137.0, 154.9, 161.3, 172.4. The dihydrochloride salt was prepared by the addition of 2 M HCl in ether to a solution of the product in ethyl acetate. Concentration gave a white solid.

Example 35

6-Methoxy-1-methyl-7-{[1-((2S)-1-methyl-5-oxo-pyrrolidin-2-ylmethyl)-(2S,3S)-2-phenyl-piperidin-3-ylamino]-methyl}-3,4-dihydro-1H-quinolin-2-one To 6-Methoxy-1-methyl-7-{[1-(5-oxo-pyrrolidin-2-ylmethyl)-(2S,3S)-2-phenyl-piperidin-3-ylamino]-methyl}-3,4-dihydro-1H-quinolin-2-one (194 mg, 0.408 mmol) in 5 mL of THF at room temperature was added 18 mg (0.448 mmol) of 60% sodium hydride suspended in mineral oil and stirred for 20 minutes. Methyl iodide (0.028 mL, 0.448 mmol) was then added and stirred for 1 hour 18 mg (0.448 mmol) of 60% sodium hydride suspended in mineral oil was added and stirred overnight. A small amount of water was added and the solvent was removed under vacuum. The residue was dissolved in ethyl acetate, washed twice with water, dried over MgSO$_4$, filtered, and concentrated. Silica gel chromatography using (95:5 ethyl acetate/methanol) as the eluent gave 25 mg (13%) of the title compound, a pale yellow oil. R$_f$=0.07 (9:1 ethyl acetate/methanol). MS (M+H)$^+$=491.2; $^1$H NMR (400 MHz, CDCl$_3$): δ 1.42–1.60 (m, 3H), 1.84–1.88 (dd, J=13.4 Hz, 4.8 Hz, 1H), 2.01–2.14 (m, 5H), 2.17–2.24 (m, 2H), 2.54–2.57 (t, J=7.3 Hz, 3H), 2.67–2.73 (m, 1H), 2.76–2.78 (t, J=7.3 Hz, 2H), 2.88 (s, 3H), 3.13 (s, 3H), 3.21–3.24 (d, J=10.9 Hz, 1H), 3.32–3.33 (d, J=3.0 Hz, 1H), 3.36–3.40 (d, J=14.3 Hz, 1H), 3.56 (s, 3H), 3.61–3.68 (m, 2H), 6.49 (s, 1H), 6.65 (s, 1H), 7.18–7.34 (m, 5H). $^{13}$C NMR (100 MHz, CDCl$_3$): δ 20.4, 23.9, 25.5, 27.5, 29.6, 31.8, 45.4, 54.2, 55.5, 56.3, 58.0, 59.9, 72.7, 109.9, 116.0, 127.1, 128.1, 129.0, 133.6, 140.9, 152.8, 170.0, 175.0. The dihydrochloride salt was prepared by the addition of 2 M HCl In ether to a solution of the product in ethyl acetate. Concentration gave a white solid.

Example 36

Preparation of 6-methoxy-1-methyl-7(R) (5(S)-6(R)-phenyl-1,7-diaza-spiro[4.5]dec-3-yl)-3,4-dihyrdo-1H-quinolin-2-one Step 1

Hydroxy-(6-methoxy-1-methyl-2-oxo-1,2,3,4-tetrahydro quinolin-7-yl) acetic acid methyl ester To a suspension of 2.0 g (0.0091 m) of 6-methoxy-1-methyl-2-oxo-1,2,3,4-tetrahydro quinoin-7-carbaldehyde in 200 ml of ethyl acetate was added 15 ml (0.015 m) of a 1N solution of sodium bisulfite. A biphasic solution formed. To this mixture was added a solution of 0.6 g (0.012 m) of sodium cyanide in 10 ml of water. The reaction was stirred four hours at room temperature at which time an additional 0.2 g (0.004 m) of sodium cyanide dissolved in 10 ml of water was added, and the mixture stirred for 18 hours at room temperature. The organic layer was extracted from the water layer, washed with saturated sodium bicarbonate, dried with anhydrous sodium sulfate, and evaporated to yield crude cyanohydrin (87% pure by NMR) as a tan solid.

The crude cyanohydrin was stirred in 100 ml of methanol and HCL gas was bubbled into the mixture until a solution formed. This mixture was heated to reflux for 3 hours. The mixture was cooled to room temperature and the solvent evaporated. The residue was triturated with 25 ml of water and stirred for 30 minutes at room temperature. The mixture was extracted with ethyl acetate; the ethyl acetate was dried with sodium sulfate and evaporated. The residue was chromatographed on silica using 3/1 methylene chloride/ethyl acetate as the elutant. Appropriate fractions were combined and evaporated to yield 1.2 g (48%) of hydroxy-(6-methoxy-1-methyl-2-oxo-1,2,3,4-tetrahydro quinolin-7-yl) acetic acid methyl ester as a white amorphous solid. $^1$H NMR (CDCl$_3$) δ 2.51 (m, 2H), 2.80 (m, 2H), 3.20 (s, 3H), 3.66 (s, 3H), 3.74 (s, 3H), 5.25 (s, 1Hs), 6.66 (s, 1H), 6.87 (s, 1H). Mass spectrum: m/e=280.0 (p+1). TLC (3/1 chloroform/ethyl acetate) Rf=0.3.

Step 2

(6-methoxy-1-methyl-2-oxo-1,2,3,4-tetrahydro-quinolin-7-yl)-oxo-acetic acid methyl ester To a solution of 1.2 g (0.0043 m) of hydroxy-(6-methoxy-1-methyl-2-oxo-1,2,3,4-tetrahydro-quinolin-7-yl) acetic acid methyl ester dissolved in 40 ml of acetone was added dropwise 1.6 ml of a 2.67 m solution of chromic acid in sulfuric acid/H$_2$O (Jones reagent). The mixture was stirred for 90 minutes at room temperature. The acetone was decanted from the green precipitate and evaporated. The residue was dissolved in ethyl acetate and washed with saturated sodium bicarbonate. The ethyl acetate solution was dried with sodium sulfate and evaporated to yield 1.0 g (84%) of (6-methoxy-1-methyl-2-oxo-1,2,3,4-tetrahydro-quinolin-7-yl)-oxo acetic acid as a yellow amorphous solid. $^1$H NMR (CDCl$_3$) δ 2.60 (m, 2H), 2.90 (m, 2H), 3.20 (s, 3H), 3.80 (s, 3H), 3.90 (s, 3H), 6.80 (s, 1H), 7.40 (s, 1H). Mass spectrum: m/e=277.9 (p+1). TLC (3/1 chloroform/ethyl acetate) Rf=0.8.

Step 3

2-(6-methoxy-1-methyl-2-oxo-1,2,3,4-tetrahydro-quinolin-7-yl) acrylic acid methyl ester A suspension of 3.1 g (0.0087 m) of methyl-triphenylphosphonium bromide in 100 ml of tetrahydrofuran was cooled to −20° C. To this suspension was added dropwise 3.5 ml (0.0087 m) of a 2.5 M solution of n-butyl lithium in tetrahydrofuran. The mixture was slowly. warmed to +5° C. at which time a yellow solution formed. The mixture was cooled to −20° C. and 2.2 g (0.0079 m) of (6-methoxy-1-methyl-2-oxo-1,2,3,4-tetrahydro-quinolin-7-yl)-oxo-acetic acid methyl ester was added. The reaction mixture was warmed to room temperature and stirred for 18 hours. The reaction mixture was filtered, and the filtrate evaporated to yield a brown oily residue. This material was chromatographed on 75 grams of silica using chloroform as the elutant. Appropriate fractions were combined and evaporated to yield 1.8 g (83%) of 2-(6-methoxy-1-methyl-2-oxo-1,2,3,4-tetrahydro-quinolin-7-yl) acrylic acid methyl ester as an amorphous solid. $^1$H NMR (CDCl$_3$) δ 2.58 (m, 2H), 2.82 (m, 2H), 3.15 (s, 3H), 3.70 (s, 6H), 5.70 (s, 1H), 6.25 (s, 1H), 6.65 (s, 1H), 6.80 (s, 1H). Mass spectrum: m/e=276 (p+1). TLC (5/1 methylene chloride/ethyl acetate) Rf=0.90.

Step 4 trans-3-nitro-2-phenyl-piperidine-1-carboxylic acid tert-butyl ester

A mixture of 3.7 grams (0.018 m) of trans-3-nitro-2-phenyl-piperidine and 7.8 grams (0.036 m) of N-tert-butyloxycarbonyl anhydride was dissolved in 50 ml of methylene chloride. To this solution was added 2.5 ml (0.018 m) of triethylamine and this mixture stirred for 20 hours at room temperature. The reaction mixture was then extracted with 20 ml of water and 20 ml of 2 N HCl. The organic layer was dried with sodium sulfate and evaporated. The residue was chromatographed on 100 grams of silica using 5/1 hexane/methylene chloride as the elutant. Appropriate fractions were combined to yield 2.8 g (51%) trans-3-nitro-2-phenyl-piperidine-1-carboxylic acid tert-butyl ester as a yellow oil. $^1$H NMR (CDCl$_3$) δ 1.40 (s, 9H), 1.45 (m, 1H), 1.80 (m, 2H), 2.45 (m, 1H), 2.80 (m, 1H), 4.10 (d, 1H), 5.0 (s, 1H), 6.22 (s, 1H), 7.2–7.4 (m, 5H). TLC (3/1 chloroform/ethyl acetate). Rf=0.65

Step 5

3-[2-Methoxy carbonyl-2-(6-methoxy-1-methyl-2-oxo-1,2,3,4-tetrahydro-quinolin-7-yl)-ethyl]-cis-3-nitro-2-phenyl-piperidine-1-carboxylic acid tert-butyl ester A mixture of 2.2 grams (0.0072 m) of trans-3-nitro-2-phenyl-piperdine-1-carboxylic acid tert-butyl ester and 1.8 grams (0.0065 m) of 2-(6-methoxy-1-methyl-2-oxo-1,2,3,4-tetrahydro-quinolin-7-yl) acrylic acid methyl ester were combined in 20 ml of tetrahydrofuran. To this was added 0.2 ml (0.0014 m) of 1,8-diazebicyclo [5.4.0]undec-7-ene (DBU) and the mixture refluxed for 18 hours. The reaction mixture was cooled to room temperature and the solvent evaporated. The residue was dissolved in 40 ml of ethyl acetate and washed with 20 ml of 1 N hydrochloride acid. The ethyl acetate solution was dried with sodium sulfate and evaporated. The residue was chromatographed on 50 grams of silica using chloroform as the elutant. Appropriate fractions were combined to yield 2.9 grams (77%) of 3-[2-methoxy carbonyl-2-(6-methoxy-1-methyl-2-oxo-1,2,3,4-tetrahydro-quinoin-7-yl)-ethyl]-cis-3-nitro-2-phenyl-piperdine-1-carboxylic acid tert butyl ester as a diastereomeric mixture of an amorphous solid. TLC (3/1 methyl chloride/ethyl acetate) Rf=0.45. Mass spectrum m/e=582 (p+1), 526 (p-56), 482 (p-100).

Step 6

3-[3(R,S)-Hydroxy-2-(6-methoxy-1-methyl-2-oxo-1,2,3,4-tetrachydro-quinolin-7-yl)-propyl-3(R)-nitro-2(S)-phenyl-piperdine-1-carboxylic acid tert-butyl ester and 3-[3(R,S)-hydroxy-2-(6-methoxy-1-methyl-2-oxo-1,2,3,4-tetrahydro-quinolin-7-yl)-propyl-3(S)-nitro-2(R)-phenyl-piperdine-1-carboxylic acid tert-butyl ester To a solution of 2.9 g (0.005 m) of 3-[2-methoxy carbonyl-2-(6-methoxy-1-methyl-2-oxo-1,2,3,4-tetrahydro-quinolin-7-yl)-ethyl-cis-3-nitro-2-phenyl-piperdine-1-carboxylic acid tert-butyl ester in 200 ml of ether was added 0.26 g (0.012 m) of lithium borohydride. A white solid precipitate formed. The mixture was stirred for 18 hours at room temperature. An additional 0.26 g (0.012 m) of lithium borohydride was added and the mixture stirred an additional 24 hours. The solvent was evaporated and the residue was dissolved in 100 ml of a 50/50 ethyl acetate/water mixture and stirred for 0.5 hours. The ethyl acetate layer was then separated from the water layer, dried with sodium sulfate and evaporated. The residue was chromatographed on 80 grams of silica using 2/1 methylenechloride/ethyl acetate as the elutant. Two pure products were isolated as amorphous solids. The first product (TLC Rf=0.41; 1/1 chloroform/ethyl acetate) was assigned as a diastereomeric mixture of 3-[3(R,S)-hydroxy-2-(6-methoxy-1-methyl-2-oxo-1,2,3,4-tetrahydro-quinolin-7-yl)-propyl-3(R)-nitro-2(S)-phenyl-piperdine-1-carboxylic acid tert-butyl ester based on x-ray analysis of the final product. $^1$H NMR (CDCl$_3$) δ 1.42 (s, 9H), 1.42–1.6 (m, 2H), 2.20 (m, 2H), 2.4–2.9 (m, 9H), 3.30 (s, 3H), 3.50–3.90 (m, 3H), 3.80 (s, 3H), 6.65 (s, 1H), 6.75 (s, 1H), 7.20 (s, 5H). The second product. (TLC Rf=0.32) was assigned as a diastereomeric mixture of 3-[(3(R,S)-hydroxy-2-(6-methoxy-1-methyl-2-oxo-1,2,3,4-tetrahydro-quinolin-7-yl)propyl-3(S)-nitro-2(R)-phenyl piperdine-1-carboxylic acid tert-butyl ester based on x-ray analysis of the final product. $^{13}$C NMR (CDCl$_3$) δ 1.40 (s, 9H), 1.5–2.0 (m, 4H), 2.4–2.55 (m, 4H), 2.55–3.0 (m, 5H), 3.25 (s, 3H), 3.35 (m, 1H), 3.60–3.80 (m, 3H), 3.80 (s, 3H), 6.58 (s, 1H), 6.60 (s, 1H), 7.1–7.3(m, 5H).

Step 7

3(S)-Amino [3(R,S)-hydroxy-2-(6-methoxy-1-methyl-2-oxo-1,2,3,4-tetrahydro-quinoin-7-ly)-propyl]-2(R)-phenyl-piperdine-1-carboxylic acid tert-butyl ester To a solution of 0.5 grams (0.0009 m) of 3-[3(R,S)-hydroxy-2-(6-methoxy-1-methyl-2-oxo-1,2,3,4-tetrahydro-quinolin-7-yl) propyl-3(S)-nitro-2(R)-phenyl-piperdine-1-carboxylic acid tert-butyl ester in 50 ml of ethanol was added approximately 500 mg of Raney nickel and the mixture was hydrogenated at 50 PSI (room temperature) for 18 hours. The mixture was filtered and the solvent evaporated. The residue was dissolved in 20 ml of water/ethyl acetate (50/50) and the pH adjusted to 2.0 with 1N HCl. The ethyl acetate extract was dried and evaporated to yield 0.23 grams of the starting nitro alcohol. The pH of the water layer was adjusted to 8.5 with 1N NaOH and the water extracted with ethyl acetate. The ethyl acetate extracts were combined, dried with anhydrous sodium sulfate and evaporated to yield 0.22 grams of 3(S)-amino [3(R,S)-hydroxy-2-(6-methoxy-1-methyl-2-oxo-1,2,3,4-tetrahydro-quinolin-7-yl)-propyl]-2(R)-phenyl-piperdine-1-carboxylic acid tert-butyl ester as an amorphous solid. $^1$H NMR (CDCl$_3$) δ 1.30 (s, 9H), 1.65 (m, 1H), 1.78 (m, 3H), 2.0 (m, 1H), 2.40 (m, 1H), 2.60 (t, 2H), 2.82(t, 2H), 3.20 (m, 1H), 3.30 (s, 3H), 3.60 (m, 1H), 3.70 (d, 2H), 3.80 (s, 3H), 4.05 (m, 1H), 5.38 (s, 1H), 6.65 (s, 1H), 6.80 (s, 1H), 7.25 (m, 3H), 7.35 (m, 2H). Mass spectrum: m/e=524 (p+1). TLC (1/1 methylenechloride/hexane) Rf=0.05.

Step 7A

3(R)-Amino [3-(R,S)-hydroxy-2-(6-methoxy-1-methyl-2-oxo-1,2,3,4-tetrahydro-quinolin-7-yl)-propyl]-2(S)-phenyl-piperdine-1-carboxylic acid tert-butyl ester $^1$H NMR (CDCl$_3$) δ 1.2 (s, 9H), 1.6–1.8 (m, 5H), 2.2 (m, 1H), 2.4 (m, 1H), 2.55 (m, 2H), 2.8 (m, 2H), 3.2 (m, 2H), 3.25 (s, 3H), 3.4 (m, 1H), 3.55 (m, 1H), 3.70 (m, 2H), 3.75 (s, 3H), 3.95 (m, 1H), 4.65 (s, 1H), 6.62 (s, 1H), 6.68 (s, 1H), 7.2–7.4 (m, 5H). Mass spectrum m/e=524.1 (p+1) TLC (1/1 ethyl acetate/methylene chloride) Rf=0.1

Step 8

3(R,S)-(1-Methyl-2-oxo-1,2,3,4-tetrahydro quinolin-7-yl)-5(S)-6(R)-phenyl-1,7-diaza-spiro[4.5]decane-7-carboxylic acid tert-butyl ester A solution of 0.22 g (0.00042 m) of 3(S)-amino[3(R,S)-hydroxy-2-(6-methoxy-1-methyl-2-oxo-1,2,3,4-tetrahydro-quinolin-7-yl)-propyl]-2(R)-phenyl-piperdine-1-carboxylic acid tert-butyl ester in 15 ml of methylene chloride was cooled to 5° C. To this solution was added 0.08 ml (0.0006 m) of triethylamine and 0.032 ml (0.00042 m) of methanesulfonyl chloride and the reaction mixture was stirred for 15 minutes. The reaction mixture was washed with dilute sodium bicarbonate, the methylene chloride extract dried with anhydrous sodium sulfate and evaporated to yield 0.16 g (75%) of 3(R,S)-(1-methyl-2-oxo-1,2,3,4-tetrahydro-quinolin-7-yl)-5(S)-6(R)-phenyl-1,7-diaza-spiro[4.5]decane-7-carboxylic acid tert-butyl ester as a diastereomeric mixture. Mass Spectrum: m/e=506.1 (p+1).

Step 8A

3(R,S)-(1-Methyl-2-oxo-1,2,3,4-tetrahydro-quinolin-7-yl)-5(R)-6(S)-phenyl-1,7-diaza-spiro[4.5]decane-7-carboxylic acid tert-butyl ester as a diastereomeric mixture Mass Spectrum: m/e=506.1 (p+1).

Separation of 3(S)-(6-methoxy-1-methyl-2-oxo-1,2,3,4-tetrahydro-quinolin-7-yl)-5(S)-6(R)-phenyl-1,7-diaza-spiro[4.5]decane-7-carboxylic acid tert-butyl ester and 3(R)-(6-methoxy-1-methyl-2-oxo-1,2,3,4-tetrahydro-quinolin-7-yl)-5(S)-6(R)-phenyl-1,7-diaza-spiro[4.5]decane-7-carboxylic acid tert-butyl ester.

A 200 mg sample of the diastereomeric mixture prepared in step 8 was chromatographed on a Chiralpak AD (5 cm×25 cm) column using a 90/10 mixture of hexane/isopropyl alcohol containing 0.1% diethylamine as the elutant. Fraction 1 (90 mg) eluted at 13.7 minutes and was assigned 3(R)-(6-methoxy-1-methyl-2-oxo-1,2,3,4-tetrahydro-quinolin-7-yl)-5(S)-6(R)-phenyl-1,7-diaza-spiro[4.5]decane-7-carboxylic acid tert-butyl ester. $^1$H NMR (CDCl$_3$) δ 1.40 (s, 9H), 1.60–1.80 (m, 4H), 2.20 (m, 1H), 2.48 (m, 1H), 2.60 (m, 2H), 2.80 (m, 2H), 2.85–3.0 (m, 2H), 3.35 (s, 3H), 3.38 (m, 1H), 3.70 (m, 1H), 3.80 (s, 3H), 3.95 (m, 1H), 5.20 (s, 1H), 6.65 (s, 1H), 6.88 (s, 1H), 7.2–7.4 (m, 3H), 7.6 (m, 2H). Mass Spectrum: m/e=506.1 (p+1). Fraction 2 (90 mg) eluted at 21.3 minutes and was assigned as 3(S)-(6-methoxy-1-methyl-2-oxo-1,2,3,4-tetrahydro-quinoin-7-yl)5(S)-6(R)-phenyl-1,7-diaza-spiro[4.5]decane-7-carboxylic acid tert-butyl ester. $^{13}$C NMR (CDCl$_3$) δ 1.40 (s, 9H), 1.6–1.8 (m, 4H), 2.25 (m, 1H), 2.45 (m, 1H), 2.60 (m, 2H), 2.80 (m, 2H), 2.90 (m, 2H), 3.35 (s, 3H), 3.38 (m, 1H), 3.70 (m, 1H), 3.80 (s, 3H), 4.0 (m, 1H), 5.2 (s, 1H), 6.62 (s, 1H), 6.82 (s, 1H), 7.30 (m, 3H), 7.58 (m, 2H). Mass Spectrum: m/e −506.1 (p+1).

Step 9

6-Methoxy-1-methyl-7(R)-(5(S)-6(R)-phenyl-1,7-diaza-spiro-[4.5]dec-3-yl]-3,4-dihydro-1H-quinolin-2-one hydrochloride A solution of 100 mg (0.0002 m) of 3(R)-(6-methoxy-1-methyl-2-oxo-1,2,3,4-tetrahydro-quinolin-7-yl)5(S)-6(R)-phenyl-1,7-diaza-spiro-[4.5]decane-7-carboxylic acid tert-butyl ester in 10 ml of dioxane was saturated with gaseous hydrochloric acid. The reaction mixture was stirred for 18 hours at room temperature. The solvent was evaporated and the residue was triturated with methanol/isopropyl ether to give 28 mg of 6-methoxy-1-methyl-7(R)-(5(S)-6(R)-phenyl-1,7-diaza spiro[4.5]dec-3-yl]-3,4-dihydro-1H-quinolin-2-one hydrochloride as a tan solid. Mass spectrum: m/e=406.0 (p+1). A 10 mg amount of the above hydrochloride salt was dissolved in a small amount of ethyl acetate/water and the pH adjusted to 9.5. The ethyl acetate layer was dried with anhydrous sodium sulfate and evaporated to give 6-methoxy-1-methyl-7(R)-5(S)-6(R)-phenyl-1,7-diaza-sprio[4.5]dec-3-yl]-3,4-dehydro-1H-quinolin-2-one as the free base. $^1$H NMR (CDCl$_3$) δ 1.2–2.2 (m, 13H), 2.55 (m, 2H), 2.75 (m, 4H), 2.90 (m, 1H), 3.15 (m, 1H), 3.22 (s, 3H), 6.30 (s, 1H), 6.62 (s, 1H), 7.30 (m, 3H), 7.50 (m, 2H).

Example 37

6-methoxy-1-Methyl-7-(S)-(5(S)-6(R)-phenyl-1,7-diaza-spiro[4.5]dec-3-yl]-3-4-dihydro-1H-quinolin-2-one hydrochloride Mass Spectrum: m/e=406.1 (p+1). $^1$H NMR (D$_6$ DMSO) δ 1.8–2.35 (m, 8H), 2.4–2.6 (m, 4H), 2.7 (m, 2H), 3.1–3.3 (m, 3H), 3.22 (s, 3H), 3.3–3.5 (m, 3H), 3.60 (s, 3H), 4.8 (br s, 1H), 6.75 (s, 1H), 6.95 (s, 1H), 7.6 (s, 3H), 8.0 (s, 2H).

Example 38

6-methoxy-1-Methyl-7(R,S)-(5(R)-6(S)-phenyl-1,7-diaza-spiro[4.5]dec-3-yl]-3-4-dihydro-1H-quinolin-2-one hydrochloride Mass Spectrum: m/e=406.1 (p+1). $^1$H NMR (CDCl$_3$; free base) δ 1.5–2.1 (m, 6H), 2.20 (m, 2H), 2.80 (m, 4H), 3.0 (s, 3H), 3.1 (m, 1H), 3.22 (m, 1H), 3.65 (s, 3H), 3.70 (m, 2H), 5.95 (s, 1H), 6.55 (s, 1H), 7.30 (m, 3H), 7.52 (m, 2H).)

Preparation 34

6-Hydroxy-1-methyl-3,4-dihydro-1H-quinolin-2-one 5.74 ml of 1.0 M BBr$_3$/CH$_2$Cl$_2$ solution was added to a dry CH$_2$Cl$_2$ solution of 6-methoxy-1-methyl-3,4-dihydro-1H-quinolin-2-one (500 mg, 2.62 mmol) under nitrogen. The reaction mixture was stirred for 2 hours, poured into ice water and extracted with ethyl acetate (150 ml). The combined organic extract was washed with brine, dried (MgSO$_4$) and the solvent was evaporated under reduced pressure to yield the title compound as a pink solid (392 mg, 84%). $^1$H NMR (400 MHz, CD$_3$OD) δ 2.52–2.56 (2H, m), 2.77–2.81 (2H, m), 3.28 (3H, s), 6.62–6.67 (2H, m), 6.92 (1H, d, J=8.72 Hz). m/z (APCI$^-$) 176 (M−1). HPLC (aqueous 200 Mm ammonium acetate buffer/acetonitrile gradient, 3.0 ml/min, Hewlett Packard ODS Hypersil 5 μM, 125×4 mm column), 2.51 minutes.

Preparation 35

1-Methyl-6-(1-phenylsulfanyl-cyclopropoxy)-3,4-dihydro-1H-quinolin-2-one

To a dry toluene solution of [1-Iodo-cyclopropylsulfanyl]-benzene (375 mg, 1.36 mmol) was added 6-Hydroxy-1-methyl-3,4-dihydro-1H-quinolin-2-one (200 mg, 1.13 mmol) and silver carbonate (312 mg, 1.13 mmol) under nitrogen and the reaction mixture was heated to 55° C. It took 3 more additions of the reagents to take the reaction to completion. The reaction was cooled to room temperature, filtered to remove the silver iodide and concentrated under vacuum to yield crude material. This was flash chromatograhed using 30% ethyl acetate/hexane to yield the title compound as a viscous oil (64 mg, 17% yield). $^1$H NMR (400 MHz, CDCl$_3$) δ 1.31–1.33 (2H, m), 1.41–1.43 (2H, m), 2.59–2.62 (2H, m), 2.83–2.87 (2H, m), 3.31 (3H, s), 6.86–6.98 (4H, m), 7.20–7.31 (2H, m), 7.44–7.47 (2H, m). m/z (APCI$^+$) 326 (M+1). HPLC (aqueous 200 Mm ammonium acetate buffer/acetonitrile gradient, 3.0 ml/min, Hewlett Packard ODS Hypersil 5 μM, 125×4 mm column), 6.59 minutes.

Preparation 36

6-Cyclopropoxy-1-methyl-3,4-dihydro-1H-quinolin-2-one

Naphthalene (1.0 g, 7.85 mmol) was dissolved in THF (7.5 ml) under nitrogen and freshly cut lithium metal (54 mg, 7.85 mmol) was added. The mixture was stirred at room temperature until a dark green solution of lithium naphthalenide was obtained. This solution was cooled to −78° C., then 1-Methyl-6-(1-phenylsulfanyl-cyclopropoxy)-3,4-dihydro-1H-quinolin-2-one (170 mg, 0.53 mmol) in THF was added over 1 minute. The reaction was stirred for 17 minutes and then water and ethyl acetate were added. The layers were separated and the aqueous layer was extracted with ethyl acetate. The combined organic extract was dried (MgSO$_4$) and the solvent was evaporated under reduced pressure. The residue was purified by column chromatography using 30% ethylacetate/hexane to give the title compound (42 mg, 36% yield).

$^1$H NMR (400 MHz, CDCl$_3$) δ 0.72–0.75 (4H, m), 2.58–2.62 (2H, m), 2.82–2.86 (2H, m), 3.30 (3H, s), 3.66–3.70 (1H, m), 6.82–6.92 (3H, m). m/z (APCI$^+$) 218 (M+1). HPLC (aqueous 200 Mm ammonium acetate buffer/acetonitrile gradient, 3.0 ml/min, Hewlett Packard ODS Hypersil 5 μM, 125×4 mm column), 4.713 min.

Preparation 37

6-Cyclopropoxy-1-methyl-2-oxo-1,2,3,4-tetrahydro-quinoline-7-carbaldehyde

TFA (1.38 ml) solution of hexamethylenetetramine (58 mg, 0.42 mmol) was heated to 70° C. for 1 hour under nitrogen. Another TFA (0.69 ml) solution of 6-Cyclopropoxy-1-methyl-3,4-dihydro-1H-quinolin-2-one (30 mg, 0.138 mmol) was then added to the above at room temperature and the reaction mixture was heated to 65° C. for an overnight. It was then cooled to room temperature, quenched with water and extracted with ethyl acetate (30 ml). The combined fractions were dried (MgSO$_4$) and the solvent was evaporated under reduced pressure. The residue was chromatographed using 40% ethylacetate/hexane to yield the title compound as a solid (13 mg, 37% yield). $^1$H NMR (400 MHz, CDCl$_3$) δ 0.84–0.87 (4H, m), 2.64–2.267 (2H, m), 2.94–2.98 (2H, m), 3.35 (3H, s), 3.80–3.85 (1H, m), 7.17 (1H, s), 7.39 (1H, s), 10.33 (1H, s). m/z (APCI$^+$) 246 (M+1). HPLC (aqueous 200 Mm ammonium acetate buffer/acetonitrile gradient, 3.0 ml/min, Hewlett Packard ODS Hypersil 5 μM, 125×4 mm column), 4.454 min.

Example 39

6-Cyclopropoxy-1-methyl-7-[(2S-phenyl-piperidin-3S-ylamino)-methyl]-3,4-dihydro-1H-quinolin-2-one Dihydrochloride A dry toluene (0.5 ml) solution of 6-Cyclopropoxy-1-methyl-2-oxo-1,2,3,4-tetrahydro-7-carbaldehyde (12.5 mg, 0.051 mmol) and 2(S)-Phenyl-piperidin-3(S)-ylamine (13.5 mg, 0.077 mmol) was heated to reflux for 3 hours. The reaction mixture was then cooled to room temperature and sodium triacetoxyborohydride (32.4 mg, 0.153 mmol) was added and left stirring at room temperature for an overnight. The reaction was concentrated and the residue chromatographed using 5% methanol/methylene chloride to yield the free base of the title compound (9 mg, 44% yield). The dihydrochloride salt was made using 1.0M HCl/Et$_2$O (45 μl) to give the title compound. $^1$H NMR (free base, 400 MHz, CDCl$_3$) δ 0.66–0.89 (4H, m), 1.63–1.74 (1H, m), 1.98 (1H, m), 2.03–2.15 (1H, m), 2.21–2.23 (1H, m), 2.57–2.60 (2H, m), 2.76–2.82 (2H, m), 2.70–3.16 (2H, m), 3.29–3.32 (1H, m), 3.22 (3H, s), 3.51 (2H, d, J=13.8 Hz), 3.63–3.66 (1H, m), 4.19 (1H, s), 6.65 (1H, s), 6.90 (1H, s), 7.19–7.35 (5H, m). m/z (APCI$^+$) 406 (M+1). HPLC (aqueous 200 Mm ammonium acetate buffer/acetonitrile gradient, 3.0 ml/min, Hewlett Packard ODS Hypersil 5 μM, 125×4 mm column), 4.701 min.

Example 40

7-{[2R,S-(4-Fluoro-phenyl)-piperidin-3R,S-ylamino]-methyl}-6-methoxy-1-methyl-3,4-dihydro-1H-quinolin-2-one A dry toluene (5 ml) solution of 6-Methoxy-1-methyl-2-oxo-1,2,3,4-tetrahydro-quinoline-7-carbaldehyde (150 mg, 0.687 mmol) and 2R,S-(4-Fluoro-phenyl)-piperidin-3R,S-ylamine (200 mg, 1.03 mmol) was heated to reflux for 2 hours and then cooled to room temperature. Sodium triacetoxyborohydride (437 mg, 2.06 mmol) was added and the reaction mixture was stirred for an overnight. The solvent was evaporated under reduced pressure and the residue was chromatographed using 2–10% methanol/methylene chloride to yield the title compound (218 mg, 80% yield). $^1$H NMR (400 MHz, CDCl$_3$) δ 1.52–1.56 (1H, m), 1.62–1.69 (1H, m), 1.95–1.99 (1H, m), 2.02–2.12 (1H, m), 2.53–2.57 (2H, m), 2.76–2.79 (2H, m), 2.87–2.95 (2H, m), 3.20 (3H, s), 3.33–3.38 (1H, m), 3.40 (1H, d, J=13.9 Hz), 3.46 (3H, s), 3.67 (1H, d, J=13.9 Hz), 4.16 (1H, d, J=1.7 Hz), 6.49 (1H, s), 6.62 (1H, s), 6.96–7.01 (2H, m), 7.23–7.27 (2H, m). m/z (APCI$^+$) 398 (M+1). HPLC (aqueous 200 Mm ammonium acetate buffer/acetonitrile gradient, 3.0 ml/min, Hewlett Packard ODS Hypersil 5 μM, 125×4 mm column), 3.978 min. The dihydrochloride salt was prepared by using 1.0M HCl/Et$_2$O and obtained as a solid.

Example 41

6-Methoxy-1-methyl-7-[1-(2-oxo-6-methoxy-1-methyl-3,4-dihydro-1H-quinolin)-7-ylmethyl-2-(4-fluoro-phenyl)-piperidin-3-ylamino]methyl-3,4-dihydro-1H-quinolin-2-one The reaction used for the preparation of 7-{[2R,S-(4-Fluoro-phenyl)-piperidin-3R,S-ylamino]-methyl}-6-methoxy-1-methyl-3,4-dihydro-1H-quinolin-2-one also yielded the title compound (82 mg, 19% yield). m/z (APCI$^+$) 601 (M+1). HPLC (aqueous 200 Mm ammonium acetate buffer/acetonitrile gradient, 3.0 ml/min, Hewlett Packard ODS Hypersil 5 μM, 125×4 mm column), 5.436 min.

Example 42

7-{[2S-(4-Fluoro-phenyl)-piperidin-3S-ylamino]-methyl}-6-methoxy-1-methyl-3,4-dihydro-1H-quinolin-2-one Preparative HPLC chiral separation of 7-{[2R,S-(4-Fluoro-phenyl)-piperidin-3R,S-ylamino]-methyl}-6-methoxy-1-methyl-3,4-dihydro-1H-quinolin-2-one (200 mg) yielded the title compound (72 mg). $^1$H NMR (free base, 400 MHz, CDCl$_3$) δ 1.48–1.59 (1H, m), 1.61–1.66 (1H, m), 1.97–2.02 (1H, m), 2.10–2.14 (1H, m), 2.56–2.59 (2H, m), 2.78–2.83 (2H, m), 2.84–2.86 (2H, m), 3.23 (3H, s), 3.34 (1H, m), 3.41 (1H, d, J=14.1 Hz), 3.51 (3H, s), 3.65 (1H, d, J=14.1 Hz), 3.98 (1H, d), 6.51 (1H, s), 6.69 (1H, s), 6.97–7.01 (2H, m), 7.30–7.34 (2H, m). m/z (APCI$^+$) 398 (M+1). HPLC (aqueous 200 Mm ammonium acetate buffer/acetonitrile gradient, 3.0 ml/min, Hewlett Packard ODS Hypersil 5 μM, 125×4 mm column), 4.221 min.

Preparation 38

6-Ethoxy-1-methyl-3,4-dihydro-1H-quinolin-2-one 1.0M potassium t-butoxide/THF (5.65 ml, 5.65 mmol) was added to 6-Hydroxy-1-methyl-3,4-dihydro-1H-quinolin-2-one (200 mg, 1.13 mmol) followed by the addition of ethyl iodide (452 μl, 5.65 mmol). The reaction mixture was stirred at room temperature for 2 hours and heated to 45° C. for an overnight. The salts were filtered off, rinsed with ethyl acetate and the combined filtrate was concentrated down to a residue. This was chromatographed using 1:1 ethylacetate/hexane to yield the title compound as a white solid (76 mg, 33% yield). $^1$H NMR (400 MHz, CDCl$_3$) δ 1.36 (3H, t, J=6.9 Hz), 2.58 (2H, m), 2.82 (2H, m), 3.29 (3H, s), 3.96 (2H, q, J=7.0 Hz), 6.71 (2H, m), 6.84 (1H, d, J=8.7 Hz). m/z (APCI$^+$) 206 (M+1). HPLC (aqueous 200 Mm ammonium acetate buffer/acetonitrile gradient, 3.0 ml/min, Hewlett Packard ODS Hypersil 5 μM, 125×4 mm column), 4.453 min.

Preparation 39

6-Ethoxy-1-methyl-2-oxo-1,2,3,4-tetrahydro-quinoline-7-carbaldehyde

The title compound was prepared according to the procedure used for the preparation of 6-cyclopropyl-1-methyl-2-oxo-1,2,3,4-tetrahydro-quinoline-7-carbaldehyde as a yellow solid. $^1$H NMR (400 MHz, CDCl$_3$) δ 1.47 (3H, t, J=7.0 Hz), 2.65 (2H, m), 2.93 (2H, m), 3.36 (3H, s), 4.14 (2H, q, 7.1 Hz), 6.81 (1H, s), 7.42 (1H, s), 10.45 (1H, s). m/z (APCI⁺) 233.9 (M+1). HPLC (aqueous 200 Mm ammonium acetate buffer/acetonitrile gradient, 3.0 ml/min, Hewlett Packard ODS Hypersil 5 μM, 125×4 mm column), 4.167 min.

Example 43

6-Ethoxy-1-methyl-7-[(2S-phenyl-piperidin-3S-ylamino)-methyl]-3,4-dihydro-1H-quinolin-2-one Dihydrochloride A dry toluene (3.86 ml) solution of 6-Ethoxy-1-methyl-2-oxo-1,2,3,4-tetrahydro-quinoline-7-carbaldehyde (90 mg, 0.386 mmol) and 2S-phenyl-piperidin-3S-ylamine (102 mg, 0.579 mmol) was heated to reflux for 2 hours and cooled down to room temperature. Sodium triacetoxyborohydride (245 mg, 1.158 mmol) was then added and the reaction mixture was stirred for an overnight. The solvent was evaporated under reduced pressure and the residue was chromatographed using 5–10% methanol/methylene chloride to yield the free base of the title compound as a viscous gum (122 mg, 81% yield). The title compound was obtained using 1.0 M HCl/Et$_2$O (620 μl) and filtering the precipitate. $^1$H NMR (free base, 400 MHz, CDCl$_3$) δ 1.10 (3H, t, 7.0 Hz), 1.42–1.45 (1H, m), 1.88–1.95 (1H, m), 2.02–2.12 (1H, m), 2.53 (2H, m), 2.76 (2H, m), 2.84 (2H, m), 3.13 (3H, s), 3.27 (1H, m), 3.37 (1H, d, J=13.9 Hz), 3.58 (1H, d, J=13.9 Hz), 3.67 (1H, m), 3.73 (1H, m), 3.92 (1H, d, J=2.1 Hz), 6.46 (1H, s), 6.57 (1H, s), 7.18–7.28 (5H, m). m/z (APCI⁺) 394 (M+1). HPLC (aqueous 200 Mm ammonium acetate buffer/acetonitrile gradient, 3.0 ml/min, Hewlett Packard ODS Hypersil 5 μM, 125×4 mm column), 4.436 min.

Example 44

6-Hydroxy-1-methyl-7-[(2S-phenyl-piperidin-3S-ylamino)-methyl]-3,4-dihydro-1H-quinolin-2-one Dihydrochloride A dry toluene (9.0 ml) solution of 6-Hydroxy-1-methyl-2-oxo-1,2,3,4-tetrahydro-quinoline-7-carbaldehyde (200 mg, 0.976 mmol) and 2S-phenyl-piperidin-3S-ylamine (258 mg, 1.46 mmol) was heated to reflux for 2 hours and cooled down to room temperature. Sodium triacetoxyborohydride (620 mg, 2.93 mmol) was then added and the reaction mixture was stirred for an overnight. The solvent was evaporated under reduced pressure and the residue was redissolved in ethylacetate and washed once with dilute sodium bicarbonate. The organic layer was dried (MgSO$_4$) and concentrated down under reduced pressure to an oil. 1.95 ml of 1.0 M HCl/Et$_2$O addition yielded a dark solid which was crystallized from isopropanol/isopropylether to yield the title compound as yellow crystals (270 mg, 63% yield). $^1$H NMR (400 MHz, CD$_3$OD) δ 1.97–2.01(1H,m), 2.28–2.32 (1H, m), 2.45–2.48 (1H, m), 2.49–2.52 (1H, m), 2.52–2.56 (2H, m), 2.79–2.82 (2H, m), 3.29 (3H, s), 3.34 (1H, m), 3.66 (1H, m), 3.86 (1H, d, J=13.3 Hz), 4.03 (1H, bs), 4.12 (1H, d, J=13.1 Hz), 5.01 (1H, bs), 6.62 (1H, s), 6.93 (1H, s), 7.53–7.55 (3H, m), 7.69–7.70 (2H, m). m/z (APCI⁺) 366 (M+1). HPLC (aqueous 200 Mm ammonium acetate buffer/acetonitrile gradient, 3.0 ml/min, Hewlett Packard ODS Hypersil 5 μM, 125×4 mm column), 3.006 min.

Example 45

7-{[2R,S-(4-Fluoro-phenyl)-piperidin-3R,S-ylamino]-methyl}-6-methoxy-3,4-dihydro-1H-quinolin-2-one Dihydrochloride A dry toluene (5 ml) solution of 6-Methoxy-2-oxo-1,2,3,4-tetrahydro-quinoline-7-carbaldehyde (115 mg, 0.561 mmol) and 2R,S-(4-Fluoro-phenyl)-piperidin-3R,S-ylamine (163 mg, 0.841 mmol) was heated to reflux for 2 hours and then cooled to room temperature. Sodium triacetoxyborohydride (357 mg, 1.68 mmol) was added and the reaction mixture was stirred overnight. The solvent was evaporated under reduced pressure and the residue was chromatographed using 5–15% methanol/methylene chloride to yield the free base of the title compound (120 mg, 56% yield). The title compound was made by using 1.0 M HCl/Et$_2$O and obtained as an off-white solid. $^1$H NMR (free base, 400 MHz, CDCl$_3$) δ 1.50–1.54 (1H, m), 1.63–1.68 (1H, m), 1.97–2.01 (1H, m), 2.07–2.11 (1H, m), 2.52 (2H, m), 2.84 (2H, m), 2.91 (2H, m), 3.30 (1H, d, J=14.1 Hz), 3.37 (1H, m), 3.47 (3H, s), 3.58 (1H, d, J=14.1 Hz), 4.12 (1H, d, J=1.5 Hz), 6.47 (1H, s), 6.64 (1H, s), 6.96–7.01 (2H, m), 7.23–7.28 (2H, m). m/z (APCI⁺) 384 (M+1). HPLC (aqueous 200 Mm ammonium acetate buffer/acetonitrile gradient, 3.0 ml/min, Hewlett Packard ODS Hypersil 5 μM, 125×4 mm column), 3.592 min.

Preparation 40

7-Iodo-6-methoxy-1-methyl-3,4-dihydro-1H-quinolin-2-one

Silver trifluoroacetate (2.32 g, 10.48 mmol) was added to a dry methylene chloride (100 ml) solution of 6-Methoxy-1-methyl-3,4-dihydro-1H-quinolin-2-one (1.0 g, 5.24 mmol) followed by the dropwise addition of methylene chloride (100 ml) solution of iodine (1.33 g, 10.48 mmol) over 15 minutes. The reaction mixture was stirred overnight and the precipitated silver iodide salts were filtered off. The filtrate was concentrated down to a residue which was chromatographed using 50% ethylacetate/hexane to yield the title compound (795 mg, 48% yield). $^1$H NMR (400 MHz, CDCl$_3$) δ 2.57–2.61 (2H, m), 2.81–2.85 (2H, m), 3.27 (3H, s), 3.82 (3H, s), 6.62 (1H, s), 7.31 (1H, s). m/z (APCI⁺) 318 (M+1). HPLC (aqueous 200 Mm ammonium acetate buffer/acetonitrile gradient, 3.0 ml/min, Hewlett Packard ODS Hypersil 5 μM, 125×4 mm column), 4.959 min.

Preparation 41

(3R,S-5R,S-6S)-3-(6-Methoxy-1-methyl-2-oxo-1,2,3,4-tetrahydro-quinolin-7-yl)-6-phenyl-1-oxa-7-(tert-butoxycarbonyl)aza-spiro[4.5]decane A mixture of (5R,S-6S)-6-Phenyl-1-oxa-7-aza-spiro[4.5] dec-3-ene-7-carboxylic acid tert-butyl ester (1.0 g, 3.17 mmol), 7-Iodo-6-methoxy-1-methyl-3,4-dihydro-1H-quinolin-2-one (2.51 g, 7.93 mmol), tetra-n-butylammonium chloride (0.88 g, 3.17 mmol), lithium chloride (14 mg, 0.032 mmol) and potassium formate (0.81 g, 9.61 mmol) in dimethylformamide (40 ml) was degassed and kept under nitrogen. Palladium acetate (80 mg, 0.32 mmol) was added and the mixture was degassed and stirred at 60° C. for 15 hours, then further 7-Iodo-6-methoxy-1-methyl-3,4-dihydro-1H-quinolin-2-one (0.5 g, 1.58 mmol), potassium formate (0.4 g, 4.8 mmol) and palladium acetate (40 mg, 0.16 mmol) were added. The mixture was stirred at 60° C. for an overnight, cooled and filtered. The solvent was evaporated under reduced pressure, water (100 ml) was added and the mixture was extracted with ethyl acetate (2×100 ml). The combined organic fractions were washed with brine, dried (MgSO$_4$) and the solvent was evaporated under reduced pressure. The residue was purified by flash column chromatography on silica gel, eluting with 35% ethyl acetate/hexane to yield the title compound as a white solid (580 mg, 36% yield). $^1$H NMR (400 MHz, CDCl$_3$) δ 1.44 (9H, s), 1.65 (2H, m), 1.75 (1H, m), 1.85 (1H, m), 2.20 (1H, m), 2.59 (2H, m). 2.70 (1H, m), 2.82 (2H, m), 3.32 (3H, s), 3.78 (3H m), 3.83–3.85 (2H, m), 3.86 (1H, m), 4.26 (1H, m), 5.34 (1H, s), 6.66 (1H, s), 6.83 (1H, s), 7.22 (1H, m), 7.23–7.32 (2H, m), 7.57–7.60 (2H, m). m/z (APCI$^+$) 507.5 (M+1). HPLC (aqueous 200 Mm ammonium acetate buffer/acetonitrile gradient, 3.0 ml/min, Hewlett Packard ODS Hypersil 5M, 125×4 mm column), 7.414 min.

Example 46

(3R,S-6S-5R,S) 3-(6-Methoxy-1-methyl-2-oxo-1,2,3,4-tetrahydro-quinolin-7-yl)-6-phenyl-1-oxa-7-aza-spiro[4.5]decane Hydrochloride Trifluoroacetic acid (0.230 ml) was added dropwise to a stirred, cooled (0° C.) solution of (3R,S-5R,S-6S)-3-(6-Methoxy-1-methyl-2-oxo-1,2,3,4-tetrahydro-quinolin-7-yl)-6-phenyl-1-oxa-7-(tert-butoxycarbonyl)aza-spiro[4.5]decane (45 mg, 0.89 mmol) in dichloromethane (8 ml) and the mixture was stirred at room temperature for an overnight. The mixture was poured into water (10 ml), the pH was adjusted to 10.0 with aqueous sodium hydroxide (4 M) and the mixture was extracted with dichloromethane (3×25 ml). The combined organic fractions were dried (MgSO$_4$) and the solvent was evaporated under reduced pressure. The residue was redissolved into ethyl acetate and treated with 1.0M HCl/ether (0.09 ml). Resuspending it into isopropanol and filtering it yielded the title compound as a solid (19 mg, 49% yield). $^1$H NMR (400 MHz, CDCl$_3$) δ 1.60 (2H, m), 1.98 (1H, m), 2.16 (1H, m), 2.30 (1H, m), 2.58 (2H, m), 2.62 (1H, m), 2.80 (2H, m), 2.82 (1H, m), 3.20–3.23 (2H, m), 3.26 (3H, s), 3.52 (1H, s), 3.61 (3H, s), 3.70 (1H, m), 3.90 (lH, m), 6.53 (1H, s), 6.56 (1H, s), 7.28–7.34 (3H, m), 7.45–7.47 (2H, m). m/z (APCI$^+$) 407 (M+1). HPLC (aqueous 200 Mm ammonium acetate buffer/acetonitrile gradient, 3.0 ml/min, Hewlett Packard ODS Hypersil 5 μM, 125×4 mm column), 4.170 min.

Example 47

S,S-7-[(1-Dimethylaminoacetyl-2-phenyl-piperidin-3-ylamino)-methyl]-6-methoxy-1-methyl-3,4-dihydro-1H-quinolin-2-one dihydrochloride Combined 95 mg of S,S-6-Methoxy-1-methyl-7-[(2-phenyl-piperidin-3-ylamino)-methyl]-3,4-dihydro-1H-quinolin-2-one (0.25 mmol) with 26 mg of N,N-dimethylaminoacetic acid (0.25 mmol) in 670 μl of CH$_2$Cl$_2$ under nitrogen Added 139 μl of triethylamine (1.00 mmol) followed by 59 mg of bis-(2-oxo-3-oxazolidinyl) phosphinic chloride (0.25 mmol). The yellow solution was stirred at room temperature overnight. The reaction was diluted with CH$_2$Cl$_2$ and partitioned with H$_2$O. The aqueous layer was extracted once with CH$_2$Cl$_2$. The combined organic fractions were dried (MgSO$_4$) and the solvent was evaporated under reduced pressure. The yellow residue was purified first by chromatography on a Biotage Flash 12, eluting with 9:1 CH$_2$Cl$_2$/CH$_3$OH, then flash chromatography on 230–400 Å mesh silica gel, eluting with a gradient of 95:5 to 85:15 CH$_2$Cl$_2$/CH$_3$OH to give 64 mg of the title compound (55%). $^1$H NMR (400 MHz, CD$_3$OD) δ 1.65 (1H, m), 1.92 (3H, m), 2.23 (6H, s), 2.56 (2H, t, J=7.24 Hz), 2.82 (2H, t, J=7.24 Hz), 2.93 (1H, m), 3.10 (1H, m), 3.17 (2H, d, J=5.8 Hz), Hz), 3.27 (3H, s), 3.62 (3H, s), 3.64 (1H, d, J=15.76 Hz), 3.77 (2H, m), 5.98 (1H, d, J=5.8 Hz), 6.75 (1H, s), 6.98 (1H, s), 7.27 (3H, m), 7.54 (2H, d, J=7.3 Hz). M/z (APCI$^+$) 465 (M+1). HPLC (aqueous 200 mM ammonium acetate buffer/acetonitrile gradient, 3.0 ml/min, Hewlett Packard ODS Hypersil 5 uM, 125×4 mm column) 3.080.

The dihydrochloride salt was prepared by dissolving the product in CH$_3$OH, adding 1 ml of 1.0 M HCl in Et$_2$O, and evaporating under reduced pressure.

Example 48

S,S-6-Methoxy-1-methyl-7-{[2-phenyl-1-(pyridin-2-yl-acetyl)-piperidin-3-ylamino]-methyl}-3,4-dihydro-1H-quinolin-2-one dihydrochloride Combined 95 mg of S,S-6-Methoxy-1-methyl-7-[(2-phenyl-piperidin-3-ylamino)-methyl]-3,4-dihydro-1H-quinolin-2-one (0.25 mmol) with 43 mg of 2-pyridylacetic acid (0.25 mmol) in 670 μl of CH$_2$Cl$_2$. Added 139 μl of triethylamine (1.00 mmol) followed by 59 mg of bis-(2-oxo-3-oxazolidinyl) phosphinic chloride (0.25 mmol). The yellow solution was shaken at room temperature overnight. The reaction was diluted with CH$_2$Cl$_2$ and partitioned with saturated NaHCO$_3$. The aqueous layer was extracted twice with CH$_2$Cl$_2$. The combined organic fractions were dried (MgSO$_4$) and the solvent was evaporated under reduced pressure. The residue was purified by flash chromatography on 230–400 Å mesh silica gel, eluting with 95:5 CH$_2$Cl$_2$/CH$_3$OH to give 50 mg of the title compound (40%). $^1$H NMR (400 MHz, CD$_3$OD) δ m), 1.86 (3H, m), 2.54 (2H, t, J=8.05 Hz), 2.82 (2H, t, J=8.05 Hz), 2.97 (1H, m), 3.14 (1H, m), 3.25 (3H, s), 3.63 (3H, s), 3.77 (3H, m), 3.89 (1H, d, J=15.31 Hz), 3.96 (1H, d, J=15.31 Hz), 6.02 (1H, d, J=5.8 Hz), 6.73 (1H, s), 6.96 (1H, s), 7.32 (5H, m), 7.56 (2H, m), 7.72 (1H, m), 8.43 (1H, m). M/z (APCI$^+$) 499.1 (M+1). HPLC (aqueous 200 mM ammonium acetate buffer/acetonitrile gradient, 3.0 ml/min, Hewlett Packard ODS Hypersil 5 uM, 125×4 mm column) 4.008.

The dihydrochloride salt was prepared by dissolving the product in CH$_3$OH, adding 1 ml of 1.0 M HCl in Et$_2$O, and evaporating under reduced pressure.

Example 49

S,S-6-Methoxy-1-methyl-7-{[2-phenyl-1-(pyridin-3-yl-acetyl)-piperidin-3-ylamino]-methyl}-3,4-dihydro-1H-quinolin-2-one dihydrochloride Combined 95 mg of S,S-6-Methoxy-1-methyl-7-[(2-phenyl-piperidin-3-ylamino)-methyl]-3,4-dihydro-1H-quinolin-2-one (0.25 mmol) with 43 mg of 3-pyridylacetic acid (0.25 mmol) in 670 μl of CH$_2$Cl$_2$. Added 139 μl of triethylamine (1.00 mmol) followed by 59 mg of bis-(2-oxo-3-oxazolidinyl) phosphinic chloride (0.25 mmol). The yellow solution was shaken at room temperature overnight. The reaction was diluted with CH$_2$Cl$_2$ and partitioned with saturated NaHCO$_3$. The aqueous layer was extracted twice with CH$_2$Cl$_2$. The combined organic fractions were dried (MgSO$_4$) and the solvent was evaporated under reduced pressure. The residue was purified by flash chromatography on 230–400 Å mesh silica gel, eluting with 95:5 CH$_2$Cl$_2$/CH$_3$OH to give 66 mg of the title compound (53%). $^1$H NMR (400 MHz, CD$_3$OD) δ 1.97(3H, m), 2.53 (2H, t, J=7.68 Hz), 2.82 (2H, t, J=7.68 Hz), 2.99 (1H, m), 3.15 (1H, m), 3.25 (3H, s), 3.62 (3H, s), 3.64 (1H, d, J=14.11 Hz), 3.81 (4H, m), 6.01 (1H, d, J=5.60 Hz), 6.73 (1H, s), 6.95 (1H, s), 7.32 (5H, m), 7.53 (2H, m), 8.37 (2H, m). M/z (APCI$^+$) 499.1 (M+1). HPLC (aqueous 200 mM ammonium acetate buffer/acetonitrile gradient, 3.0 ml/min, Hewlett Packard ODS Hypersil 5 uM, 125×4 mm column) 3.690.

The dihydrochloride salt was prepared by dissolving the product in CH$_3$OH, adding 1 ml of 1.0 M HCl in Et$_2$O, and evaporating under reduced pressure.

Example 50

S,S-6-Methoxy-1-methyl-7-{[2-phenyl-1-(pyridin-4-yl-acetyl)-piperidin-3-ylamino]-methyl}-3,4-dihydro-1H-quinolin-2-one dihydrochloride Combined 95 mg of S,S-6-Methoxy-1-methyl-7-[(2-phenyl-piperidin-3-ylamino)-methyl]-3,4-dihydro-1H-quinolin-2-one (0.25 mmol) with 43 mg of 4-pyridylacetic acid (0.25 mmol) in 670 µl of CH$_2$Cl$_2$. Added 139 µl of triethylamine (1.00 mmol) followed by 59 mg of bis-(2-oxo-3-oxazolidinyl) phosphinic chloride (0.25 mmol). The yellow solution was shaken at room temperature overnight. The reaction was diluted with CH$_2$Cl$_2$ and partitioned with saturated NaHCO$_3$. The aqueous layer was extracted twice with CH$_2$Cl$_2$. The combined organic fractions were dried (MgSO$_4$) and the solvent was evaporated under reduced pressure. The residue was purified by flash chromatography on 230–400 Å mesh silica gel, eluting with 95:5 CH$_2$Cl$_2$/CH$_3$OH to give 51 mg of the title compound (41%). $^1$H NMR (400 MHz, CD$_3$OD) δ 1.51 (1H, m), 1.88 (3H, m), 2.54 (2H, t, J=7.89 Hz), 2.83 (2H, t, J=7.89 Hz), 2.97 (1H, m), 3.17 (1H, m), 3.26 (3H, s), 3.63 (3H, s), 3.77 (5H, m), 6.01 (1H, d, J=5.81 Hz), 6.74 (1H, s), 6.96 (1H, s), 7.18 (2H, m), 7.32 (3H, m), 7.53 (2H, d), 8.40 (2H, d). M/z (APCI$^+$) 499.1 (M+1). HPLC (aqueous 200 mM ammonium acetate buffer/acetonitrile gradient, 3.0 ml/min, Hewlett Packard ODS Hypersil 5 uM, 125×4 mm column) 3.589.

The dihydrochloride salt was prepared by dissolving the product in CH$_3$OH, adding 1 ml of 1.0 M HCl in Et$_2$O, and evaporating under reduced pressure.

Example 51

S,S-7-{[1-(Imidazol-1-yl-acetyl)-2-phenyl-piperidin-3-ylamino]-methyl}-6-methoxy-1-methyl-3,4-dihydro-1H-quinolin-2-one dihydrochloride Combined 95 mg of S,S-6-Methoxy-1-methyl-7-[(2-phenyl-piperidin-3-ylamino)-methyl]-3,4-dihydro-1H-quinolin-2-one (0.25 mmol) with 31 mg of imidazol-1-yl-acetic acid (0.25 mmol)) in 670 µl of CH$_2$Cl$_2$. Added 139 µl of triethylamine (NEt$_3$) (1.00 mmol) followed by 59 mg of bis (2-oxo-3-oxazolidinyl) phosphinic chloride (0.25 mmol). The yellow solution was shaken at room temperature overnight. The reaction was diluted with CH$_2$Cl$_2$ and partitioned twice with saturated NaHCO$_3$. The organic layer was dried (MgSO$_4$) and the solvent was evaporated under reduced pressure. The residue was purified by flash chromatography on 230–400 Å mesh silica gel, eluting with 95:5 CH$_2$Cl$_2$/CH$_3$OH to yield 85 mg of product (70%). $^1$H NMR (400 MHz, CD$_3$OD) δ 1.70 (1H, m), 1.96 (3H, m), 2.52 (2H, t, J=7.66 Hz), 2.82 (2H, t, J=7.66 Hz), 2.99 (1H, m), 3.24 (3H, s), 3.25 (1H, m), 3.61 (3H, s), 3.61 (3H, m), 4.96 (1H, d, J=16.94 Hz), 5.07 (1H, d, J=16.94 Hz), 5.92 (1H, d, J=5.6 Hz), 6.75 (1H, s), 6.93 (2H, d, J=3.9 Hz), 7.00 (1H, s), 7.34 (3H, m), 7.51 (3H, m). M/z (APCI$^+$) 488.1 (M+1). HPLC (aqueous 200 mM ammonium acetate buffer/acetonitrile gradient, 3.0 ml/min, Hewlett Packard ODS Hypersil 5 uM, 125×4 mm column) 2.896.

The dihydrochloride salt was prepared by dissolving the product in CH$_3$OH, adding 1 ml of 1.0 M HCl in Et$_2$O, and evaporating under reduced pressure.

Imidazol-1-yl-acetic acid methyl ester

Under nitrogen, combined 1.0 g of imidazole (14.7 mmol) with 824 mg of potassium hydroxide (14.7 mmol), 2.0 g of potassium carbonate (14.7 mmol) and 82 mg of benzyltriethylammonium chloride (7.34 mmol) in 40 ml of CH$_2$Cl$_2$. Added 695 µl of methylbromoacetate. Reaction is stirred at room temperature for 3 hours. Filtered off solids, rinsed with CH$_2$Cl$_2$, and evaporated the filtrate under reduced pressure to give colorless oil. Product is purified by flash chromatography on a Biotage Flash 40 (Eluent: 95:5 CH$_2$Cl$_2$/CH$_3$OH), yielding 300 mg of a white solid (27%). $^1$H NMR (400 MHz, CD$_3$OD) δ 3.75 (3H, s), 4.91 (2H, s), 6.96 (1H, s), 7.10 (1H, s), 7.64 (1H, s).

Imidazol-1-yl-acetic acid

Under nitrogen, refluxed 300 mg of imidazol-1-yl-acetic acid methyl ester in 12 ml of H$_2$O for 6 hours. Evaporated in vacuo after cooling to yield 240 mg of white solid (97%) $^1$H NMR (400 MHz, CD$_3$OD) δ 4.79 (2H, s), 7.41 (1H, s), 7.48 (1H, s), 8.70 (1H, s).

Example 52

S,S-6-Methoxy-1-methyl-7-[(1-[1,2,4]oxadiazol-3-ylmethyl-2-phenyl-piperidin-3-ylamino)-methyl]-3,4-dihydro-1H-quinolin-2-one dihydrochloride Combined 95 mg of S,S-6-methoxy-1-methyl-7-[(2-phenyl-piperidin-3-ylamino)-methyl]-3,4-dihydro-1H-quinolin-2-one (0.25 mmol) with 30 mg of 3-(chloromethyl) [1,2,4] oxadiazole (0.25 mmol), 105 µl of diisopropylamine and 2 ml of acetonitrile and shaken overnight. Removed solvent in vacuo, partitioned residue two times between CH$_2$Cl$_2$ and saturated NaHCO$_3$. The organic layer was dried (MgSO$_4$) and the solvent was evaporated under reduced pressure. The yellow gum was purified by flash chromatography on 230–400 Å mesh silica gel, eluting with 95:5 CH$_2$Cl$_2$/CH$_3$OH to give 73 mg of product (63%). $^1$H NMR (400 MHz, CD$_3$OD) δ 1.49 (1H, m), 2.03 (2H, m), 2.30 (1H, m), 2.52 (2H, m), 2.67 (1H, s), 2.80 (2H, m), 3.08 (1H, d, J=11.0 Hz), 3.20 (3H, s), 3.33 (3H, m), 3.44 (3H, s), 3.59 (1H, d, J=13.7 Hz), 3.63 (1H, d, J=2.9 Hz), 3.81 (1H, d, J=14.7), 6.62 (1H, s), 6.74 (1H, s), 7 27 (1H, t, J=7.3 Hz), 7.33 (2H, m), 7.41 (2H, d, J=6.9 Hz), 9.10 (1H, s). M/z (APCI$^+$) 462.1 (M+1). HPLC (aqueous 200 mM ammonium acetate buffer/acetonitrile gradient, 3.0 ml/min, Hewlett Packard ODS Hypersil 5 uM, 125×4 mm column) 4.461.

The dihydrochloride salt was prepared by dissolving the product in CH$_3$OH, adding 1 ml of 1.0 M HCl in Et$_2$O, and evaporating under reduced pressure.

Example 53

S,S-6-Methoxy-7-{[1-(2-methoxy-ethyl)-2-phenyl-piperidin-3-ylamino]-methyl}-1-methyl-3,4-dihydro-1H-quinolin-2-one dihydrochloride Dissolved 23.5 µl of 2-bromoethyl methyl ether (0.25 mmol) in 2 ml of acetonitrile. Added 95 mg of S,S-6-methoxy-1-methyl-7-[(2-phenyl-piperidin-3-ylamino)-methyl]-3,4-dihydro-1H-quinolin-2-one (0.25 mmol) and 105 µl of diisopropylamine. Reaction was shaken for 2 days. Removed solvent in vacuo, partitioned residue two times between $CH_2Cl_2$ and saturated $NaHCO_3$. The organic layer was dried ($MgSO_4$) and the solvent was evaporated under reduced pressure. The residue was first purified by flash chromatography on 230–400 Å mesh silica gel, eluting with 9:1,1% $CH_2Cl_2/CH_3OH$/triethylamine, then by flash chromatography on 230–400 Å mesh silica gel, eluting with 9:1, 0.1% $CH_2Cl_2/CH_3OH$/triethylamine to give 26 mg of product (24%). $^1$H NMR (400 MHz, $CD_3OD$) δ 1.54 (2H, m), 2.02 (3H, m), 2.20 (1H, m), 2.51 (2H, m), 2.70 (2H, m), 2.79 (2H, m), 3.20 (3H, s), 3.22 (3H, s), 3.23 (1H, m), 3.38 (4H, m), 3.43 (3H, s), 3.64 (1H, d, J=13.7 Hz), 6.63 (1H, s), 6.75 (1H, s), 7.29 (5H, m). M/z ($APCI^+$) 438.3 (M+1). HPLC (aqueous 200 mM ammonium acetate buffer/acetonitrile gradient, 3.0 ml/min, Hewlett Packard ODS Hypersil 5 uM, 125×4 mm column) 4.720.

The dihydrochloride salt was prepared by dissolving the product in $CH_3OH$, adding 1 ml of 1.0 M HCl in $Et_2O$, and evaporating under reduced pressure.

Example 54

S,S-7-{[1-(2,3-Dihydroxy-propyl)-2-phenyl-piperidin-3-ylamino]-methyl}-6-methoxy-1-methyl-3,4-dihydro-1H-quinolin-2-one dihydrochloride Dissolved 21.9 µl of 3-bromo-1,2-propanediol (0.25 mmol) in 2 ml of acetonitrile. Added 95 mg of S,S,-6-methoxy-1-methyl-7-[(2-phenyl-piperidin-3-ylamino)-methyl]-3,4-dihydro-1H-quinolin-2-one (0.25 mmol) and 105 µl of diisopropylamine 95 mg of 6-methoxy-1-methyl-7-[(2-phenyl-piperidin-3-ylamino)-methyl]-3,4-dihydro-1H-quinolin-2-one (0.25 mmol) and 105 µl of diisopropylamine. Reaction was shaken for 2 days. Removed solvent in vacuo, partitioned residue two times between $CH_2Cl_2$ and saturated $NaHCO_3$. The organic layer was dried ($MgSO_4$) and the solvent was evaporated under reduced pressure. The residue was first purified by flash chromatography on 230–400 Å mesh silica gel, eluting with 9:1, 0.1% $CH_2Cl_2/CH_3OH$/triethylamine, then by flash chromatography on 230–400 Å mesh silica gel, eluting with 98:2, 0.05% $CH_2Cl_2/CH_3OH$/triethylamine to give 19 mg of product (17%). $^1$H NMR (400 MHz, $CD_3OD$) δ 1.52 (1H, m), 1.79 (1H, m), 2.08 (3H, m), 2.51 (2H, m), 2.61 (2H, m), 2.80 (2H, t, J=7.4 Hz), 3.20 (3H, s), 3.31 (6H, m), 3.35 (3H, s), 3.68 (1H, d, J=13.1 Hz), 3.85 (1H, m), 6.64 (1H, s), 6.79 (1H, s), 7.30 (5H, m). M/z ($APCI^+$) 454.2 (M+1). HPLC (aqueous 200 mM ammonium acetate buffer/acetonitrile gradient, 3.0 ml/min, Hewlett Packard ODS Hypersil 5 uM, 125×4 mm column) 3.608.

The dihydrochloride salt was prepared by dissolving the product in $CH_3OH$, adding 1 ml of 1.0 M HCl in $Et_2O$, and evaporating under reduced pressure.

Example 55

S,S-7-{[1-(2-Dimethylamino-ethyl)-2-phenyl-piperidin-3-ylamino]-methyl}-6-methoxy-1-methyl-3,4-dihydro-1H-quinolin-2-one dihydrochloride Combined 36 mg of 2-(N,N-Dimethylamino)ethyl chloride (0.25 mmol) with 95 mg of S,S-6-methoxy-1-methyl-7-[(2-phenyl-piperidin-3-ylamino)-methyl]-3,4-dihydro-1H-quinolin-2-one (0.25 mmol) and 105 µl of diisopropylamine in 2 ml of acetonitrile. Reaction was shaken for 2 days. Removed solvent in vacuo, partitioned residue two times between $CH_2Cl_2$ and saturated $NaHCO_3$. The organic layer was dried ($MgSO_4$) and the solvent was evaporated under reduced pressure. The residue was purified by flash chromatography on 230–400 Å mesh silica gel, eluting with gradient of 9:1 $CH_2Cl_2/CH_3OH$ to 8:2 $CH_3OH$/triethylamine, to give 24 mg of product (21%). $^1$H NMR (400 MHz, $CD_3OD$) δ 1.51 (2H, m), 2.02 (3H, m), 2.10 (6H, s), 2.17 (1H, m), 2.50 (4H, m), 2.64 (2H, m), 2.81 (2H, t, J=7 88 Hz), 3.18 (1H, m), 3.21 (3H, s), 3.36 (1H, d, J=13.5 Hz), 3.44 (3H, s), 3.44 (1H, m), 3.62 (1H, d, J=13.7 Hz), 6.63 (1H, s), 6.75 (1H, s), 7.30 (5H, m). M/z ($APCI^+$) 451.3 (M+1). HPLC (aqueous 200 mM ammonium acetate buffer/acetonitrile gradient, 3.0 ml/min, Hewlett Packard ODS Hypersil 5 uM, 125×4 mm column) 3.346.

The dihydrochloride salt was prepared by dissolving the product in $CH_3OH$, adding 1 ml of 1.0 M HCl in $Et_2O$, and evaporating under reduced pressure.

Example 56

6-Methoxy-1-methyl-7-[(2-phenyl-octahydro-cyclopenta[b]pyrrol-3-ylamino)-methyl]-3,4-dihydro-1H-quinolin-2-one dihydrochloride Dissolved 441 mg of 3-[(6-Methoxy-1-methyl-2-oxo-1,2,3,4-tetrahydro-quinolin-7-ylmethyl)-amino]-2-phenyl-hexahydro-cyclopenta[b]pyrrole-1-carboxylic acid benzyl ester (0.82 mmol) in 40 ml of EtOH. Added 55 mg of 10% palladium on carbon and placed on Parr shaker for 4.25 hours under 45 lbs. of hydrogen. Filtered over celite, rinsed catalyst with EtOH several times and evaporated the filtrate under reduced pressure. The residue was purified on a Biotage Flash 40, eluting with 96:4 $CH_2Cl_2/CH_3OH$ to give 222 mg of racemic product (69%). $^1$H NMR (400 MHz, $CDCl_3$) δ 1.35 (2H, m), 1.71 (2H, m), 1.94 (2H, m), 2.60 (3H, m), 2.82 (2H, t, J=7.47 Hz), 2.95 (1H, d, J=3.11 Hz), 3.26 (3H, s), 3.49 (1H, d, J=7.68 Hz), 3.54 (3H, s), 3.73 (1H, d, J=13.1 Hz), 4.05 (1H, m), 4.33 (1H, d, J=4.6 Hz), 6.56 (1H, s), 6.65 (1H, s), 7.38 (5H, m). M/z ($APCI^+$) 406.2 (M+1). HPLC (aqueous 200 mM ammonium acetate buffer/acetonitrile gradient, 3.0 ml/min, Hewlett Packard ODS, Hypersil 5 uM, 125×4 mm column) 4.200.

The enantiomers were separated by chiral preparative HPLC (80/20/0.025% hexanes/EtOH/diethylamine, 75 ml/min, Chiralpak AD, 5 cm×50 cm) to give the S,S-enantiomer at retention time 6.512 min and the R, R-enantiomer at retention time 12.078 min.

The dihydrochloride salts were prepared by dissolving the product in $CH_3OH$, adding 1 ml of 1.0 M HCl in $Et_2O$, and evaporating under reduced pressure.

Preparation 42

3-[(6-Methoxy-1-methyl-2-oxo-1,2,3,4-tetrahydro-quinolin-7-ylmethyl)-amino]-2-phenyl-hexahydro-cyclopenta[b]pyrrole-1-carboxylic acid benzyl ester Under nitrogen, combined 606 mg of 3-Amino-2-phenyl-hexahydro-cyclopenta[b]pyrrole-1-carboxylic acid benzyl ester (1.80 mmol) with 395 mg of 6-Methoxy-1-methyl-2-oxo-1,2,3,4-tetrahydro-quinoline-7-carbaldehyde (1.80 mmol) in 10 ml of $CH_2Cl_2$ and stirred for 15 minutes. Added 1.15 g of sodium triacetoxyborohydride (5.40 mmol) and stirred overnight. The reaction mixture was washed three times with saturated $NaHCO_3$. The organic layer was dried ($MgSO_4$) and the solvent was evaporated under reduced pressure. The residue was purified by flash chromatography on a Biotage Flash 40, eluting first with 1:1 EtOAc/Hexanes, then with EtOAc to give 323 mg of product (33%). Another lot (241 mg, 25%) is isolated after a second chromatography. M/z (APCI$^+$) 539.9 (M+1). HPLC (aqueous 200 mM ammonium acetate buffer/acetonitrile gradient, 3.0 ml/min, Hewlett Packard ODS Hypersil 5 uM, 125×4 mm column) 6.367.

Example 57

6-Methoxy-1,3,3-trimethyl-5-[(2-phenyl-octahydro-cyclopenta[b]pyrrol-3-ylamino)-methyl]-1,3-dihydro-indol-2-one dihydrochloride Dissolved 326 mg of 3-[(6-Methoxy-1,3,3-trimethyl-2-oxo-2,3-dihydro-1H-indol-5-ylmethyl)-amino]-2-phenyl-hexahydro-cyclopenta[b]pyrrole-1-carboxylic acid phenyl ester (0.59 mmol) in 32 ml of EtOH. Added 32 mg of 10% palladium on carbon and placed on Parr shaker for 4.5 hours under 39 pounds of hydrogen. Filtered over celite, rinsed catalyst with EtOH several times and evaporated the filtrate under reduced pressure. The residue was purified on a Biotage Flash 40, eluting with 95:5 $CH_2Cl_2/CH_3OH$, then $CH_3OH$, to give 150 mg of racemic product (61%). $^1$H NMR (400 MHz, $CDCl_3$) δ 1.27 (6H, s), 1.32 (3H, m), 1.68 (1H, m), 1.92 (2H, m), 2.62 (1H, m), 2.88(1H, m), 3.16 (3H, s), 3.54 (1H, d, J=13.53 Hz), 3.56 (3H, s), 3.72 (1H, d, J=13.52 Hz), 4.04 (1H, m), 4.29 (1H, d, J=4.6 Hz), 6.27 (1H, s), 6.81 (1H, s), 7.27 (5H, m). M/z (APCI$^+$) 420.4 (M+1). HPLC (aqueous 200 mM ammonium acetate buffer/acetonitrile gradient, 3.0 ml/min, Hewlett Packard ODS Hypersil 5 uM, 125×4 mm column) 4.522.

The enantiomers were separated by chiral preparative HPLC (85/15/0.025% Hexanes/Isopropanol/Diethylamine, 80 ml/min, Chiralpak AD, 5 cm×50 cm) to give the S,S-enantiomer at retention time 9.358 minutes and the R,R-enantiomer at retention time 13.946 minutes.

The dihydrochloride salts were prepared by dissolving the product in $CH_3OH$, adding 1 ml of 1.0 M HCl in $Et_2O$, and evaporating under reduced pressure.

Preparation 43

6-Methoxy-1,3,3-trimethyl-1,3-dihydro-indol-2-one

In a flame-dried flask under nitrogen, 490 mg of 60% sodium hydride (12.26 mmol) was slurried three times with Hexanes, and the Hexanes were syringed off. Added 6.25 ml of N,N-dimethylformamide, followed by 500 mg of 6-Methoxy-1,3-dihydro-indol-2-one (3.06 mmol) and stirred at room temperature for 5 minutes. Chilled in ice-$H_2O$ bath and added 763 μl of methyl iodide (12.26 mmol) dropwise. After 10 minutes, warmed to room temperature and stirred for 1.5 hours. Chilled in ice-$H_2O$ bath and added 20 ml of $H_2O$ dropwise. Extracted three times with 2:1 EtOAc/toluene. The combined organics were washed with sodium thiosulfate, $H_2O$ and brine, dried ($MgSO_4$) and the solvent removed in vacuo to crude red oil. Purified on Biotage Flash 40, eluting with 4:1 Hexanes/EtOAc to give 285 mg of a white solid (45%). $^1$H NMR (400 MHz, $CDCl_3$) δ 1.31 (6H, s), 3.16 (3H, s), 3.80 (3H, s), 6.41 (1H, d, J=2.28 Hz), 6.53 (1H, m), 7.06 (1H, d, J=8.1 Hz). M/z (APCI$^+$) 206.0 (M+1).

Preparation 44

6-Methoxy-1,3,3-trimethyl-2-oxo-2,3-dihydro-1H-indole-5-carbaldehyde

Under nitrogen, combined 282 mg of 6-Methoxy-1,3,3-trimethyl-1,3-dihydro-indol-2-one (1.37 mmol) with 10 ml of $CH_2Cl_2$ and chilled in ice-$H_2O$ bath. Added 4.1 ml of 1.0 M titanium tetrachloride in $CH_2Cl_2$ (4.1 mmol) dropwise. Stirred in cold for 1.5 hours. Added 186 μl of α,α-dichloromethyl methyl ether (2.06 mmol and stirred in cold for 15 minutes, then at room temperature overnight. Poured over ice-$H_2O$, extracted three times with $CH_2Cl_2$. The combined organics were extracted with brine, sat. $NaHCO_3$, brine, dried ($MgSO_4$) and the solvent evaporated in vacuo to 289 mg of green solid (91%). $^1$H NMR (400 MHz, $CDCl_3$) δ 1.35 (6H, s), 3.25 (3H, s), 3.98 (3H, s), 6.42 (1H, s), 7.68 (1H, s), 10.35 (1H, s), M/z (APCI$^+$) 234.0 (M+1).

Preparation 45

3-[(6-Methoxy-1,3,3-trimethyl-2-oxo-2,3-dihydro-1H-indol-5-ylmethyl)-amino]-2-phenyl-hexahydro-cyclopenta[b]pyrrole-1-carboxylic acid phenyl ester Under nitrogen, combined 288 mg of 3-Amino-2-phenyl-hexahydro-cyclopenta[b]pyrrole-1-carboxylic acid benzyl ester (0.86 mmol) with 200 mg of 6-Methoxy-1,3,3-trimethyl-2-oxo-2,3-dihydro-1H-indole-5-carbaldehyde (0.86 mmol) in 5 ml of $CH_2Cl_2$ and stirred for 10 minutes. Added 545 mg of sodium triacetoxyborohydride (2.57 mmol) and stirred overnight. The reaction mixture was extracted two times with saturated $NaHCO_3$. The organic layer was dried ($MgSO_4$) and the solvent was evaporated under reduced pressure. The residue was purified by flash chromatography on a Biotage Flash 40, eluting with 1:1 EtOAc/Hexanes to give 336 mg of product (71%). M/z (APCI$^+$) 554.2 (M+1). HPLC (aqueous 200 mM ammonium acetate buffer/acetonitrile gradient, 3.0 ml/min, Hewlett Packard ODS Hypersil 5 uM, 125×4 mm column) 6.531.

Example 58

S,S-6-Ethoxy-1,3,3-trimethyl-5-[(2-phenyl-piperidin-3-ylamino)-methyl]-1,3-dihydro-indol-2-one dihydrochloride Under nitrogen, dissolved 50 mg of S,S-2-Phenyl-piperidin-3-ylamine (0.20 mmol) in 1.5 ml of $CH_2Cl_2$ and 0.5 ml of DMF. Added 49 mg of 6-ethoxy-1,3,3-trimethyl-2-oxo-2,3-dihydro-1H-indole-5-carbaldehyde (0.20 mmol) and stirred for 45 minutes. Added 127 mg of sodium triacetoxyborohydride (0.60 mmol) and stirred for 40 hours. Diluted with $CH_2Cl_2$ and extracted with saturated $NaHCO_3$, dried ($MgSO_4$), and removed solvent under reduced pressure.

Purified by chromatography on a Biotage Flash 40, eluting with 95:5 CH$_2$Cl$_2$/CH$_3$OH, then 85:15 CH$_2$Cl$_2$/CH$_3$OH to give 40 mg of product (49%). $^1$H NMR (400 MHz, CD$_3$OD) δ 1.08 (3H, t, J=7.05 Hz), 1.26 (6H, d, J=8.3 Hz), 1.43 (1H, d, J=13.28 Hz), 1.73 (1H, m), 1.87 (1H, m), 2.22 (1H, d, J=13.49 Hz), 2.76 (1H, m), 2.86 (1H, d, J=2.49 Hz), 3.17 (3H, s), 3.21 (1H, m), 3.36 (1H, d, J=13.07 Hz), 3.65 (1H, d, J=13.28 Hz), 3.77 (2H, m), 3.94 (1H, d, J=2.07 Hz), 6.50 (1H, s), 6.93 (1H, s), 7.25 (5H, m). M/z (APCI$^+$) 408.3 (M+1). HPLC (aqueous 200 mM ammonium acetate buffer/acetonitrile gradient, 3.0 ml/min, Hewlett Packard ODS Hypersil 5 uM, 125×4 mm column) 4.514.

The dihydrochloride salt was prepared by dissolving the product in CH$_3$OH, adding 1 ml of 1.0 M HCl in Et$_2$O, and evaporating under reduced pressure.

Example 59

6-Ethoxy-1,3,3-trimethyl-5-[(2-phenyl-octahydro-cyclopenta[b]pyrrol-3-ylamino)-methyl]-1,3-dihydro-indol-2-one dihydrochloride Dissolved 279 mg of 3-[(6-Ethoxy-1,3,3-trimethyl-2-oxo-2,3-dihydro-1H-indol-6-ylmethyl)-amino]-2-phenyl-hexahydro-cyclopenta[b]pyrrole-1-carboxylic acid phenyl ester (0.49 mmol) in 28 ml of EtOH. Added 28 mg of 10% palladium on carbon and placed on Parr shaker under 52 lbs. of hydrogen overnight. Filtered over celite, rinsed catalyst with EtOH several times and evaporated the filtrate under reduced pressure. The residue was purified on a Biotage Flash 40, eluting with 95:5 CH$_2$Cl$_2$/CH$_3$OH, then 90:10 CH$_2$Cl$_2$/CH$_3$OH to give 92 mg of racemic product (43%). $^1$H NMR (400 MHz, CDCl$_3$) δ 1.10 (3H, t, J=6.85 Hz), 1 29 (1H, m), 1.45 (2H, m), 1.70 (1H, m), 1.96 (2H, m), 2.68 (1H, q, J=8.1 Hz), 2.89 (1H, q, J=4.4 Hz), 3.17 (3H, s), 3.53 (1H, d, J=13.7 Hz), 3.83 (3H, m), 4.07 (1H, q, J=7.9 Hz), 4.30 (1H, d, J=4.4 Hz), 6.29 (1H, s), 6.84 (1H, s), 7.28 (5H, m). M/z (APCI$^+$) 434.3 (M+1). HPLC (aqueous 200 mM ammonium acetate buffer/acetonitrile gradient, 3.0 ml/min, Hewlett Packard ODS Hypersil 5 uM, 125×4 mm column) 5.172.

The enantiomers were separated by chiral preparative HPLC (90/10/0.025% Hexanes/Isopropanol/Diethylamine, 45 ml/min, Chiralpak AD, 5 cm×50 cm) to give the S,S-enantiomer at retention time 12.915 min and the R,R-enantiomer at retention time 15.159 min.

The dihydrochloride salts were prepared by dissolving the product in CH$_3$OH, adding 1 ml of 1.0 M HCl in Et$_2$O, and evaporating under reduced pressure.

Preparation 46

6-Hydroxy-1,3,3-trimethyl-1,3-dihydro-indol-2-one

Under nitrogen, combined 2.05 g of 6-Methoxy-1,3,3-trimethyl-1,3-dihydro-indol-2-one (10.0 mmol) with 28 ml of CH$_2$Cl$_2$. Added 22 ml of 1.0 M boron tribromide in CH$_2$Cl$_2$ dropwise over 10 minutes. Stirred at room temperature for 3.5 hours. Poured over ice-H$_2$O and filtered to give 2.32 g of beige solid. $^1$H NMR (400 MHz, CD$_3$OD) δ 1.25 (6H, s), 3.13 (3H, s), 6.42 (1H, d, J=2.08 Hz), 6.45 (1H, d, J=7.9 Hz), 7.02 (1H, d, J=8.1 Hz). M/z (APCI$^+$) 192.1 (M+1). HPLC (aqueous 200 mM ammonium acetate buffer/acetonitrile gradient, 3.0 ml/min, Hewlett Packard ODS Hypersil 5 uM, 125×4 mm column) 3.262.

Preparation 47

6-Ethoxy-1,3,3-trimethyl-1,3-dihydro-indol-2-one

Under nitrogen, combined 1.16 g of 6-Hydroxy-1,3,3-trimethyl-1,3-dihydro-indol-2-one (5.0 mmol) with 10 ml of THF. Added 2.8 g of potassium t-butoxide (25.0 mmol) and stirred for 45 minutes. Added 2.0 ml of ethyl iodide (25.0 mmol) and stirred overnight. The reaction mixture was diluted with EtOAc and extracted three times with H$_2$O, combined organics were dried (MgSO$_4$), and the solvent was evaporated under reduced pressure to give 864 mg of yellow solid (78%). $^1$H NMR (400 MHz, CDCl$_3$) δ 1.33 (6H, s), 1.41 (3H, t, J=7.05 Hz), 3.17 (3H, s), 4.04 (2H, q, J=7.06 Hz), 6.43 (1H, d, J=2.07 Hz), 6.54 (1H, d, J=8.3 Hz), 7.06 (1H, d, J=8.3 Hz). M/z (APCI$^+$) 220.2 (M+1). HPLC (aqueous 200 mM ammonium acetate buffer/acetonitrile gradient, 3.0 ml/min, Hewlett Packard ODS Hypersil 5 uM, 125×4 mm column) 5.220.

Preparation 48

6-Ethoxy-1,3,3-trimethyl-2-oxo-2,3-dihydro-1H-indole-5-carbaldehyde

Under nitrogen, added 3.5 ml of trifluoroacetic acid to 859 mg of hexamethylenetetramine (6.13 mmol) and heated in 70° C. oil bath for 1 hour. Added 448 mg of 6-Ethoxy-1,3,3-trimethyl-1,3-dihydro-indol-2-one dissolved in 1.0 ml of trifluoroacetic acid. Heated at 70° C. for 4 hours, then at 50° C. for 18 hours. Cooled to room temperature. Added 4.0 ml of H$_2$O and extracted three times with EtOAc. Combined organics were dried (MgSO$_4$), evaporated in vacuo and purified by chromatography on a Biotage Flash 40, eluting with 2:1 Hexanes/EtOAc to give 335 mg of a green solid (66%). $^1$H NMR (400 MHz, CDCl$_3$) δ 1.35 (6H, s), 1.50 (3H, t, J=7.05 Hz), 3.24 (3H, s), 4.19 (2H, q, J=7.06 Hz), 6.40 (1H, s), 7.68 (1H, s), 10.37 (1H, s). M/z (APCI$^+$) 248.1 (M+1). HPLC (aqueous 200 mM ammonium acetate buffer/acetonitrile gradient, 3.0 ml/min, Hewlett Packard ODS Hypersil 5 uM, 125×4 mm column) 4.815.

Preparation 49

3-[(6-Ethoxy-1,3,3-trimethyl-2-oxo-2,3-dihydro-1H-indol-6-ylmethyl)-amino]-2-phenyl-hexahydro-cyclopenta[b]pyrrole-1-carboxylic acid phenyl ester Under nitrogen, combined 202 mg of 3-Amino-2-phenyl-hexahydro-cyclopenta[b]pyrrole-1-carboxylic acid benzyl ester (0.60 mmol) with 148 mg of 6-Ethoxy-1,3,3-trimethyl-2-oxo-2,3-dihydro-1H-indole-5-carbaldehyde (0.60 mmol) in 5 ml of CH$_2$Cl$_2$ and stirred for 45 minutes. Added 381 mg of sodium triacetoxyborohydride (1.80 mmol) and stirred for 40 hours. The reaction mixture was extracted with saturated NaHCO$_3$. The organic layer was dried (MgSO$_4$) and the solvent was evaporated under reduced pressure. The residue was purified by flash chromatography on a Biotage Flash 40, eluting with 1:2 EtOAc/Hexanes to give 279 mg of product (82%). M/z (APCI$^+$) 568.3 (M+1). HPLC (aqueous 200 mM ammonium acetate buffer/acetonitrile gradient, 3.0 ml/min, Hewlett Packard ODS Hypersil 5 uM, 125×4 mm column) 7.058.

Example 60

S,S-6-Isopropoxy-1,3,3-trimethyl-5-[(2-phenyl-piperidin-3-ylamino)-methyl]-1,3-dihydro-indol-2-one dihydrochloride Under nitrogen, dissolved 50 mg of S,S-2-Phenyl-piperidin-3-ylamine (0.20 mmol) in 1.5 ml of $CH_2Cl_2$ and 0.5 ml of DMF. Added 52 mg of 6-Isopropoxy-1,3,3-trimethyl-2-oxo-2,3-dihydro-1H-indole-5-carbaldehyde (0.20 mmol) and stirred for 1 hour. Added 127 mg of sodium triacetoxyborohydride (0.60 mmol) and slurried overnight. Diluted with $CH_2Cl_2$ and extracted with sat. $NaHCO_3$, dried ($MgSO_4$), and removed solvent under reduced pressure. Purified by chromatography on a Biotage Flash 40, eluting with 9:1 $CH_2Cl_2/CH_3OH$, then 8:2 $CH_2Cl_2/CH_3OH$, and finally with 1:1 $CH_2Cl_2/CH_3OH$ to give 40 mg of product (48%). $^1H$ NMR (400 MHz, $CD_3OD$) δ 1.03 (6H, dd, J=6.02 Hz), 1.24 (6H, d, J=3.11 Hz), 1.42 (1H, m), 1.80 (2H, m), 2.22 (1H, m), 2.75 (1H, m), 2.92 (1H, m), 3.14 (3H, s), 3.17 (1H, m), 3.34 (1H, d, J=12.66 Hz), 3.54 (1H, d, J=12.87 Hz), 3.93 (1H, d, J=2.08 Hz), 4.64 (1H, m), 6.51 (1H, s), 6.92 (1H, s), 7.26 (5H, m). M/z ($APCI^+$) 422.4 (M+1). HPLC (aqueous 200 mM ammonium acetate buffer/acetonitrile gradient, 3.0 ml/min, Hewlett Packard ODS Hypersil 5 uM, 125×4 mm column) 5.053.

The dihydrochloride salt was prepared by dissolving the product in $CH_3OH$, adding 1 ml of 1.0 M HCl in $Et_2O$, and evaporating under reduced pressure.

Example 61

6-Isopropoxy-1,3,3-trimethyl-5-[(2-phenyl-octahydro-cyclopenta[b]pyrrol-3-ylamino)-methyl]-1,3-dihydro-indol-2-one dihydrochloride Dissolved 307 mg of 3-[(6-Isopropoxy-1,3,3-trimethyl-2-oxo-2,3-dihydro-1H-indol-6-ylmethyl)-amino]-2-phenyl-hexahydro-cyclopenta[b]pyrrole-1-carboxylic acid phenyl ester (0.53 mmol) in 30 ml of EtOH. Added 30 mg of 10% palladium on carbon and placed on Parr shaker under 42 pounds of hydrogen overnight. Filtered over celite, rinsed catalyst with EtOH several times and evaporated the filtrate under reduced pressure. The residue was purified on a Biotage Flash 40, eluting with 95:5 $CH_2Cl_2/CH_3OH$, then 1:1 $CH_2Cl_2/CH_3OH$ to give 148 mg of racemic product (63%). $^1H$ NMR (400 MHz, $CDCl_3$) δ 1.08 (6H, dd, J=19.5 Hz), 1.28 (6H, s), 1.36 (1H, m), 1.82 (5H, m), 2.63 (1H, q, J=8.1 Hz), 2.90 (1H, d, J=4.57 Hz), 3.13 (3H, s), 3.49 (1H, d, J=13.29 Hz), 3.71 (1H, d, J=13.7 Hz), 4.03 (1H, m), 4.26 (1H, d, J=4.57 Hz), 4.37 (1H, m), 6.27 (1H, s), 6.82 (1H, s), 7.30 (5H, m). M/z ($APCI^+$) 448.2 (M+1). HPLC (aqueous 200 mM ammonium acetate buffer/acetonitrile gradient, 3.0 ml/min, Hewlett Packard ODS Hypersil 5 uM, 125×4 mm column) 5.426.

The enantiomers were separated by chiral preparative HPLC (90/10/0.05% Hexanes/Isopropanol/Diethylamine, 100 ml/min, Chiralpak AD, 5 cm×50 cm) to give the S,S-enantiomer at retention time 8.832 minutes and the R,R-enantiomer at retention time 12.563 minutes.

The dihydrochloride salts were prepared by dissolving the product in $CH_3OH$, adding 1 ml of 1.0 M HCl in $Et_2O$, and evaporating under reduced pressure.

Preparation 50

6-Isopropoxy-1,3,3-trimethyl-1,3-dihydro-indol-2-one

Under nitrogen, combined 1.16 g of 6-Hydroxy-1,3,3-trimethyl-1,3-dihydro-indol-2-one (5.0 mmol) with 10 ml of THF. Added 2.8 g of potassium t-butoxide (25.0 mmol) and stirred for 45 minutes. Added 2.5 ml of 2-iodopropane (25.0 mmol) and stirred overnight. The reaction mixture was diluted with EtOAc and extracted with $H_2O$, combined organics were dried ($MgSO_4$), and the solvent was evaporated under reduced pressure. Purified by flash chromatography on a Biotage Flash 40, eluting with 3:1 Hexanes/EtOAc to give 490 mg of yellow solid (42%). $^1H$ NMR (400 MHz, $CDCl_3$) δ 1.34 (12H, m), 3.17 (3H, s), 4.54 (1H, m), 6.41 (1H, d, J=2.28 Hz), 6.53 (1H, d, J=8.1 Hz), 7.05 (1H, d, J=8.1 Hz). M/z ($APCI^+$) 234.2 (M+1). HPLC (aqueous 200 mM ammonium acetate buffer/acetonitrile gradient, 3.0 ml/min, Hewlett Packard ODS Hypersil 5 uM, 125×4 mm column) 5.648.

Preparation 51

6-Isopropoxy-1,3,3-trimethyl-2-oxo-2,3-dihydro-1H-indole-5-carbaldehyde

Under nitrogen, added 3.5 ml of trifluoroacetic acid to 880 mg of hexamethylenetetramine (6.30 mmol) and heated in 70° C. sand bath for 1 hour. Added 490 mg of 6-Isopropoxy-1,3,3-trimethyl-1,3-dihydro-indol-2-one dissolved in 1.5 ml of trifluoroacetic acid. Heated at 70° C. for 1 hour, then at 50° C. for 18 hours. Cooled to room temperature. Added 4.5 ml of $H_2O$ and extracted three times with EtOAc. Combined organics were dried ($MgSO_4$), evaporated in vacuo and purified by chromatography on a Biotage Flash 40, eluting with 2:1 Hexanes/EtOAc to give 241 mg of a green solid (49%). $^1H$ NMR (400 MHz, $CDCl_3$) δ 1.33 (6H, s), 1.41 (6H, d, J=6.22 Hz), 3.21 (3H, s), 4.68 (1H, m), 6.38 (1H, s), 7.66 (1H, s), 10.33 (1H, s). M/z ($APCI^+$) 262.2 (M+1). HPLC (aqueous 200 mM ammonium acetate buffer/acetonitrile gradient, 3.0 ml/min, Hewlett Packard ODS Hypersil 5 uM, 125×4 mm column) 5.050.

Preparation 52

3-[(6-Isopropoxy-1,3,3-trimethyl-2-oxo-2,3-dihydro-1H-indol-6-ylmethyl)-amino]-2-phenyl-hexahydro-cyclopenta[b]pyrrole-1-carboxylic acid phenyl ester Under nitrogen, combined 202 mg of 3-Amino-2-phenyl-hexahydro-cyclopenta[b]pyrrole-1-carboxylic acid benzyl ester (0.60 mmol) with 157 mg of 6-Isopropoxy-1,3,3-trimethyl-2-oxo-2,3-dihydro-1H-indole-5-carbaldehyde (0.60 mmol) in 5 ml of $CH_2Cl_2$ and stirred for 1 hour. Added 381 mg of sodium triacetoxyborohydride (1.80 mmol) and stirred for 1 week. Partitioned between $CH_2Cl_2$ and saturated $NaHCO_3$. The organic layer was dried ($MgSO_4$) and the solvent was evaporated under reduced pressure. The residue was purified by flash chromatography on a Biotage Flash 40, eluting with 975/25 $CH_2Cl_2/CH_3OH$ to give 312 mg of product (89%). HPLC (aqueous 200 mM ammonium acetate buffer/acetonitrile gradient, 3.0 ml/min, Hewlett Packard ODS Hypersil 5 uM, 125×4 mm column) 7.476.

Example 62

S,S-7-Isopropoxy-1-methyl-6-[(2-phenyl-piperidin-3-ylamino)-methyl]-3,4-dihydro-1H-quinolin-2-one dihydrochloride Under nitrogen, combined 50 mg of S,S-2-Phenyl-piperidin-3-ylamine (0.20 mmol) with 49 mg of 7-Isopropoxy-1-methyl-2-oxo-1,2,3,4-tetrahydro-quinoline-6-carbaldehyde (0.20 mmol) in 1.5 ml of $CH_2Cl_2$ and 0.5 ml of DMF and stirred at room temperature for 15 minutes. Added 127 mg of sodium triacetoxyborohydride (0.60 mmol) and stirred overnight. Diluted reaction with $CH_2Cl_2$ and extracted twice with sat. $NaHCO_3$, dried ($MgSO_4$), and evaporated under reduced pressure. The residue was purified on a Biotage Flash 40, eluting with 9:1 $CH_2Cl_2/CH_3OH$ to give 39 mg of product (48%). $^1H$ NMR (400 MHz, $CD_3OD$) δ 1.03 (6H, dd, J=8.10 Hz), 1.42 (1H, m), 1.78 (2H, m), 2.19 (1H, m), 2.53 (2H, m), 2.74 (3H, m), 2.88 (1H, d, J=2.7 Hz), 3.16 (1H, m), 3.27 (3H, s), 3.32 (1H, d, J=13.08 Hz), 3.50 (1H, d, J=13.08 Hz), 3.92 (1H, d, J=2.3 Hz), 4.40 (1H, m), 6.51 (1H, s), 6.79 (1H, s), 7.25 (5H, m). M/z ($APCI^+$) 408.6 (M+1). HPLC (aqueous 200 mM ammonium acetate buffer/acetonitrile gradient, 3.0 ml/min, Hewlett Packard ODS Hypersil 5 uM, 125×4 mm column) 4.147.

The dihydrochloride salt was prepared by dissolving the product in $CH_3OH$, adding 1 ml of 1.0 M HCl in $Et_2O$, and evaporating under reduced pressure.

Preparation 53

3-Chloro-N-(3-methoxy-phenyl)-propionamide

Under nitrogen, added 4.5 ml of m-anisidine (0.04 mol) to a vigorously stirred mixture of 25 ml of $CH_2Cl_2$ and 25 ml of sat. $NaHCO_3$. Added 3.82 ml of 3-chloropropionyl chloride dropwise over 15 minutes, at a rate to prevent reflux. Stirred for 15 minutes after addition completed, separated layers, extracted aqueous layer with $CH_2Cl_2$, dried combined organics ($MgSO_4$), and evaporated solvent off under reduced pressure to give 7.93 g of tan solid (93%). $^1H$ NMR (400 MHz, $CDCl_3$) δ 2.78 (2H, t, J=6.23 Hz), 3.77 (3H, s), 3.85 (2H, t, J=6.44 Hz), 6.65 (1H, dd, J=8.30 Hz), 6.94 (1H, d, J=7.89 Hz), 7.21 (3H, m). M/z ($APCI^+$) 215.9, 213.9 (M+1). HPLC (aqueous 200 mM ammonium acetate buffer/acetonitrile gradient, 3.0 ml/min, Hewlett Packard ODS Hypersil 5 uM, 125×4 mm column) 4.131.

Preparation 54

7-Hydroxy-3,4-dihydro-1H-quinolin-2-one

Under nitrogen with outlet to back of hood, added 12.37 g of aluminum chloride powder (0.093 mol) to 7.93 g of 3-Chloro-N-(3-methoxy-phenyl)-propionamide (0.037 mol). Placed in preheated 160° C. sand bath, and heated for 4 hours, raising bath temperature to 200° C., until no more HCl is observed. Cooled to room temperature, chilled in ice bath and cautiously added ice-$H_2O$. Extracted three times with EtOAc, dried ($MgSO_4$), and evaporated under reduced pressure. Purified by flash chromatography on 230–400 Å mesh silica gel, eluting with 1:1 EtOAc/Hexanes to give 3.3 g of beige solid (55%). $^1H$ NMR (400 MHz, $CDCl_3$) δ 2.60 (2H, q, J=6.23 Hz), 2.88 (2H, t, J=6.85 Hz), 6.23 (1H, d, J=2.49 Hz), 6.44 (1H, q, J=2.49 Hz), 7.00 (1H, d, J=8.09 Hz). M/z ($APCI^+$) 163.7 (M+1).

Preparation 55

7-Methoxy-1-methyl-3,4-dihydro-1H-quinolin-2-one

Under nitrogen, combined 3.2 g of 7-Hydroxy-3,4-dihydro-1H-quinolin-2-one (0.0196 mol) with 25 ml of THF. Added 5.1 g of potassium t-butoxide (0.0451 mol) and stirred for 1.25 hours. Added 4.3 ml of dimethyl sulfate (0.0451 mol), followed by 10 ml of THF and stirred overnight. The reaction mixture was diluted with EtOAc and extracted three times with $H_2O$, dried ($MgSO_4$), and evaporated under reduced pressure. Purified by chromatography on Biotage Flash 40, eluting with 3:1 Hexanes/EtOAc to give 1.7 g of white solid (45%). $^1H$ NMR (400 MHz, $CDCl_3$) δ 2.62 (2H, q, J=5.39 Hz), 2.83 (2H, q, J=6.85 Hz), 3.32 (3H, s), 3.81 (3H, s), 6.53 (1H, d, J=2.49 Hz), 6.54 (1H, d, J=1.87 Hz), 7.05 (1H, d, J=7.68 Hz). M/z ($APCI^+$) 192.1 (M+1). HPLC (aqueous 200 mM ammonium acetate buffer/acetonitrile gradient, 3.0 ml/min, Hewlett Packard ODS Hypersil 5 uM, 125×4 mm column) 4.068.

Preparation 56

7-Hydroxy-1-methyl-3,4-dihydro-1H-quinolin-2-one

Under nitrogen, combined 1.3 g of 7-Methoxy-1-methyl-3,4-dihydro-1H-quinolin-2-one (6.8 mmol) with 18 ml of $CH_2Cl_2$. Added 15 ml of 1.0 M boron tribromide in $CH_2Cl_2$ (15.0 mmol) dropwise over 3 minutes. Stirred reaction for 5 hours, poured over ice-$H_2O$, slurried for 15 minutes and filtered 818 mg of off-white solid (68%). $^1H$ NMR (400 MHz, $CD_3OD$) δ 2.56 (2H, t, J=7.88 Hz), 2.78 (2H, t, J=6.85 Hz), 3.29 (3H, s), 6.45 (1H, d, J=8.09 Hz), 6.54 (1H, d, J=2.07 Hz), 6.98 (1H, d, J=8.09 Hz). M/z ($APCI^+$) 178.0 (M+1). HPLC (aqueous 200 mM ammonium acetate buffer/acetonitrile gradient, 3.0 ml/min, Hewlett Packard ODS Hypersil 5 uM, 125×4 mm column) 2.826.

Preparation 57

7-isopropoxy-1-methyl-3,4-dihydro-1H-quinolin-2-one

Under nitrogen, combined 818 mg of 7-Hydroxy-1-methyl-3,4-dihydro-1H-quinolin-2-one (4.62 mmol) with 7 ml of THF. Added 2.59 g of potassium t-butoxide (23.1 mmol) and stirred thick suspension for 1 hour. Added 2.3 ml of 2-iodopropane (23.1 mmol) and stirred for 9 days. The reaction mixture was diluted with EtOAc and extracted three times with $H_2O$, dried ($MgSO_4$), and evaporated under reduced pressure. Residue was purified by chromatography on Biotage Flash 40, eluting with 3:1 Hexanes/EtOAc to give 408 mg of colorless oil (41%). $^1H$ NMR (400 MHz, $CDCl_3$) δ 1.31 (6H, d, J=6.02 Hz), 2.59 (2H, m), 2.79 (2H, m), 3.29 (3H, s), 4.51 (1H, m), 6.49 (1H, d, J=2.49 Hz), 6.51 (1H, d, J=1.87 Hz), 7.00 (1H, m). M/z ($APCI^+$) 220.2 (M+1). HPLC (aqueous 200 mM ammonium acetate buffer/acetonitrile gradient, 3.0 ml/min, Hewlett Packard ODS Hypersil 5 uM, 125×4 mm column) 5.044.

Preparation 58

7-Isopropoxy-1-methyl-2-oxo-1,2,3,4-tetrahydro-quinoline-6-carbaldehyde

Under nitrogen, added 3.0 ml of trifluoroacetic acid to 771 mg of hexamethylenetetramine (5.50 mmol) and heated in 70° C. sand bath for 1 hour. Added 402 mg of 7-Isopropoxy-1-methyl-3,4-dihydro-1H-quinolin-2-one dissolved in 1.0 ml of trifluoroacetic acid. Heated at 70° C. for 5 hours, then at 50° C. overnight. Cooled to room temperature, added 3.6 ml of $H_2O$. Partitioned with EtOAc three times, dried ($MgSO_4$), and evaporated under reduced pressure. Residue was purified by flash chromatography on Biotage Flash 40, eluting with 1:1 EtOAc/Hexanes to give 169 mg of white solid (37%). $^1$H NMR (400 MHz, $CDCl_3$) δ 1.41 (6H, d, J=6.02 Hz), 2.65 (2H, t, J=7.88 Hz), 2.86 (2H, t, J=6.85 Hz), 3.36 (3H, s), 4.66 (1H, m), 6.52 (1H, s), 7.62 (1H, s), 10.34 (1H,s). M/z (APCI$^+$) 248.1 (M+1). HPLC (aqueous 200 mM ammonium acetate buffer/acetonitrile gradient, 3.0 ml/min, Hewlett Packard ODS Hypersil 5 uM, 125×4 mm column) 4.802.

Preparation 59

6-methoxy-1 methyl-3,3-spirocyclopropyl-1,3-dihydroindol-2-one

To a stirred ice cold solution of 6-methoxyoxindole (433 mg, 2.6 mmol) in 12 mL of dry DMF was added sodium hydride (60% in mineral oil, 117 mg, 2.92 mmol) The suspension was stirred for 10 minutes. To the resultant gray mixture was added dropwise methyl iodide (414 mg, 2.92 mmol) and the mixture was warmed to room temperature and stirred for 3 hours. The reaction mixture was cooled to 0° C. and quenched with 25 mL of water. The solution pH was adjusted with saturated aqueous bicarbonate solution and the mixture was extracted with EtOAc, washed with brine and the extracts were dried with $Na_2SO_4$, The mixture was filtered and concentrated to a syrup. Silica gel chromatography (1:3 EtOAc/hexanes) gave 202 mg (51%) of the title compound. Mass spectrum m/e M+H=178.

Preparation 59A 6-methoxy-1 methyl-3,3-spirocyclopropyl-1,3-dihydroindol-2-one

To a stirred ice cold solution of 6-methoxy-1-methyloxindole (1.97 g, 12.1 mmol) in 60 mL of dry DMF was added sodium hydride (60% in mineral oil, 0.97 g, 24.4 mmol) The suspension was stirred for 10 minutes. To the resultant gray mixture was added dropwise 1,2-dibromoethane (3.34 g, 17.7 mmol) and the mixture was warmed to room temperature and stirred for 3 hours. The reaction mixture was cooled to 0° C. and quenched with 25 mL of water. The solution pH was adjusted with saturated aqueous bicarbonate solution and the mixture was extracted with EtOAc, washed with brine and the extracts were dried with $Na_2SO_4$, The mixture was filtered and concentrated to a syrup. Silica gel chromatography (1:3 EtOAc/hexanes) gave 1.5 g (68%) of the title compound. Mass spectrum m/e M+H=204.

Preparation 60

6-Methoxy-1-methyl-3,3-spirocyclopropyl-2-oxo-2,3-dihydro-1H-indole-5-carbaldehyde To a stirred ice-cold solution of 6-methoxy-1-methyl-3,3-spirocyclopropyl-1,3-dihydroindol-2-one (0.41 g, 2.0 mmol) in 60 mL of $CH_2Cl_2$ was added TiCl4 (20 mL of a 1 M soln in $CH_2Cl_2$, 20 mmol) followed by α,α-dichloromethyl methyl ether (0.91 mL, 10.1 mmol). The reaction was stirred overnight at room temperature and was then quenched with 20 mL of water. The aqueous layer was extracted with $CH_2Cl_2$ (2×20 mL) and the combined organic portions were washed successively with satd $NaHCO_3$, brine and water, dried with $Na_2SO_4$, and concentrated. The crude product was chromatographed on silica gel eluting with 50% ethyl acetate in hexane to afford 450 mg (98%) of the desired product as a yellow solid. Mass spectrum m/z 232 p+1.

Example 63

6-Methoxy-1-methyl-,3,3-cyclopropyl-5-[(2-phenyl-piperidin-3-ylamino)-methyl]-1,3-dihydro-indol-2-one By a procedure similar to the previous examples 1 and 2: 352 mg (2.00 mmole) cis-(2S,3S)-3-amino, 2-phenylpiperidine and 455 mg (1.97 mmole) 6-Methoxy-1-methyl-3,3-spirocyclopropyl-2-oxo-2,3-dihydro-1H-indole-5-carbaldehyde were converted to the above named product as the hydrochloride in 33% overall yield (302 mg). Mp 244–246° C. MS, APCI m/e 392 (p+1).

Preparation 61

5-Methoxy-1-methyl-3,3-spirocyclopropyl-2-oxo-2,3-dihydro-1H-indole-6-carbaldehyde By a procedure similar to Preparations 59, 59a and 60, beginning with 5-methoxyoxindole, there was obtained 66 mg of the desired material. Mass spectrum m/z 232 p+1.

Example 64

5-Methoxy-1-methyl-,3,3-spirocyclopropyl-6-[(2-phenyl-piperidin-3-ylamino)-methyl]-1,3-dihydro-indol-2-one By a procedure similar to the previous examples 1, 2 and 63: 389 mg (2.21 mmole) cis-(2S,3S)-3-amino, 2-phenylpiperidine and 485 mg (2.1 mmole) 5-Methoxy-1-methyl-3,3-spirocyclopropyl-2-oxo-2,3-dihydro-1H-indole-6-carbaldehyde were converted to the above named product as the hydrochloride in 67% overall yield (200 mg). Mp 240° C. decompose MS, APCI m/e 392 (p+1).

Preparation 62

5-Methoxy-1-methyl-3,3-spirocyclobutane-2-oxo-2,3-dihydro-1H-indole-6-carbaldehyde By a procedure similar to Preparations 59, 59A and 60, beginning with 5-methoxyoxindole and 1,3-dibromopropane, there was obtained 570 mg of the desired material. Mass spectrum m/z 246 p+1.

Example 65

5-Methoxy-1-methyl-,3,3-cyclobutane-6-[(2-phenyl-piperidin-3-ylamino)-methyl]-1,3-dihydro-indol-2-one By a procedure similar to the previous examples 1, 2 and 63: 144 mg (0.82 mmole) cis-(2S,3S)-3-amino, 2-phenylpiperidine and 183 mg (0.75 mmole) 5-Methoxy-1-methyl-3,3-spirocyclobutyl-2-oxo-2,3-dihydro-1H-indole-6-carbaldehyde were converted to the above named product as the hydrochloride (143 mg). Mp 285–288° C. decompose MS, APCI m/e 406 (p+1).

Preparation 63

6-Methoxy-1-methyl-3,3-spirocyclopentyl-2-oxo-2,3-dihydro-1H-indole-5-carbaldehyde By a procedure similar to Preparations 59, 59A and 60, beginning with 5-methoxyoxindole and 1,4-dibromobutane there was obtained 215 mg of the desired material. Mass spectrum m/z 260 p+1.

Example 66

6-Methoxy-1-methyl-,3,3-cyclopentyl-5-[(2-phenyl-piperidin-3-ylamino)-methyl]-1,3-dihydro-indol-2-one By a procedure similar to the previous examples 1, 2 and 63: 74 mg (0.42 mmole) cis-(2S,3S)-3-amino, 2-phenylpiperidine and 109 mg (0.42 mmole) 6-Methoxy-1-methyl-3,3-spirocyclopentyl-2-oxo-2,3-dihydro-1H-indole-5-carbaldehyde were converted to the above named product as the hydrochloride in 65% overall yield (133 mg). Mp>300° C. MS, APCI m/e 420 (p+1).

Preparation 64

6-Methoxy-1-methyl-3,3-spirocyclohexyl-2-oxo-2,3-dihydro-1H-indole-5-carbaldehyde By a procedure similar to Preparations 59, 59A and 60, beginning with 5-methoxyoxindole and 1,5-dibromopentane, there was obtained 260 mg of the desired material. Mass spectrum m/z 274 p+1.

Example 67

6-Methoxy-1-methyl-,3,3-cyclohexyl-5-[(2-phenyl-piperidin-3-ylamino)-methyl]-1,3-dihydro-indol-2-one By a procedure similar to the previous examples 1, 2 and 63: 79 mg (0.45 mmole) cis-(2S,3S)-3-amino, 2-phenylpiperidine and 125 mg (0.42 mmole) 6-Methoxy-1-methyl-3,3-spirocyclohexyl-2-oxo-2,3-dihydro-1H-indole-5-carbaldehyde were converted to the above named product as the hydrochloride in 65% overall yield (147 mg). Mp>300° C. MS, APCI m/e 434 (p+1).

Preparation 65

2-Phenyl-3-hydroxypyridine

To a 1 liter round bottom flask equipped with a nitrogen inlet and a condenser was introduced 25 gm. (143.68 mmol) 2-bromo-3-hydroxypyridine, 19.27 gm. (156 mmol) phenylboronic acid, 5 gm (4.31 mmol) tetrakistriphenylphosphine palladium (0). The contents were dissolved in 300 ml of benzene and 100 ml of 2M aqueous sodium carbonate solution. The reaction mixture was heated under reflux for a period of 18 hours. The mixture was allowed to cool to room temperature and extracted with ethyl acetate (4×100 ml). The organic phase was dried over sodium sulfate and concentrated in vacuo. The residue was taken up in chloroform followed by treatment with ether to afford a solid precipitate. Upon filtration there was obtained 10.4 gm (42%) of 2-phenyl-3-hydroxypyridine. $^1$H NMR (CDCl$_3$, 400 MHz) δ 8.22 (d, 1H), 7.71 (d, 2H), 7.51–7.40 (m, 2H), 7.22 (d, 2H), 7.15 (m, 1H) ppm. Mass spectrum APCI m/z 172 (p+1).

Preparation 66

1-Benzyl-3-hydroxy-2-phenyl-pyridinium bromide

To a flame dried round bottom flask equipped with a nitrogen inlet and a condenser was introduced 1.3 gm. (7.59 mmol) 2-phenyl-3-hydroxypyridine, 3.25 gm. 2.26 ml (18.96 mmol) benzylbromide. The contents were dissolved in 30 ml of acetonitrile and the reaction mixture was heated under reflux for a period of 18 hours. The mixture was allowed to cool to room temperature and evaporated in vacuo. The residue was taken up in chloroform followed by treatment with ether to afford a solid precipitate. Upon filtration there was obtained 2.09 gm (81%) of 1-phenylmethyl-2-phenyl-3-hydroxypyridinium bromide. $^1$H NMR (CDCl$_3$, 400 MHz) δ 8.70 (d, 1H), 8.25 (d, 1H), 7.50 (m, 2H), 7.40 (m, 2H), 7.30–7.20 (m, 5H), 6.90 (d, 2H), 5.60 (s, 2H) ppm. Mass spectrum APCI m/z 262.

Preparation 67

6-Benzenesulfonyl-8-benzyl-1-phenyl-8-aza-bicyclo[3.2.1]oct-3-en-2-one

To 7.35 gm (21.5 mmol) 1-phenylmethyl-2-phenyl-3-hydroxypyridinium bromide in 20 ml of methanol was added 8.69 gm Amberlyst AG1-X8 resin ⁻OH form 20–40 mesh. The mixture was stirred for a short period and then filtered and the resin washed with methanol. The solvent was removed in vacuo. The solid residue was taken up in toluene (150 ml) and treated with 50 mg of hydroquinone and 6.84 gm (37.1 mmol) phenyl vinylsulfone. The reaction mixture was heated under reflux for 18 hours and then cooled to room temperature. The solvent was removed in vacuo and the residue was chromatographed on silica gel eluting with 8:2/hexane:ethyl acetate to afford 5.87 gm (64%) of a light yellow solid. $^1$H NMR (CDCl$_3$, 400 MHz) δ 7.71–7.61 (m, 5H), 7.46 (t, 2H, J=8 Hz), 7.37–7.23 (m, 8H), 6.84 (dd, 1H, J=9 Hz, J=5 Hz), 6.20 (d, 1H, J=9 Hz), 4.22 (d, 1H, J=5 Hz), 3.63 (d, 1H, J=14 Hz), 3.54 (dd, 1H, J=9 Hz, J=4 Hz), 3.40 (d, 1H, J=13 Hz), 2.80 (dd, 1H, J=15 Hz, J=3 Hz), 2.53 (dd, 1H, J=15 Hz, J=5 Hz) ppm. $^{13}$C NMR (CDCl$_3$, 125 MHz) δ 196.9, 144.9, 138.3, 138.0, 137.7, 134.3, 130.9, 129.9, 129.8, 129.5, 129.2, 129.2, 129.0, 129.0, 128.9, 128.7, 128.2, 128.1, 127.9, 75.1, 66.3, 57.9, 49.1, 38.1 ppm. Mass spectrum APCI m/z 430 (p+1).

Preparation 68

6-Benzenesulfonyl-8-benzyl-1-phenyl-8-aza-bicyclo[3.2.1]octan-2-one

To a 500 ml round bottom flask equipped with nitrogen inlet and condenser was placed 5.87 gm (13.68 mmol) of the 6-Benzenesulfonyl-8-benzyl-1-phenyl-8-aza-bicyclo[3.2.1]oct-3-en-2-one together with 150 ml of methanol, 17.25 gm (273.66 mmol) ammonium formate and 1.95 gm palladium hydroxide. The reaction mixture was heated under reflux for 1.5 hours and then cooled to room temperature. The sus pension was filtered through a bed of celite which was then washed with methanol. The combined organics were evaporated in vacuo and the residue was taken up in chloroform and partitioned with saturated aqueous bicarbonate solution. The organics were washed with saturated brine solution and then dried over a bed of sodium sulfate. The mixture was filtered and the filtrate evaporated in vacuo. The residue was chromatographed on silica gel eluting with 8:2/hexane:ethyl acetate to afford 4.04 gm (68%) of an off white solid. $^1$H NMR (CDCl$_3$, 400 MHz) δ 7.79 (d, 2H, J=7 Hz), 7.66 (t, 1H, J=7 Hz), 7.51 (t, 2H, J=8 Hz), 7.40–7.19 (m, 10H), 3.93 (br.s., 1H), 3.70 (d, 1H, J=15 Hz), 3.62 (t, 1H, J=7 Hz), 3.35 (d, 1H, J=14 Hz), 2.70–2.5 (m, 4H), 1.79–1.70 (m, 1H), 1.55 (br.s., 1H) ppm. Mass spectrum APCI m/z 432 (p+1).

Preparation 69

6-Benzenesulfonyl-8-benzyl-1-phenyl-8-aza-bicyclo[3.2.1]octan-2-one O-methyl-oxime

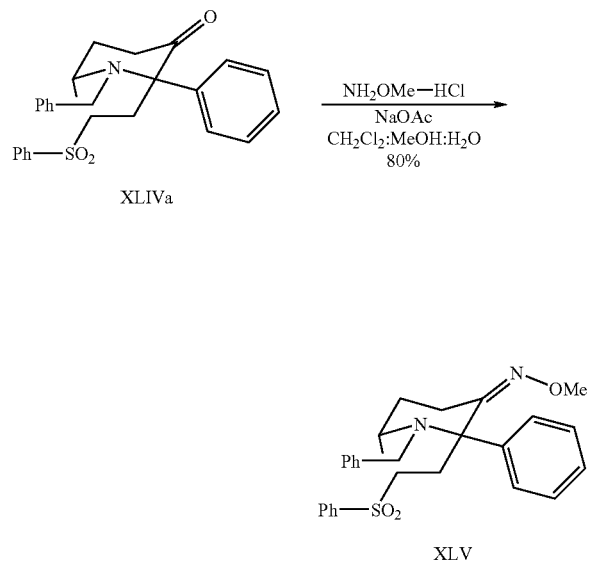

To a solution of the ketone (4.04 gm; 9.37 mmol) in 300 ml of 1:1 methylene chloride methanol was added a second solution of 2.94 gm (35.24 mmol) methoxyamine hydrochloride and 1.86 gm (22.68 mmol) sodium acetate in 30 ml of water. The reaction mixture is heated under reflux for 18 hours. The reaction mixture was allowed to cool and then diluted with 100 ml of water. The aqueous phase is extracted with methylene chloride and the combined organics were washed with brine, dried over sodium sulfate and evaporated in vacuo. The residue was chromatographed on silica gel eluting with 8:2/hexane:ethyl acetate to afford 3.45 gm (80%) of a white solid. $^1$H NMR (CDCl$_3$, 400 MHz) δ 7.72 (d, 2H, J=7 Hz), 7.6 (t, 1H, J=8 Hz), 7.46 (t, 2H, J=7 Hz), 7.41 (d, 2H, J=9 Hz), 7.35 (br.s., 4H), 7.32–7.20 (m, 4H), 3.85 (br.s., 1H), 3.78 (s, 3H), 3.71 (d, 1H, J=14 Hz), 3.56 (dd, 1H, J=9 Hz, J=6 Hz), 3.34 (d, 1H, J=14 Hz), 3.32 (obsc. dd, 1H, J=9 Hz, J=7 Hz), 2.56 (ddd, 2H, J=15 Hz, J=10 Hz, J=6 Hz), 2.32–2.23 (br.m., 1H), 2.15–2.07 (br.m., 1H), 1.44 (dd, 1H, J=14 Hz, J=7 Hz) ppm. Mass spectrum APCI m/z 461 (p+1).

Preparation 70

N-(6-Benzenesulfonyl-8-benzyl-1-phenyl-8-aza-bicyclo[3.2.1]oct-2-yl)-O-methyl-hydroxylamine

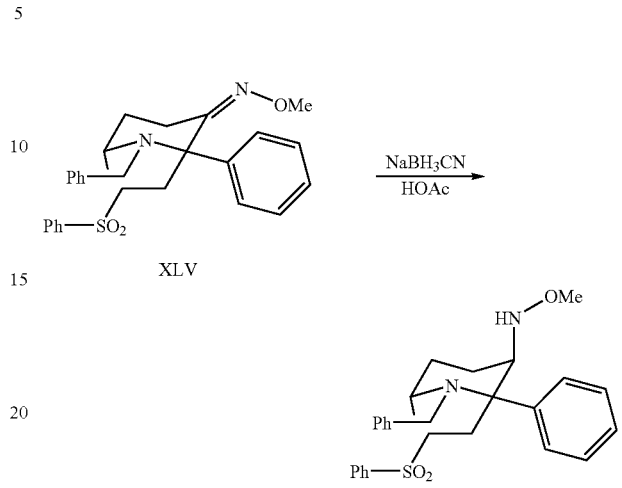

A solution of oxime (3.45 gm; 7.5 mmol) in 80 ml of acetic acid was treated with 0.71 gm (11.25 mmol) of sodium cyanoborohydride and the reaction mixture was stirred at room temperature for 2 hours. The reaction mixture was quenched into 50 ml of ice/water and stirred. The aqueous mixture was made basic to pH 10 by the addition of aqueous sodium hydroxide. The formation of a precipitate was evident and after filtration the resultant white solid was taken up in methylene chloride and dried over sodium sulfate. The organic phase was evaporated in vacuo to afford 3.01 gm (87%) of a white solid. $^1$H NMR (CDCl$_3$, 400 MHz) δ 7.62 (d, 2H, J=7 Hz), 7.54 (t, 1H, J=8 Hz), 7.46 (d, 4H, J=8 Hz), 7.38–7.32 (m, 6H), 7.29–7.22 (m, 2H), 4.03 (d, 1H, J=15 Hz), 3.80 (br.s., 1H), 3.56 (d, 1H, J=4 Hz), 3.53 (s, 3H), 3.53–3.50 (obsc.d, 1H), 3.46–3.43 (br.m., 1H), 2.34–2.26 (br.m., 3H), 2.11 (dd, 1H, J=15 Hz, J=4 Hz), 2.05 (s, 1H), 1.80–1.70 (br.m., 1H), 1.05–0.95 (br.m., 1H) ppm. Mass spectrum APCI m/z 463 (p+1).

Preparation 71

8-Benzyl-1-phenyl-8-aza-bicyclo[3.2.1]oct-2-ylamine

A flame dried 3/N round bottom flask equipped with an NH$_3$ (g) inlet, dry ice condenser and magnetic stir bar was cooled to −78° C. and ammonia gas was introduced. A solution of 464 mg (1.0 mmol) of the N-(6-Benzenesulfonyl-8-benzyl-1-phenyl-8-aza-bicyclo[3.2.1]oct-2-yl)-O-methyl-hydroxylamine in 10 ml of THF was added followed by 323 mg (14.05 mmol) sodium metal portionwise. A deep blue color was evident and the reaction mixture was stirred at −78° C. for 30 min. The reaction was quenched by the addition of solid ammonium chloride and the ammonia was allowed to evaporate. The residue was taken up in water and methylene chloride. The aqueous phase was washed once again with methylene chloride. The combined organic layers were washed with brine, dried of sodium sulfate and evaporated in vacuo. There was obtained 203 mg (68%) of a clear oil. Enantiomeric separation was completed on a 5 cm×50 cm Chirlpak AS column eluting at 25 ml/min with 93/7 hexane/ethanol containing 0.025% diethyl amine. The retention times were 4.6 minutes and 6.6 minutes respectively. $^1$H NMR (CDCl$_3$, 400 MHz) δ 7.49–7.41 (m, 2H), 7.37–7.27 (br.m., 5H), 7.24–7.18 (br.m., 3H), 3.97 (d, 1H, J=15 Hz), 3.26–3.24 (br.s., 1H), 2.97 (d, 1H, J=15 Hz), 2.54–2.53 (br.s., 1H), 2.40 (br.s., 2H), 2.33–2.15 (br.m., 3H), 2.03–1.86 (br.m., 2H), 1.72–1.64 (br.m., 2H), 1.33–1.28 (br.m., 1H) ppm. Mass spectrum APCI m/z 293 (p+1).

Preparation 72

(1S,2S,5R) or (1R,2R,5S) 1-Phenyl-8-aza-bicyclo[3.2.1]oct-2-ylamine

To a 25 ml round bottom flask equipped with nitrogen inlet and condenser was placed 37 mg (0.127 mmol) of either the (1S,2S,5R) (or the (1R,2R,5S)) 8-Benzyl-1-phenyl-8-aza-bicyclo[3.2.1]oct-2-ylamine together with 10 ml of methanol, 80 mg (1.27 mmol) ammonium formate and 12 mg palladium hydroxide. The reaction mixture was treated with 21 ul of conc aq HCl and then heated under reflux for 40 mins and then cooled to room temperature. The suspension was filtered through a bed of celite which was then washed with methanol. The combined organics were evaporated in vacuo and the residue was taken up in chloroform and partitioned with saturated aqueous bicarbonate solution. The organics were washed with saturated brine solution and then dried over a bed of sodium sulfate. The mixture was filtered and the filtrate evaporated in vacuo to afford 20 mg of the desired (1S,2S,5R) (or the (1R,2R,5S)) diamine. $^1$H NMR (CDCl$_3$, 400 MHz) δ 7.31–7.16 (br.m., 5H), 3.64–3.63 (br.s., 1H), 2.95 (dd, 1H, J=5 Hz, J=2 Hz), 2.25–2.19 (br.m., 1H), 2.03–1.89 (br.m., 2H), 1.87–1.78 (br.m, 5H), 1.72–1.66 (br.m., 1H), 1.54–1.49 (br.m., 1H), 1.33–1.28 (br.m., 1H) ppm. Mass spectrum APCI m/z 203 (p+1).

Example 68

(1S,1aR)-6-Methoxy-3-methyl-5-[(1S,2S,5R)-(1-phenyl-8-aza-bicyclo[3.2.1]oct-2-ylamino)-methyl]-1,1a,3,7b-tetrahydro-3-aza-cyclopropa[a]naphthalen-2-one or (1R,1aS)-6-Methoxy-3-methyl-5-[(1R,2R,5S)-(1-phenyl-8-aza-bicyclo[3.2.1]oct-2-ylamino)-methyl]-1,1a,3,7b-tetrahydro-3-aza-cyclopropa[a]naphthalen-2-one By a procedure similar to previous examples 1 and 2: 20 mg (0.099 mmole) (1S,2S,5R) (or the (1R,2R,5S)) 1-Phenyl-8-aza-bicyclo[3.2.1]oct-2-ylamine and 23 mg (0.099 mmole) (1S,1aR) (or (1R,1aS))-6-Methoxy-3-methyl-2-oxo-1a,2,3,7b-tetrahydro-1H-3-aza-cyclopropa[a]naphthalene-5-carbaldehyde were combined in 20 ml of toluene and heated under reflux for 18 hours over a Dean-Stark trap. The crude imine (MS APCI m/e=390 p+1) solution was evaporated in vacuo and redissolved in 20 ml dichloroethane. The solution was treated with 32 mg (0.148 mmol) sodium triacetoxyborohydride and stirred at room temperature for 16 hours. The reaction mixture was washed with saturated aqueous bicarbonate solution followed by brine and then dried over sodium sulfate. After evaporation, the crude residue was chromatographed on silica gel eluting with 96/4/1 methylene chloride, methanol, ammonium hydroxide (NH$_4$OH) to afford 20 mg of the desired product. Mass spectrum APCI m/z 418 (p+1).

Example 69

5-Methoxy-1-methyl-,3,3-cyclopropyl-6-[(1S,2S, 5R)-(1-phenyl-8-azabicyclo[3.2.1]oct-2-yl)-amine)-methyl]-1,3-dihydro-indol-2-one By a procedure similar to the previous example 68, there was obtained the above named product. Mass spectrum APCI m/z 418 (p+1).

Preparation 73

N-(4-Methoxy-2-methyl-phenyl)-methanesulfonamide

To a solution of 6.85 gm (50 mmol) 4-methoxy-2-methylaniline in 70 ml of methylene chloride was introduced 8.5 gm (ml; mmol) pyridine followed by dropwise addition of 6.87 gm (60 mmol) methanesulfonylchloride. The reaction mixture was stirred at room temperature for 16 hours. The reaction mixture was washed with 1N HCl and then with saturated aqueous brine. The organics were dried with sodium sulfate and then evaporated in vacuo. The residue was triturated in diethyl ether to afford 7.5 gm (79%) of a light purple solid. Mass spectrum APCI (m/z) 216 (p+1).

Preparation 74

N-(4-Methoxy-2-methyl-phenyl)-N-methyl-methanesulfonamide

To a solution of 860 mg (4.0 mmol) N-(4-methoxy-2-methyl-phenyl)-methanesulfonamide in 15 ml DMF at ambient temperature was added 192 mg (48 mmol) 60% sodium hydride dispersion and the resulting mixture was treated with 1.14 gm, 0.5 ml (8.0 mmol) methyl iodide. The reaction mixture was stirred at room temperature for 2 hours and 0.5 ml of methyl iodide was introduced and the reaction mixture was stirred at room temperature for 16 hours. The reaction mixture was diluted with 1N HCl and then extracted with ethyl acetate. The organics were washed with brine, dried with sodium sulfate and then evaporated in vacuo to afford 293 mg (X %) of a light purple solid. Mass spectrum APCI (m/z) 230 (p+1).

Preparation 75

N-(2-Bromomethyl-4-methoxy-phenyl)-N-methyl-methanesulfonamide

A solution of 532 mg (2.33 mmol) N-(4-Methoxy-2-methyl-phenyl)-N-methyl-methanesulfonamide in 20 ml carbon tetrachloride was treated with 500 mg (2.79 mmol) N-bromosuccinimide and a small catalytic amount of azaobisisobutyronitrile. The reaction mixture was heated to reflux over a flood lamp for a period of 16 hours. The reaction mixture was cooled to ambient temperature and diluted with ethyl acetate. The reaction mixture wss filtered through a pad of celite and the filtrate was evaporated in vacuo. The residue was chromatographed on silica with 70:30/hexane:ethyl acetate to afford 231 mg of the desired bromide. Mass spectrum APCI (m/z) 308, 310 (p+1).

Preparation 76

6-Methoxy-1-methyl-3,4-dihydro-1H-benzo[c][1,2]thiazine 2,2-dioxide

A solution of 291 mg (0.95 mmol) N-(2-Bromomethyl-4-methoxy-phenyl)-N-methyl-methanesulfonamide in 15 ml of DMF was treated with 45 mg (1.14 mmol) 60% NaH and the reaction mixture was stirred at 75° C. for 4 hours. The reaction was quenched with water and extracted with ethyl acetate. The organic layer was dried over sodium sulfate, dried and evaporated. The residue was passed through a short plug of silica gel eluting with 25% ethyl acetate in hexane. There was obtained 123 mg (57%) of the desired product. Mass spectrum APCI (m/z) 228 (p+1).

Preparation 77

6-Methoxy-1-methyl-2,2-dioxo-1,2,3,4-tetrahydro-2$\lambda^6$-benzo[c][1,2]thiazine-7-carbaldehyde To a solution of sultam (11 mg; 0.04 mmol) in 3 ml methylene chloride at ambient temperature was treated with 0.4 ml (0.4 mmol) titanium tetrachloride and the solution was stirred for 15 minutes. Dichloromethylmethylether (23 mg; 0.2 mmol) was added dropwise at ambient temperature to the reaction mixture which was then stirred for 16 hours. The reaction mixture was diluted with 1 N HCl and then extracted with methylene chloride. The organics were washed with brine, dried with sodium sulfate and then evaporated in vacuo. The residue was chromatographed on silica with 50:50/hexane:ethyl acetate to afford 6 mg of the aldehyde. Mass spectrum APCI (m/z) 256 (p+1).

Example 70

(6-Methoxy-1-methyl-2,2-dioxo-1,2,3,4-tetrahydro-2$\lambda^6$-benzo[c][1,2]thiazin-7-ylmethyl)-(2-phenyl-piperidin-3-yl)-amine By a procedure similar to previous examples 1 and 2: 65 mg (0.37 mmole) 2-phenyl-3-aminopiperidine and 92 mg (0.36 mmole) the sultam-5-carbaldehyde were combined in 20 ml of toluene and heated under reflux for 18 hours over a Dean-Stark trap. The crude imine (MS APCI m/e=414 p+1) solution was evaporated in vacuo and redissolved in 20 ml dichloroethane. The solution was treated with 154 mg (0.72 mmol) sodium triacetoxyborohydride and stirred at room temperature for 16 hours. The reaction mixture was washed with saturated aqueous bicarbonate solution followed by brine and then dried over sodium sulfate. After evaporation, the crude residue was chromatographed on silica gel eluting with 94/5/1 methylene chloride, methanol, ammonium hydroxide (NH$_4$OH) to afford 95 mg of the desired product. Mass spectrum APCI (m/z) 416 (p+1).

Example 71

5-Methoxy-1,3,3-trimethyl-6-[(2(S)-phenyl-piperidin-3(S)-ylamino)-methyl]-1,3-dihydro-pyrrolo[3,2-b]pyridin-2-one Step 1

5-Methoxy-1,3,3-trimethyl-1,3-dihydro-pyrrolo[3,2-b]pyridin-2-one

A solution of 0.2 g (1.22 mmol) 5-methoxy-1,3-dihydro-pyrrolo[3,2-b]pyridin-2-one (*J. Het. Chem.* 1996, 33, 287–93) was dissolved in 10 ml of DMF and cooled to 0° C. under a nitrogen atmosphere in a flame dried round bottom flask. To this solution was added 4.02 ml (4.02 mmol) of a 1M solution of potassium t-butoxide in THF and the solution was stirred for 10 minutes. To this solution was added dropwise 0.3 ml (4.88 mmol) of MeI, and the reaction was stirred for 15 minutes at 0° C. The reaction was quenched with water and extracted with ethyl acetate. The ethyl acetate extracts were dried (Na$_2$SO$_4$) and evaporated. The residue was chromatographed on 6 g of silica using 3:1 hexanes/ethyl acetate as the elutant. Appropriate fractions were combined and evaporated to yield 0.14 g of 5-methoxy-1,3,3-trimethyl-1,3-dihydro-pyrrolo[3,2-b]pyridin-2-one. $^1$H NMR (CDCl$_3$) δ 7.02 (d, 1H), 6.58 (d, 1H), 3.90 (s, 3H), 3.18 (s, 3H), 1.38 (s, 6H). Mass spectrum: m/e=207 (P+1).

Step 2

5-Methoxy-6-bromo-1,3,3-trimethyl-1,3-dihydro-pyrrolo[3,2-b]pyridin-2-one

To a solution of 0.14 g (0.853 mmol) 5-methoxy-1,3,3-trimethyl-1,3-dihydro-pyrrolo[3,2-b]pyridin-2-one dissolved in 2 ml of acetic acid was added 0.136 g (0.0853 mmol) of bromine. The solution was heated to 60° C. for 1 hour. The reaction was cooled to room temperature and quenched with 5 ml of water. The pH was adjusted to 7.5 and the mixture extracted with ethyl acetate. The ethyl acetate extracts were combined, dried (Na$_2$SO$_4$) and evaporated. The residue was chromatographed on silica using chloroform as the elutant. Appropriate fractions were combined and evaporated to yield 138 mg of 5-methoxy-6-bromo-1,3,3-trimethyl-1,3-dihydro-pyrrolo[3,2-b]pyridin-2-one. Mass spectrum: m/e=285,287.

Step 3

5-Methoxy-1,3,3-trimethyl-6-vinyl-1,3-dihydro-pyrrolo[3,2-b]pyridin-2-one

A mixture of 138 mg (0.048 mmol) 5-methoxy-6-bromo-1,3,3-trimethyl-1,3-dihydro-pyrrolo[3,2-b]pyridin-2-one, 138 mg (0.48 mmol) of tri-n-butyl-vinyltin and 15 mg of bis(triphenylphosphine-palladium(II) chloride in 1 ml of HMPA was heated under nitrogen to 65° C. for 14 hours. The reaction mixture was cooled to room temperature and diluted with water and ethyl acetate. The ethyl acetate solution was washed with water several times. To this ethyl acetate solution was added 1 ml of saturated KF, and the mixture filtered. The filtrate was dried (Na$_2$SO$_4$), evaporated, and the residue chromatographed on silica using 1:1 ethyl acetate/hexanes as the elutant. Appropriate fractions were combined and evaporated to afford 82 mg of 5-methoxy-1,3,3-trimethyl-6-vinyl-1,3-dihydro-pyrrolo[3,2-b]pyridin-2-one. $^1$H NMR (CDCl$_3$) δ 6.90 (d,d 1H), 5.75 (d, 1H), 5.30 (d, 1H), 3.95 (s, 3H), 3.20 (s, 3H), 1.40 (s, 6H).

Step 4

5-Methoxy-1,3,3-trimethyl-2-oxo-2,3-dihydro-1H-pyrrolo[3,2-b]pyridine-6-carbaldehyde A 65 mg (0.28 mmol) solution of 5-methoxy-1,3,3-trimethyl-6-vinyl-1,3-dihydro-pyrrolo[3,2-b]pyridin-2-one in 16 ml of methylene chloride and 4 ml of methanol was cooled to −70° C. Ozone (via an ozone generator) was bubbled into the solution until a blue color was achieved. The reaction mixture was stirred at −70° C. for 30 minutes and warmed to room temperature. Approximately 0.5 ml of dimethyl sulfide was added and the reaction was evaporated. This residue (0.6 g) was used directly in the next step. $^1$H NMR (CDCl$_3$) δ 10.20 (s, 1H). Mass spectrum: m/e =235 (p+1).

Step 5

5-Methoxy-1,3,3-trimethyl-6-[(2(S)-phenyl-piperidin-3(S)-ylamino)-methyl]-1,3-dihydro-pyrrolo[3,2-b]pyridin-2-one The crude 5-methoxy-1,3,3-trimethyl-2-oxo-2,3-dihydro-1H-pyrrolo[3,2-b]pyridine-6-carbaldehyde prepared in step 4 (0.6 g; 0.15 mmol) was dissolved in 5 ml of dichloroethane. To this was added 0.05 g (0.2 mmol) of 2-(S)-phenyl-piperidin-3(S)-ylamine and 0.06 ml (0.4 mmol) of triethylamine, and the mixture was stirred for 60 minutes at room temperature. To this mixture was added 0.1 g (0.5 mmol) of sodium triacetoxyborohydride, and the reaction mixture was stirred at room temperature for 18 hours. The reaction was quenched with water and stirred at room temperature for 30 minutes. The pH of the mixture was adjusted to 2 with 1N HCl and extracted with ethyl acetate. The pH of the water layer was adjusted to 7.0 with sodium bicarbonate and extracted with ethyl acetate. The pH=7 ethyl acetate extracts were combined, dried (Na$_2$SO$_4$), and evaporated to yield 50 mg of a yellow amorphous solid. $^1$H NMR (CDCl$_3$) δ 7.2–7.4 (m, 5H), 6.75 (s, 1H), 3.90 (s, 1H), 3.65 (s, 3H), 3.60,3.40, (d,d 2H), 3.25 (d, 1H), 3.05 (s, 3H), 2.80 (m, 3H), 2.10 m, 1H), 1.90 (m, 2H), 1.60 (m, 1H), 1.40 (m, 1H), 1.28 (s, 3H), 1.22 (s, 3H). Mass spectrum: m/e=395 (p+1). TLC: Rf=0.2; (10:1 chloroform/methanol).

Example 72

6-Methoxy-1,3,3-trimethyl-5-[(2(S)-phenyl-piperidin-3(S)-ylamino)-methyl]-1,3-dihydro-pyrrolo[2,3-b]pyridin-2-one Step 1

6-Chloro-1,3,3-trimethyl-1,3-dihydro-pyrrolo[2,3-b]pyridin-2-one

A solution of 0.25 g (1.5 mmol) 6-chloro-1,3-dihydro-pyrrolo[2,3-b]pyridin-2-one (WO9910349 A1) was dissolved in 5 ml of DMF and cooled to 5° C. To this solution was added 4.5 ml (4.5 mmol) of potassium t-butoxide (1M solution in THF) followed by 0.37 ml (6.0 mmol) of methyl iodide. The reaction mixture was stirred at 5° C. for 1 hour. The reaction mixture was poured into 50 ml of water and extracted with ethyl acetate. The ethyl acetate extract was dried (Na$_2$SO$_4$) and evaporated to yield 0.25 g of 6-chloro-1,3,3-trimethyl-1,3-dihydro-pyrrolo[2,3-b]pyridin-2-one as a dark amorphous solid. TLC: Rf=0.8 (1:1 hexane/ethyl acetate). $^1$H NMR (CDCl$_3$) δ 7.38 (d, 1H), 6.95 (d, 1H), 3.25 (s, 3H), 1.38 (s, 3H). Mass spectrum: m/e=211,213 (p+1, p+3).

Step 2

6-Methoxy-1,3,3-trimethyl-1,3-dihydro-pyrrolo[2,3-b]pyridin-2-one

A mixture of 0.3 g (1.4 mmol) 6-chloro-1,3,3-trimethyl-1,3-dihydro-pyrrolo[2,3-b]pyridin-2-one, 0.6 ml (2.8 mmol) of sodium methoxide (4.6M in methanol), and 1.2 mg of CuI in 6 ml of DMF was heated to 145° C. for 18 hours. The reaction mixture was cooled to room temperature and added to 25 ml of water. The mixture was extracted with ethyl acetate. The ethyl acetate extract were was washed with 25 ml of saturated sodium bisulfite, dried (Na$_2$SO$_4$) and evaporated. The residue was triturated twice with hot hexane, and the hexane decanted. The residue 6-methoxy-1,3,3-trimethyl-1,3-dihydro-pyrrolo[2,3-b]pyridin-2-one (0.25 g) was used without further purification. TLC: Rf=0.7 (5:1 hexane/ethyl acetate). $^1$H NMR (CDCl$_3$) δ 7.35 (d, 1H), 6.38 (d, 1H), 3.92 (s, 3H), 3.22 (s, 3H), 1.33 (s, 3H). Mass spectrum: m/e=207.3 (p+1).

Step 3

6-Methoxy-1,3,3-trimethyl-2-oxo-2,3-dihydro-1H-pyrrolo[2,3-b]pyridine-5-carbaldehyde A 0.16 g (0.8 mmol) solution of 6-methoxy-1,3,3-trimethyl-1,3-dihydro-pyrrolo[2,3-b]pyridin-2-one in 5 ml of methylene chloride was cooled to 5° C. To this solution was added 3.2 ml (3.2 mmol) of titanium tetrachloride (1M solution in methylene chloride). The reaction was stirred for 90 minutes at 5° C. To this mixture was added 0.11 ml (1.2 mmol) of 1,1-dichloromethylmethyl ether and the reaction mixture stirred at room temperature for 48 hours. The reaction mixture was then quenched with ice and stirred for 30 minutes. The organic layer was dried (Na$_2$SO$_4$) and evaporated to yield 0.16 g of an amorphous white solid. Mass spectrum and NMR indicated that the solid was a 50/50 mixture of desired 6-methoxy-1,3,3-trimethyl-2-oxo-2,3-dihydro-1H-pyrrolo[2,3-b]pyridine-5-carbaldehyde and starting of 6-methoxy-1,3,3-trimethyl-1,3-dihydro-pyrrolo[2,3-b]pyridin-2-one. $^1$H NMR (CDCl$_3$) δ 10.12 (s, 1H). TLC: Rf=0.5 (5:1 hexane/ethyl acetate) Mass spectrum: m/e=235 (p+1). This material was used directly in the next step.

Step 4

6-Methoxy-1,3,3-trimethyl-5-[(2(S)-phenyl-piperidin-3(S)-ylamino)-methyl]-1,3-dihydro-pyrrolo[2,3-b]pyridin-2-one The crude 6-methoxy-1,3,3-trimethyl-2-oxo-2,3-dihydro-1H-pyrrolo[2,3-b]pyridine-5-carbaldehyde prepared in step 3 (0.16 g; 0.34 mmol) was dissolved in 5 ml of dichloroethane. To this was added 0.1 g (0.4 mmol) of 2-(S)-phenyl-piperidin-3(S)-ylamine and 0.11 ml (0.8 mmol) of triethylamine, and the mixture was stirred for 60 minutes at room temperature. To this mixture was added 0.2 g (1.0 mmol) of sodium triacetoxyborohydride, and the reaction mixture was stirred at room temperature for 18 hours. The reaction was quenched with water and stirred at room temperature for 30 minutes. The pH of the mixture was adjusted to 2 with 1N HCl and extracted with ethyl acetate. The pH of the water layer was adjusted to 7.0 with sodium bicarbonate and extracted with ethyl acetate. The pH=7 ethyl acetate extracts were combined, dried (Na$_2$SO$_4$) and evaporated to yield an amorphous solid. $^1$H NMR (CDCl$_3$) δ 7.30 (m, 5H), 7.0 (s, 1H), 3.9 (s, 1H), 3.65 (s, 3H) 3.5,3.3 (d,d, 2H), 3.25 (d, 1H), 2.8 (m, 3H), 2.1 (d, 1H), 1.95 (m, 2H), 1.6 (m, 1H), 1.4 (m, 1H), 1.22 (s, 3H), 1.20 (s, 3H). Mass spectrum: m/e=395.3 (p+1). The amorphous solid was dissolved in isopropyl alcohol, and to this solution was added 0.2 ml of concentrated HCl. The mixture was stirred for 10 minutes and the solvent was evaporated to a brown solid. This solid was triturated with isopropyl ether, and then recrystallized from isopropyl alcohol/methanol to yield 75 mg of a white solid. TLC: Rf=0.3 (10:1 chloroform/methanol). Mass spectrum: m/e=395.3 (p+1).

Example 73

6-Methoxy-1-methyl-7-[(2(S)-phenyl-piperidin-3(S)-ylamino)-methyl]-3,4-dihydro-1H-[1,8]naphthyridin-2-one Step 1

3-Methoxy-6-nitro-2-vinyl-pyridine

To a solution of 1.0 g (4.3 mmol) 2-bromo-3-methoxy-6-nitropyridine (J. Lombardino, *J. Med. Chem.* 1981, 24, 39–42) in 25 ml of toluene was added 1.9 ml (6.4 mmol) of tri-n-butyl-vinyltin and a catalytic amount of bis(triphenylphosphine-palladium(II) chloride, and the reaction was refluxed under a nitrogen atmosphere for 2 hours. The reaction mixture was cooled to room temperature and the solvent evaporated. The residue was chromatographed on silica using chloroform as the elutant. Appropriate fractions were combined to yield 0.63 g of 3-methoxy-6-nitro-2-vinyl-pyridine as an oil. TLC: Rf=0.5 (5:1 hexane/ethyl acetate). $^1$H NMR (CDCl$_3$) δ 8.15 (d, 1H), 7.35 (d, 1H), 7.10 (m, 1H), 6.55 (d, 1H), 5.65 (d, 1H), 4.0 (s, 3H). Mass spectrum: m/e=181.1 (p+1).

Step 2

3-Methoxy-6-nitro-pyridine-2-carbaldehyde

A solution of 0.63 g (3.5 mmol) 3-methoxy-6-nitro-2-vinyl-pyridine in 50 ml of CH$_2$Cl$_2$ and 10 ml of methanol was cooled to –70° C. Ozone was bubbled into the solution until a blue color persisted. The mixture was stirred for 60 minutes at –70° C. and then quenched with excess dimethyl sulfide. The reaction was warmed to room temperature and the solvent evaporated. The residue was dissolved in ethyl acetate and water. The pH of the solution was adjusted to 2.0 with 1N HCl and the mixture stirred for 30 minutes. The pH of the solution was then adjusted to 8.0 with 1N NaOH. The mixture was extracted with excess ethyl acetate. The ethyl acetate extracts were combined, dried (Na$_2$SO$_4$) and evaporated to yield 0.6 g of 3-methoxy-6-nitro-pyridine-2-carbaldehyde as a tan solid. TLC: Rf=0.2 (1.1 ethyl acetate/hexane). $^1$H NMR (CDCl$_3$) δ 10.1 (s, 1H), 8.5 (d, 1H), 7.85 (d, 1H), 4.15 (s, 3H).

Step 3

2-[1,3]Dioxolan-2-yl-3-methoxy-6-nitro-pyridine

A mixture of 0.55 g (0.3 mmol) 3-methoxy-6-nitro-pyridine-2-carbaldehyde, 0.8 ml (15 mmol) of ethylene glycol, and 10 mg (catalytic amount) of p-toluene sulfonic acid was refluxed in 50 ml of toluene using a Dean-Stark trap to trap water. After 90 minutes, the reaction mixture was cooled to room temperature and the solvent evaporated. The residue was chromatographed on silica using 5:1 (chloroform/ethyl acetate) as the elutant. Appropriate fractions were combined and evaporated to yield 0.6 g of 2-[1,3]dioxolan-2-yl-3-methoxy-6-nitro-pyridine as an oil. TLC: Rf=0.9 (1:1 chloroform/ethyl acetate). $^1$H NMR (CDCl$_3$) δ 8.25 (d, 1H), 7.40 (d, 1H), 6.30 (s, 1H), 4.30 (m, 2H), 4.10 (m, 2H), 4.0 (s, 3H). Mass Spectrum: m/e=227.2 (p+1).

Step 4

3-Benzenesulfonylmethyl-6-[1,3]dioxolan-2-yl-5-methoxy-2-nitro-pyridine

A mixture of 0.6 g (2.6 mmol) 2-[1,3]dioxolan-2-yl-3-methoxy-6-nitro-pyridine, 0.55 g (2.9 mmol) of chloromethylphenylsulfone and 2.9 ml (2.9 mmol) of potassium t-butoxode (1M solution in THF) in 5 ml of DMF were combined at 5° C. and stirred at ambient temperature for 18 hours. The reaction mixture was quenched with 25 ml of water and extracted with ethyl acetate. The ethyl acetate extracts were combined, dried (Na$_2$SO$_4$), and evaporated. The residue was chromatographed on silica using 5:1 chloroform/ethyl acetate as the elutant. Appropriate fractions were combined and evaporated to yield 0.28 g of 3-benzenesulfonylmethyl-6-[1,3]dioxolan-2-yl-5-methoxy-2-nitro-pyridine as an oil. TLC: Rf=0.4 (1:1 chloroform/ethyl acetate). $^1$H NMR (CDCl$_3$) δ 7.7 (m, 3H), 7.55 (m, 2H), 7.42 (s, 1H), 6.30 (s, 1H), 4.90 (s, 2H), 4.30 (m, 2H), 4.10 (m, 2H), 4.02 (s, 3H).). Mass Spectrum: m/e=381.0 (p+1).

Step 5

3-(6-[1,3]Dioxolan-2-yl-5-methoxy-2-nitro-pyridin-3-yl)-acrylic acid ethyl ester A mixture of 0.28 g (0.73 mmol) 3-benzenesulfonylmethyl-6-[1,3]dioxolan-2-yl-5-methoxy-2-nitro-pyridine and 0.8 ml (0.73 mmol) of ethyl bromoacetate was dissolved in 10 ml of ethanol. To this solution was added 0.5 ml of potassium t-butoxide (1M in t-butyl alcohol) and the reaction mixture was stirred at room temperature for 1 hour. The solvent was evaporated and the residue was added to 5 ml of water. The suspension was extracted with ethyl acetate. The ethyl acetate extract was dried (Na$_2$SO$_4$) and evaporated to yield approximately 0.3 g of an oil. Mass spectrum: m/e=325.1 (p+1). This material was used directly in step 6.

Step 6

7-[1,3]Dioxolan-2-yl-6-methoxy-3,4-dihydro-1H-[1,8]naphthyridin-2-one

The oil isolated in step 5 was dissolved in 30 ml of ethanol and hydrogenated for 90 minutes at 50 PSI using 10% Pd/C as the catalyst. The reaction mixture was filtered and evaporated to yield the intermediate 3-(2-amino-6-[1,3]dioxolan-2-yl-5-methoxy-pyridin-3-yl)-propionic acid ethyl ester as a dark oil. Mass Spectrum: m/e=297.1 (p+1). This material was dissolved in 10 ml of toluene and heated to reflux for 4 hours. The solution was cooled to room temperature and evaporated to yield 0.1 g of 7-[1,3]dioxolan-2-yl-6-methoxy-3,4-dihydro-1H-[1,8]naphthyridin-2-one as a dark oil. Mass spectrum: m/e=251 (p+1). $^1$H NMR (CDCl$_3$) δ 7.10 (s, 1H), 6.10 (s, 1H), 4.30 (m, 2H), 4.10 (m, 2H), 3.90 (s, 3H), 2.90 (m, 2H), 2.75 (m, 2H). This material was used without further purification in step 7.

Step 7

3-Methoxy-8-methyl-7-oxo-5,6,7,8-tetrahydro-[1,8]naphthyridine-2-carbaldehyde

To a solution of 0.1 g (0.4 mmol) 7-[1,3]dioxolan-2-yl-6-methoxy-3,4-dihydro-1H-[1,8]naphthyridin-2-one in 1 ml of DMF cooled to 5° C. was added 0.5 ml (0.5 mmol) of potassium t-butoxide (1M solution in THF). The reaction mixture was stirred fo 30 minutes. To this mixture was added 0.06 ml (1 mmol) of methyl iodide and the reaction stirred at ambient temperature for 2 hours. The reaction mixture was diluted with 5 ml of water and extracted with ethyl acetate. The ethyl acetate extract was dried (Na$_2$SO$_4$) and evaporated to yield intermediate 7-[1,3]dioxolan-2-yl-6-methoxy-1-methyl-3,4-dihydro-1H-[1,8]naphthyridin-2-one as a dark oil. Mass spectrum: m/e=205.1 (p+1). This material was dissolved in 5 ml of acetone containing 0.1 g of para-toluenesulfonic acid and refluxed for 2 hours. The reaction mixture was evaporated and the residue triturated with saturated NaHCO$_3$. This mixture was extracted with ethyl acetate. The ethyl acetate extract was dried (Na$_2$SO$_4$) and evaporated and the residue chromatographed on silica using 3:1 chloroform/ethyl acetate as the elutant. Appropriate fractions were combined to yield 12 mg of 3-methoxy-8-methyl-7-oxo-5,6,7,8-tetrahydro-[1,8]naphthyridine-2-carbaldehyde as an oil. Mass spectrum: m/e=221.1 (p+1). $^1$H NMR (CDCl$_3$) δ 10.1 (s, 1H), 7.25 (s, 1H), 3.95 (s, 3H), 3.50 (s, 3H), 3.0 (m, 2H), 2.90 (m, 2H).

Step 8

6-Methoxy-1-methyl-7-[(2(S)-phenyl-piperidin-3(S)-ylamino)-methyl]-3,4-dihydro-1H-[1,8]naphthyridin-2-one The 3-methoxy-8-methyl-7-oxo-5,6,7,8-tetrahydro-[1,8]naphthyridine-2-carbaldehyde prepared in step 7 (12 mg; 0.05 mmol) was dissolved in 3 ml of dichloroethane. To this was added 25 mg (0.1 mmol) of 2-(S)-phenyl-piperidin-3(S)-ylamine and 0.014 ml (0.1 mmol) of triethylamine, and the mixture was stirred for 60 minutes at room temperature. To this mixture was added 32 mg (0.15 mmol) of sodium triacetoxyborohydride, and the reaction mixture was stirred at room temperature for 18 hours. The reaction was quenched with water and stirred at room temperature for 30 minutes. The pH of the mixture was adjusted to 2 with 1N HCl and extracted with ethyl acetate. The pH of the water layer was adjusted to 7.0 with sodium bicarbonate and extracted with ethyl acetate. The pH=7 ethyl acetate extracts were combined, dried(Na$_2$SO$_4$) and evaporated to yield 7 mg of a yellow amorphous solid. $^1$H NMR (CDCl$_3$) δ 7.2–7.4 (m, 5H), 6.85 (s, 1H), 3.95 (s, 1H), 3.85 (s, 3H), 3.62 (d,d 2H), 3.30 (d, 1H), 3.10 (s, 3H), 3.0 (s, 1H), 2.80 (m, 2H), 2.60 (m, 2H), 2.2–2.4 (m, 3H), 1.9 (m, 2H), 1.7 (m, 2H), 1.4 (m, 1H). Mass spectrum: m/e=381.1 (p+1). TLC: Rf=0.4; (5:1 chloroform/methanol).

Example 74

6-Methoxy-1-methyl-7-[(2(S)-phenyl-piperidin-3(S)-ylamino)-methyl]-3,4-dihydro-1H-[1,5]naphthyridin-2-one Step 1

6-Methoxy-3,4-dihydro-1H-[1,5]naphthyridin-2-one

A 2.2 g (8.7 mmol) solution of 3-(6-methoxy-3-nitropyridin-2-yl)-acrylic acid ethyl ester (M. Makosza, A. Tryula *Synthesis*, 1987, 1142–1144) in 50 ml of ethanol containing a catalytic amount of 10% Pd/C was hydrogenated at 50 PSI for 2 hours. The reaction was filtered and the solvent evaporated to afford crude intermediate 3-(3-amino-6-methoxy-pyridin-2-yl)-propionic acid ethyl ester. This material was disolved in 5 ml of acetic acid and heated on a steam bath for 30 minutes. The solution was cooled to room temperature and the solvent evaporated. The residue was dissolved in 25 ml of ethyl acetate and washed with saturated NaHCO$_3$. The ethyl acetate solution was dried (Na$_2$SO$_4$) and evaporated to yield a brown solid residue. This material was chromatographed on silica using 5:1 chloroform/ethyl acetate as the elutant. Appropriate fractions were combined and evaporated to yield 1.2 g of 6-methoxy-3,4-dihydro-1H-[1,5]naphthyridin-2-one. TLC: Rf=0.55 (5:1 ethyl acetate:hexane). $^1$H NMR (CDCl$_3$) δ 8.6 (s, 1H), 7.1 (d, 1H), 6.6 (d, 1H), 3.9 (s, 3H), 3.05 (m, 2H), 2.7 (m, 2H). Mass Spectrum: m/e=179.2 (p+1).

Step 2

6-Methoxy-1-methyl-3,4-dihydro-1H-[1,5]naphthyridin-2-one

A solution of 1.2 g (6.7 mmol) 6-methoxy-3,4-dihydro-1H-[1,5]naphthyridin-2-one in 15 ml of DMF was cooled to 5° C. and to this solution was slowly added 6.7 ml (6.7 mmol) of potassium t-butoxide (1M solution in THF). The mixture was stirred for 10 minutes followed by addition of 0.46 ml (7.4 mmol) methyl iodide. After addition was complete, the reaction mixture was stirred for 1 hour at 5° C. The reaction mixture was poured into saturated NaCl. The mixture was extracted with ethyl acetate. The ethyl acetate extracts were dried (Na$_2$SO$_4$) and evaporated. The residue was chromatographed on silica using 5:1 chloroform/ethyl acetate as the elutant. Appropriate fractions were combined and evaporated to yield 0.83 g of 6-methoxy-1-methyl-3,4-dihydro-1H-[1,5]naphthyridin-2-one. TLC Rf=0.6 (1:10 ethyl acetate/chloroform). $^1$H NMR (CDCl$_3$) δ 7.2 (d, 1H), 6.6 (d, 1H), 3.9 (s, 3H), 3.3 (s, 3H), 3.0 (m, 2H), 2.7 (m, 2H). Mass Spectrum: m/e 193.2 (p+1).

Step 3

7-Bromo-6-methoxy-1-methyl-3,4-dihydro-1H-[1,5]naphthyridin-2-one

To a solution of 0.6 g (3.1 mmol) 6-methoxy-1-methyl-3,4-dihydro-1H-[1,5]naphthyridin-2-one in 8 ml of acetic acid was added 8 ml of water. To this mixture was added 0.32 ml (6.2 mmol) of bromine. The reaction mixture was heated to 60° C. for 1 hour. The reaction mixture was cooled to room temperature and poured into 50 ml of water. The suspension was extracted with ethyl acetate. The ethyl acetate extracts were dried (Na$_2$SO$_4$) and evaporated. The residue was chromatographed on silica using chloroform as the elutant. Appropriate fractions were combined and evaporated to yield 0.69 g of 7-bromo-6-methoxy-1-methyl-3,4-dihydro-1H-[1,5]naphthyridin-2-one. TLC Rf=0.8 (10:1 ethyl acetate/chloroform). $^1$H NMR (CDCl$_3$) δ 7.42 (s, 1H), 4.0 (s, 3H), 3.3 (s, 3H), 3.0 (m, 2H), 2.7 (m, 2H). Mass Spectrum: m/e=271.2, 273.2 (p+1,3).

Step 4

6-Methoxy-1-methyl-7-vinyl-3,4-dihydro-1H-[1,5]naphthyridin-2-one

A mixture of 690 mg (2.5 mmol) of 7-bromo-6-methoxy-1-methyl-3,4-dihydro-1H-[1,5]naphthyridin-2-one, 0.8 ml (2.7 mmol) of tri-n-butyl-vinyltin and 100 mg of bis(triphenylphosphine-palladium(II) chloride in 20 ml of dioxane was heated under nitrogen to 100° C. for 6 hours. The reaction mixture was cooled to room temperature and diluted with water and ethyl acetate. The ethyl acetate solution was washed with water several times. To this ethyl acetate solution was added 1 ml of saturated KF, and the mixture filtered. The filtrate was dried, evaporated, and the residue chromatographed on silica using 1 5 ethyl acetate/hexanes as the elutant. Appropriate fractions were combined and evaporated to afford 200 mg of 6-methoxy-1-methyl-7-vinyl-3,4-dihydro-1H-[1,5]naphthyridin-2-one. $^1$H NMR (CDCl$_3$) δ 7.28 (s, 1H), 6.90 (d,d 1H), 5.75 (d, 1H), 5.35 (d, 1H), 3.95 (s, 3H), 3.26 (s, 3H), 3.0 (m, 2H), 2.7 (m, 2H) Mass spectrum: m/e=219.3 (p+1).

Step 5

2-Methoxy-5-methyl-6-oxo-5,6,7,8-tetrahydro-[1,5]naphthyridine-3-carbaldehyde

A 1.1 g (5.0 mmol) solution of 6-methoxy-1-methyl-7-vinyl-3,4-dihydro-1H-[1,5]naphthyridin-2-one in 50 ml of methylene chloride and 10 ml of methanol was cooled to −70° C. Ozone (via an ozone generator) was bubbled into the solution until a blue color was achieved. The reaction mixture was stirred at −70° C. for 30 minutes and quenched with 4.0 ml of dimethyl sulfide. The reaction mixture was stirred for 18 hours at room temperature. The reaction mixture was poured into 50 ml of water. The organic layer was dried (Na$_2$SO$_4$) and evaporated. This residue was chromatographed on silica using 10:1 chloroform/ethyl acetate as the elutant. Appropriate fractions were combined to yield 0.52 g of 2-methoxy-5-methyl-6-oxo-5,6,7,8-tetrahydro-[1,5]naphthyridine-3-carbaldehyde. TLC Rf=0.4 (1:1 ethyl acetate:hexane). $^1$H NMR (CDCl$_3$) δ 10.18 (s, 1H), 7.7 (s, 1H), 4.05 (s, 3H), 3.3 (s, 3H), 3.0 (m, 2H), 2.7 (m, 2H). Mass spectrum: m/e=221.1, (p+1).

Step 6

6-Methoxy-1-methyl-7-[(2(S)-phenyl-piperidin-3(S)-ylamino)-methyl]-3,4-dihydro-1H-[1,5]naphthyridin-2-one The 2-methoxy-5-methyl-6-oxo-5,6,7,8-tetrahydro-[1,5]naphthyridine-3-carbaldehyde prepared in step 5 (0.35 g; 1.4 mmol) was dissolved in 20 ml of dichloroethane. To this was added 250 mg (1.1 mmol) of 2-(S)-phenyl-piperidin-3(S)-ylamine and 0.4 ml (2.8 mmol) of triethylamine, and the mixture was stirred for 60 minutes at room temperature. To this mixture was added 0.7 g (3.3 mmol) of sodium triacetoxyborohydride, and the reaction mixture was stirred at room temperature for 18 hours. The reaction was quenched with water and stirred at room temperature for 30 minutes. The pH of the mixture was adjusted to 8.5 with Na$_2$CO$_3$. The organic layer was separated from the water layer. An additional 20 ml of water was added to the organic layer. The pH of the mixture was adjusted to 2 with 1N HCl and extracted with ethyl acetate. The pH of the water layer was adjusted to 7.5 with sodium bicarbonate and extracted with ethyl acetate. The pH=7.5 ethyl acetate extracts were combined, dried (Na$_2$SO$_4$), and evaporated to yield 300 mg of 6-methoxy-1-methyl-7-[(2(S)-phenyl-piperidin-3(S)-ylamino)-methyl]-3,4-dihydro-1H-[1,5]naphthyridin-2-one. $^1$H NMR (CDCl$_3$) δ 7.2–7.4 (m, 5H), 6.85 (s, 1H), 3.90 (s, 1H), 3.85 (s, 3H), 3.60,3.38 (d,d 2H), 3.30 (d, 1H), 3.10 (s, 3H), 3.0 (s, 1H), 2.90 (m, 2H), 2.80 (m, 2H), 2.66 (m, 2H), 2.0–2.2 (m, 3H), 1.9 (m, 1H), 1.6 (m, 1H), 1.45 (m, 1H). Mass spectrum: m/e=381.1 (p+1). TLC: Rf=0.5; (5:1 chloroform/methanol).

Example 75

6-Methoxy-1-methyl-7-[(6(S)-methyl-2(S)-phenyl-piperidin-3(S)-ylamino)-methyl]-3,4-dihydro-1H-[1,5]naphthyridin-2-one By a procedure similar to the previous example 74: starting with 6(S)-methyl-2(S)-phenyl-piperidin-3(S)-ylamine (Scheme J) and 2-methoxy-5-methyl-6-oxo-5,6,7,8-tetrahydro-[1,5]naphthyridine-3-carbaldehyde (Example 74, step 5) and using the above coupling procedure (Example 74, step 6) 6-methoxy-1-methyl-7-[(6(S)-methyl-2(S)-phenyl-piperidin-3(S)-ylamino)-methyl]-3,4-dihydro-1H-[1,5]naphthyridin-2-one was obtained. $^1$H NMR (CDCl$_3$) δ 7.2–7.4 (m, 5H), 7.0 (s, 1H), 4.28 (s, 1H), 3.70 (s, 3H), 3.60,3.42 (d,d 2H) 3.45 (m, 1H), 3.15 (s, 3H), 2.90 (m, 3H), 2.60 (m, 2H), 2.0–2.2 (m, 3H), 1.85 (m, 3H), 1.1 (d, 3H). Mass spectrum: m/e=395.2 (p+1). TLC: Rf=0.55; (5:1 chloroform/methanol). [47595-203, 276]

Example 76

7-[(6(S)-Ethyl-2(S)-phenyl-piperidin-3(S)-ylamino)-methyl]-6-methoxy-1-methyl-3,4-dihydro-1H-[1,5]naphthyridin-2-one By a procedure similar to the previous example 74: starting with cis-2-phenyl-3-amino-trans-6-ethyl-piperidine (scheme J) and 2-methoxy-5-methyl-6-oxo-5,6,7,8-tetrahydro-[1,5]naphthyridine-3-carbaldehyde (Example 74, step 5) and using the above coupling procedure (Example 74, step 6) 7-[(6-ethyl-2-phenyl-piperidin-3-ylamino)-methyl]-6-methoxy-1-methyl-3,4-dihydro-1H-[1,5]naphthyridin-2-one was obtained. Using a CHIRALPAK AD (10×50 cm) and a mobil phase of 95:5 heptane/ethanol containing 0.025% diethyl amine (flow rate=275 ml/min) 7-[(6(S)-ethyl-2(S)-phenyl-piperidin-3(S)-ylamino)-methyl]-6-methoxy-1-methyl-3,4-dihydro-1H-[1,5]naphthyridin-2-one (retention time 13.545 min) was isolated as a pure enantiomer. $^1$H NMR (CDCl$_3$) δ 7.40 (m, 2H), 7.35 (m, 2H), 7.2 (m, 1H), 4.20 (s, 1H), 3.75 (s, 3H), 2.82, 2.42 (d,d, 2H), 3.17 (s, 3H), 3.08 (m, 1H), 2.90 (m, 2H), 2.85 (m, 1H), 2.65 (m, 2H), 1.8–2.2 (m, 6H), 1.7 (m, 1H), 1.55 (m, 1H), 1.38 (m, 1H), 0.9 (t, 3H). Mass spectrum: m/e=409.2 (p+1). The corresponding 7-[(6(R)-ethyl-2(R)-phenyl-piperidin-3(R)-ylamino)-methyl]-6-methoxy-1-methyl-3,4-dihydro-1H-[1,5]naphthyridin-2-one enantiomer (retenton time 14.539 min) was also isolated. NMR and mass spectrum was identical to the above spectra.

Example 77

6-Methoxy-1-methyl-7-[(2-phenyl-6-propyl-piperidin-3-ylamino)-methyl]-3,4-dihydro-1H-[1,5]naphthyridin-2-one By a procedure similar to the previous example 74: starting with cis-2-phenyl-3-amino-trans-6-(n-propyl)-piperidine (Scheme J) and 2-methoxy-5-methyl-6-oxo-5,6,7,8-tetrahydro-[1,5]naphthyridine-3-carbaldehyde (Example 74, step 5) and using the above coupling procedure (Example 74, step 6) 7-[(6-ethyl-2-phenyl-piperidin-3-ylamino)-methyl]-6-methoxy-1-methyl-3,4-dihydro-1H-[1,5]naphthyridin-2-one was obtained. Using a CHIRALPAK AD (10×50 cm) and a mobil phase of 95:5 heptane/ethanol containing 0.025% diethyl amine (flow rate=275 ml/min) 6-methoxy-1-methyl-7-[(2(S)-phenyl-6(S)-propyl-piperidin-3(S)-ylamino)-methyl]-3,4-dihydro-1H-[1,5]naphthyridin-2-one (retention time 11.479 min) was isolated as a pure enantiomer. $^1$H NMR (CDCl$_3$) δ 7.40 (m, 2H), 7.30 (m, 2H), 7.22 (m, 1H), 6.95 (s, 1H), 4.20 (s, 1H), 3.72 (s, 3H), 3.80, 3.62 (d,d, 2H), 3.20 (m, 1H), 3.10 (s, 3H), 2.90 (m, 2H), 2.85 (m, 1H), 2.62 (m, 2H), 2.10 (m, 2H), 1.90 (m, 3H), 1.70 (m, 1H), 1.42 (m, 1H), 1.30 (m, 3H), 0.9 (t, 3H). Mass spectrum: m/e=423.2 (p+1). The corresponding enantiomer 6-methoxy-1-methyl-7-[(2(R)-phenyl-6(R)-propyl-piperidin-3(R)-ylamino)-methyl]-3,4-dihydro-1H-[1,5]naphthyridin-2-one (retention time 11.592 min) was also isolated. NMR and mass spectrum was identical to the above spectra.

Example 78

6-Methoxy-1-methyl-3,3-spirocyclopropyl-5-[(2R,S-(4-fluoro-phenyl)-piperidin-3R,S-ylamino)-methyl]-1,3-dihydro-indol-2-one To a stirred solution of 2R,S-(4-fluoro-phenyl)-piperidin-3R,S-ylamine (169 mg, 0.63 mmol) in 2 ml of methylene chloride under nitrogen, was added 6-methoxy-1-methyl-3,3-spirocyclopropyl-2-oxo-2,3-dihydro-1H-indole-5-carbaldehyde (146 mg, 0.63 mmol) (prepared by the method described in Preparation 60). After 5 minutes, added sodium triacetoxyborohydride (401 mg, 1.9 mmol) and stirred at room temperature overnight. The reaction was diluted with methylene chloride and extracted (3×) with saturated NaHCO$_3$. The organics were dried over anhydrous MgSO$_4$, concentrated and the residue was chromatographed using 0.1% triethylamine, 5% methanol/methylene chloride to yield the title compound (88 mg, 34% yield). $^1$H NMR (400 MHz, CDCl$_3$) δ 1.32–1.43 (3H, m), 1.54–1.67 (3H, m), 1.88–2.17 (5H, m), 2.74–2.81 (2H, m), 3.24 (4H, s), 3.35–3.38 (1H, d), 3.56 (3H, s), 3.62–3.66 (1H, d), 3.86 (1H, s), 6.31 (1H, s), 6.45 (1H, s), 6.95–6.99 (2H, t), 7.22–7.26 (2H, m). m/z (APCI$^+$) 410 (M+1). HPLC (aqueous 200 Mm ammonium acetate buffer/acetonitrile gradient, 3.0 ml/min, Hewlett Packard ODS Hypersil 5 μM, 125×4 mm column), 4.241.

Example 79

6-Methoxy-1-methyl-3,3-spirocyclopropyl-5-[(2R-(4-fluoro-phenyl)-piperidin-3R-ylamino)-methyl]-1,3-dihydro-indol-2-one Preparative HPLC chiral separation (Chiralpak AD column, 5 cm×50 cm, Eluent: 85/15Hexanes/Isopropanol, 0.025% Diethylamine, 50 ml/min) of 6-Methoxy-1-methyl-3,3-spirocyclopropyl-5-[(2R,S-(4-fluoro-phenyl)-piperidin-3R,S-ylamino)-methyl]-1,3-dihydro-indol-2-one yielded the title compound. (41 mg).

Example 80

6-Methoxy-1-methyl-3,3-spirocyclopropyl-5-[(2S-(4-fluoro-phenyl)-piperidin-3S-ylamino)-methyl]-1,3-dihydro-indol-2-one Preparative HPLC chiral separation (Chiralpak AD column, 5 cm×50 cm, Eluent: 85/15Hexanes/Isopropanol, 0.025% Diethylamine, 50 ml/min) of 6-Methoxy-1-methyl-3,3-spirocyclopropyl-5-[(2R,S-(4-fluoro-phenyl)-piperidin-3R,S-ylamino)-methyl]-1,3-dihydro-indol-2-one yielded the title compound. (43 mg).

Example 81

5-Methoxy-1-methyl-3,3-spirocyclopropyl-6-[(2S-(4-fluoro-phenyl)-piperidin-3S-ylamino)-methyl]-1,3-dihydro-indol-2-one To a stirred solution of 2S-(4-fluoro-phenyl)-piperidin-3S-ylamine (39 mg, 0.20 mmol) in 1 ml of methylene chloride under nitrogen, was added 5-methoxy-1-methyl-3,3-spirocyclopropyl-2-oxo-2,3-dihydro-1H-indole-6-carbaldehyde (46 mg, 0.20 mmol) (prepared by the method described in Preparation 61). After 5 minutes, added sodium triacetoxyborohydride (127 mg, 0.60 mmol) and stirred at room temperature overnight. The reaction was diluted with methylene chloride, then quenched with saturated NaHCO$_3$. A pH workup gave the title compound (16 mg). $^1$H NMR (400 MHz, CDCl$_3$) δ 1.42–1.45 (3H, m), 1.60–1.74 (4H, m), 2.14–2.18(1H, d), 2.80–2.87 (3H, m), 3.20 (3H, s), 3.32–3.35 (1H,d), 3.46–3.49 (1H, d), 3.49 (3H, s), 3.67–3.69 (1H, d), 3.94 (1H, s), 6.24 (1H, s), 6.62 (1H, s), 6.96–7.05 (3H, m), 7.30–7.32 (2H, m). m/z (APCI$^+$) 410 (M+1). HPLC (aqueous 200 Mm ammonium acetate buffer/acetonitrile gradient, 3.0 ml/min, Hewlett Packard ODS Hypersil 5 μM, 125×4 mm column), 4.235.

Example 82

5-Methoxy-1-methyl-3,3-spirocyclopropyl-6-[(2R-(4-fluoro-phenyl)-piperidin-3R-ylamino)-methyl]-1,3-dihydro-indol-2-one To a stirred solution of 2R-(4-fluoro-phenyl)-piperidin-3R-ylamine (39 mg, 0.20 mmol) in 1 ml of methylene chloride under nitrogen, was added 5-methoxy-1-methyl-3,3-spirocyclopropyl-2-oxo-2,3-dihydro-1H-indole-6-carbaldehyde (46 mg, 0.20 mmol) (prepared by the method described in Preparation 61). After 5 minutes, added sodium triacetoxyborohydride (127 mg, 0.60 mmol) and stirred at room temperature overnight. The reaction was diluted with methylene chloride, then quenched with saturated NaHCO$_3$. A pH workup gave the title compound (21 mg). $^1$H NMR (400 MHz, CDCl$_3$) δ 1.42–1.45 (3H, m), 1.60–1.74 (4H, m), 2.14–2.18(1H, d), 2.80–2.87 (3H, m), 3.20 (3H, s), 3.32–3.35 (1H, d), 3.46–3.49 (1H, d), 3.49 (3H, s), 3.67–3.69 (1H, d), 3.94 (1H, s), 6.24 (1H, s), 6.62 (1H, s), 6.96–7.05 (3H, m), 7.30–7.32 (2H, m). m/z (APCI$^+$) 410 (M+1). HPLC (aqueous 200 Mm ammonium acetate buffer/ acetonitrile gradient, 3.0 ml/min, Hewlett Packard ODS Hypersil 5 μM, 125×4 mm column), 4.314.

Example 83

5-{[2-(4-Fluoro-phenyl)-piperidin-3-ylamino]-methyl}-6-methoxy-3-methyl-1,1a,3,7b-tetrahydro-3-aza-cyclopropa[a]naphthalen-2-one To a stirred solution of 2S-(4-fluoro-phenyl)-piperidin-3S,-ylamine (39 mg, 0.20 mmol) in 1 ml of methylene chloride under nitrogen, was added 6-methoxy-3-methyl-2-oxo-1a,2,3,7b-tetrahydro-1H-3-aza-cyclopropa[a]napthalene-5-carbaldehyde (46 mg, 0.20 mmol) (prepared by the method described in Preparation 22 and/or 22A and/or 22B). After 45 minutes, added sodium triacetoxyborohydride (127 mg, 0.60 mmol) and stirred at room temperature overnight. The reaction was diluted with $CH_2Cl_2$, then quenched with $H_2O$. A pH workup gave the title compound (69 mg). Prepared HCl salt in isopropanol and concentrated hydrochloric acid, azeotroped off the $H_2O$ and recrystallized from methanol/isopropanol. $^1H$ NMR (400 MHz, $CD_3OD$) δ 0.50 (1H, m), 1.65 (1H, m), 2.0(1H, d), 2.25 (2H, m), 2.45 (2H, m), 2.65 (1H, m), 3.65 (1H, d), 3.75 (3H, s), 3.85 (1H, d), 3.95 (1H, s), 4.2 (1H, d), 4.95 (1H, s), 7.05 (2H, d), 7.30 (3H, m), 7.75 (2H, m). m/z ($APCI^+$) 410 (M+1). HPLC (aqueous 200 Mm ammonium acetate buffer/acetonitrile gradient, 3.0 ml/min, Hewlett Packard ODS Hypersil 5 μM, 125×4 mm column), 4.210.

Example 84

5-{[2-(4-Fluoro-phenyl)-piperidin-3-ylamino]-methyl}-6-methoxy-3-methyl-1,1a,3,7b-tetrahydro-3-aza-cyclopropa[a]naphthalen-2-one To a stirred solution of 2S-(4-fluoro-phenyl)-piperidin-3S-ylamine (39 mg, 0.20 mmol) in 1 ml of methylene chloride under nitrogen, was added 6-methoxy-3-methyl-2-oxo-1a,2,3,7b-tetrahydro-1H-3-aza-cyclopropa[a]napthalene-5-carbaldehyde (46 mg, 0.20 mmol) (prepared by the method described in Preparation 22 and/or 22A and/or 22B). After 45 minutes, added sodium triacetoxyborohydride (127 mg, 0.60 mmol) and stirred at room temperature overnight. The reaction was diluted with $CH_2Cl_2$, then quenched with $H_2O$. A pH workup gave the title compound (69 mg). Prepared HCl salt in isopropanol and concentrated hydrochloric acid, azeotroped off the $H_2O$ and recrystallized from methanol/isopropanol. $^1H$ NMR (400 MHz, $CD_3OD$) δ 0.50 (1H, m), 1.65 (1H, m), 2.0(1H, d), 2.25 (2H, m), 2.45 (2H, m), 2.65 (1H, m), 3.65 (1H, d), 3.75 (3H, s), 3.85 (1H, d), 3.95 (1H, s), 4.2 (1H, d), 4.95 (1H, s), 7.05 (2H, d), 7.30 (3H, m), 7.75 (2H, m). m/z ($APCI^+$) 410 (M+1). HPLC (aqueous 200 Mm ammonium acetate buffer/acetonitrile gradient, 3.0 ml/min, Hewlett Packard ODS Hypersil 5 μM, 125×4 mm column), 4.214.

Preparation 78a

1-Nitroheptan-4-one

To 53.4 g (544 mmol) of 1-hexen-3-one in 250 mL of methanol and 294 mL (5440 mmol) of nitromethane was added as a slow, steady stream 30 mL (136 mmol) of 25% NaOMe in methanol. The resultant yellow solution was warmed to −5° C. over 1 h, and kept between −5° C. and −10° C. for an additional 3 h. The solution was warmed to 0° C. for 1 h and was then quenched with 250 mL of saturated $NH_4Cl$. The mixture was diluted with 200 mL brine to aid in layer separation, and extracted with ether (2×250 mL). The combined ether extracts were washed with Brine, dried with $MgSO_4$, filtered and concentrated to give 75.7 g (88%) of a yellow liquid. $^1H$ NMR revealed the presence of ca. 10% of 7-nitro-trideca-4,10-dione arising from the combination of one molar equivallent of nitromethane with two molar equivalents of 1-hexen-3-one. The products are insepararable by silica gel chromatography (EtOAc/hexanes), so the material was generally used in the next step without purification. Title compound: mass spectrum m/e=144 (M−1).

Preparation 79a-1

1-Nitrohexan-4-one

To ethyl vinyl ketone (90.1 g, 1285 mmol) in 550 mL of methanol and 556 mL (10282 mmol) of nitromethane at −40° C. was added as a steady stream 84 mL (ca. 386 mmol) of 25% methanolic NaOMe. The resultant pale yellow slurry was allowed to warm to rt over 5 h, and was stirred overnight. The mixture was quenched with 300 mL of saturated $NH_4Cl$ followed by 250 mL water and 250 mL brine. The mixture was then extracted with $CH_2Cl_2$ (250 mL×4). The extracts were treated with $MgSO_4$ and decolorizing carbon, filtered and concentrated to yield 154 g (92%) pale yelow liquid: $^1H$ NMR: δ 4.43 (t, J=6.6 Hz, 2H), 2.56 (t, J=6.6 Hz, 2H), 2.44 (t, J=7.5 Hz, 2H), 2.25 (m, 2H), 1.06 (t, J=7.5 Hz, 3H).

Preparation 79a-2

1-Nitrohexan-4-one

To ethylvinylketone (41.4 g, 493 mmol) in MeOH (150 mL) and nitromethane (160 mL) was added sodium methoxide (ca. 123 mmol; 27 mL of a 25% solution in MeOH). The mixture was warmed to −10° C. over 30 min. After 1.5 h at −10° C., the mixture was quenched with saturated $NH_4Cl$ (250 mL) and water (250 mL). The mixture was pured into a separatory funnel and the lower organic layer was removed. The aqueous portion was extracted with $CH_2Cl_2$ (2×250 mL) and the combined organic portions were dried with $MgSO_4$ and concentrated. The resultant liquid was reconcentrated from toluene (2×250 mL) followed by methanol (1×250 mL) to yield the desired material.

Preparation 80a

1-Nitropentan-4-one

Prepared by a procedure similar to Preparation 79a-1. Mass spectrum m/e=130 (M−1).

Preparation 81a

6-Ethyl-3-nitro-2-phenyl-2,3,4,5-tetrahydro-pyridine

The crude product (1-nitrohexan-4-one) was then dissolved in MeOH (90 mL) and trimethylorthoformate (90 mL) and treated with camphorsulfonic acid (5.7 g, 24.7 mmol). After 30 min was added ammonium acetate (75.9 g, 986 mmol) and MeOH (200 mL), followed by benzaldehyde (110 g, 1035 mmol). The solution was stirred for 7 h, and then seeded to induce crystallization. After stirring the resultant slurry overnight, the crystals were collected and rinsed with 300 mL of cold methanol to yield 100 g (53%) of benzylidene-(5,5-dimethoxy-2-nitro-1-phenyl-heptyl)- amine as a white powder. The material was dissolved in EtOAc (300 mL) and to the stirred solution was added a solution of p-toluenesulfonic acid (54.3 g, 286 mmol) in 300 mL of warm EtOAc. The mixture was stirred overnight and the resultant crystals were isolated and rinsed with 250 mL of EtOAc followed by 250 mL of ether to yield 92 g (48%) of the title compound as a white powder consisting of a ca. 1:1 cis/trans mixture. Mass spectrum calcd for $C_{13}H_{16}N_2O_2$ (M-pTsO$^-$) 233. Found 233.

Preparation 82a

6-Methyl-3-nitro-2-phenyl-2,3,4,5-tetrahydro-pyridine

Prepared by a procedure similar to Preparation 81a. Mass spectrum m/e=219 (M+1).

Preparation 83a

6-Propyl-3-nitro-2-phenyl-2,3,4,5-tetrahydro-pyridine

Prepared by a procedure similar to Preparation 81a. Mass spectrum m/e=247 (M+1).

Preparation 84a

6-Ethyl-3,3-dimethoxy-2-phenyl-2,3,4,5-tetrahydro-pyridine camphorsulfonate

To 6-Methyl-3-nitro-2-phenyl-2,3,4,5-tetrahydro-pyridine (50.0 g, 216 mmol) in 180 mL MeOH was added 25% NaOMe/MeOH solution (180 mL, ca. 864 mmol). The solution was stirred at rt for 25 min, and then was added dropwise over 1 h to 2 M methanolic $H_2SO_4$ (1080 mL, 2160 mmol) at 0° C. The mixture was warmed to rt and stirred for 3.5 h. The mixture was then poured carefully into a solution of 362 g (4320 mmol) of NaHCO$_3$ in 2 L of water. The mixture was then diluted with 2 L of ether and 1 L of water and stirred well for 5 min. The layers were separated and the aqueous portion was extracted with ether (1×2 L). The ether portion was extracted with 5% HOAc (aq) (3×750 mL). HOAc extracts were basified with 500 mL of saturated Na$_2$CO$_3$ and extracted with CH$_2$Cl$_2$ (2×700 mL). The extracts were dired (MgSO$_4$) and concentrated to yield 33.2 g of a viscous red oil. The oil was dissolved in EtOAC (100 mL) and with vigorous stirring a solution of (+/−)-camphorsulfonic acid (31.3 g, 13.5 mmol) in 50 mL of warm THF was added. A precipitate formed within 30 s. The resultant thick slurry was diluted with EtOAc (100 mL) and cooled on ice. After 1 h the precipitate was collected via filtration and rinsed with EtOAc (200 mL) followed by ether (200 mL) to yield 48.0 g (47%) of an off-white powder: $^1$H NMR (300 MHz, CDCl3) δ 7.40–7.03 (comp, 3H), 7.20–7.17 (comp, 2H), 5.55 (s, 1H), 3.4 (s, 3H), 3.20 (s, 3H), 3.11 (d, J=14.6, 1H), 3.06–2.96 (comp, 3H), 2.65 (d, J=14.6, 1H), 2.54 (ddd, J=4.2, 12, 15 Hz, 1H), 2.38–2.22 (comp, 2H), 2.08–2.16 (m, 1H), 1.98 (t, J=3.6 Hz, 1H), 1.73–1.94 (comp, 3H), 1.46 (par obsc m, 1H), 1.44 (t, J=7.8, 3H), 1.19–1.28 (m, 1H), 1.01 (s, 3H), 0.74 (s, 3H).

Preparation 85a

6-Methyl-3,3-dimethoxy-2-phenyl-2,3,4,5-tetrahydro-pyridine camphorsulfonate

Prepared by a procedure similar to Preparation 84a.

Preparation 86a

6-Propyl-3,3-dimethoxy-2-phenyl-2,3,4,5-tetrahydro-pyridine camphorsulfonate

Prepared by a procedure similar to Preparation 84a.

Preparation 87a trans-6-Ethyl-3,3-dimethoxy-2-phenyl-piperidine

The imine salt 6-Ethyl-3,3-dimethoxy-2-phenyl-2,3,4,5-tetrahydro-pyridine camphorsulfonate was partitioned between saturated NaHCO$_3$ (1×100 mL) and ether (2×100 mL). The extracts were washed with brine, dried with MgSO4 and concentrated. The resultant oil was dissolved in 40 mL THF and cooled to −78° C. Triethylaluminum (35 mL, 35 mmol of a 1 M solution in heptane) was added and the solution was stirred for 10 min. This was followed by the addition of pre-cooled LiAlH$_4$ (39 mL, 39 mmol of a 0.5 M solution in THF), added rapidly via jacketed addition funnel at −78° C. After stirring for 1 h, the mixture was quenched carefully via dropwise addition of 2 M Rochelle's salt solution. When vigorous bubbling stopped, the mixture was diluted with 100 mL of additional 2 M Rochelle's salt solution and stirred overnight. The mixture was then diluted with water and extracted once with ether. The extract was washed with brine, dried with MgSO$_4$ and concentrated to give 8.9 g (99%) of the title compound as a colorless oil: δ 7.78 (d, J=7.5 Hz, 2H), 7.25–7.40 (comp, 3H), 4.15 (s, 1H), 3.23 (s, 3H), 3.19 (s, 3H), 2.43 (m, 1H), 1.91–2.10 (comp, 2H), 1.68–1.74 (m, 1H), 1.29–1.50 (comp, 3H), 0.89 (t, J=7.5, 3H); mass spectrum m/e=250 (base) [$C_{15}H_{23}NO_2$ (M+1) requires 250], 218.

Preparation 88a trans-6-Methyl-3,3-dimethoxy-2-phenyl-piperidine

Prepared by a procedure similar to Preparation 87a. Mass spectrum m/e=236 (base) [$C_{15}H_{23}NO_2$ (M+1) requires 236], 204.

Preparation 89a trans-6-Propyl-3,3-dimethoxy-2-phenyl-piperidine

Prepared by a procedure similar to Preparation 87a. Mass spectrum m/e=264 (base) [$C_{15}H_{23}NO_2$ (M+1) requires 264], 232.

Preparation 90a 3,3-Dimethoxy-1,2,3,4,5,6-hexahydro-[2,3']bipyridinyl

Prepared by a procedure similar to Preparation 87a. Mass spectrum m/e=223 (M+1, base), 191.

Preparation 91a

6-Ethyl-2-phenyl-piperidin-3-one oxime

To a mixture of trans-6-Ethyl-3,3-dimethoxy-2-phenyl-piperidine (6.3 g, 25.3 mmol) and 17.5 g (253 mmol) of hydroxylamine hydrochloride in 250 ml of 50% aqueous acetonitrile was added 9.7 ml (126 mmol) of trifluroacetic acid. The resulting solution was heated to 60° C. for 3 hours. The reaction mixture was cooled to 5° C. and the pH adjusted to 7.0 with saturated sodium bicarbonate. The mixture was extracted with methylene chloride. The methylene chloride extracts were dried ($Na_2SO_4$) and evaporated to yield 5.1 g of a dark oil. The oil was dissolved in 70 ml of ethyl acetate and 30 ml of water and the pH adjusted to 3.4 with 1 N HCl. The aqueous layer was extracted with ethyl acetate. The aqueous layer was then diluted with an equal volume of ethyl acetate and the pH adjusted to 7.5 with saturated sodium bicarbonate. The ethyl acetate layer was dried ($Na_2SO_4$) and evaporated to yield 3.67 grams (66%) of product as a mixture of cis- and trans-oxime isomers. NMR ($CDCl_3$) δ 7.2–7.4 (m, 5H), 5.75,4.7 (s, 1H), 1.1–3.4 (m, 8H), 0.9 (t. 3H): mass spectrum: m/e=219 (base; m+1), 201.

Preparation 92a

(+/−)-6-Methyl-2-phenyl-piperidin-3-one oxime

Prepared by a procedure similar to Preparation 91a. Mass spectrum 205 (M+1, base), 187.

Preparation 93a

6-Propyl-2-phenyl-piperidin-3-one oxime

Prepared by a procedure similar to Preparation 91a. Mass spectrum 233 (M+1, base), 215.

Preparation 94a

1,4,5,6-Tetrahydro-2H-[2,3']bipyridinyl-3-one oxime

Prepared by a procedure similar to Preparation 91a. Mass spectrum 191 (M+1, base), 173.

Preparation 95a

6-Ethyl-2-phenyl-piperidin-3-ylamine

6-Ethyl-2-phenyl-piperidin-3-one oxime was dissolved in EtOH (20 mL) and hydrogenated at 52 p.s.i. over freshly prepared Raney Nickel catalyst (6.0 g of a wet slurry) for 20 h. The mixture was carefully filtered through celite and concentrated. The ditosylate salt was prepared by treatment with p-touenesulphonic acid (12.3 g, 65 mmol) in MeOH/EtOAc to give 7.2 g (40%) of off-white crystals. Recrystallization from 2-propanol gave 3.80 g (21%) of a white powder: mass spectrum 205 (base), 188.

Preparation 96a

6-Methyl-2-phenyl-piperidin-3-ylamine

Prepared by a procedure similar to Preparation 95a. Mass spectrum (M+1)=191 (base), 174.

Preparation 97a

6-Propyl-2-phenyl-piperidin-3-ylamine

Prepared by a procedure similar to Preparation 95a. Mass spectrum (M+1)=219 (base), 202.

Preparation 98a

1,2,3,4,5,6-Hexahydro-[2,3']bipyridinyl-3-ylamine

Prepared by a procedure similar to Preparation 95a. Mass spectrum (M+1)=176.

Preparation 99a

Chiral salt resolution of (+/−)-6-Ethyl-2-phenyl-piperidin-3-ylamine

(2S,3S,6S)-6-Ethyl-2-phenyl-piperidin-3-ylamine dibenzoyl-L-tartrate (+/−)-6-Ethyl-2-phenyl-piperidin-3-ylamine (102 mg, 0.50 mmol) and (−) dibenzoyltartaric acid were dissolved by heating in 5 mL 2-propanol and 1 mL water. The resultant solid (26 mg, 25%) was determined to be 94% enriched in the (2S,3S,6S)-enantiomer.

Preparation 78b

Cis-6-Ethyl-3-nitro-2-phenyl-2,3,4,5-tetrahydro-pyridine

To a flame dried round bottomed flask under nitrogen was added 250 mg (1.07 mmol) 6-Ethyl-3-nitro-2-phenyl-2,3,4,5-tetrahydro-pyridine as a mixture of cis and trans isomers and 5 ml of anhydrous THF (TLC rf.=Trans 0.6; Cis 0.4; eluting solvent hexane:ethylacetate/50:50). The reaction mixture was cooled to −78° C. and 1.07 ml (1.07 mmol) of 1N lithium bis(trimethylsilyl)amide solution in THF was introduced. The reaction mixture was stirred for 20 min, and then quenched directly into a well stirred solution of 2 gm Baker Silica Gel (40 uM Flash Chromatography Packing). The solids were filtered and the filtrate was concentrated in vacuo to afford an orange red oil, 0.23 gm (92%) as the desired cis isomer, Cis-6-Ethyl-3-nitro-2-phenyl-2,3,4,5-tetrahydro-pyridine (TLC rf.=0.4, hexane:ethylacetate/50:50). Mass spectrum APCI (m/z) 233 (p+1).

Preparation 79b

(2S,3S,6S)-6-Ethyl-2-phenyl-piperidin-3-ylamine

To a solution of Cis-6-Ethyl-3-nitro-2-phenyl-2,3,4,5-tetrahydro-pyridine prepared above (322 mg; 1.39 mmol) in 5 ml of THF at −78° C. was added 1.39 ml (1.39 mmol) of 1M triethylaluminum in hexane solution. The reaction mixture was stirred for 5 min prior to the addition of 1.39 ml (1.39 mmol) 1M lithium aluminum hydride in THF and again stirred for 5 minutes. The reaction mixture was treated directly at −78° C. with 5 ml of 6N HCl solution and allowed to warm to room temperature. The mixture was treated with 1.81 gm of zinc dust (27.7 mmol) and then heated under reflux for 30 minutes. The mixture was allowed to cool and then treated with 20% aqueous sodium hydroxide solution. The mixture was extracted with ethyl acetate, washed with saturated brine solution, dried over sodium sulfate and evaporated in vacuo to a clear oil. The oil was dissolved in ethyl acetate (25 mg/ml) and treated with 176 mg (0.757 mmol) camphorsulfonic acid and then stirred overnight at room temperature. The resulting solids were filtered to afford 70 mg of mainly (2S,3S,6S)-6-Ethyl-2-phenyl-piperidin-3-ylamine as the camphorsulfonic acid salt. Mass spectrum APCI (m/z) 204 (p+1).

Preparation 78c

Cis-6-Ethyl-3-nitro-2-phenyl-1,2,3,4,-tetrahydro-2H-pyridine-1-carboxylic acid benzyl ester A solution of the cis-6-Ethyl-3-nitro-2-phenyl-2,3,4,5-tetrahydro-pyridine (12 gm; 29.7 mmol) in saturated aqueous sodium bicarbonate solution (50 ml) and methylene chloride (100 ml) was treated with 5.08 ml (35.6 mmol) benzylchloroformate. The mixture was rapidly stirred and heated to 45° C. for 3 hours followed by a return to ambient temperature. The layers were separated and the aqueous layer was washed once more with methylene chloride. The combined organic layers were concentrated and the residue was treated with isopropyl ether (80 ml). In this case, a solid precipitated. However, in the event that no precipitation occurred, the mixture was cooled to −78° C. for 2 hrs. The solids were collected as a first crop 4.92 gm (45%). A second crop was obtained from the filtrate 1.18 gm (11%). TLC and NMR identified this material as the cis isomer cis-6-Ethyl-3-nitro-2-phenyl-1,2,3,4,-tetrahydro-2H-pyridine-1-carboxylic acid benzyl ester. $^1$H NMR (CDCl$_3$, 400 MHz) δ 7.4–7.1 (br.m, 10H), 6.22 (d, 1H, J=5 Hz), 5.25–5.05 (br.m), 4.96 (br.t), 4.90 (m), 2.8–2.5 (m), 1.0 (t, 3H) ppm. Mass spectra m/z=367 (p+1).

Preparation 79c (2S,3S,6S)-6-Ethyl-3-nitro-2-phenyl-piperidine-1-carboxylic acid benzyl ester To a three-neck flask with nitrogen inlet, addition funnel and magnetic stir bar was charged 81 ml (1.05 mol) trifluoroacetic acid (TFA) and 80 ml of methylene chloride. The solution was cooled to −15° C. whereupon TFA as a white solid often precipitated. The addition funnel was charged with 38.75 gm (105.8 mmol) of Cis-6-Ethyl-3-nitro-2-phenyl-1,2,3,4,-tetrahydro-2-H-pyridine-1-carboxylic acid benzyl ester and 46.4 ml (291.0 mmol) triethylsilane in 45 ml of methylene chloride. The contents of the addition funnel were added slowly over 20 minutes to the reaction flask and stirring was continued for 15 minutes. The reaction was judged to be complete by TLC and was then evaporated in vacuo to I, as a thick red oil. The material was used directly in the next transformation. $^1$H NMR (CDCl$_3$, 400 MHz) δ 7.4–7.0 (br.m, 10H), 5.95 (d, 1H, J=5 Hz), 5.30–4.95 (br.m), 3.85 (br.t), 4.90 (m), 2.3–2.0 (m), 2.0–1.75 (m), 1.5–1.4 (m), 0.95 (t, 3H) ppm. Mass spectra m/z=369 (p+1).

Preparation 80c (2S,3S,6S)-6-Ethyl-3-nitro-2-phenyl-piperidine (2S,3S,6S)-6-Ethyl-3-nitro-2-phenyl-piperidine-1-carboxylic acid benzyl ester (40 gm; 108 mmol) was dissolved in 80 ml of 30% HBr in propionic acid at room temperature. There was a rapid evolution of gas and the desired product precipitated after 3–5 minutes. The mixture was stirred at room temperature for 16 hours. The tan solids were collected, washed with ether and dried in vacuo to afford 29 gm of the (2S,3S,6S)-6-Ethyl-3-nitro-2-phenyl-piperidine HBr salt. $^1$H NMR (D$_2$O, 400 MHz) δ 7.4–7.2 (br.m, 5H), 5.25 (m, 1H), 4.95 (d), 3.65 (br.m.), 2.4–2.0 (m), 1.9–1.55 (m), 0.85 (t, 3H) ppm. Mass spectra m/z=235 (p+1).

Preparation 81c (2S,3S,6S)-6-Ethyl-2-phenyl-piperidin-3-ylamine

To a 250 ml Parr bottle was charged 1 gm (3.18 mmol) of the (2S,3S,6S)-6-Ethyl-3-nitro-2-phenyl-piperidine HBr salt prepared above in 60 ml of methanol. To the resulting solutionwas added an excess of commercial Raney nickel which had been exhaustively washed with deionized water until the supernatant was pH 7.00. The reaction mixture was placed under 50 p.s.i. in a Parr Hydrogenator and shaken for 4 hrs. The reaction mixture was filtered through celite and the filtrate was evaporated in vacuo. The residue was partitioned between methylene chloride and 1N NaOH. The combined organics were washed with brine and then dried and evaporated to afford 0.47 gm (72%) of crude racemic 6-Ethyl-2-phenyl-piperidin-3-ylamine. Such racemate was resolved through the formation of a salt with (−)-O,O'-dibenzoyl-L-tartaric acid in isopropanol water. $^1$H NMR (CDCl$_3$, 400 MHz) δ 7.4–7.2 (br.m, 5H), 4.05 (d), 3.0 (br.t), 2.90 (m), 1.98 (m), 1.75 (m), 1.6–1.4 (m), 0.80 (t, 3H), ppm. Mass spectra m/z=205 (p+1).

Example 85

5-[(6-Ethyl-2-phenyl-piperidin-3-ylamino)-methyl]-6-methoxy-3-methyl-1,1a,3,7b-tetrahydro-3-azacyclopropa[a]naphthalen-2-one By a procedure similar to the previous examples 9 and 9A: prepared through the reaction of 6-Ethyl-2-phenyl-piperidin-3-ylamine [or (2S,3S,6S)-6-Ethyl-2-phenyl-piperidin-3-ylamine or (2R,3R,6R)-6-Ethyl-2-phenyl-piperidin-3-ylamine] with 6-Methoxy-3-methyl-2-oxo-1a,2,3,7b-tetrahydro-1H-3-aza-cyclopropa[a]naphthalene-5-carbaldehyde [or (1S,1aR)-6-Methoxy-3-methyl-2-oxo-1a,2,3,7b-tetrahydro-1H-3-aza-cyclopropa[a]naphthalene-5-carbaldehyde or (1R,1aS)-6-Methoxy-3-methyl-2-oxo-1a,2,3,7b-tetrahydro-1H-3-aza-cyclopropa[a]naphthalene-5-carbaldehyde]. Melting Point: 231–234° C. (dec); $^1$H-NMR (dihydrochloride, 400 MHz, CD$_3$OD): δ 0.48 (app. q, J=5.0 Hz, 1H), 1.02 (t, J=7.5 Hz, 3H), 1.64 (ddd, J=4.2, 9.1, 9.1 Hz, 1H), 1.70–1.85 (comp, 3H), 2.21 (ddd, J=5.0, 7.5, 9.5 Hz, 1H), 2.35–2.50 (comp, 3H), 2.61 (ddd, J=8.3, 8.3, 5.5 Hz, 1H), 3.28 (s, 3H), 3.61 (m, 1H), 3.71 (s, 3H), 4.00 (m, 1H), 4.14 (ab q, J=13.3, 6.2 Hz, 2H), 5.12 (d, J=4.97 Hz, 1H), 7.09 (d, J=12.9 Hz, 2H), 7.59–7.60 (m, 3H), 7.80–7.82 (m, 2H).

Mass spectrum APCI (m/z) 420 (p+1).

Example 86

6-Methoxy-3-methyl-5-[(6-methyl-2-phenyl-piperidin-3-ylamino)-methyl]-1,1a,3,7b-tetrahydro-3-azacyclopropa[a]naphthalen-2-one By a procedure similar to the previous examples 9 and 9A: prepared through the reaction of 6-Methyl-2-phenyl-piperidin-3-ylamine [or (2S,3S,)-6-methyl-2-phenyl-piperidin-3-ylamine or (2R,3R,6R)-6-methyl-2-phenyl-piperidin-3-ylamine] with 6-Methoxy-3-methyl-2-oxo-1a,2,3,7b- tetrahydro-1H-3-aza-cyclopropa[a]naphthalene-5-carbaldehyde [or (1S,1aR)-6-Methoxy-3-methyl-2-oxo-1a,2,3,7b-tetrahydro-1H-3-aza-cyclopropa[a]naphthalene-5-carbaldehyde or (1R, 1aS)-6-Methoxy-3-methyl-2-oxo-1a,2,3,7b-tetrahydro-1H-3-aza-cyclopropa[a]naphthalene-5-carbaldehyde].

Mass spectrum APCI (m/z) 406 (p+1).

Example 87

6-Methoxy-3-methyl-5-[(2-phenyl-6-propyl-piperidin-3-ylamino)-methyl]-1,1a,3,7b-tetrahydro-3-aza-cyclopropa[a]naphthalen-2-one By a procedure similar to the previous examples 9 and 9A: prepared through the reaction of 6-propyl-2-phenyl-piperidin-3-ylamine [or (2S,3S,6S)-6-propyl-2-phenyl-piperidin-3-ylamine or (2R,3R,6R)-6-propyl-2-phenyl-piperidin-3-ylamine] with 6-Methoxy-3-methyl-2-oxo-1a,2,3,7b-tetrahydro-1H-3-aza-cyclopropa[a]naphthalene-5-carbaldehyde [or (1S,1aR)-6-Methoxy-3-methyl-2-oxo-1a,2,3,7b-tetrahydro-1H-3-aza-cyclopropa[a]naphthalene-5-carbaldehyde or (1R,1aS)-6-Methoxy-3-methyl-2-oxo-1a,2,3,7b-tetrahydro-1H-3-aza-cyclopropa[a]naphthalene-5-carbaldehyde].

Mass spectrum APCI (m/z) 434 (p+1).

Example 88

6-Methoxy-1-methyl-7-[(2-phenyl-6-propyl-piperidin-3-ylamino)-methyl]-3,4-dihydro-1H-quinolin-2-one By a procedure similar to the previous examples 9 and 9A: prepared through the reaction of 6-propyl-2-phenyl-piperidin-3-ylamine [or (2S,3S,6S)-6-propyl-2-phenyl-piperidin-3-ylamine or (2R,3R,6R)-6-propyl-2-phenyl-piperidin-3-ylamine] with 6-Methoxy-1-methyl-2-oxo-1,2,3,4-tetrahydro-quinoline-7-carbaldehyde.

Mass spectrum APCI (m/z) 422 (p+1).

Example 89

7-[(6-Ethyl-2-phenyl-piperidin-3-ylamino)-methyl]-6-methoxy-1-methyl-3,4-dihydro-1H-quinolin-2-one By a procedure similar to the previous examples 9 and 9A: prepared through the reaction of 6-ethyl-2-phenyl-piperidin-3-ylamine [or (2S,3S,6S)-6-ethyl-2-phenyl-piperidin-3-ylamine or (2R,3R,6R)-6-ethyl-2-phenyl-piperidin-3-ylamine] with 6-Methoxy-1-methyl-2-oxo-1,2,3,4-tetrahydro-quinoline-7-carbaldehyde.

Mass spectrum APCI (m/z) 408 (p+1).

Example 90

6-Methoxy-1-methyl-7-[(6-methyl-2-phenyl-piperidin-3-ylamino)-methyl]-3,4-dihydro-1H-quinolin-2-one By a procedure similar to the previous examples 9 and 9A: prepared through the reaction of 6-methyl-2-phenyl-piperidin-3-ylamine [or (2S,3S,6S)-6-methyl-2-phenyl-piperidin-3-ylamine or (2R,3R,6R)-6-methyl-2-phenyl-piperidin-3-ylamine] with 6-Methoxy-1-methyl-2-oxo-1,2,3,4-tetrahydro-quinoline-7-carbaldehyde.

Mass spectrum APCI (m/z) 394 (p+1).

Example 91

7-[((2S,3S,6S)-6-Isopropyl-2-phenyl-piperidin-3-ylamino)-methyl]-6-methoxy-1-methyl-3,4-dihydro-1H-quinolin-2-one hydrochloride By a procedure similar to the previous examples 9 and 9A: prepared through the reaction of 6-isopropyl-2-phenyl-piperidin-3-ylamine with 6-Methoxy-1-methyl-2-oxo-1,2,3,4-tetrahydro-quinoline-7-carbaldehyde Mass spectrum calcd for $C_{26}H_{36}N_3O_2$ (M+1) 423; found 423.

Example 92

7-[((2S,3S,6S)-6-Isopropyl-2-phenyl-piperidin-3-ylamino)-methyl]-6-methoxy-1-methyl-3,4-dihydro-1H-[1,5]naphthyridin-2-one By a procedure similar to the previous examples 9 and 9A: prepared through the reaction of 6-isopropyl-2-phenyl-piperidin-3-ylamine with 2-Methoxy-5-methyl-6-oxo-5,6,7,8-tetrahydro-[1,5]naphthyridine-3-carbaldehyde. Mass spectrum calcd for $C_{25}H_{34}N_4O_2$ (M+1) 423; found 423.

Preparation 100

3-Benzylamino-3-methyl-butan-1-ol

To a slurry of 3-Benzylamino-3-methyl-butyric acid (1.00 g, 4.83 mmol) in THF was added borane (9.7 mmol, 9.7 mL of a 1.0 M solution in THF). After stirring for 1 h, the mixture was quenched by pouring into a mixture of 1 M HCl and crushed ice. The mixture was neutralized with $K_2CO_3$ and extracted 1× with $CHCl_3$. The material was dried via passage through cotton and concentrated to give 441 mg (47%) of the title compound: Rf 0.40 (12:88 MeOH/$CHCl_3$).

Preparation 101

(3-Hydroxy-1,1-dimethyl-propyl)-carbamic acid tert-butyl ester

To 3-Benzylamino-3-methyl-butan-1-ol (3.75 g, 36.0 mmol) in 30 mL THF and 76 mL water was added $NaHCO_3$ (4.0 g, 47.6 mmol) followed by di-tert-butyldicarbonate (7.8 g, 36 mmol). After stirring overnight, the mixture was washed with 2 M $NaHSO_4$ (3×30 mL) followed by brine. Concentration gave 5.13 g (70%) of the title compound as a colorless oil: mass spectrum (M−100)=103.

Preparation 102

(1,1-Dimethyl-3-oxo-propyl)-carbamic acid tert-butyl ester (3-Hydroxy-1,1-dimethyl-propyl)-carbamic acid tert-butyl ester (6.0 g, 30 mmol) was dissolved in $CH_2Cl_2$ (50 mL) and treated with Dess-Martin periodinane (20.0 g, 44 mmol). After stirring overnight 50 mL of water was added followed by $NaHCO_3$ and $Na_2S_2O_3$. The resultant mixture was stirred vigorously for 30 min and then was extracted with $CH_2Cl_2$ (3–50 mL). The extracts were dried with $MgSO_4$ and concentrated to give 3.26 g (54%) of an orange oil. This material was used in the next step without purification.

Preparation 103

(3-Hydroxy-1,1-dimethyl-4-nitro-butyl)-carbamic acid tert-butyl ester (1,1-Dimethyl-3-oxo-propyl)-carbamic acid tert-butyl ester (3.20 g, 16 mmol) was dissolved in EtOH (10 mL). Nitromethane (976 mg, 16 mmol) was added followed by NaOH solution (640 mg in 1.6 mL water) added dropwise. The pH of the solution was reduced to ca. 6.0 with HOAc and the mixture was extracted with EtOAc (3×20 mL). Extracts were washed with brine, dried with $MgSO_4$ and concentrated. Chromatography (9:1 hexanes/EtOAc) gave 2.17 g (52%) of a pale yellow oil: mass spectrum 144.

Preparation 104

(1,1-Dimethyl-4-nitro-but-3-enyl)-carbamic acid tert-butyl ester

To (3-Hydroxy-1,1-dimethyl-4-nitro-butyl)-carbamic acid tert-butyl ester (2.00 g, 7.6 mmol) and triethylamine (2.73 g, 27.0 mmol) in 50 mL $CH_2Cl_2$ at −10° C. was added dropwise over 5 min. methanesulfonyl chloride. The mixture was warmed to rt for 1 h, and then was diluted with water and extracted with CH2Cl2 (3×30 mL). The extracts were washed sequentially with 1% HCl, water and brine and were dried over $MgSO_4$ and concentrated. Silica gel chromatography (10:1 hexane/EtOAc) gave 1.07 g (60%) of a colorless oil: 1H NMR (300 MHz, $CD_3OD$) d 7.1–7.4 (comp, 2H), 2.72 (d, 2H, J 7.5 Hz), 1.46(s, 9H), 1.31 (s, 6H).

Preparation 105

(1,1-Dimethyl-4-nitro-butyl)-carbamic acid tert-butyl ester

To (1,1-Dimethyl-4-nitro-but-3-enyl)-carbamic acid tert-butyl ester (2.0 g, 8.2 mmol) in 20 mL of EtOH was added $NaBH_4$ (500 mg, 13.5 mmol). The mixture was stirred 1 h and then quenched with saturated $NH_4Cl$ (40 mL). The solution was extracted with EtOAc (2×25 mL), the extracts were washed with brine, dried with $MgSO_4$ and concentrated. Silica gel chromatography (10:1 hexane/EtOAc) gave 1.57 g (78%) of a colorless oil: mass spectru m/e=147 (M−100).

Preparation 106

1,1-Dimethyl-4-nitro-butylamine trifluoroacetate

To (1,1-Dimethyl-4-nitro-butyl)-carbamic acid tert-butyl ester (1.0 g, 4.0 mmol) in 25 mL $CH_2Cl_2$ at −10° C. was added 2.5 mL TFA. The mixture was warmed to rt and monitored by TLC. When judged complete by TLC analysis, the mixture was concentrated to give the 518 mg (88%) of the title compound as an orange oil: mass spectrum m/e=147 (M+1).

Preparation 107 trans-2,2-Dimethyl-5-nitro-6-phenyl-piperidine

To 1,1-Dimethyl-4-nitro-butylamine (0 mg, 0.344 mmol) in 1 mL of MeOH was added $NH_4OAc$ (53 mg, 0.69 mmol) and benzaldehyde (69 mg, 0.688 mmol). The mixture was stirred at rt overnight, diluted with water, and extracted with $CHCl_3$. The extracts were dried via filtration through cotton and concentrated. Chromatography (20:1 hexanes/EtOAc) gave 17 mg (21%) of a white solid: mass spectrum m/e=235 (M+1).

Preparation 108 cis-2,2-Dimethyl-5-nitro-6-phenyl-piperidine

The trans nitropiperidine (500 mg, 2.45 mmol) was dissolved in 10 mL methanol and treated with 4 mL of 25% NaOMe/MeOH solution. After stirring for 30 min the reaction was added dropwise to a slurry of 5 g of silica gel in EtOAc. The silica gel was removed via filtration and the filtrate was concentrated. Silica gel chromatography (1:9 EtOAc/hexanes) gave 155 g (32%) of the title compound and 227 mg of trans-starting material. Title compound: mass spectrum m/e 205 (M+1).

Preparation 109

6,6-Dimethyl-2-phenyl-piperidin-3-ylamine

To 2,2-Dimethyl-5-nitro-6-phenyl-piperidine in 0.4 mL of THF was added 0.2 mL of 6 M HCl and 100 mg (1.5 mmol) of zinc powder. The mixture was stirred at rt until complete by TLC analysis. The mixture was filtered through celite, rinsing with 5 mL of water. The aqueous solution was washed with $Et_2O$ (3×5 mL) and was then basified with 1 N NaOH to pH=12. The mixture was extracted with CHCl3 and the extracts were dried via filtration through a plug of cotton and concentrated to give 6 mg (69%) of the title compound as a colorless oil: mass spectrum m/e=205 (M+1)

Example 93

7-[(6,6-Dimethyl-2-phenyl-piperidin-3-ylamino)-methyl]-6-methoxy-1-methyl-3,4-dihydro-1H-quinolin-2-one By a procedure similar to the previous examples 9 and 9A: prepared through the reaction of 6,6-dimethyl-2-phenyl-piperidin-3-ylamine with 6-Methoxy-1-methyl-2-oxo-1,2,3,4-tetrahydro-quinoline-7-carbaldehyde. Mass spectrum calcd for $C_{25}H_{34}N_3O_2$ (M+1) 408; found 408.

Preparation 110

3-Nitro-2,3,4,5-tetrahydro-1H-[2,2']bipyridinyl-6-one

To 4-Nitro-butyric acid methyl ester (29.4 g, 200 mmol) in 350 mL of EtOH was added pyridine-3-carboxaldehyde (21.4 g, 200 mmol). The mixture was refluxed overnight, and the was cooled to ice-bath temperature. The solids were collected via filtration, rinsing with cold EtOH followed by ether to give 36.8 g (83%) of a pale yellow solid: mass spectrum m/e=221 (M+1).

Preparation 111

3,3-Dimethoxy-2,3,4,5-tetrahydro-1H-[2,3']bipyridinyl-6-one

The lactam 3-Nitro-2,3,4,5-tetrahydro-1H-[2,3']bipyridinyl-6-one was dissolved in 2.6 M methanolic sodium methoxide (160 mL) and stirred at rt for 40 min. The solution was then added dropwise to 4M methanolic sulfuric acid (300 mL) at −10° C. The resultant green solution was warmed to room temperature and stirred for 2 h. The bulk of the methanol was removed under vacuum and the viscous liquid remaining was diluted with 300 mL of $CH_2Cl_2$. With stirring, the mixture was carefully diluted with 1 L of satd $NaHCO_3$. The resultant mixture was extracted with $CH_2Cl_2$ (6–500 mL) and the extracts were dried via passage through a cotton wad and concentrated. The residue was re-concentrated from 250 mL of EtOAc to near-dryness. The resultant precipitate was collected via filtration and washed with ice-cold, 1:1 Et2O/EtOAc followed by $Et_2O$ to give 13.2 g (41%) of a white solid: mass spectrum m/e=237 (M+1), 205.

Preparation 112

3,3-Dimethoxy-1,2,3,4,5,6-hexahydro-[2,3']bipyridinyl

To 3,3-Dimethoxy-2,3,4,5-tetrahydro-1H-[2,3']bipyridinyl-6-one (1.0 g, 421 mmol) in 3 mL THF was added borane-dimethylsulfide complex (3.0 mL, 6.0 mmol of a 2 M solution in THF) at 0° C. The solution was stirred at rt overnight, and was then quenched with methanol and heated at reflux for 2 h. The methanol was removed under vacuum and the residue was partitioned between water and chloroform. The mixture was acidified to pH=3 and washed with $CHCl_3$ (3–10 mL). The aqueous material was then basified to pH=8 with solid $NaHCO_3$ and then was extracted with $CHCl_3$ (3×15 mL). The extracts were dried over $MgSO_4$ and concentrated to give 812 mg (86%) of a pale yellow oil: mass spectrum m/e=223.

The invention claimed is:
1. A compound of the formula

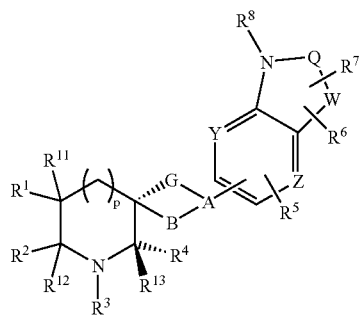

I wherein Q is C=NH, C=$CH_2$, C=S, C=O, SO or $SO_2$;
B is hydrogen, methylene, or ethylene;
when B is hydrogen, A is $CH_2$, $CH(C_1–C_6)$alkyl, or $CH(CF_3)$; and B is not directly bonded to A;
when B is methylene or ethylene, A is CH, $CH(C_1–C_6)$ alkyl or $CH(CF_3)$; and B is directly bonded to A;
Y is N and Z is CH, or Y is CH and Z is N;
G is $NH(CH_2)_q$, $S(CH_2)_q$ or $O(CH_2)_q$, wherein q is zero or one;
with the proviso that when q is zero, G is —NH—, —S— or —O—;
W is a one carbon linking group (i.e., methylene) or a saturated or unsaturated two or three carbon linking group, wherein each of the foregoing W groups can optionally be substituted with one substituent $R^7$ or two substituents $R^7$ and $R^6$, or W is a one carbon linking group that is substituted with a 2, 3, 4 or 5 carbon chain that together with W, forms a 3, 4, 5 or 6 membered spiro ring, respectively;
or W is a saturated two carbon chain linking group that forms, together with a separate 1, 2 or 3 carbon chain, a fused 3, 4 or 5 membered ring, respectively;
or W is a saturated two carbon chain linking group, wherein one of the two carbons in the chain forms, together with a separate 2, 3, 4 or 5 carbon chain, a 3, 4, 5 or 6 membered spiro ring, respectively;
p is one;
$R^3$ is selected from hydrogen, $COR^9$, $CO_2R^9$, optionally substituted phenyl, and optionally substituted $(C_1–C_8)$ alkyl wherein one of the $CH_2$ groups of said $(C_1–C_8)$ alkyl may optionally be replaced with a sulfur, oxygen or carbonyl group and wherein said $(C_1–C_8)$alkyl can optionally be unsubstituted or substituted with one to three substituents, independently selected from hydroxy, oxo, phenyl-$(C_1–C_3)$alkoxy, phenyl, cyano, halo, optionally substituted heterocyclic rings, $NR^9COR^{10}$, $NR^9CO_2R^{10}$, $CONR^9R^{10}$, $COR^9$, $CO_2R^9$, $NR^9R^{10}$, and $(C_1–C_6)$alkoxy optionally substituted with from one to seven fluorine atoms, preferably with from zero to three fluorine atoms;
and wherein the heterocyclic ring substituents on the alkyl groups of $R^3$ are selected, independently, from 3 to 7 membered saturated or unsaturated monocyclic rings containing from 1 to 4 ring heteroatoms, and 8 to 12 membered saturated or unsaturated bicyclic rings containing from 1 to 4 ring heteroatoms, wherein said heteroatoms are selected, independently, from oxygen, nitrogen and sulfur, with the proviso that there can not be two adjacent ring oxygen atoms or two adjacent ring sulfur atoms in either the monocyclic or bicyclic heterocyclic rings, and with the proviso that heterocyclic rings formed from $NR^9R^{10}$ or $CONR^9R^{10}$ must contain at least one nitrogen atom;
and wherein the heterocyclic ring substituents on the alkyl groups of $R^3$ can optionally be unsubstituted or substituted with one or more substituents, independently selected from oxo, hydroxy, thioxo, halo, cyano, phenyl, $(CH_2)_mNR^9R^{10}$, $NR^9COR^{10}$, $(CH_2)_mOR^9$, wherein m is zero, one or two, and $(C_1–C_6)$alkyl optionally substituted with one or more substituents, independently selected from halo, $CF_3$, methoxy and phenyl;
and wherein the phenyl groups of $R^3$ and the phenyl substituents in the alkyl groups of $R^3$ can optionally be unsubstituted or substituted with one or more substitutents, independently selected from the group consisting of halo, cyano, nitro, $CF_3$, $(CH_2)_mNR^9R^{10}$, wherein m is zero, one or two, $NR^9COR^{10}$, $NR^9CO_2R^{10}$, $CONR^9R^{10}$, $CO_2NR^9R^{10}$, $COR^9$, $CO_2R^9$, $(C_1–C_6)$alkyl optionally substituted with from one to seven fluorine atoms, preferably with from zero to three fluorine atoms, $(C_1–C_6)$alkoxy optionally substituted with from one to seven fluorine atoms, preferably with from zero to three fluorine atoms, and $(C_2–C_6)$alkenyl optionally unsusbstituted or substituted with from one to seven fluorine atoms;
each of $R^1$, $R^2$, $R^{11}$, $R^{12}$ and $R^{13}$ are selected, independently, from hydrogen and $(C_1–C_6)$alkyl optionally unsubstituted or substituted with one or more substituents, that are selected independently from hydroxy, oxo, $(C_1–C_6)$alkoxy and cyano;
or $R^1$ and $R^2$, together with the carbon atoms to which they are attached, or $R^2$ and $R^3$, together with the carbon and nitrogen to which they are attached, respectively, form a 5 or 6 membered saturated heterocyclic ring containing one or two heteroatoms that are selected, independently, from nitrogen, oxygen and sulfur, with the proviso that said ring can not contain two adjacent oxygen atoms or two adjacent sulfur atoms; or $R^1$ and $R^2$, together with the carbons to which they are attached, form a 5 or 6 membered, saturated or unsaturated carbocyclic ring, and wherein said heterocyclic and carbocyclic rings formed by $R^1$ and $R^2$ or by $R^2$ and $R^3$ can be unsubstituted or substituted with one or more substituents independently selected from halo, oxo, $NR^9R^{10}$, $(C_1-C_6)$alkyl optionally unsubstituted or substituted with from one to seven fluorine atoms;

or $R^{12}$ and $R^{13}$, together with the carbon atoms to which they are attached, form a 5 or 6 membered saturated heterocyclic ring containing one or two heteroatoms that are selected, independently, from nitrogen, oxygen and sulfur, with the proviso that said ring can not contain two adjacent oxygen atoms or two adjacent sulfur atoms, or $R^{12}$ and $R^{13}$, together with the carbons to which they are attached, form a 5 or 6 membered, saturated or unsaturated carbocyclic ring, and wherein said heterocyclic and carbocyclic rings formed by $R^{12}$ and $R^{13}$ can be unsubstituted or substituted with one or more substituents, independently selected from $NR^9R^{10}$, halo, phenyl-S—, phenyl-SO—, phenyl-$SO_2$—, oxo, $(C_1-C_6)$alkoxy optionally unsubstituted or substituted with from one to seven fluorine atoms, and $(C_1-C_6)$alkyl optionally substituted with from one to seven fluorine atoms;

with the proviso that no more than one of $R^1$ and $R^2$, $R^2$ and $R^3$, and $R^{12}$ and $R^{13}$ can form a ring;

$R^4$ is selected from phenyl, 2-, 3- or 4-pyridyl, 2- or 3-thienyl, and pyrimidyl, wherein $R^4$ can be optionally substituted with one or more substituents, preferably with zero or one substituent, selected, independently, from halo, $(C_1-C_6)$alkyl optionally substituted with from one to seven fluorine atoms, preferably with from zero to three fluorine atoms, $(C_1-C_6)$alkoxy optionally unsubstituted or substituted with from one to seven fluorine atoms and $(C_2-C_6)$alkenyl optionally unsubstituted or substituted with from one to seven fluorine atoms;

$R^5$ and $R^6$ are selected, independently, from hydrogen, —SO($C_1-C_6$)alkyl, —$SO_2$—($C_1-C_6$)alkyl, —SO-aryl, —$SO_2$-aryl, $CF_3$, halo, phenyl, phenyl-($C_1-C_2$)alkyl, hydroxy, aryloxy, heteroaryloxy, pyridyl, tetrazolyl, oxazolyl, thiazolyl, $(C_1-C_6)$alkoxy optionally substituted with from one to seven fluorine atoms, $(C_1-C_6)$ alkyl unsubstituted or substituted with one to seven fluorine atoms, and $(C_1-C_6)$alkyl unsubstituted or substituted with one or more substituents, selected, independently, from hydroxy, oxo, $(C_1-C_6)$alkoxy, phenyl-$(C_1-C_3)$alkoxy, phenyl, cyano, chloro, bromo, iodo, $NR^9R^{10}$, $NR^9COR^{10}$, $NR^9CO_2R^{10}$, $CONR^9R^{10}$, $COR^9$ and $CO_2R^9$;

$R^6$ and $R^7$ are selected, independently, from —SO($C_1-C_6$) alkyl, —$SO_2$—($C_1-C_6$)alkyl, —SO-aryl, —$SO_2$-aryl, $CF_3$, halo, phenyl, phenyl-($C_1-C_2$)alkyl, hydroxy, aryloxy, heteroaryloxy, pyridyl, tetrazolyl, oxazolyl, thiazolyl, $(C_1-C_6)$alkoxy optionally unsubstituted or substituted with from one to seven fluorine atoms, $(C_1-C_6)$ alkyl optionally unsubstituted or substituted with from one to seven fluorine atoms, and $(C_1-C_6)$alkyl substituted with one or more substituents, preferably with from zero to two substituents selected, independently, from hydroxy, oxo, $(C_1-C_6)$alkoxy, phenyl-$(C_1-C_3)$ alkoxy, phenyl, cyano, chloro, bromo, iodo, $NR^9R^{10}$, $NR^9COR^{10}$, $NR^9CO_2R^{10}$, $CONR^9R^{10}$, $COR^9$ and $CO_2R^9$;

each $R^9$ and each $R^{10}$ is selected, independently, from hydrogen, $(C_1-C_6)$alkyl, hydroxy$(C_1-C_6)$alkyl, phenyl and $CF_3$;

or $R^9$ and $R^{10}$, when $R^3$ is $NR^9R^{10}$ or $CONR^9R^{10}$, can form, together with the nitrogen to which they are attached, an optionally substituted heterocyclic ring that contains at least one nitrogen atom;

and wherein the phenyl groups in the definition of $R^5$, $R^6$, $R^7$ and $R^8$ and the phenyl moiety of phenyl $(C_1-C_2)$ alkyl in the definition of $R^5$, $R^6$, $R^7$ and $R^8$ can optionally be unsubstituted or substituted with one or more substituents, that are selected, independently, from halo, hydroxy, $(C_1-C_6)$alkoxy optionally unsubstituted or substituted with from one to seven fluorine atoms, preferably with from zero to three fluorine atoms, and $(C_1-C_6)$alkyl optionally substituted with from one to seven fluorine atoms, preferably with from zero to three fluorine atoms;

or a pharmaceutically acceptable salt thereof.

2. A compound according to claim 1, wherein $R^3$ is an alkyl group substituted with an optionally substituted heterocyclic ring, wherein said heterocyclic ring is selected from the following: pyrimidinyl, benzoxazolyl, 2,3-dihydro-3-oxobenzisosulfonazol-2-yl, morpholin-1-yl, thiomorpholin-1-yl, benzofuranyl, benzothienyl, indolyl, isoindolyl, isoquinolinyl, furyl, pyridyl, isothiazolyl, oxazolyl, triazolyl, tetrazolyl, quinolyl, thiazolyl, and thienyl, and groups of the formulas

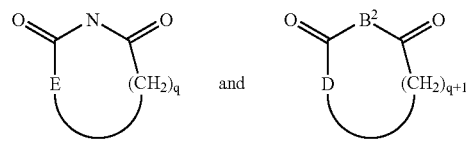

wherein $B^2$ and D are selected from carbon, oxygen and nitrogen, and at least one of $B^2$ and D is other than carbon; E is carbon or nitrogen; q is an integer from 1 to 5; any one of the carbon atoms of said $(CH_2)_q$ and $(CH_2)_{q+1}$ may be optionally substituted with $(C_1-C_6)$ alkyl or $(C_1-C_6)$ spiroalkyl; and either any one pair of the carbon atoms of said $(CH_2)_q$ and $(CH_2)_{q+1}$ may be bridged by a one or two carbon atom linkage, or any one pair of adjacent carbon atoms of said $(CH_2)_q$ and $(CH_2)_{q+1}$ may form, together with from one to three carbon atoms that are not members of the carbonyl containing ring, a $(C_3-C_5)$ fused carbocyclic ring.

3. A compound according to claim 1, wherein B is absent and A is $CH_2$.

4. A compound according to claim 1, wherein Q is a carbonyl group.

5. A compound according to claim 1, wherein Y and Z are both CH.

6. A compound according to claim 1, wherein B is ethylene, A is CH and G is $NHCH_2$.

7. A compound according to claim 1, wherein B is ethylene, A is CH and G is $SCH_2$.

8. A compound according to claim 1, wherein $R^3$ is hydrogen.

9. A compound according to claim 1, wherein $R^3$ is $CO_2R^9$.

10. A compound according to claim 1, wherein B is absent, G is NH and A is $CH_2$.

11. A compound according to claim 1, wherein W is ethylene.

12. A compound according to claim 1, wherein $R^4$ is phenyl.

13. A compound according to claim 1, wherein $R^4$ is phenyl and $R^8$ is hydrogen.

14. A compound according to claim 1, wherein p is one.

15. A compound according to claim 1, wherein $R^2$ is $(C_1-C_6)$alkyl.

16. A compound according to claim 1, wherein $R^2$ is $(C_1-C_6)$alkyl wherein the stereochemical configuration at the chiral carbon to which $R^2$ is attached is "S".

17. A compound according to claim 1, wherein $R^4$ is 2-, 3- or 4-pyridyl.

18. A compound according to claim 1, wherein $R^2$ and $R^{12}$ are selected, independently, from methyl and ethyl.

19. A compound according to claim 3, wherein Q is a carbonyl group.

20. A compound according to claim 2, wherein Q is a carbonyl group.

21. A compound according to claim 1, wherein Q is C=O and W is methylene optionally substituted with one or two substituents independently selected from $(C_1-C_6)$alkyl and $CF_3$.

22. A compound according to claim 1, wherein Q is C=O and W is ethylene optionally substituted with one or two substituents independently selected from $(C_1-C_6)$alkyl and $CF_3$.

23. A compound according to claim 1, wherein Q is SO.

24. A compound according to claim 1, wherein Q is $SO_2$.

25. A compound according to claim 1, wherein Q is C=S.

26. A compound according to claim 3 wherein $R^8$ is hydrogen.

27. A compound according to claim 1 wherein $R^3$ is an alkyl group substituted with a heterocyclic ring.

28. A compound according to claim 1 wherein $R^3$ is an alkyl group substituted with a heterocyclic ring selected from imidazolyl, 5-oxo-4,5-dihydro-1H-[1,2,4]triazol-3-yl, benzoxazol-2-yl, and 5-oxo-pyrrolidin-2-yl.

29. A compound according to claim 1 wherein $R^4$ is optionally substituted pyridyl.

30. A compound according to claim 1 wherein $R^2$ and $R^{12}$ are selected from $(C_1-C_3)$alkyl.

31. A compound according to claim 27 wherein Q is a carbonyl group.

32. A compound according to claim 2 wherein B is ethylene, A is CH and G is $NHCH_2$.

33. A compound according to claim 2 wherein B is ethylene, A is CH and G is $SCH_2$.

34. A compound according to claim 3 wherein $R^3$ is hydrogen.

35. A compound according to claim 3 wherein B is ethylene, A is CH and G is $NHCH_2$.

36. A compound according to claim 3 wherein $R^3$ is $CO_2R^9$.

37. A compound according to claim 3 wherein G is NH.

38. A compound according to claim 3 wherein W is ethylene.

39. A compound according to claim 3 wherein $R^4$ is phenyl.

40. A compound according to claim 3 wherein $R^4$ is phenyl and $R^8$ is hydrogen.

41. A compound according to claim 3 wherein $R^2$ is $(C_1-C_6)$alkyl.

42. A compound according to claim 3 wherein $R^2$ is $(C_1-C_6)$alkyl wherein the stereochemical configuration at the chiral carbon to which $R^2$ is attached is "S".

43. A compound according to claim 3, wherein $R^4$ is 2-, 3- or 4-pyridyl.

44. A compound according to claim 3 wherein $R^2$ and $R^{12}$ are selected, independently, from hydrogen, methyl, ethyl and propyl.

45. A compound according to claim 3 wherein both $R^2$ and $R^{12}$ are other than hydrogen.

46. A compound according to claim 2 wherein Y is CH and Z is nitrogen.

47. A compound according to claim 3 wherein Q is C=O and W is methylene optionally substituted with one or two substituents independently selected from $(C_1-C_6)$alkyl and $CF_3$.

48. A compound according to claim 3 wherein Q is C=O and W is ethylene optionally substituted with one or two substituents independently selected from $(C_1-C_6)$alkyl and $CF_3$.

49. A compound according to claim 3 wherein Q is SO.

50. A compound that is selected from isomers and mixtures of isomers of the following compounds, wherein said isomers or mixtures of isomers have the sterochemistry depicted in structural formula I, according to claim 1:
   6-Methoxy-1-methyl-7-[(2-phenyl-piperidin-3-ylamino)-methyl]-3,4-dihydro-1H-[1,5]naphthyridin-2-one;
   6-Methoxy-1-methyl-7-[(2-phenyl-piperidin-3-ylamino)-methyl]-3,4-dihydro-1H-[1,5]naphthyridin-2-one;
   7-[(6-Ethyl-2-phenyl-piperidin-3-ylamino)-methyl]-6-methoxy-1-methyl-3,4-dihydro-1H-[1,5]naphthyridin-2-one;
   6-Methoxy-1-methyl-7-[(2-phenyl-6-propyl-piperidin-3-ylamino)-methyl]-3,4-dihydro-1H-[1,5]naphthyridin-2-one;
   or a pharmaceutically acceptable salt thereof.

51. A compound according to claim 1, selected from the group consisting of:
   7-[((2S,3S,6S)-6-Isopropyl-2-phenyl-piperidin-3-ylamino)-methyl]-6-methoxy-1-methyl-3,4-dihydro-1H-quinoline-2-one;
   and pharmaceutically acceptable salts thereof.

* * * * *